United States Patent
Genung et al.

(10) Patent No.: US 12,180,205 B2
(45) Date of Patent: Dec. 31, 2024

(54) O-GLYCOPROTEIN-2-ACETAMIDO-2-DEOXY-3-D-GLUCOPYRANOSIDASE INHIBITORS

(71) Applicant: BIOGEN MA INC., Cambridge, MA (US)

(72) Inventors: Nathan Genung, Charlestown, MA (US); Kevin M. Guckian, Northborough, MA (US); Jeffrey Vessels, Marlborough, MA (US); Lei Zhang, Westford, MA (US); Ryan Gianatassio, Everett, MA (US); Edward Yin Shiang Lin, Ashland, MA (US); Zhili Xin, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 853 days.

(21) Appl. No.: 17/276,502

(22) PCT Filed: Sep. 18, 2019

(86) PCT No.: PCT/US2019/051661
§ 371 (c)(1),
(2) Date: Mar. 16, 2021

(87) PCT Pub. No.: WO2020/061150
PCT Pub. Date: Mar. 26, 2020

(65) Prior Publication Data
US 2022/0041586 A1    Feb. 10, 2022

Related U.S. Application Data

(60) Provisional application No. 62/750,000, filed on Oct. 24, 2018, provisional application No. 62/733,484, filed on Sep. 19, 2018.

(51) Int. Cl.
*C07D 417/14* (2006.01)
*A61P 25/28* (2006.01)
*C07D 417/06* (2006.01)

(52) U.S. Cl.
CPC .......... *C07D 417/14* (2013.01); *A61P 25/28* (2018.01); *C07D 417/06* (2013.01)

(58) Field of Classification Search
CPC ............... C07D 417/14; C07D 417/06; A61K 31/427
See application file for complete search history.

(56) References Cited

U.S. PATENT DOCUMENTS

2021/0040080 A1    2/2021    Genung et al.

FOREIGN PATENT DOCUMENTS

| KR | 20150079711 A | 7/2015 |
|---|---|---|
| WO | 2002/055496 A1 | 7/2002 |
| WO | 2006/034341 A2 | 3/2006 |
| WO | 2010/075376 A2 | 7/2010 |
| WO | 2011/143495 A1 | 11/2011 |
| WO | 2013/170072 A2 | 11/2013 |
| WO | 2014/159234 A1 | 10/2014 |
| WO | 2015/101957 A2 | 7/2015 |
| WO | 2016/107603 A1 | 7/2016 |
| WO | 2018/109198 A1 | 6/2018 |
| WO | 2018/109202 A1 | 6/2018 |
| WO | 2018/140299 A1 | 8/2018 |
| WO | 2019/178191 A1 | 9/2019 |
| WO | 2019/243531 A1 | 12/2019 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Acute Leukemia, Merck Manual (Online Edition) 6 p. pp. 1-6 (2013).*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 1, 20018, 84(10): 1424-31.*
International Search Report and Written Opinion for Application No. PCT/US2019/051661, dated Dec. 5, 2019, 12 pages.

* cited by examiner

*Primary Examiner* — Deepak R Rao
(74) *Attorney, Agent, or Firm* — McCarter & English, LLP; Xin Zhang; Zhongyu Wang

(57) ABSTRACT

Described herein are compounds represented by formulas (IA) or (IB) or a pharmaceutically acceptable salt thereof, pharmaceutical compositions comprising the same and methods of preparing and using the same. The variables $R^1$, $R^3$, $R^4$, $Y^1$, $Y^2$, Ar, Z and n are as defined herein.

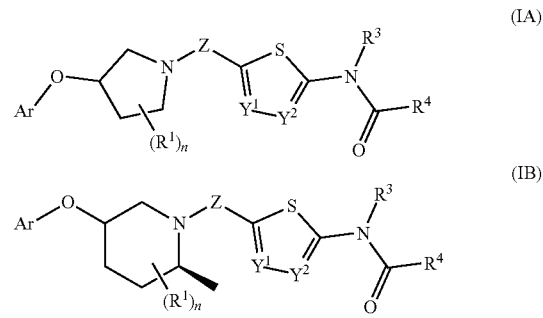

20 Claims, No Drawings

O-GLYCOPROTEIN-2-ACETAMIDO-2-DEOXY-3-D-GLUCOPYRANOSIDASE INHIBITORS

RELATED APPLICATIONS

This application is a 35 U.S.C. § 371 national stage filing of International Application No. PCT/US2019/051661, filed on Sep. 18, 2019, which in turn claims priority to U.S. Provisional Patent Application Nos. 62/733,484, filed Sep. 19, 2018; and 62/750,000, filed Oct. 24, 2018. The disclosure or content of the aforementioned applications is incorporated herein by reference, each in its entirety.

BACKGROUND

A wide range of cellular proteins, both nuclear and cytoplasmic, are post-translationally modified by the addition of the monosaccharide 2-acetamido-2-deoxy-β-D-glucopyranoside (β—N-acetyl glucosamine) which is attached via an O-glycosidic linkage. This monosaccharide is generally referred to as O-linked N-acetylglucosamine or O-GlcNAc. The enzyme responsible for post-translationally linking β—N-acetylglucosamine (GlcNAc) to specific serine and threonine residues of numerous nucleocytoplasmic proteins is O-GlcNAc transferase (OGTase). A second enzyme, known as O-glycoprotein-2-acetamido-2-deoxy-3-D-glucopyranosidase or O-GlcNAcase or OGA, removes this post-translational modification to liberate proteins, making the O-GlcNAc-modification a dynamic cycle occurring several times during the lifetime of a protein.

O-GlcNAc-modified proteins regulate a wide range of vital cellular functions including, e.g., transcription, proteasomal degradation and cellular signaling. O-GlcNAc is also found on many structural proteins, including the cytoskeletal protein "tau" which is responsible for stabilizing a key cellular network of microtubules that is essential for distributing proteins and nutrients within neurons. Importantly, tau has been clearly implicated in the etiology of several diseases including tauopathies, Alzheimer's disease, Parkinson's disease, dementia and cancer.

It is well established that Alzheimer's disease and a number of related tauopathies including Progressive Supranuclear Palsy (PSP) and amyotrophic lateral sclerosis (ALS) are characterized, in part, by the development of neurofibrillary tangles (NFTs). These NFTs are aggregates of paired helical filaments (PHFs) and are composed of an abnormal form of tau. In AD patients, tau becomes hyperphosphorylated, thereby disrupting its normal function, forming PHFs and ultimately aggregating to form NFTs.

Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups.

It has recently emerged that increases in phosphorylation levels result in decreased O-GlcNAc levels and conversely, increased O-GlcNAc levels correlate with decreased phosphorylation levels. It has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase, which prevents hyperphosphorylation of tau by preventing removal of O-GlcNac from tau, should compensate for the age-related impairment of glucose metabolism within the brains of health individuals as well as patients suffering from Alzheimer's disease or related neurodegenerative diseases.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β—N-acetylglucosaminidases, existing compounds that act to block O-GlcNAcase function are non-specific and act potently to inhibit the lysosomal β-hexosaminidases.

In view of foregoing technical challenge, and given the potential for regulation of O-GlcNAcase for treatment of AD, tauopathies and other neurological diseases, there remains a need for development of potent and selective O-GlcNAcase inhibitors.

SUMMARY

Described herein are compounds that are useful treating various diseases, disorders and medical conditions, including but not limited to those associated with proteins that are modified by O-GlcNAcase.

A first embodiment of a compound of the present invention is represented by the following structural formula:

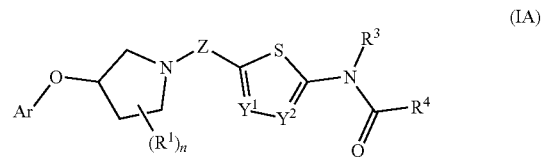

(IA)

or a pharmaceutically acceptable salt thereof, wherein:

Ar is an optionally substituted monocyclic aryl or optionally substituted monocyclic heteroaryl;

$Y^1$ and $Y^2$ are each $CR^c$ or N, wherein at least one of $Y^1$ or $Y^2$ is N;

Z is $CR^zR^z$, $C(=O)$, $(CR^zR^z)_2$, or $CH_2C(=O)$;

$R^c$ is —H, halo, $C_1$-$C_4$ alkyl, or $C_1$-$C_4$ haloalkyl;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^z$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl;

or alternatively two $R^z$ together with the carbon atom to which they are attached form a $C_3$-$C_{10}$ cycloalkyl;

$R^3$ is —H or $C_1$-$C_4$ alkyl; and $R^4$ is —H, $C_1$-$C_4$ alkyl, $C_1$-$C_4$ haloalkyl, or $C_3$-$C_6$ cycloalkyl;

or alternatively $R^3$ and $R^4$ taken together with their intervening atoms form an optionally substituted 5-to 7-membered heterocyclyl.

Another embodiment of a compound of the present invention is represented by the following structural formula:

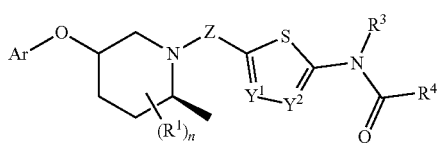

(IB)

or a pharmaceutically acceptable salt thereof, wherein:
Ar is an optionally substituted monocyclic aryl or optionally substituted monocyclic heteroaryl;
$Y^1$ and $Y^2$ are each $CR^c$ or N, wherein at least one of $Y^1$ or $Y^2$ is N;
Z is $CR^zR^z$, C(=O), $(CR^zR^z)_2$, or $CH_2C(=O)$;
$R^c$ is —H, halo, $C_1$-$C_4$ alkyl, or $C_1$-$C_4$ haloalkyl;
n is 0 or an integer from 1 to 7;
when n is other than 0, $R^1$, for each occurrence, is independently halo, $C_1$-$C_4$ alkyl, $C_1$-$C_4$ haloalkyl, or $C_1$-$C_4$ alkoxy;
$R^z$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl;
or alternatively two $R^z$ together with the carbon atom to which they are attached form a $C_3$-$C_{10}$ cycloalkyl;
$R^3$ is —H or $C_1$-$C_4$ alkyl; and
$R^4$ is —H, $C_1$-$C_4$ alkyl, $C_1$-$C_4$ haloalkyl, or $C_3$-$C_6$ cycloalkyl;
or alternatively $R^3$ and $R^4$ taken together with their intervening atoms form an optionally substituted 5-to 7-membered heterocyclyl.

Provided is a pharmaceutical composition comprising at least one compound described herein, or a pharmaceutically acceptable salt thereof, and at least one pharmaceutically acceptable excipient.

Also provided is a method of treating a subject with a disease or condition selected from a neurodegenerative disease, a tauopathy, diabetes, cancer and stress, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of inhibiting O-GlcNAcase in a subject in need thereof, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of treating a disease or condition characterized by hyperphosphorylation of tau in the brain, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient. In one embodiment, the disease or condition characterized by hyperphosphorylation of tau in the brain is Alzheimer's disease.

DETAILED DESCRIPTION

Described herein are compounds that are useful treating various diseases, disorders and medical conditions, including but not limited to those associated with proteins that are modified by O-GlcNAcase.

In a first embodiment, a compound of the present invention is represented by the following structural formula:

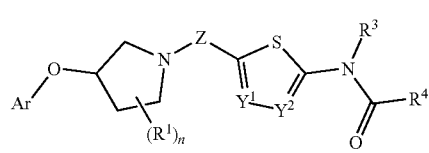

(IA)

or a pharmaceutically acceptable salt thereof, wherein the variables are as defined above in the summary for a compound represented by formula (IA).

In a second embodiment, a compound of the present invention is represented by the following structural formula:

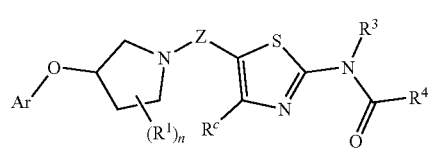

(IIA)

or a pharmaceutically acceptable salt thereof; wherein $R^1$ is halo, $C_1$-$C_4$ alkyl, $C_1$-$C_4$ haloalkyl, or $C_1$-$C_4$ alkoxy; $R^c$ is halo, $C_1$-$C_4$ alkyl, or $C_1$-$C_4$ haloalkyl; and n is an integer from 1 to 7; wherein the remaining variables are as defined in the first embodiment.

In a third embodiment, a compound of the present invention is represented by the following structural formula:

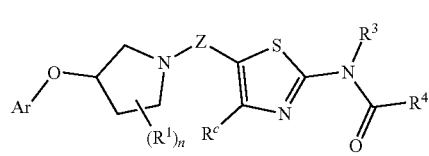

(IIA)

or a pharmaceutically acceptable salt thereof, wherein Rt is halo or $C_1$-$C_4$ alkyl; wherein the remaining variables are as defined in the first embodiment.

In a fourth embodiment, a compound of the invention is represented by the following structural formula:

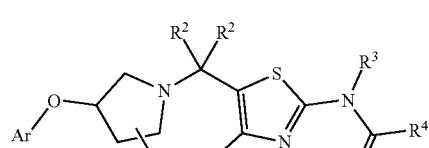

(IIIA)

or a pharmaceutically acceptable salt thereof; wherein $R^z$, for each occurrence, is independently —H or $C_1$-$C_4$ alkyl;

and wherein the remaining variables are as defined the variables in the first, second, or third embodiment.

In a fifth embodiment, a compound of the invention is represented by the following structural formula:

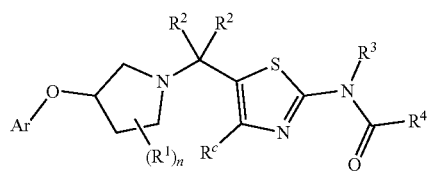

(IIIA)

or a pharmaceutically acceptable salt thereof; wherein $R^z$, for each occurrence, is independently —H or $C_1$-$C_4$ alkyl, $R^c$ is halo or $C_1$-$C_4$ alkyl; and n is an integer from 1 to 7; wherein the remaining variables are as defined in the first, second, third, or fourth embodiment.

In a sixth embodiment, a compound of the invention is represented by one of the following structural formulas:

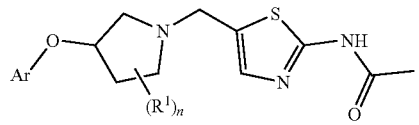

(IVA-1)

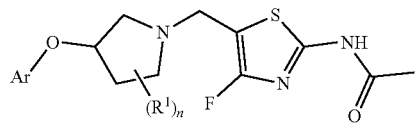

(IVA-2)

wherein the remaining variables are as defined in the first, second, third, fourth, or fifth embodiment.

In a seventh embodiment, a compound of the invention is represented by one of the following structural formulas:

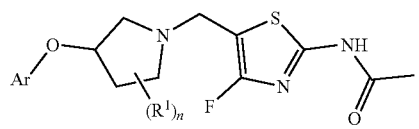

(IVA-2)

or a pharmaceutically acceptable salt thereof; wherein n is an integer from 1 to 7; wherein the remaining variables are as defined in the first, second, third, fourth, fifth, or sixth embodiment.

In an eighth embodiment, a compound of the invention is represented by one of the following structural formulas:

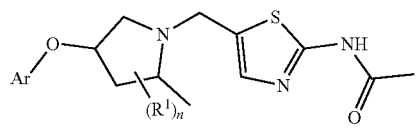

(VA-1)

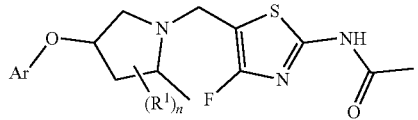

(VA-2)

or a pharmaceutically acceptable salt thereof; wherein n is 0 or an integer from 1 to 7; and wherein the remaining variables are as defined in the first, second, third, fourth, fifth, sixth, or seventh embodiment.

In a ninth embodiment, a compound of the invention is represented by one of the following structural formulas:

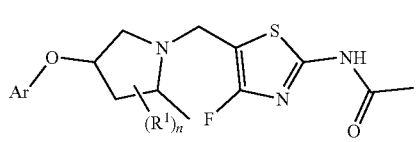

(VA-2)

or a pharmaceutically acceptable salt thereof; wherein n is 0 or an integer from 1 to 6; and wherein the remaining variables are as defined in the first, second, third, fourth, fifth, sixth, seventh, or eighth embodiment.

In a tenth embodiment, a compound of the invention is represented by one of the following structural formulas:

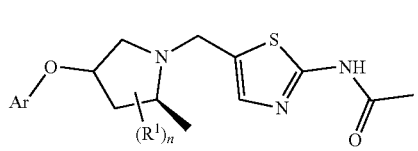

(VIA-1)

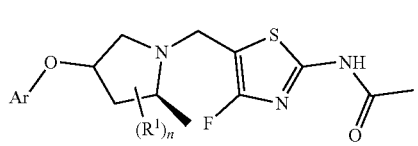

(VIA-2)

or a pharmaceutically acceptable salt thereof; wherein n is 0 or an integer from 1 to 3; and wherein the remaining variables are as defined in the first, second, third, fourth, fifth, sixth, seventh, eighth, or ninth embodiment.

In an eleventh embodiment, a compound of the invention is represented by the following structural formula:

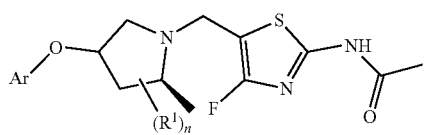

(VIA-2)

or a pharmaceutically acceptable salt thereof; wherein n is 0 or an integer from 1 to 3; and wherein the remaining variables are as defined in the first, second, third, fourth, fifth, sixth, seventh, eighth, ninth, or tenth embodiment.

In a twelfth embodiment, a compound of the invention is represented by the following structural formula:

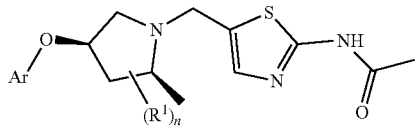
(VIIA-1)

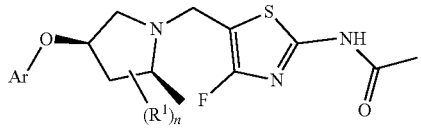
(VIIA-2)

or a pharmaceutically acceptable salt thereof; wherein n is 0, 1, or 2; and wherein the remaining variables are as defined in the first, second, third, fourth, fifth, sixth, seventh, eighth, ninth, tenth, or eleventh embodiment.

In a thirteenth embodiment, a compound of the invention is represented by the following structural formula:

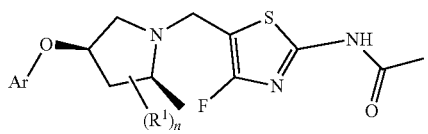
(VIIA-2)

or a pharmaceutically acceptable salt thereof; wherein n is 0, 1, or 2; and wherein the remaining variables are as defined in the first, second, third, fourth, fifth, sixth, seventh, eighth, ninth, tenth, eleventh, or twelfth embodiment.

In a fourteenth embodiment, a compound of the invention is represented by the following structural formula:

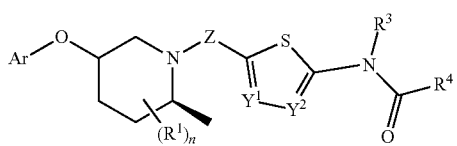
(IB)

or a pharmaceutically acceptable salt thereof; wherein the variables are as defined above in the summary for a compound represented by formula (IB) or a pharmaceutically acceptable salt thereof.

In a fifteenth embodiment, a compound of the invention is represented by one of the following structural formulas:

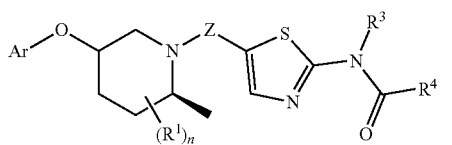
(IIB-1)

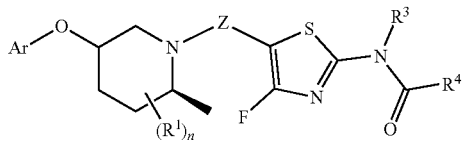
(IIB-2)

or a pharmaceutically acceptable salt thereof; wherein $R^1$ is halo or $C_1$-$C_4$ alkyl; and wherein the remaining variables are as defined in the fourteenth embodiment.

In a sixteenth embodiment, a compound of the invention is represented by one of the following structural formulas:

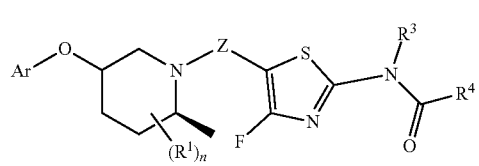
(IIB-2)

or a pharmaceutically acceptable salt thereof; wherein $R^1$ is halo or $C_1$-$C_4$ alkyl; and wherein the remaining variables are as defined in the fourteenth or fifteenth embodiment.

In a seventeenth embodiment, a compound of the invention is represented by one of the following structural formulas:

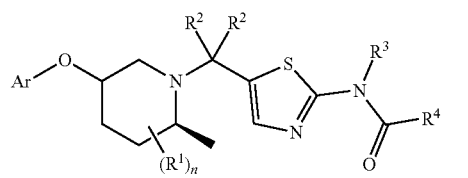
(IIIB-1)

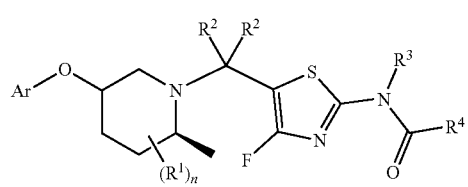
(IIIB-2)

or a pharmaceutically acceptable salt thereof; wherein $R^2$, for each occurrence, is independently —H or $C_1$-$C_4$ alkyl; wherein n is 0 or an integer from 1 to 3; and wherein the remaining variables are as defined in the fourteenth, fifteenth, or sixteenth embodiment.

In an eighteenth embodiment, a compound of the invention is represented by one of the following structural formulas:

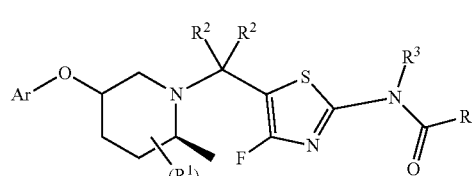
(IIIB-2)

or a pharmaceutically acceptable salt thereof; wherein $R^2$, for each occurrence, is independently —H or $C_1$-$C_4$ alkyl; wherein n is 0 or an integer from 1 to 3; and wherein the remaining variables are as defined in the fourteenth, fifteenth, sixteenth, or seventeenth embodiment.

In a nineteenth embodiment, a compound of the invention is represented by one of the following structural formulas:

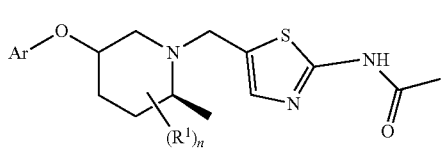
(IVB-1)

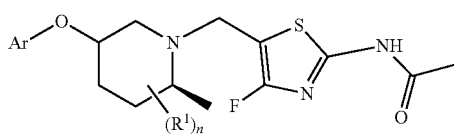
(IVB-2)

or a pharmaceutically acceptable salt thereof; wherein n is 0, 1, or 2; and wherein the remaining variables are as defined in the fourteenth, fifteenth, sixteenth, seventeenth, or eighteenth embodiment.

In a twentieth embodiment, a compound of the invention is represented by one of the following structural formulas:

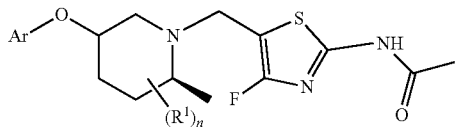
(IVB-2)

or a pharmaceutically acceptable salt thereof; wherein n is 0, 1, or 2; and wherein the remaining variables are as defined in the fourteenth, fifteenth, sixteenth, seventeenth, eighteenth, or nineteenth embodiment.

In a twenty-first embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiments, or a pharmaceutically acceptable salt thereof, Ar is an optionally substituted 5- or 6-membered monocyclic heteroaryl.

In a twenty-second embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiments, or a pharmaceutically acceptable salt thereof, Ar is an optionally substituted monocyclic heteroaryl comprising one or more nitrogen atoms.

In a twenty-third embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiments, or a pharmaceutically acceptable salt thereof, Ar is optionally substituted pyridinyl, optionally substituted pyrimidinyl, optionally substituted pyrazinyl, or optionally substituted pyridazinyl.

In a twenty-fourth embodiment, in a compound of the invention in accordance to the first, second, third, fourth, fifth, sixth, seventh, eighth, ninth, tenth, eleventh, twelfth, thirteenth, fourteenth, fifteenth, seventeenth, eighteenth, nineteenth, twentieth, twenty-first, twenty-second, or twenty-third embodiments, or a pharmaceutically acceptable salt thereof, Ar is optionally substituted pyridinyl, optionally substituted pyrimidinyl, or optionally substituted pyrazinyl.

In a twenty-fifth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment, or a pharmaceutically acceptable salt thereof, Ar is optionally substituted

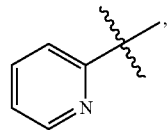 [SMILES: *c1ccccn1]

optionally substituted

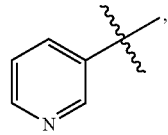 [SMILES: *c1cccnc1]

optionally substituted

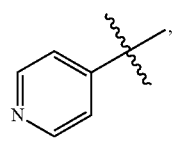 [SMILES: *c1ccncc1]

optionally substituted

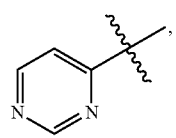 [SMILES: *c1ccncn1]

optionally substituted

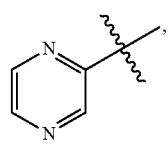

or optionally substituted

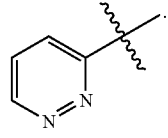 [SMILES: *c1cccnn1]

In a twenty-sixth embodiment, in a compound of the invention in accordance to the first, second, third, fourth, fifth, sixth, seventh, eighth, ninth, tenth, eleventh, twelfth, thirteenth, fourteenth, fifteenth, sixteenth, eighteenth, nineteenth, twentieth, twenty-first, twenty-second, twenty-third, twenty-fourth, or twenty-fifth embodiment, or a pharmaceutically acceptable salt thereof, Ar is optionally substituted

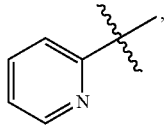, optionally substituted

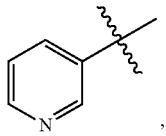 [SMILES: *c1cccnc1], optionally substituted

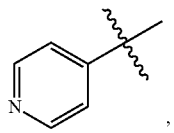, optionally substituted

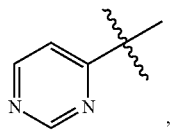, or optionally substituted

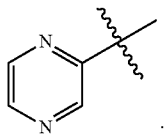,

In a twenty-seventh embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment, or a pharmaceutically acceptable salt thereof, Ar is optionally substituted

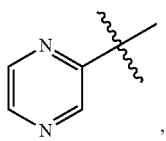, optionally substituted

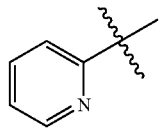 [SMILES: *c1ccccn1]

or optionally substituted

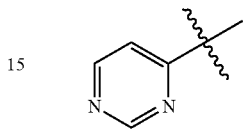.

In a twenty-eighth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment, or a pharmaceutically acceptable salt thereof, Ar is optionally substituted

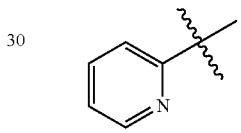

or optionally substituted

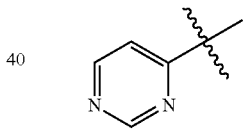.

In a twenty-ninth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth embodiment, or a pharmaceutically acceptable salt thereof, Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —NO$_2$, —OR$^z$, —NR$^x$R$^y$, —S(O)$_t$R$^x$, —NR$^x$S(O)$_t$R$^y$, —S(O)$_t$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR(C=O)NR$^x$R$^y$, —NR(C=S)NR$^x$R$^y$, —C(=S)R$^x$, —C(=O)R$^x$, phenyl and monocyclic heteroaryl;
  wherein
    the $C_1$-$C_4$ alkyl group substituent on Ar is optionally substituted with —CN, —NO$_2$, —OR$^z$, —NR$^x$R$^y$, —S(O)$_t$R$^x$, —NR$^x$S(O)$_t$R$^y$, —S(O)$_t$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$—NR$^x$C(=S)R$^y$, —NR$^x$(C=O)OR$^y$, —O(C=O)NR$^x$R$^y$, —NR(C=S)OR$^y$, —O(C=S)NR$^x$R$^y$, —NR(C—O)NR$^x$R$^y$, —NR$^x$(C=S)NR$^x$R$^y$, —C(=S)R$^x$, —C(=O)R$^y$, C$_3$-C$_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy and halomethoxy) or phenyl (optionally substituted with one or more groups selected from —CH$_3$, halomethyl, halo, methoxy and halomethoxy);

the C$_3$-C$_6$ cycloalkyl, C$_3$-C$_6$ heterocyclyl, phenyl and monocyclic heteroaryl group substituent on Ar are optionally and independently substituted with C$_1$-C$_4$ alkyl, C$_1$-C$_4$haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, or —C(=O)R$^x$;

each R$^x$ and each R$^y$ is independently —H, C$_1$-C$_4$ alkyl, or C$_3$-C$_8$ cycloalkyl; wherein the C$_1$-C$_4$ alkyl or C$_3$-C$_8$ cycloalkyl represented by R$^x$ or R$^y$ is optionally substituted with one or more substituents selected from halo, hydroxyl, C$_1$-C$_4$ alkyl, C$_1$-C$_4$ alkoxy, C$_3$-C$_6$ cycloalkyl and phenyl (optionally substituted with one or more groups selected from –CH$_3$, halomethyl, halo, methoxy and halomethoxy);

R$^z$ is —H, C$_1$-C$_4$ alkyl, C$_3$-C$_8$ cycloalkyl, or C$_3$-C$_8$ heterocyclyl; wherein the C$_1$-C$_4$alkyl, C$_3$-C$_8$ cycloalkyl, or C$_3$-C$_8$ heterocyclyl group represented by R$^z$ is optionally substituted with one or more substituents selected from —CN, halo, hydroxyl, C$_1$-C$_4$ alkyl, C$_1$-C$_4$ alkoxy, C$_3$-C$_6$ cycloalkyl and phenyl (optionally substituted with one or more groups selected from —CH$_3$, halomethyl, halo, methoxy and halomethoxy); and i is 0, 1, or 2.

In a thirtieth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth embodiment, or a pharmaceutically acceptable salt thereof, Ar is optionally substituted with one or more groups selected from C$_1$-C$_4$ alkyl, C$_1$-C$_4$ haloalkyl, C$_3$-C$_6$ cycloalkyl, C$_3$-C$_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl;

wherein
the C$_1$-C$_4$ alkyl group substituent on Ar is optionally substituted with —CN, —NO$_2$, —OR$^x$, —NR$^x$R$^y$, —S(O)$_i$R$^x$, —NR$^x$S(O)$_i$R$^y$, —S(O)—NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$—NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^y$, C$_3$-C$_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy and halomethoxy) or phenyl (optionally substituted with one or more groups selected from —CH$_3$, halomethyl, halo, methoxy and halomethoxy);

the C$_3$-C$_6$ cycloalkyl, C$_3$-C$_6$ heterocyclyl, phenyl and monocyclic heteroaryl group substituent on Ar are optionally and independently substituted with C$_1$-C$_4$ alkyl, C$_1$-C$_4$haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$;

each R$^x$ and each R$^y$ is independently —H, C$_1$-C$_4$ alkyl, or C$_3$-C$_8$ cycloalkyl; wherein the C$_1$-C$_4$ alkyl or C$_3$-C$_8$ cycloalkyl represented by R$^x$ or R$^y$ is optionally substituted with one or more substituents selected from halo, hydroxyl, C$_3$-C$_6$ cycloalkyl and phenyl (optionally substituted with one or more groups selected from —CH$_3$, halomethyl, halo, methoxy and halomethoxy);

R$^z$ is —H, C$_1$-C$_4$ alkyl, C$_1$-C$_4$ alkoxy, C$_3$-C$_8$ cycloalkyl, or C$_3$-C$_8$ heterocyclyl; wherein the C$_1$-C$_4$ alkyl or C$_3$-C$_8$ cycloalkyl group represented by R$^z$ is optionally substituted with one or more substituents selected from —CN, halo, hydroxyl, C$_1$-C$_4$ alkyl, C$_1$-C$_4$ alkoxy, C$_3$-C$_6$ cycloalkyl and phenyl (optionally substituted with one or more groups selected from —CH$_3$, halomethyl, halo, methoxy and halomethoxy); and i is 0, 1, or 2.

In a thirty-first embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, or thirtieth embodiment, or a pharmaceutically acceptable salt thereof, Ar is optionally substituted with one or more groups selected from optionally substituted C$_1$-C$_4$ alkyl, C$_1$-C$_4$ haloalkyl, optionally substituted C$_3$-C$_6$ cycloalkyl, optionally substituted C$_3$-C$_6$ heterocyclyl, halo, —CN, —OR$^z$, —NR$^x$R$^y$, —C(=O)NR$^x$R$^y$, —C(=S)NR$^x$R$^y$, —O(C=O)NR$^x$R$^y$, —O(C=S)NR$^x$R$^y$, —C(=O)R$^x$, —C(=O)OR$^z$, —NR$^x$C(=O)R$^y$, phenyl and optionally substituted monocyclic heteroaryl.

In a thirty-second embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment, or a pharmaceutically acceptable salt thereof, Ar is optionally substituted with one or more groups selected from C$_1$-C$_4$ alkyl, C$_1$-C$_4$ haloalkyl, C$_3$-C$_6$ cycloalkyl, halo, —CN, —OR$^z$, —NR$^x$R$^y$, —C(=O)NR$^x$R$^y$, —C(=S)NR$^x$R$^y$, —O(C=O)NR$^x$R$^y$, —O(C=S)

NR$^x$R$^y$, —C(=O)OR$^x$, —NR$^x$C(=O)R$^y$, phenyl and optionally substituted monocyclic heteroaryl.

In a thirty-third embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment or a pharmaceutically acceptable salt thereof, Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —OR$^z$, —NR$^x$R$^y$, and —C(=O)R$^x$; wherein the $C_3$-$C_6$ cycloalkyl and $C_3$-$C_6$ heterocyclyl substituent group on Ar are each optionally substituted with one or more groups independently selected from halo, $C_1$-$C_4$ alkyl and $C_1$-$C_4$ alkoxy; R$^x$ and R$^y$ are each independently —H, $C_1$-$C_4$ alkyl or $C_3$-$C_6$cycloalkyl, wherein the $C_1$-$C_4$ alkyl group represented by R$^x$ and R$^y$ is optionally substituted with one or more substituents independently selected from halo and $C_1$-$C_4$alkoxy; and R$^z$ is H, $C_1$-$C_4$ alkyl, $C_3$-$C_8$ cycloalkyl or $C_3$-$C_6$ heterocyclyl, wherein the $C_1$-$C_4$ alkyl, $C_3$-$C_8$cycloalkyl and $C_3$-$C_6$ heterocyclyl represented by R$^z$ are each optionally and independently substituted with one or more substituents independently selected from halo, —CN, $C_1$-$C_4$ alkyl and $C_1$-$C_4$ alkoxy.

In a thirty-fourth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, or thirty-third embodiment, Ar is optionally substituted with one with one or more groups selected from $C_1$-$C_4$ alkyl, $C_1$-$C_4$haloalkyl, halo, —CN, and —OR$^z$; wherein R$^z$ is $C_1$-$C_4$ alkyl optionally substituted with one or more halo groups.

In a thirty-fifth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, or thirty-third embodiments, or a pharmaceutically acceptable salt thereof, Ar is optionally substituted with one or more groups selected from —CH$_3$, —CF$_3$, —CHF$_2$, —F, —Cl, —CN, —OCH$_3$, —OCHF$_2$, —OC$_2$H$_5$, —OCH$_2$CF$_3$, —O(CH$_2$)$_2$(O)CH$_3$, —OCH(CH$_3$)$_2$, —O-(3-methoxycyclobutyl), —O-cyclobutyl, —O-cyclopentyl,

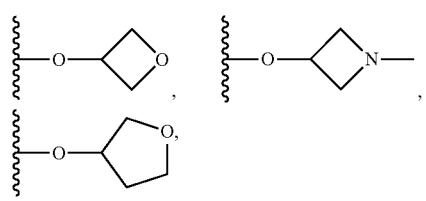

—COCH$_3$, —N(H)CH$_3$, —N(CH$_3$)C$_2$H$_5$, —N(H)cyclobutyl, —NHCH$_2$CH$_3$, —NHCH(CH$_3$)$_2$, —N(CH$_3$), —N(CH$_3$)CH$_2$CH$_2$(O)CH$_3$, —OH, azetidinyl,

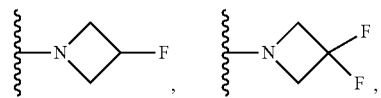 [SMILES: *N1CC(F)C1 ; *N1CC(F)(F)C1]

oxetanyl, pyrrolidinyl, morpholinyl, 4-methylpiperazinyl, and piperazinyl,

In a thirty-sixth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth embodiment, or a pharmaceutically acceptable salt thereof, Ar is optionally substituted with one with one or more groups selected from —CH$_3$, —CF$_3$, —CHF$_2$, —F, —Cl, —CN, —OCH$_3$, —O(CH$_2$)$_2$(O)CH$_3$, and —OCHF$_2$.

In a thirty-seventh embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth embodiment, or a pharmaceutically acceptable salt thereof, Ar is optionally substituted with one with one or more groups selected from —CH$_3$, —CF$_3$, —CHF$_2$, —F, —Cl, —CN, —OCH$_3$, and —OCHF$_2$.

In a thirty-eighth embodiment, in a compound of the invention in accordance to the eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth or thirty-seventh embodiment, n is 0.

In a thirty-ninth embodiment, a compound of the invention is represented by one of the following structural formulas:

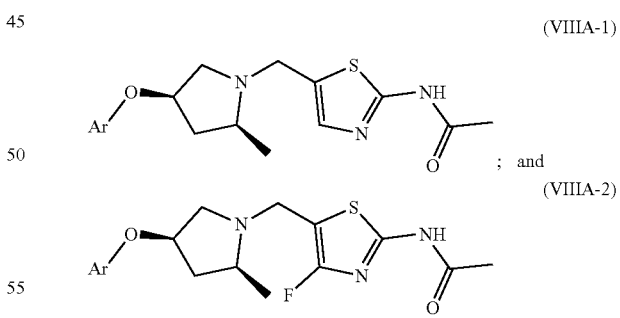

or a pharmaceutically acceptable salt thereof, wherein Ar is

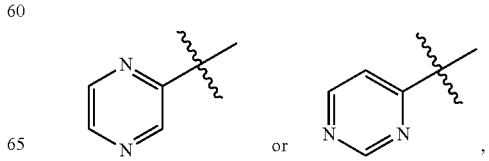

each of which is optionally substituted with one substituent $R^{Ar}$ selected from selected from $C_1$-$C_4$ alkyl, $C_1$-$C_4$haloalkyl, halo, —CN, and —$OR^z$; $R^z$ is H, $C_1$-$C_4$ alkyl, $C_3$-$C_8$ cycloalkyl or $C_3$-$C_6$ heterocyclyl, wherein the $C_1$-$C_4$ alky, $C_3$-$C_8$ cycloalkyl and $C_3$-$C_6$ heterocyclyl represented by $R^z$ are each optionally and independently substituted with one or more substituents independently selected from halo, —CN, $C_1$-$C_4$ alkyl and $C_1$-$C_4$ alkoxy.

In a fortieth embodiment, in a compound of the invention in accordance to the thirty-ninth embodiment, Ar is represented by the following formula:

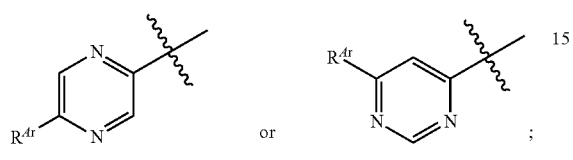

and the remaining variables are as defined in the thirty-ninth embodiment.

In a forty-first embodiment, in a compound of the invention in accordance to the thirty-ninth or fortieth embodiment, $R^{Ar}$ is $C_1$-$C_4$ alkyl or —$OR^z$; $R^z$ is H or $C_1$-$C_4$ alkyl optionally substituted with one to three substituents independently selected from halo, —CN, $C_1$-$C_4$ alkyl and $C_1$-$C_4$ alkoxy; and the remaining variables are as defined in thirty-ninth or fortieth embodiment.

In one embodiment, a compound of the invention is selected from:

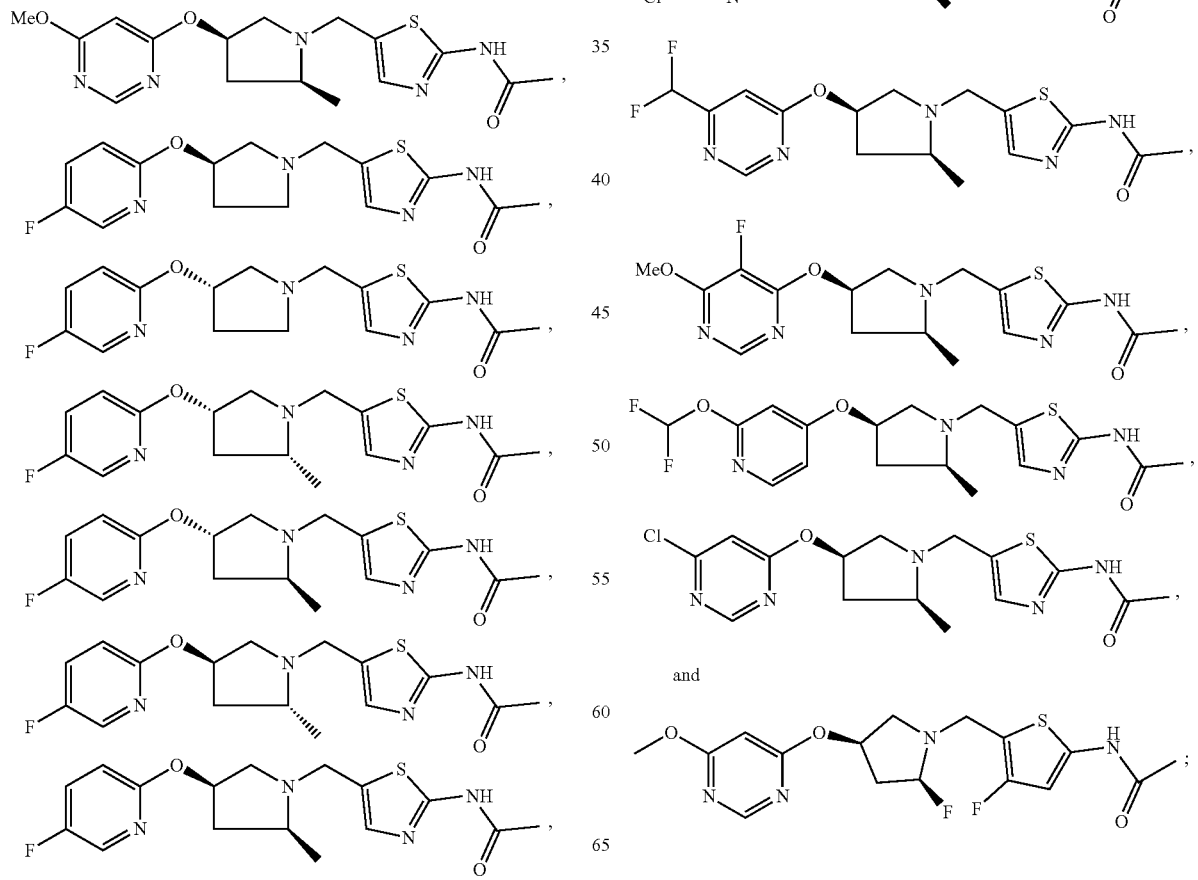

or a pharmaceutically acceptable salt thereof.

In another embodiment, a compound of the invention is selected from:
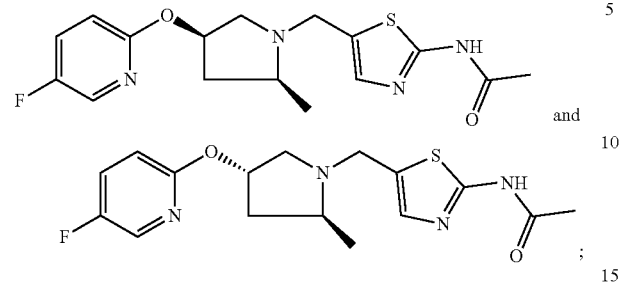
and
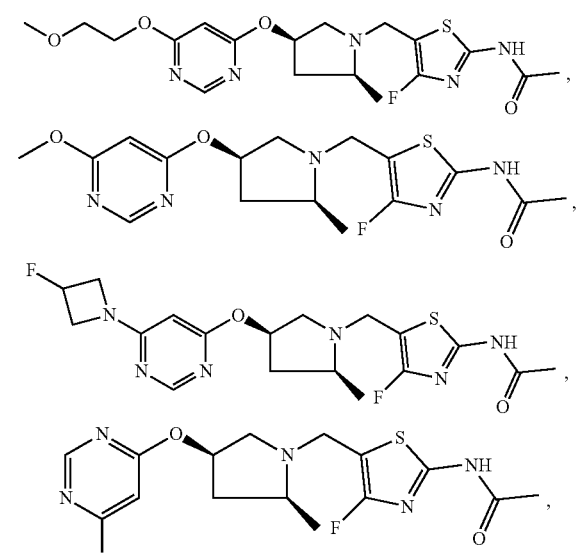
;
or a pharmaceutically acceptable salt thereof.
In another embodiment, a compound of the invention is selected from:
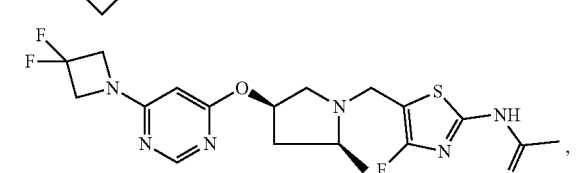
,
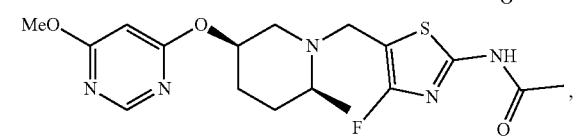
,
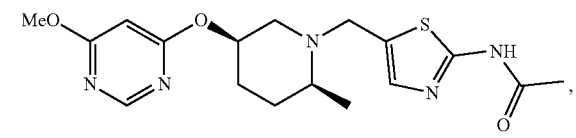
,
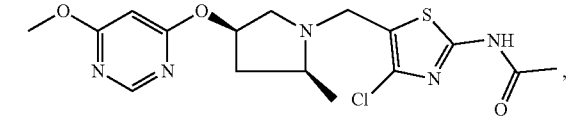
,
-continued
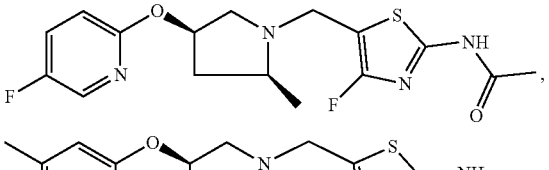
,
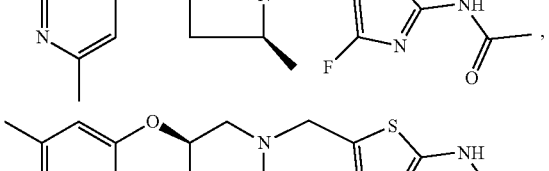
,
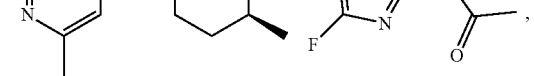
,
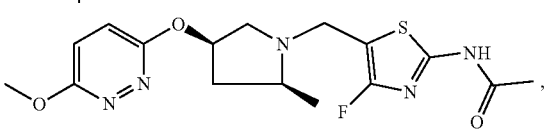
,
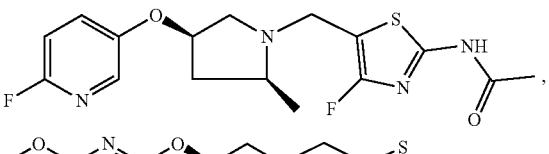
,
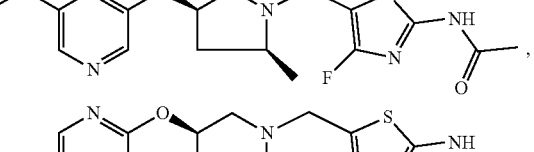
,
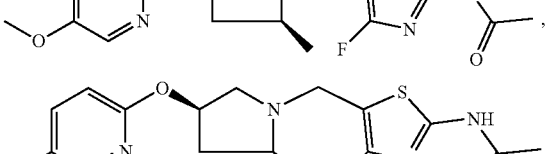
,
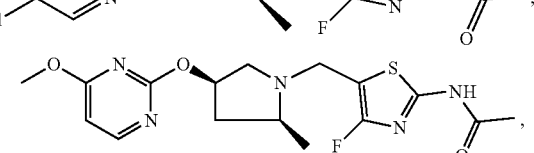
,
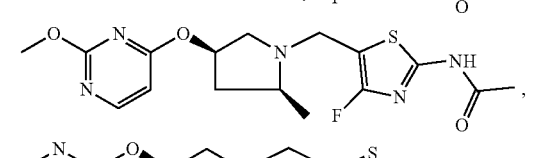
,
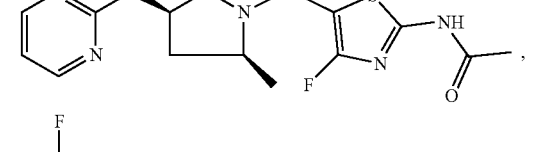
,
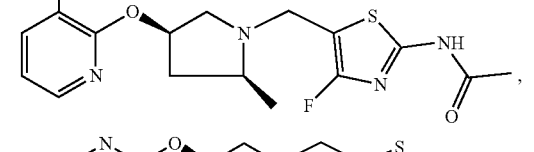
,
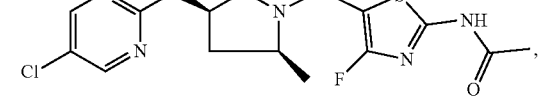
,

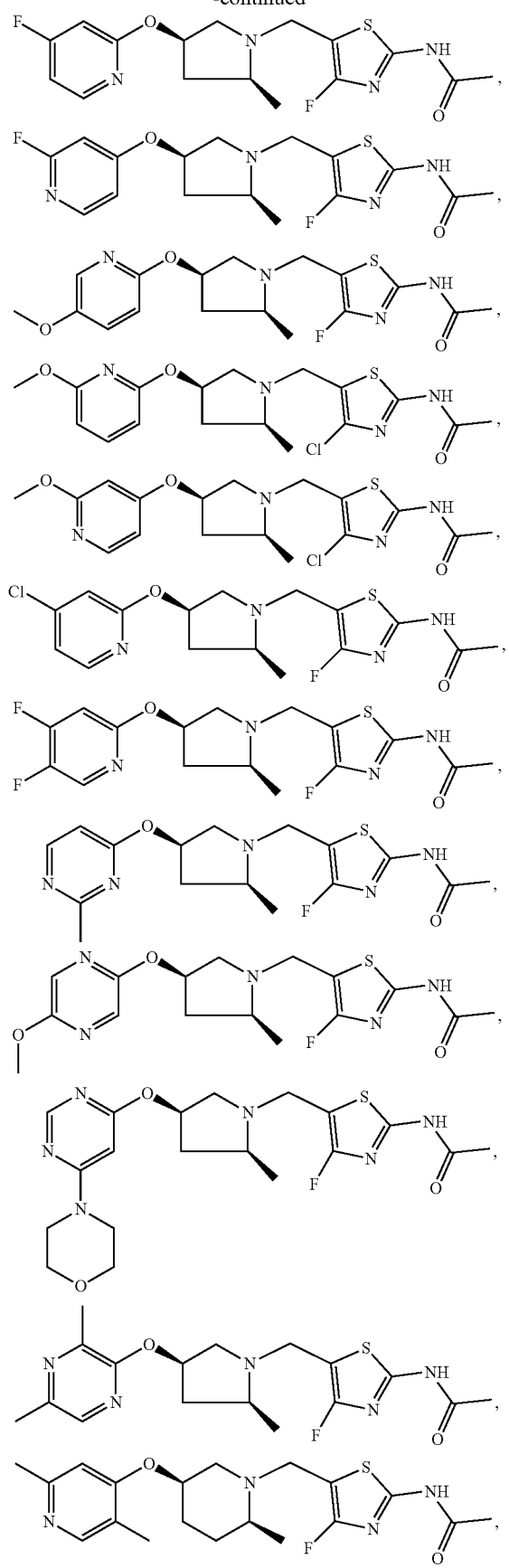
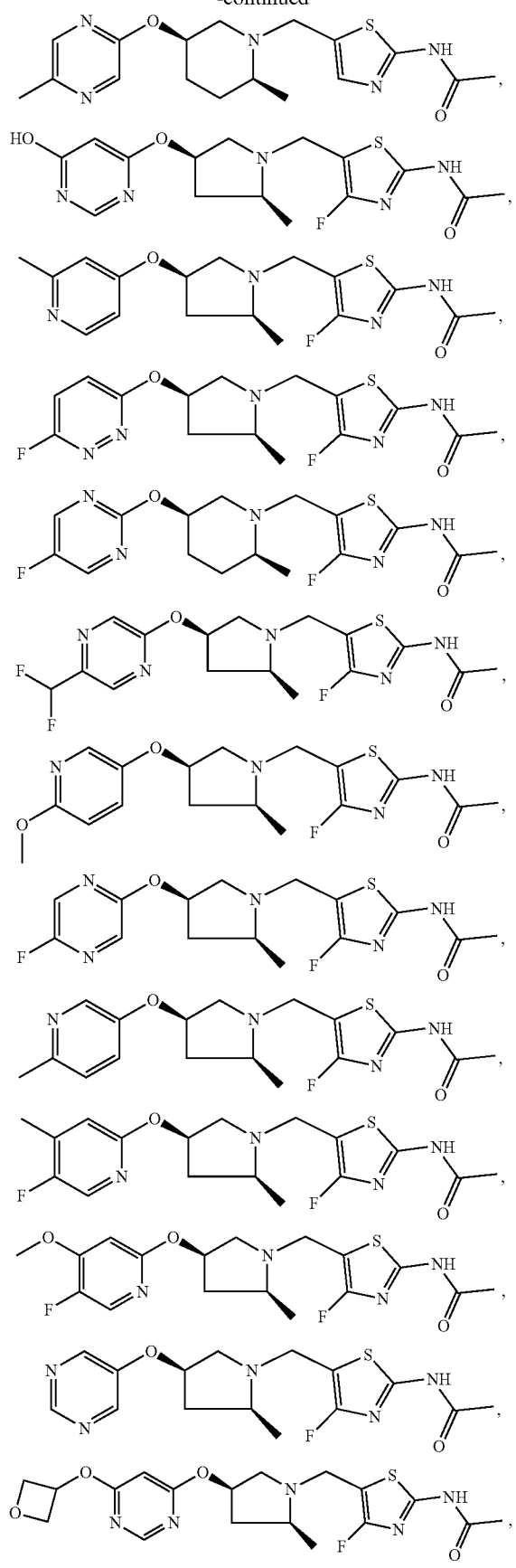

-continued
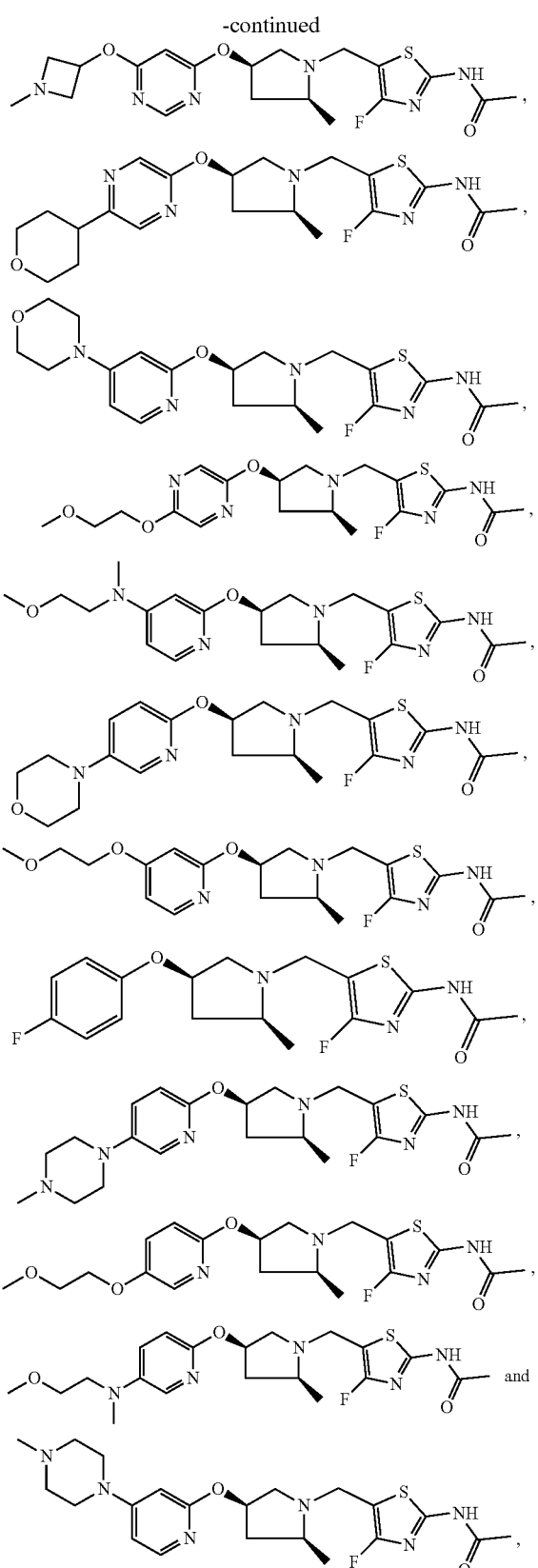
In another embodiment, a compound of the invention is selected from the compounds described in the exemplifications herein.
In yet another embodiment, a compound of the invention is selected from the following:
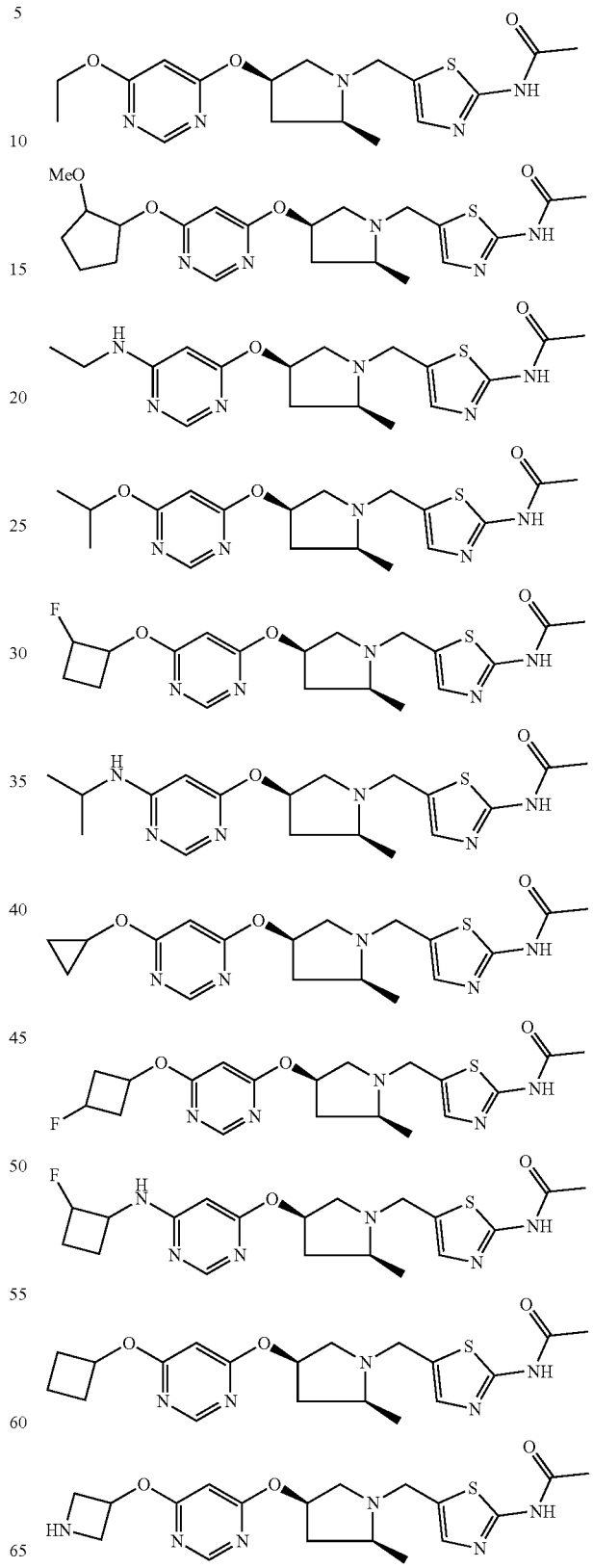

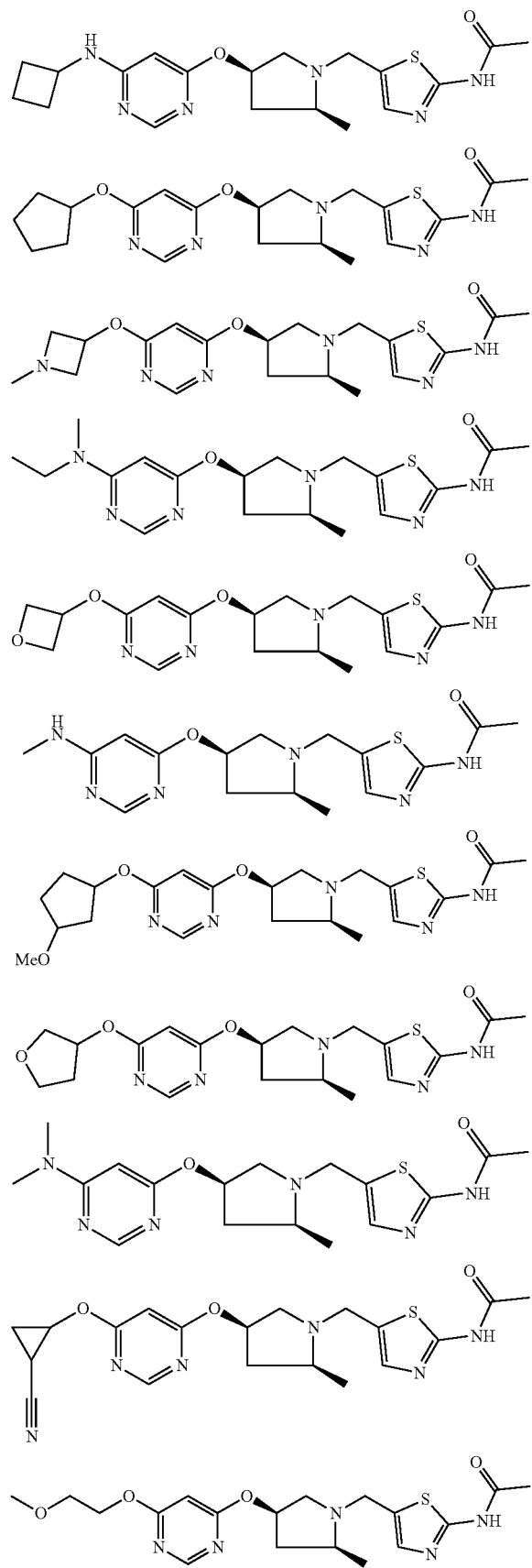

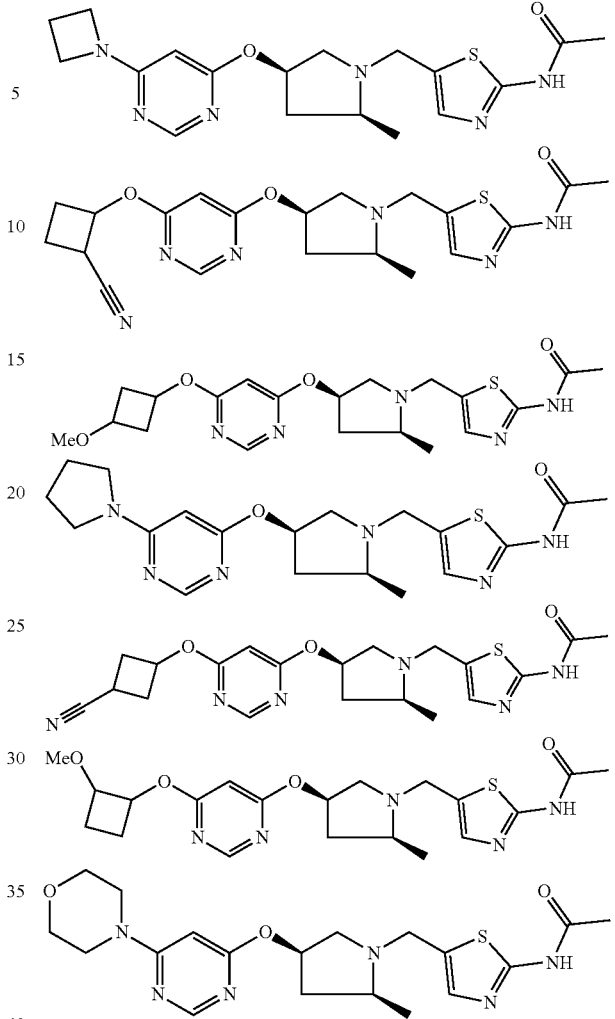

In one embodiment, a compound of the invention, such as a compound in accordance with the first or fourteenth embodiments, is selected from the following:

N-(5-(((2S,4R)-4-((6-methoxypyrimidin-4-yl)oxy)-2-methylpyrrolidin-1-yl)methyl)thiazol-2-yl)acetamide;
N-(5-(((2S,5R)-5-((5-fluoropyridin-2-yl)oxy)-2-methylpiperidin-1-yl)methyl)thiazol-2-yl)acetamide;
N-(5-(((2S,5S)-5-((5-fluoropyridin-2-yl)oxy)-2-methylpiperidin-1-yl)methyl)thiazol-2-yl)acetamide;
(R)-N-(5-((3-((5-fluoropyridin-2-yl)oxy)pyrrolidin-1-yl)methyl)thiazol-2-yl)acetamide;
(S)-N-(5-((3-((5-fluoropyridin-2-yl)oxy)pyrrolidin-1-yl)methyl)thiazol-2-yl)acetamide;
N-(5-(((2R,4S)-4-((5-fluoropyridin-2-yl)oxy)-2-methylpyrrolidin-1-yl)methyl)thiazol-2-yl)acetamide;
N-(5-(((2S,4S)-4-((5-fluoropyridin-2-yl)oxy)-2-methylpyrrolidin-1-yl)methyl)thiazol-2-yl)acetamide;
N-(5-(((2R,4R)-4-((5-fluoropyridin-2-yl)oxy)-2-methylpyrrolidin-1-yl)methyl)thiazol-2-yl)acetamide;
N-(5-(((2S,4R)-4-((5-fluoropyridin-2-yl)oxy)-2-methylpyrrolidin-1-yl)methyl)thiazol-2-yl)acetamide;
N-(5-(((2S,4R)-4-((6-methoxypyrazin-2-yl)oxy)-2-methylpyrrolidin-1-yl)methyl)thiazol-2-yl)acetamide;
N-(5-(((2S,4R)-4-((5-(difluoromethyl)pyridin-2-yl)oxy)-2-methylpyrrolidin-1-yl)methyl)thiazol-2-yl)acetamide;

N-(5-(((2S,4R)-2-methyl-4-(pyridin-2-yloxy)pyrrolidin-1-yl)methyl)thiazol-2-yl)acetamide;
N-(5-(((2S,4R)-4-((5-fluoro-6-methylpyridin-2-yl)oxy)-2-methylpyrrolidin-1-yl)methyl)thiazol-2-yl)acetamide;
N-(5-(((2S,4R)-4-((5-cyanopyridin-2-yl)oxy)-2-methylpyrrolidin-1-yl)methyl)thiazol-2-yl)acetamide;
N-(5-(((2S,4R)-4-((6-chloro-4-methylpyridin-3-yl)oxy)-2-methylpyrrolidin-1-yl)methyl)thiazol-2-yl)acetamide;
N-(5-(((2S,4R)-4-((6-(difluoromethyl)pyrimidin-4-yl)oxy)-2-methylpyrrolidin-1-yl)methyl)thiazol-2-yl)acetamide;
N-(5-(((2S,4R)-4-((5-fluoro-6-methoxypyrimidin-4-yl)oxy)-2-methylpyrrolidin-1-yl)methyl)thiazol-2-yl)acetamide;
N-(5-(((2S,4R)-4-((2-(difluoromethoxy)pyridin-4-yl)oxy)-2-methylpyrrolidin-1-yl)methyl)thiazol-2-yl)acetamide;
N-(4-fluoro-5-(((2S,4R)-4-((6-(2-methoxyethoxy)pyrimidin-4-yl)oxy)-2-methylpyrrolidin-1-yl)methyl)thiazol-2-yl)acetamide;
N-(5-(((2S,4R)-4-((6-(azetidin-1-yl)pyrimidin-4-yl)oxy)-2-methylpyrrolidin-1-yl)methyl)-4-fluorothiazol-2-yl)acetamide;
N-(4-fluoro-5-(((2S,4R)-4-((6-(3-fluoroazetidin-1-yl)pyrimidin-4-yl)oxy)-2-methylpyrrolidin-1-yl)methyl)thiazol-2-yl)acetamide;
N-(5-(((2S,4R)-4-((6-(3,3-difluoroazetidin-1-yl)pyrimidin-4-yl)oxy)-2-methylpyrrolidin-1-yl)methyl)-4-fluorothiazol-2-yl)acetamide;
(S)-N-(4-fluoro-5-((3-((6-methoxypyrimidin-4-yl)oxy)pyrrolidin-1-yl)methyl)thiazol-2-yl)acetamide;
(R)-N-(4-fluoro-5-((3-((6-methoxypyrimidin-4-yl)oxy)pyrrolidin-1-yl)methyl)thiazol-2-yl)acetamide;
N-(4-fluoro-5-(((2R,4R)-4-((6-methoxypyrimidin-4-yl)oxy)-2-methylpyrrolidin-1-yl)methyl)thiazol-2-yl)acetamide;
N-(4-fluoro-5-(((2S,4S)-4-((6-methoxypyrimidin-4-yl)oxy)-2-methylpyrrolidin-1-yl)methyl)thiazol-2-yl)acetamide;
N-(4-fluoro-5-(((2R,4S)-4-((6-methoxypyrimidin-4-yl)oxy)-2-methylpyrrolidin-1-yl)methyl)thiazol-2-yl)acetamide;
N-(4-fluoro-5-(((2S,5S)-5-((6-methoxypyrimidin-4-yl)oxy)-2-methylpiperidin-1-yl)methyl)thiazol-2-yl)acetamide;
N-(4-fluoro-5-(((2S,5R)-5-((6-methoxypyrimidin-4-yl)oxy)-2-methylpiperidin-1-yl)methyl)thiazol-2-yl)acetamide;
(S)-N-(5-((3-((6-methoxypyrimidin-4-yl)oxy)pyrrolidin-1-yl)methyl)thiazol-2-yl)acetamide;
(R)-N-(5-((3-((6-methoxypyrimidin-4-yl)oxy)pyrrolidin-1-yl)methyl)thiazol-2-yl)acetamide;
N-(5-(((2R,4R)-4-((6-methoxypyrimidin-4-yl)oxy)-2-methylpyrrolidin-1-yl)methyl)thiazol-2-yl)acetamide;
N-(5-(((2S,4S)-4-((6-methoxypyrimidin-4-yl)oxy)-2-methylpyrrolidin-1-yl)methyl)thiazol-2-yl)acetamide;
N-(5-(((2R,4S)-4-((6-methoxypyrimidin-4-yl)oxy)-2-methylpyrrolidin-1-yl)methyl)thiazol-2-yl)acetamide;
N-(5-(((2S,5S)-5-((6-methoxypyrimidin-4-yl)oxy)-2-methylpiperidin-1-yl)methyl)thiazol-2-yl)acetamide;
N-(5-(((2S,5R)-5-((6-methoxypyrimidin-4-yl)oxy)-2-methylpiperidin-1-yl)methyl)thiazol-2-yl)acetamide;
(R)-N-(4-fluoro-5-((3-((6-methoxypyrimidin-4-yl)oxy)pyrrolidin-1-yl)methyl)thiazol-2-yl)propionamide;
N-(4-fluoro-5-(((2S,4R)-4-((5-fluoropyridin-2-yl)oxy)-2-methylpyrrolidin-1-yl)methyl)thiazol-2-yl)acetamide;
(S)-N-(5-((3-((2,6-dimethylpyridin-4-yl)oxy)pyrrolidin-1-yl)methyl)-4-fluorothiazol-2-yl)acetamide;
(R)-N-(5-((3-((2,6-dimethylpyridin-4-yl)oxy)pyrrolidin-1-yl)methyl)-4-fluorothiazol-2-yl)acetamide;
N-(5-(((2S,4R)-4-((2,6-dimethylpyridin-4-yl)oxy)-2-methylpyrrolidin-1-yl)methyl)-4 fluorothiazol-2-yl)acetamide;
N-(5-(((2R,4R)-4-((2,6-dimethylpyridin-4-yl)oxy)-2-methylpyrrolidin-1-yl)methyl)-4-fluorothiazol-2-yl)acetamide;
N-(5-(((2S,4S)-4-((2,6-dimethylpyridin-4-yl)oxy)-2-methylpyrrolidin-1-yl)methyl)-4-fluorothiazol-2-yl)acetamide;
N-(5-(((2R,4S)-4-((2,6-dimethylpyridin-4-yl)oxy)-2-methylpyrrolidin-1-yl)methyl)-4-fluorothiazol-2-yl)acetamide;
N-(5-(((2S,5S)-5-((2,6-dimethylpyridin-4-yl)oxy)-2-methylpiperidin-1-yl)methyl)-4-fluorothiazol-2-yl)acetamide;
N-(5-(((2S,5R)-5-((2,6-dimethylpyridin-4-yl)oxy)-2-methylpiperidin-1-yl)methyl)-4-fluorothiazol-2-yl)acetamide;
(S)-N-(5-((3-((2,6-dimethylpyridin-4-yl)oxy)pyrrolidin-1-yl)methyl)thiazol-2-yl)acetamide;
(R)-N-(5-((3-((2,6-dimethylpyridin-4-yl)oxy)pyrrolidin-1-yl)methyl)thiazol-2-yl)acetamide;
N-(5-(((2S,4R)-4-((2,6-dimethylpyridin-4-yl)oxy)-2-methylpyrrolidin-1-yl)methyl)thiazol-2-yl)acetamide;
N-(5-(((2R,4R)-4-((2,6-dimethylpyridin-4-yl)oxy)-2-methylpyrrolidin-1-yl)methyl)thiazol-2-yl)acetamide;
N-(5-(((2S,4S)-4-((2,6-dimethylpyridin-4-yl)oxy)-2-methylpyrrolidin-1-yl)methyl)thiazol-2-yl)acetamide;
N-(5-(((2R,4S)-4-((2,6-dimethylpyridin-4-yl)oxy)-2-methylpyrrolidin-1-yl)methyl)thiazol-2-yl)acetamide;
N-(5-(((2S,5S)-5-((2,6-dimethylpyridin-4-yl)oxy)-2-methylpiperidin-1-yl)methyl)thiazol-2-yl)acetamide;
N-(5-(((2S,5R)-5-((2,6-dimethylpyridin-4-yl)oxy)-2-methylpiperidin-1-yl)methyl)thiazol-2-yl)acetamide;
N-(5-(((2S,4R)-4-((6-methoxypyridazin-3-yl)oxy)-2-methylpyrrolidin-1-yl)methyl)thiazol-2-yl)acetamide;
N-(5-(((2S,4R)-2-methyl-4-((5-methylpyrazin-2-yl)oxy)pyrrolidin-1-yl)methyl)thiazol-2-yl)acetamide;
N-(5-(((2S,4R)-2-methyl-4-((1-methyl-6-oxo-1,6-dihydropyrimidin-4-yl)oxy)pyrrolidin-1-yl)methyl)thiazol-2-yl)acetamide;
N-(5-(((2S,4R)-4-((6-methoxy-5-methylpyrimidin-4-yl)oxy)-2-methylpyrrolidin-1-yl)methyl)thiazol-2-yl)acetamide;
N-(5-(((2S,4R)-4-((2,5-dimethylpyridin-4-yl)oxy)-2-methylpyrrolidin-1-yl)methyl)thiazol-2-yl)acetamide;
N-(5-(((2S,4R)-4-((5-methoxypyrazin-2-yl)oxy)-2-methylpyrrolidin-1-yl)methyl)thiazol-2-yl)acetamide;
N-(4-fluoro-5-(((2S,4R)-4-((5-methoxypyrimidin-4-yl)oxy)-2-methylpyrrolidin-1-yl)methyl)thiazol-2-yl)acetamide;
N-(5-(((2S,4R)-4-((2-methoxy-6-methylpyrimidin-4-yl)oxy)-2-methylpyrrolidin-1-yl)methyl)thiazol-2-yl)acetamide;
N-(5-(((2S,4R)-4-((6-acetylpyrimidin-4-yl)oxy)-2-methylpyrrolidin-1-yl)methyl)-4-fluorothiazol-2-yl)acetamide;
N-(4-fluoro-5-(((2S,4R)-2-methyl-4-((6-(2,2,2-trifluoroethoxy)pyrimidin-4-yl)oxy)pyrrolidin-1-yl)methyl)thiazol-2-yl)acetamide;
N-(5-(((2S,4R)-2-methyl-4-((6-(trifluoromethyl)pyrimidin-4-yl)oxy)pyrrolidin-1-yl)methyl)thiazol-2-yl)acetamide;
N-(5-(((2S,4R)-4-((3,5-dimethylpyrazin-2-yl)oxy)-2-methylpyrrolidin-1l-yl)methyl)thiazol-2-yl)acetamide;
N-(5-(((2S,4R)-2-methyl-4-((2-methylpyridin-4-yl)oxy)pyrrolidin-1-yl)methyl)thiazol-2-yl)acetamide;
N-(5-(((2S,4R)-4-((6-fluoropyridazin-3-yl)oxy)-2-methylpyrrolidin-1-yl)methyl)thiazol-2-yl)acetamide;

N-(4-fluoro-5-(((2S,4R)-4-((6-methoxypyridazin-3-yl)oxy)-2-methylpyrrolidin-1-yl)methyl)thiazol-2-yl)acetamide;
N-(4-fluoro-5-(((2S,4R)-4-((6-fluoropyridin-3-yl)oxy)-2-methylpyrrolidin-1-yl)methyl)thiazol-2-yl)acetamide;
N-(5-(((2S,4R)-4-((5-fluoropyrimidin-2-yl)oxy)-2-methylpyrrolidin-1-yl)methyl)thiazol-2-yl)acetamide;
N-(5-(((2S,4R)-4-((5-fluoro-4-methylpyridin-2-yl)oxy)-2-methylpyrrolidin-1l-yl)methyl)thiazol-2-yl)acetamide;
N-(4-fluoro-5-(((2S,4R)-4-((6-methoxypyrazin-2-yl)oxy)-2-methylpyrrolidin-1-yl)methyl)thiazol-2-yl)acetamide;
N-(4-fluoro-5-(((2S,4R)-4-((5-methoxypyrimidin-2-yl)oxy)-2-methylpyrrolidin-1-yl)methyl)thiazol-2-yl)acetamide;
N-(5-(((2S,4R)-4-((5-chloropyridin-2-yl)oxy)-2-methylpyrrolidin-1-yl)methyl)-4-fluorothiazol-2-yl)acetamide;
N-(4-fluoro-5-(((2S,4R)-4-((4-methoxypyrimidin-2-yl)oxy)-2-methylpyrrolidin-1-yl)methyl)thiazol-2-yl)acetamide;
N-(4-fluoro-5-(((2S,4R)-2-methyl-4-(pyrimidin-2-yloxy)pyrrolidin-1-yl)methyl)thiazol-2-yl)acetamide;
N-(4-fluoro-5-(((2S,4R)-4-((3-fluoropyridin-2-yl)oxy)-2-methylpyrrolidin-1-yl)methyl)thiazol-2-yl)acetamide;
N-(5-(((2S,4R)-4-((5-chloropyrimidin-2-yl)oxy)-2-methylpyrrolidin-1-yl)methyl)-4-fluorothiazol-2-yl)acetamide;
N-(4-fluoro-5-(((2S,4R)-4-((4-fluoropyridin-2-yl)oxy)-2-methylpyrrolidin-1-yl)methyl)thiazol-2-yl)acetamide;
N-(4-fluoro-5-(((2S,4R)-4-((2-fluoropyridin-4-yl)oxy)-2-methylpyrrolidin-1-yl)methyl)thiazol-2-yl)acetamide;
N-(4-fluoro-5-(((2S,4R)-4-((5-methoxypyridin-2-yl)oxy)-2-methylpyrrolidin-1-yl)methyl)thiazol-2-yl)acetamide;
N-(4-fluoro-5-(((2S,4R)-4-((6-methoxypyridin-2-yl)oxy)-2-methylpyrrolidin-1-yl)methyl)thiazol-2-yl)acetamide;
N-(4-fluoro-5-(((2S,4R)-4-((2-methoxypyridin-4-yl)oxy)-2-methylpyrrolidin-1-yl)methyl)thiazol-2-yl)acetamide;
N-(5-(((2S,4R)-4-((4-chloropyridin-2-yl)oxy)-2-methylpyrrolidin-1-yl)methyl)-4-fluorothiazol-2-yl)acetamide;
N-(5-(((2S,4R)-4-((4,5-difluoropyridin-2-yl)oxy)-2-methylpyrrolidin-1-yl)methyl)-4-fluorothiazol-2-yl)acetamide;
N-(4-fluoro-5-(((2S,4R)-2-methyl-4-((6-morpholinopyrimidin-4-yl)oxy)pyrrolidin-1-yl)methyl)thiazol-2-yl)acetamide;
N-(5-(((2S,4R)-2-methyl-4-((2-methylpyrimidin-4-yl)oxy)pyrrolidin-1-yl)methyl)thiazol-2-yl)acetamide;
N-(4-fluoro-5-(((2S,4R)-4-((5-methoxypyrazin-2-yl)oxy)-2-methylpyrrolidin-1-yl)methyl)thiazol-2-yl)acetamide;
N-(5-(((2S,4R)-4-((3,5-dimethylpyrazin-2-yl)oxy)-2-methylpyrrolidin-1-yl)methyl)-4-fluorothiazol-2-yl)acetamide;
N-(5-(((2S,4R)-4-((2,5-dimethylpyridin-4-yl)oxy)-2-methylpyrrolidin-1-yl)methyl)-4-fluorothiazol-2-yl)acetamide;
N-(4-fluoro-5-(((2S,4R)-2-methyl-4-((5-methylpyrazin-2-yl)oxy)pyrrolidin-1-yl)methyl)thiazol-2-yl)acetamide;
N-(4-fluoro-5-(((2S,4R)-4-((6-hydroxypyrimidin-4-yl)oxy)-2-methylpyrrolidin-1-yl)methyl)thiazol-2-yl)acetamide;
N-(4-fluoro-5-(((2S,4R)-4-((2-methylpyridin-4-yl)oxy)-2-methylpyrrolidin-1-yl)methyl)thiazol-2-yl)acetamide;
N-(4-fluoro-5-(((2S,4R)-4-((6-fluoropyridazin-3-yl)oxy)-2-methylpyrrolidin-1-yl)methyl)thiazol-2-yl)acetamide;
N-(4-fluoro-5-(((2S,4R)-4-((5-fluoropyrimidin-2-yl)oxy)-2-methylpyrrolidin-1-yl)methyl)thiazol-2-yl)acetamide;
N-(5-(((2S,4R)-4-((5-(difluoromethyl)pyrazin-2-yl)oxy)-2-methylpyrrolidin-1-yl)methyl)-4-fluorothiazol-2-yl)acetamide;
N-(4-fluoro-5-(((2S,4R)-4-((6-methoxypyridin-3-yl)oxy)-2-methylpyrrolidin-1-yl)methyl)thiazol-2-yl)acetamide;
N-(5-(((2S,4R)-4-((6-fluoropyridin-3-yl)oxy)-2-methylpyrrolidin-1-yl)methyl)thiazol-2-yl)acetamide;
N-(5-(((2R,4S)-2-methyl-4-((6-methylpyridin-3-yl)oxy)pyrrolidin-1-yl)methyl)thiazol-2-yl)acetamide;
N-(4-fluoro-5-(((2S,4R)-4-((5-fluoro-4-methylpyridin-2-yl)oxy)-2-methylpyrrolidin-1-yl)methyl)thiazol-2-yl)acetamide;
N-(4-fluoro-5-(((2S,4R)-4-((5-fluoro-4-methoxypyridin-2-yl)oxy)-2-methylpyrrolidin-1-yl)methyl)thiazol-2-yl)acetamide;
N-(4-fluoro-5-(((2S,4R)-2-methyl-4-(pyrimidin-5-yloxy)pyrrolidin-1-yl)methyl)thiazol-2-yl)acetamide;
N-(5-(((2S,4R)-4-((6-((1r,3R)-3-methoxycyclobutoxy)pyrimidin-4-yl)oxy)-2-methylpyrrolidin-1-yl)methyl)thiazol-2-yl)acetamide;
N-(5-(((2S,4R)-4-((6-cyclobutoxypyrimidin-4-yl)oxy)-2-methylpyrrolidin-1-yl)methyl)thiazol-2-yl)acetamide;
N-(5-(((2S,4R)-4-((6-(2-methoxyethoxy)pyrimidin-4-yl)oxy)-2-methylpyrrolidin-1-yl)methyl)thiazol-2-yl)acetamide;
N-(5-(((2S,4R)-2-methyl-4-((6-(oxetan-3-yloxy)pyrimidin-4-yl)oxy)pyrrolidin-1-yl)methyl)thiazol-2-yl)acetamide;
N-(5-(((2S,4R)-2-methyl-4-((6-((1-methylazetidin-3-yl)oxy)pyrimidin-4-yl)oxy)pyrrolidin-1-yl)methyl)thiazol-2-yl)acetamide;
N-(5-(((2S,4R)-4-((6-ethoxypyrimidin-4-yl)oxy)-2-methylpyrrolidin-1-yl)methyl)thiazol-2-yl)acetamide;
N-(5-(((2S,4R)-4-((6-isopropoxypyrimidin-4-yl)oxy)-2-methylpyrrolidin-1-yl)methyl)thiazol-2-yl)acetamide;
N-(5-(((2S,4R)-4-((2,6-dimethylpyrimidin-4-yl)oxy)-2-methylpyrrolidin-1-yl)methyl)thiazol-2-yl)acetamide;
N-(5-(((2S,4R)-2-methyl-4-((6-(pyrrolidin-1-yl)pyrimidin-4-yl)oxy)pyrrolidin-1-yl)methyl)thiazol-2-yl)acetamide;
N-(5-(((2S,4R)-2-methyl-4-((6-morpholinopyrimidin-4-yl)oxy)pyrrolidin 1-yl)methyl)thiazol-2-yl)acetamide;
N-(5-(((2S,4R)-4-((6-(dimethylamino)pyrimidin-4-yl)oxy)-2-methylpyrrolidin-1-yl)methyl)thiazol-2-yl)acetamide;
N-(5-(((2S,4R)-4-((6-(ethyl(methyl)amino)pyrimidin-4-yl)oxy)-2-methylpyrrolidin-1-yl)methyl)thiazol-2-yl)acetamide;
N-(5-(((2S,4R)-4-((6-(azetidin-1-yl)pyrimidin-4-yl)oxy)-2-methylpyrrolidin-1-yl)methyl)thiazol-2-yl)acetamide;
N-(5-(((2S,4R)-4-((6-(cyclobutylamino)pyrimidin-4-yl)oxy)-2-methylpyrrolidin-1-yl)methyl)thiazol-2-yl)acetamide;
N-(5-(((2S,4R)-4-((6-(ethylamino)pyrimidin-4-yl)oxy)-2-methylpyrrolidin-1-yl)methyl)thiazol-2-yl)acetamide;
N-(5-(((2S,4R)-4-((6-(isopropylamino)pyrimidin-4-yl)oxy)-2-methylpyrrolidin-1-yl)methyl)thiazol-2-yl)acetamide;
N-(5-(((2S,4R)-2-methyl-4-((6-(methylamino)pyrimidin-4-yl)oxy)pyrrolidin-1-yl)methyl)thiazol-2-yl)acetamide;
N-(5-(((2S,4R)-4-((6-(cyclopentyloxy)pyrimidin-4-yl)oxy)-2-methylpyrrolidin-1-yl)methyl)thiazol-2-yl)acetamide;
N-(5-(((2S,4R)-4-((6-chloropyrimidin-4-yl)oxy)-2-methylpyrrolidin-1-yl)methyl)-4-fluorothiazol-2-yl)acetamide;
N-(4-fluoro-5-(((2S,4R)-2-methyl-4-((6-(oxetan-3-yloxy)pyrimidin-4-yl)oxy)pyrrolidin-1-yl)methyl)thiazol-2-yl)acetamide;

N-(4-fluoro-5-(((2S,4R)-2-methyl-4-((6-((1-methylazetidin-3-yl)oxy)pyrimidin-4-yl)oxy)pyrrolidin-1-yl)methyl)thiazol-2-yl)acetamide;

N-(4-fluoro-5-(((2S,4R)-2-methyl-4-((5-morpholinopyrazin-2-yl)oxy)pyrrolidin-1-yl)methyl)thiazol-2-yl)acetamide;

N-(4-fluoro-5-(((2S,4R)-2-methyl-4-((4-morpholinopyridin-2-yl)oxy)pyrrolidin-1-yl)methyl)thiazol-2-yl)acetamide;

N-(4-fluoro-5-(((2S,4R)-4-((5-(2-methoxyethoxy)pyrazin-2-yl)oxy)-2-methylpyrrolidin-1-yl)methyl)thiazol-2-yl)acetamide;

N-(4-fluoro-5-(((2S,4R)-4-((4-((2-methoxyethyl(methyl)amino)pyridin-2-yl)oxy)-2-methylpyrrolidin-1-yl)methyl)thiazol-2-yl)acetamide;

N-(4-fluoro-5-(((2S,4R)-2-methyl-4-((5-morpholinopyridin-2-yl)oxy)pyrrolidin-1-yl)methyl)thiazol-2-yl)acetamide;

N-(4-fluoro-5-(((2S,4R)-4-((4-(2-methoxyethoxy)pyridin-2-yl)oxy)-2-methylpyrrolidin-1-yl)methyl)thiazol-2-yl)acetamide;

N-(4-fluoro-5-(((2S,4R)-4-(4-fluorophenoxy)-2-methylpyrrolidin-1-yl)methyl)thiazol-2-yl)acetamide;

N-(4-fluoro-5-(((2S,4R)-2-methyl-4-((5-(4-methylpiperazin-1-yl)pyridin-2-yl)oxy)pyrrolidin-1-yl)methyl)thiazol-2-yl)acetamide;

N-(4-fluoro-5-(((2S,4R)-4-((5-(2-methoxyethoxy)pyridin-2-yl)oxy)-2-methylpyrrolidin-1-yl)methyl)thiazol-2-yl)acetamide;

N-(4-fluoro-5-(((2S,4R)-4-((5-((2-methoxyethyl(methyl)amino)pyridin-2-yl)oxy)-2-methylpyrrolidin-1-yl)methyl)thiazol-2-yl)acetamide;

N-(4-fluoro-5-(((2S,4R)-2-methyl-4-((4-(4-methylpiperazin-1-yl)pyridin-2-yl)oxy)pyrrolidin-1-yl)methyl)thiazol-2-yl)acetamide;

N-(4-fluoro-5-(((2S,4R)-4-((6-methoxypyrimidin-4-yl-4,5,6-13C₃)oxy)-2-methylpyrrolidin-1-yl)methyl)thiazol-2-yl)acetamide;

N-(5-(((2S,4R)-4-((6-(methoxy-d₃)pyrimidin-4-yl)oxy)-2-methylpyrrolidin-1-yl)methyl)thiazol-2-yl)acetamide;

N-(4-fluoro-5-(((2S,4R)-4-((6-(methoxy-d)pyrimidin-4-yl)oxy)-2-methylpyrrolidin-1-yl)methyl)thiazol-2-yl)acetamide;

N-(5-(((2S,4R)-4-((6-methoxypyrimidin-4-yl)oxy)-2-methylpyrrolidin-1-yl)methyl)thiazol-2-yl)acetamide-2,2,2-d₃; N-(4-fluoro-5-(((2S,4R)-4-((6-methoxypyrimidin-4-yl)oxy)-2-methylpyrrolidin-1-yl)methyl)thiazol-2-yl)acetamide-2,2,2-d₃;

N-(5-(((2S,4R)-4-((6-methoxypyrimidin-4-yl)oxy)-2-methylpyrrolidin-1-yl)methyl-d)thiazol-2-yl)acetamide;

N-(4-fluoro-5-(((2S,4R)-4-((6-methoxypyrimidin-4-yl)oxy)-2-methylpyrrolidin-1-yl)methyl-d)thiazol-2-yl)acetamide;

N-(5-(((2S,4R)-4-((6-methoxypyrimidin-4-yl)oxy)-2-methylpyrrolidin-1-yl)methyl-d₂)thiazol-2-yl)acetamide;

N-(4-fluoro-5-(((2S,4R)-4-((6-methoxypyrimidin-4-yl)oxy)-2-methylpyrrolidin-1-yl)methyl-d₂)thiazol-2-yl)acetamide;

N-(5-(((2S,4R)-4-((6-methoxypyrimidin-4-yl)oxy)-2-methylpyrrolidin-1-yl)methyl)thiazol-2-yl-4-d)acetamide;

N-(5-(((2S,4R)-4-((6-methoxypyrimidin-4-yl)oxy)-2-methylpyrrolidin-1-yl-4-d)methyl)thiazol-2-yl)acetamide;

N-(5-(((2S,4S)-4-((6-methoxypyrimidin-4-yl)oxy)-2-methylpyrrolidin-1-yl-4-d)methyl)thiazol-2-yl)acetamide;

N-(4-Fluoro-5-(((2S,4R)-4-((6-methoxypyrimidin-4-yl)oxy)-2-methylpyrrolidin-1-yl)methyl)thiazol-2-yl)acetamide;

N-(4-fluoro-5-(((2S,4R)-4-((6-methoxypyrimidin-4-yl)oxy)-2-methylpyrrolidin-1-yl-4-d)methyl)thiazol-2-yl)acetamide; and N-(4-fluoro-5-(((2S,4S)-4-((6-methoxypyrimidin-4-yl)oxy)-2-methylpyrrolidin-1-yl-4-d)methyl)thiazol-2-yl)acetamide;

or a pharmaceutically acceptable salt thereof.

In another embodiment, a compound of the invention, such as a compound in accordance with the first or fourteenth embodiments, is selected from the following:

N-(4-fluoro-5-(((2S,4R)-4-((6-(2-methoxyethoxy)pyrimidin-4-yl)oxy)-2-methylpyrrolidin-1-yl)methyl)thiazol-2-yl)acetamide;

N-(5-(((2S,4R)-4-((6-(azetidin-1-yl)pyrimidin-4-yl)oxy)-2-methylpyrrolidin-1-yl)methyl)-4-fluorothiazol-2-yl)acetamide;

N-(4-fluoro-5-(((2S,4R)-4-((6-(3-fluoroazetidin-1-yl)pyrimidin-4-yl)oxy)-2-methylpyrrolidin-1-yl)methyl)thiazol-2-yl)acetamide;

N-(5-(((2S,4R)-4-((6-(3,3-difluoroazetidin-1-yl)pyrimidin-4-yl)oxy)-2-methylpyrrolidin-1-yl)methyl)-4-fluorothiazol-2-yl)acetamide;

N-(4-fluoro-5-(((2S,5S)-5-((6-methoxypyrimidin-4-yl)oxy)-2-methylpiperidin-1-yl)methyl)thiazol-2-yl)acetamide;

N-(4-fluoro-5-(((2S,4R)-4-((5-fluoropyridin-2-yl)oxy)-2-methylpyrrolidin-1-yl)methyl)thiazol-2-yl)acetamide;

N-(5-(((2S,4R)-4-((2,6-dimethylpyridin-4-yl)oxy)-2-methylpyrrolidin-1-yl)methyl)-4-fluorothiazol-2-yl)acetamide;

N-(4-fluoro-5-(((2S,4R)-4-((5-methoxypyrimidin-4-yl)oxy)-2-methylpyrrolidin-1-yl)methyl)thiazol-2-yl)acetamide;

N-(5-(((2S,4R)-4-((6-acetylpyrimidin-4-yl)oxy)-2-methylpyrrolidin-1-yl)methyl)-4-fluorothiazol-2-yl)acetamide;

N-(4-fluoro-5-(((2S,4R)-2-methyl-4-((6-(2,2,2-trifluoroethoxy)pyrimidin-4-yl)oxy)pyrrolidin-1-yl)methyl)thiazol-2-yl)acetamide;

N-(4-fluoro-5-(((2S,4R)-4-((6-methoxypyridazin-3-yl)oxy)-2-methylpyrrolidin-1-yl)methyl)thiazol-2-yl)acetamide;

N-(4-fluoro-5-(((2S,4R)-4-((6-fluoropyridin-3-yl)oxy)-2-methylpyrrolidin-1-yl)methyl)thiazol-2-yl)acetamide;

N-(4-fluoro-5-(((2S,4R)-4-((6-methoxypyrazin-2-yl)oxy)-2-methylpyrrolidin-1-yl)methyl)thiazol-2-yl)acetamide;

N-(4-fluoro-5-(((2S,4R)-4-((5-methoxypyrimidin-2-yl)oxy)-2-methylpyrrolidin-1-yl)methyl)thiazol-2-yl)acetamide;

N-(5-(((2S,4R)-4-((5-chloropyridin-2-yl)oxy)-2-methylpyrrolidin-1-yl)methyl)-4-fluorothiazol-2-yl)acetamide;

N-(4-fluoro-5-(((2S,4R)-4-((4-methoxypyrimidin-2-yl)oxy)-2-methylpyrrolidin-1-yl)methyl)thiazol-2-yl)acetamide;

N-(4-fluoro-5-(((2S,4R)-2-methyl-4-(pyrimidin-2-yloxy)pyrrolidin-1-yl)methyl)thiazol-2-yl)acetamide;

N-(4-fluoro-5-(((2S,4R)-4-((3-fluoropyridin-2-yl)oxy)-2-methylpyrrolidin-1-yl)methyl)thiazol-2-yl)acetamide;

N-(5-(((2S,4R)-4-((5-chloropyrimidin-2-yl)oxy)-2-methylpyrrolidin-1-yl)methyl)-4-fluorothiazol-2-yl)acetamide;

N-(4-fluoro-5-(((2S,4R)-4-((4-fluoropyridin-2-yl)oxy)-2-methylpyrrolidin-1-yl)methyl)thiazol-2-yl)acetamide;

N-(4-fluoro-5-(((2S,4R)-4-((2-fluoropyridin-4-yl)oxy)-2-methylpyrrolidin-1-yl)methyl)thiazol-2-yl)acetamide;

N-(4-fluoro-5-(((2S,4R)-4-((5-methoxypyridin-2-yl)oxy)-2-methylpyrrolidin-1-yl)methyl)thiazol-2-yl)acetamide;

N-(4-fluoro-5-(((2S,4R)-4-((6-methoxypyridin-2-yl)oxy)-2-methylpyrrolidin-1-yl)methyl)thiazol-2-yl)acetamide;
N-(4-fluoro-5-(((2S,4R)-4-((2-methoxypyridin-4-yl)oxy)-2-methylpyrrolidin-1-yl)methyl)thiazol-2-yl)acetamide;
N-(5-(((2S,4R)-4-((4-chloropyridin-2-yl)oxy)-2-methylpyrrolidin-1-yl)methyl)-4-fluorothiazol-2-yl)acetamide;
N-(5-(((2S,4R)-4-((4,5-difluoropyridin-2-yl)oxy)-2-methylpyrrolidin-1-yl)methyl)-4-fluorothiazol-2-yl)acetamide;
N-(4-fluoro-5-(((2S,4R)-2-methyl-4-((6-morpholinopyrimidin-4-yl)oxy)pyrrolidin-1-yl)methyl)thiazol-2-yl)acetamide;
N-(4-fluoro-5-(((2S,4R)-4-((5-methoxypyrazin-2-yl)oxy)-2-methylpyrrolidin-1-yl)methyl)thiazol-2-yl)acetamide;
N-(5-(((2S,4R)-4-((3,5-dimethylpyrazin-2-yl)oxy)-2-methylpyrrolidin-1-yl)methyl)-4-fluorothiazol-2-yl)acetamide;
N-(5-(((2S,4R)-4-((2,5-dimethylpyridin-4-yl)oxy)-2-methylpyrrolidin-1-yl)methyl)-4-fluorothiazol-2-yl)acetamide;
N-(4-fluoro-5-(((2S,4R)-2-methyl-4-((5-methylpyrazin-2-yl)oxy)pyrrolidin-1-yl)methyl)thiazol-2-yl)acetamide;
N-(4-fluoro-5-(((2S,4R)-4-((6-hydroxypyrimidin-4-yl)oxy)-2-methylpyrrolidin-1-yl)methyl)thiazol-2-yl)acetamide;
N-(4-fluoro-5-(((2S,4R)-2-methyl-4-((2-methylpyridin-4-yl)oxy)pyrrolidin-1-yl)methyl)thiazol-2-yl)acetamide;
N-(4-fluoro-5-(((2S,4R)-4-((6-fluoropyridazin-3-yl)oxy)-2-methylpyrrolidin-1-yl)methyl)thiazol-2-yl)acetamide;
N-(4-fluoro-5-(((2S,4R)-4-((5-fluoropyrimidin-2-yl)oxy)-2-methylpyrrolidin-1-yl)methyl)thiazol-2-yl)acetamide;
N-(5-(((2S,4R)-4-((5-(difluoromethyl)pyrazin-2-yl)oxy)-2-methylpyrrolidin-1l-yl)methyl)-4-fluorothiazol-2-yl)acetamide;
N-(4-fluoro-5-(((2S,4R)-4-((6-methoxypyridin-3-yl)oxy)-2-methylpyrrolidin-1-yl)methyl)thiazol-2-yl)acetamide;
N-(4-fluoro-5-(((2S,4R)-4-((5-fluoro-4-methylpyridin-2-yl)oxy)-2-methylpyrrolidin-1-yl)methyl)thiazol-2-yl)acetamide;
N-(4-fluoro-5-(((2S,4R)-4-((5-fluoro-4-methoxypyridin-2-yl)oxy)-2-methylpyrrolidin-1-yl)methyl)thiazol-2-yl)acetamide;
N-(4-fluoro-5-(((2S,4R)-2-methyl-4-(pyrimidin-5-yloxy)pyrrolidin-1-yl)methyl)thiazol-2-yl)acetamide;
N-(5-(((2S,4R)-4-((6-chloropyrimidin-4-yl)oxy)-2-methylpyrrolidin-1-yl)methyl)-4-fluorothiazol-2-yl)acetamide;
N-(4-fluoro-5-(((2S,4R)-2-methyl-4-((6-(oxetan-3-yloxy)pyrimidin-4-yl)oxy)pyrrolidin-1-yl)methyl)thiazol-2-yl)acetamide;
N-(4-fluoro-5-(((2S,4R)-2-methyl-4-((6-((1-methylazetidin-3-yl)oxy)pyrimidin-4-yl)oxy)pyrrolidin-1-yl)methyl)thiazol-2-yl)acetamide;
N-(4-fluoro-5-(((2S,4R)-2-methyl-4-((5-morpholinopyrazin-2-yl)oxy)pyrrolidin-1-yl)methyl)thiazol-2-yl)acetamide;
N-(4-fluoro-5-(((2S,4R)-2-methyl-4-((4-morpholinopyridin-2-yl)oxy)pyrrolidin-1-yl)methyl)thiazol-2-yl)acetamide;
N-(4-fluoro-5-(((2S,4R)-4-((5-(2-methoxyethoxy)pyrazin-2-yl)oxy)-2-methylpyrrolidin-1-yl)methyl)thiazol-2-yl)acetamide;
N-(4-fluoro-5-(((2S,4R)-4-((4-((2-methoxyethyl(methyl)amino)pyridin-2-yl)oxy)-2-methylpyrrolidin-1-yl)methyl)thiazol-2-yl)acetamide;
N-(4-fluoro-5-(((2S,4R)-2-methyl-4-((5-morpholinopyridin-2-yl)oxy)pyrrolidin-1-yl)methyl)thiazol-2-yl)acetamide;
N-(4-fluoro-5-(((2S,4R)-4-((4-(2-methoxyethoxy)pyridin-2-yl)oxy)-2-methylpyrrolidin-1-yl)methyl)thiazol-2-yl)acetamide;
N-(4-fluoro-5-(((2S,4R)-4-(4-fluorophenoxy)-2-methylpyrrolidin-1-yl)methyl)thiazol-2-yl)acetamide;
N-(4-fluoro-5-(((2S,4R)-2-methyl-4-((5-(4-methylpiperazin-1-yl)pyridin-2-yl)oxy)pyrrolidin-1-yl)methyl)thiazol-2-yl)acetamide;
N-(4-fluoro-5-(((2S,4R)-4-((5-(2-methoxyethoxy)pyridin-2-yl)oxy)-2-methylpyrrolidin-1-yl)methyl)thiazol-2-yl)acetamide;
N-(4-fluoro-5-(((2S,4R)-4-((5-((2-methoxyethyl)(methyl)amino)pyridin-2-yl)oxy)-2-methylpyrrolidin-1-yl)methyl)thiazol-2-yl)acetamide;
N-(4-fluoro-5-(((2S,4R)-2-methyl-4-((4-(4-methylpiperazin-1-yl)pyridin-2-yl)oxy)pyrrolidin-1-yl)methyl)thiazol-2-yl)acetamide;
N-(4-Fluoro-5-(((2S,4R)-4-((6-methoxypyrimidin-4-yl)oxy)-2-methylpyrrolidin-1-yl)methyl)thiazol-2-yl)acetamide;
N-(4-fluoro-5-(((2S,4R)-4-((6-methoxypyrimidin-4-yl)oxy)-2-methylpyrrolidin-1l-yl-4-d)methyl)thiazol-2-yl)acetamide; and
N-(4-fluoro-5-(((2S,4S)-4-((6-methoxypyrimidin-4-yl)oxy)-2-methylpyrrolidin-1-yl-4-d)methyl)thiazol-2-yl)acetamide, or a pharmaceutically acceptable salt thereof.

As used herein, the term "alkyl" refers to a fully saturated branched or straightchained hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkoxy" refers to the group —OR, in which R is an alkyl or a cycloalkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O-cyclopentyl and —O-cyclohexyl.

As used herein, the terms "aryl", "aryl group", "aryl ring", "aromatic group" and "aromatic ring" are used interchangeably to refer to an aromatic 5-to 12-membered monocyclic or bicyclic carbon ring system. Examples of monocyclic aryl systems include, but are not limited to, cyclopenta-1,3-dien-1-yl, phenyl and the like.

The number of carbon atoms in a group is specified herein by the prefix "$C_{x-xx}$", wherein x and xx are integers. For example, "$C_{1-4}$ alkyl" is an alkyl group which has from 1 to 4 carbon atoms.

As used herein, the term "halogen" or "halo" may be fluoro, chloro, bromo or iodo.

As used herein, the term "haloalkyl" refers to an alkyl, as defined herein, that is substituted by one or more halo groups as defined herein.

As used herein, the terms "heterocyclyl", "heterocyclyl group", "heterocyclic" and "heterocyclic ring" are used interchangeably to refer to a saturated, unsaturated, non-aromatic, monocyclic or bicyclic (e.g., fused) ring system which has from 3-to 12-ring members, or in particular 3-to 6-ring members or 5-to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(=O)), N can be oxidized (e.g., N(O)) or quaternized (e.g. N*), and S can be optionally oxidized to sulfoxide and sulfone. Examples of non-aromatic heterocyclyls include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and the like. Examples of bicyclic nonaromatic heterocyclic ring systems include benzo[1,3]dioxolyl, tetrahydroindolyl, and 2-azaspiro[3.3] heptanyl, and the like.

As used herein, the terms "heteroaryl", "heteroaryl group", "heteroaryl ring" "heteroaromatic" and "heteroaromatic ring" are used interchangeably to refer to an aromatic 5-to 12-membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone. "Heteroaryl" includes a heteroaromatic group that is fused to a phenyl group or non-aromatic heterocycle such as tetrahydrofuran, pyran, pyrrolidine, piperidine, and the like. As used herein, the heteroaryl group Ar can be attached to the rest of a compound of the invention at any ring that has an open valency. Examples of monocyclic heteroaryl ring systems include pyrrolyl, furanyl, imidazolyl, pyrazolyl, oxazolyl, isoxazolyl, thiazolyl, isothiazolyl, oxadiazolyl, thiadiazolyl, triazolyl, tetrazolyl, pyridyl, pyrazinyl, pyrimidyl, pyridazinyl, oxazinyl, thiazinyl, dioxinyl, triazinyl, tetrazinyl, azepinyl, oxepinyl, thiepinyl, thiazepinyl, 1-oxo-pyridyl, thienyl, valerolactamyl, and the like.

As used herein, the term "cycloalkyl" refers to completely saturated monocyclic or bicyclic (e.g., fused) hydrocarbon groups of 3-12 carbon atoms, 3-6 carbon atoms or 5-7 carbon atoms.

As used herein, the term "halocycloalkyl" refers to a cycloalkyl, as defined herein, that is substituted by one or more halo groups as defined herein.

A substituted alkyl, phenyl, heteroaryl, non-aromatic heterocyclyl or heterocyclyl group is an alkyl, phenyl, heteroaryl, non-aromatic heterocyclyl or heterocyclyl group that has one or more (e.g., two, three, four, five, six, etc.) substituents. In some embodiments, a substituted alkyl, phenyl, heteroaryl, non-aromatic heterocyclyl or heterocyclyl group is an alkyl, phenyl, heteroaryl, non-aromatic heterocyclyl or heterocyclyl group has one to six, one to three, or one to two substituents. Suitable substituents are those that do not significantly decrease the O-GlcNAcase inhibitory activity of a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof. Examples of suitable substituents for an alkyl, phenyl, heteroaryl, non-aromatic heterocyclyl or heterocyclyl group include but are not limited to $C_1$-$C_4$ alkyl, $C_1$-$C_4$ haloalkyl, $C_3$-$C_6$ cycloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S) R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR(C=S)OR$^y$, —O(C=S)NR$^x$R$^y$, —NR(C=O)NR$^x$R$^y$, —NR(C=S)NR$^x$R$^y$, —C(=S)R$^x$, —C(=O)R$^x$, phenyl and monocyclic heteroaryl. The $C_1$-$C_4$alkyl group substituent is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S) R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O) NR$^x$R$^y$, —NR$^x$(C=S)NR$^x$R$^y$, —C(=S)R$^x$, and —C(=O) R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy). The $C_3$-$C_6$ cycloalkyl, phenyl and monocyclic heteroaryl group substituents are optionally and independently substituted with $C_1$-$C_4$ alkyl, $C_1$-$C_4$ haloalkyl, halo, —CN, —NO$_2$, —OR$^z$, —NR$^x$R$^y$, —S(O)$_i$R$^x$, —NR$^x$S (O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O) OR$^y$, —O(C=O)NR$^x$R$^y$, —NR$^x$(C=S)OR$^y$, —O(C=S) NR$^x$R$^y$, —NR$^x$(C=O)NR$^x$R$^y$, —NR$^x$(C=S)NR$^x$R$^y$, —C(=S)R$^x$, and —C(=O)R$^x$. In these substituents, each R$^x$ and each R$^y$ is independently —H, $C_1$-$C_4$ alkyl, or $C_3$-$C_8$ cycloalkyl, where the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy). In these substituents, R$^z$ is —H, $C_1$-$C_4$ alkyl, or $C_3$-$C_8$ cycloalkyl, where the $C_1$-$C_4$ alkyl or $C_3$-$C_8$ cycloalkyl group represented by R$^z$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy and halomethoxy). In these substituents, i is 0, 1, or 2.

Pharmaceutically acceptable salts of the compounds disclosed herein are also included in the invention. In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Suitable bases include but are not limited to alkali metal hydroxides, alkaline earth metal hydroxides, carbonates, bicarbonates, and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular stereoisomer (e.g., enantiomer, diastereomer, etc.) of a compound used in the disclosed methods is depicted by name or structure, the stereochemical purity of the compounds is at least 60%, 70%, 80%, 90%, 95%, 97%, 99%, 99.5% or 99.9%. "Stereochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In one embodiment, the invention also provides isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

In one embodiment, the invention provides deuterated compounds disclosed herein, in which any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

One aspect of the invention includes a method for inhibiting a glycosidase and/or a glycosidase signaling pathway in a cell, the method comprising contacting the cell with an effective amount of a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase. In one embodiment, the cell is contacted in vitro or in vivo. In one embodiment, contacting the cell includes administering the compound to a subject.

One aspect of the invention includes a method for inhibiting a glycosidase and/or a glycosidase signaling pathway in a subject in need thereof, the method comprising administering to the subject, a therapeutically effective amount of a compound of formula (IA), (IIA), (IIIA), (IVA-1), (IVA-2), (VA-1), (VA-2), (VIA-1), (VIA-2), (VIIA), (VIIA-2), (IB), (JIB-1), (IIB-2), (IIIB-1), (IIIB-2), (IVB-1), (IVB-2), or a pharmaceutically acceptable salt thereof, thereby activating the glycosidase in the subject. The glycosidase is preferably a glycoside hydrolase, more preferably a family 84 glycoside hydrolase, even more preferably O-glycoprotein-2-acetamido-2-deoxy-3-D-glucopyanosidase (O-GlcNAcase or OGA), most preferably a mammalian O-GlcNAcase.

One aspect of the invention includes a method for promoting survival of a eukaryotic cell (e.g., a mammalian cell) or increasing the lifespan of the cell, the method comprising administering to the subject a therapeutically effective amount of a compound of formula (IA), (IIA), (IA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof, thereby promoting survival of the eukaryotic cell or increasing the lifespan of the cell.

One aspect of the invention includes a method for treating a disease or a condition that is caused, mediated and/or propagated by O-GlcNAcase activity in a subject, the method comprising administering to the subject a therapeutically effective amount of a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof. Preferably, the disease or condition is a neurological disorder, diabetes, cancer or stress. More preferably, the disease or condition is a neurological disorder. In one embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-only dementia, Huntington's disease, and Parkinson's disease. In another embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, mild cognitive impairment (MCI), Huntington's disease, and Parkinson's disease. In yet another embodiment, the neurological disorder is Alzheimer's disease.

One aspect of the invention includes a method for treating a disease or a condition that is characterized by hyperphosphorylation of tau (e.g., hyperphosphorylation of tau in the brain) in a subject, the method comprising administering to the subject a therapeutically effective amount of a compound of formula (IA), (IIA), (IA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof. In one embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-only dementia, Huntington's disease, and Parkinson's disease. In another embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, ischemic stroke, mild cognitive impairment (MCI), Huntington's disease, and Parkinson's disease. In yet another embodiment, the disease or condition is Alzheimer's disease.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder, and delaying, inhibiting or decreasing the likelihood of the progression of the disease, disorder or syndrome.

The term "an effective amount" means an amount of the compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof, reducing the likelihood of recurrence of a disease or condition treatable by a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof or one or more symptoms thereof, e.g., as determined by clinical symptoms, compared to a control. The expression "an effective amount" also encompasses the amounts which are effective for increasing normal physiological function.

Another embodiment of the present invention is a pharmaceutical composition comprising at least one compound described herein, or a pharmaceutically acceptable salt thereof, and at least one pharmaceutically acceptable carrier.

Also included are the use of a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof in the manufacture of a medicament for the treatment of one or more diseases or conditions described herein. Also included herein are pharmaceutical compositions comprising a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof optionally together with a pharmaceutically acceptable carrier, in the manufacture of a medicament for the treatment of one or more diseases or conditions described herein. Also included is a compound of formula (IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof for use the treatment of a subject with one or more diseases or conditions described herein. Further included are pharmaceutical compositions comprising a compound of formula (IA), (IIA), (IIIA), (IVA-1), (IVA-2), (VA-1), (VA-2), (VIA-1), (VIA-2), (VIIA), (VIIA-2), (TB), (IIB-1), (IIB-2), (IIIB-1), (IIIB-2), (IVB-1), (IVB-2), or a pharmaceutically acceptable salt thereof, optionally together with a pharmaceutically acceptable carrier, for use in the treatment of one or more diseases or conditions described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

A compound of formula ((IA), (IIA), (IIIA), (IVA-1), (IVA-2), (VA-1), (VA-2), (VIA-1), (VIA-2), (VIIA), (VIIA-2), (IB), (IIB-1), (IIB-2), (IIIB-1), (IIIB-2), (IVB-1), (IVB-2), or a pharmaceutically acceptable salt thereof, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

EXEMPLIFICATIONS

General Methods

Chromatography on silica gel was carried out using 20-40 uM (particle size), 250-400 mesh, or 400-632 mesh silica gel using either a Teledyne ISCO Combiflash RF or a Grace Reveleris X2 with ELSD purification systems.

Analytical HPLC

Acidic HPLC: Conducted on a Shimadza 20A instrument with an Ultimate C18 3.0×50 mm, 3 um column eluting with 2.75 mL/4 L TFA in water (solvent A) and 2.5 mL/4 L TFA in acetonitrile (solvent B) by the following methods:
- Method A: using the following elution gradient 0%-60% (solvent B) over 6 minutes and holding at 60% for 2 minutes at a flow rate of 1.2 ml/minutes. Wavelength: UV 220 nm, 215 nm and 254 nm.
- Method B: using the following elution gradient 10%-80% (solvent B) over 6 minutes and holding at 60% for 2 minutes at a flow rate of 1.2 ml/minutes. Wavelength: UV 220 nm, 215 nm and 254 nm.
- Method C: using the following elution gradient 30%-90% (solvent B) over 6 minutes and holding at 60% for 2 minutes at a flow rate of 1.2 ml/minutes. Wavelength: UV 220 nm, 215 nm and 254 nm.

Basic HPLC: Conducted on a Shimadza 20A instrument with Xbridge Shield RP-18, 5 um, 2.1×50 mm column eluting with 2 mL/4 L $NH_3H_2O$ in water (solvent A) and acetonitrile (solvent B), by the following methods:
- Method D: using the following elution gradient 0%-60% (solvent B) over 4.0 minutes and holding at 60% for 2 minutes at a flow rate of 1.2 ml/minutes.
- Method E: using the following elution gradient 10%-80% h (solvent B) over 4.0 minutes and holding at 60% for 2 minutes at a flow rate of 1.2 ml/minutes.
- Method F: using the following elution gradient 30%-90% (solvent B) over 4.0 minutes and holding at 60% for 2 minutes at a flow rate of 1.2 ml/minutes.

Analytical LCMS

Acidic LCMS: Conducted on a Agilent 1100 Series LC/MSD system with DAD/ELSD, Agilent LC/MSD VL (G1956A) SL (G1956B) mass-spectrometer, Agilent 1200 Series LC/MSD system with DAD/ELSD, Agilent LC/MSD SL (G6130A) SL (G6140A) mass-spectrometer, Shimadza 2010 Series, Shimadza 2020 Series, or Waters Acquity UPLC BEH. (MS ionization: ESI) instrument equipped with a C18 column (2.1 mm×30 mm, 3.0 mm or 2.1 mm×50 mm, C18, 1.7 um), eluting with 1.5 mL/4 L TFA in water (solvent A) and 0.75 mL/4LTFA in acetonitrile (solvent B) or Zorbax SB-C18 1.8 μm 4.6×15 mm Rapid Resolution cartridge with solvent A—acetonitrile, 0.1% formic acid, solvent B—water (0.1% formic acid) using the methods below: 1.5 minute methods:
- General method: using the following elution gradient 5%-95% (solvent B) over 0.7 minutes and holding at 95% for 0.4 minutes at a flow rate of 1.5 ml/minutes. Wavelength: UV 220 nm and 254 nm.

2 Minute Methods:
- Method A: using the following elution gradient 0%-60% (solvent B) over 0.9 minutes and holding at 60% for 0.6 minutes at a flow rate of 1.2 m/minutes. Wavelength: UV 220 nm and 254 nm.
- Method B: using the following elution gradient 10%-80% h (solvent B) over 0.9 minutes and holding at 60% for 0.6 minutes at a flow rate of 1.2 ml/minutes. Wavelength: UV 220 nm and 254 nm.

Method C: using the following elution gradient 30%-90% (solvent B) over 0.9 minutes and holding at 60% for 0.6 minutes at a flow rate of 1.2 m/minutes. Wavelength: UV 220 nm and 254 nm.

3.5 Minute Method:
Initial conditions, solvent A—95%: solvent B—5%; hold at initial from 0.0-0.1 min; Linear Ramp to solvent A—5%: solvent B—95% between 0.1-3.25 min; hold at solvent A—5%: solvent B—95% between 3.25-3.5 min. Diode array/MS detection.

4 Minute Methods:
Method A: using the following elution gradient 0%-60% (solvent B) over 3 minutes and holding at 60% for 0.5 minutes at a flow rate of 0.8 ml/minutes. Wavelength: UV 220 nm and 254 nm.

Method B: using the following elution gradient 10%-80% (solvent B) over 3 minutes and holding at 60% h for 0.5 minutes at a flow rate of 0.8 ml/minutes. Wavelength: UV 220 nm and 254 nm.

Method C: using the following elution gradient 30%-90% (solvent B) over 3 minutes and holding at 60% for 0.5 minutes at a flow rate of 0.8 m/minutes. Wavelength: UV 220 nm and 254 nm.

7 Minute Methods:
Method A: using the following elution gradient 0%-60% (solvent B) over 6 minutes and holding at 60% for 0.5 minutes at a flow rate of 0.8 m/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-900% (solvent B) over 6 minutes and holding at 60% for 0.5 minutes at a flow rate of 0.8 ml/minutes. Wavelength: UV 220 nm and 254 nm.

Basic LCMS: Conducted on a Shimadza 2020 Series or Waters Acquity UPLC BEH (MS ionization: ESI) instrument equipped with XBridge Shield RP18, 5 um column (2.1 mm×30 mm, 3.0 mm i.d.) or 2.1 mm×50 mm, C18, 1.7 um column, eluting with 2 mL/4 L $NH_3 \cdot H_2O$ in water (solvent A) and acetonitrile (solvent B) using the methods below:

3 Minute Methods:
Method A: using the following elution gradient 0%-60% (solvent B) over 2 minutes and holding at 60% for 0.48 minutes at a flow rate of 1 ml/minutes. Wavelength: UV 220 nm and 254 nm.

Method B: using the following elution gradient 10%-80% (solvent B) over 2 minutes and holding at 60% for 0.48 minutes at a flow rate of 1 ml/minutes. Wavelength: UV 220 nm and 254 nm.

Method C: using the following elution gradient 30%-90% (solvent B) over 2 minutes and holding at 60% for 0.48 minutes at a flow rate of 1 ml/minutes. Wavelength: UV 220 nm and 254 nm.

3.5 Minute Method:
Initial conditions, solvent A—95%: solvent B—5%; hold at initial from 0.0-0.1 min; Linear Ramp to solvent A—5%: solvent B—95% between 0.1-3.25 min; hold at solvent A—5%: solvent B—95% between 3.25-3.5 min. Diode array/MS detection.

7 Minute Methods:
Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-90% (solvent B) over 6 minutes and holding at 60% for 0.5 minutes at a flow rate of 0.8 ml/minutes. Wavelength: UV 220 nm and 254 nm.

SFC Analytical Separation
Instrument: Waters UPC2 analytical SFC (SFC—H). Column: ChiralCel OJ, 150×4.6 mm I.D., 3 μm. Mobile phase: A for $CO_2$ and B for Ethanol (0.05% DEA). Gradient: B 40%. Flow rate: 2.5 mL/min. Back pressure: 100 bar. Column temperature: 35° C. Wavelength: 220 nm Preparative HPLC Purification
General Method: Preparative HPLC was performed on a Gilson UV/VIS-156 with UV detection at 220/254 nm Gilson 281 automatic collection.

Acidic condition: Two acid grading systems used: Hydrochloride acid and Formic acid.

Method A: Hydrochloride acid: YMC-Actus Triart C18 150×30 mm×5 um, Gradient used 0-100% acetonitrile with water and corresponding acid (0.05% HCl).

Method B: Formic acid: Phenomenex Synergi C18 150× 30 mm×4 um, Gradient used 0-100% acetonitrile with water and corresponding acid (0.225% formic acid), the gradient shape was optimized for individual separations.

Neutral condition: Xtimate C18 150×25 mm×5 um, Gradient used 0-100% (water (10 mM $NH_4HCO_3$)-ACN), the gradient shape was optimized for individual separations.

Basic condition: Waters Xbridge Prep OBD C18 150×30 10 um, Gradient used 0-100% water (0.04% $NH_3H_2O$+ 10 mM $NH_4HCO_3$)-acetonitrile, the gradient shape was optimized for individual separations.

Preparative HPLC-MS Purification
Columns used:
Acid: Waters SunFire Prep, C18 5 um, OBD 19×100 mm
Base: Waters XSelect CSH Prep C18 5 um OBD 19×100 mm Gradient Profile: 12 min Run: Initial conditions: A—95%: B—5%; hold at initial from 0.0-0.5 min; linear ramp from A—5% to variable B—% (typical range is from B—40% to B—75%) between 0.5-7.5 min; linear ramp from B—% to B—95% from 7.5-8.0 min; hold at A—5%: B—95% between 8.0-10.0 min; end of DAD/MS detection; linear ramp down to initial conditions between 10.0-10.5 min and hold at initial for 1.5 min.

Mobile Phase: Acid: A: 0.1% trifluoroacetic acid in water (v/v); Mobile phase B: 0.1% trifluoroacetic acid in acetonitrile (v/v). Base: A: 0.1% ammonia in water (v/v); Mobile phase B: 0.1% ammonia in acetonitrile (v/v)

Preparative SFC Purification
Instrument: MG III preparative SFC (SFC-1). Column: ChiralCel OJ, 250×30 mm I.D., 5 μm. Mobile phase: A for $CO_2$ and B for Ethanol(0.1% $NH_3H_2O$). Gradient: B 50%. Flow rate: 40 ml/min. Back pressure: 100 bar. Column temperature: 38° C. Wavelength: 220 nm. Cycle time: ~8 min.

¹H-NMR

The NMR spectra were recorded on Bruker Avance III 600 MHz, Bruker AVANCE DRX 500, Bruker Avance III HD 500 MHz, Bruker Avance III 500 MHz, Bruker Avance III 400 MHz, Varian UNITY plus 400, Varian-400 VNMRS, or Varian-400 MR. Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

The following general reaction Schemes 1-6 provide useful details for preparing the instant compounds. The requisite intermediates are in some cases commercially available or can be prepared according to literature procedures. The illustrative reaction schemes are not limited by the compounds listed or by any particular substituents employed for illustrative purposes substituent labeling (i.e. R groups) as shown in the reaction schemes do not necessarily correlate to that used in the claims and often, for clarity, a single substituent is shown attached to the compound where multiple substituents are allowed under the definitions of Formulas (IA) or (IB) hereinabove.

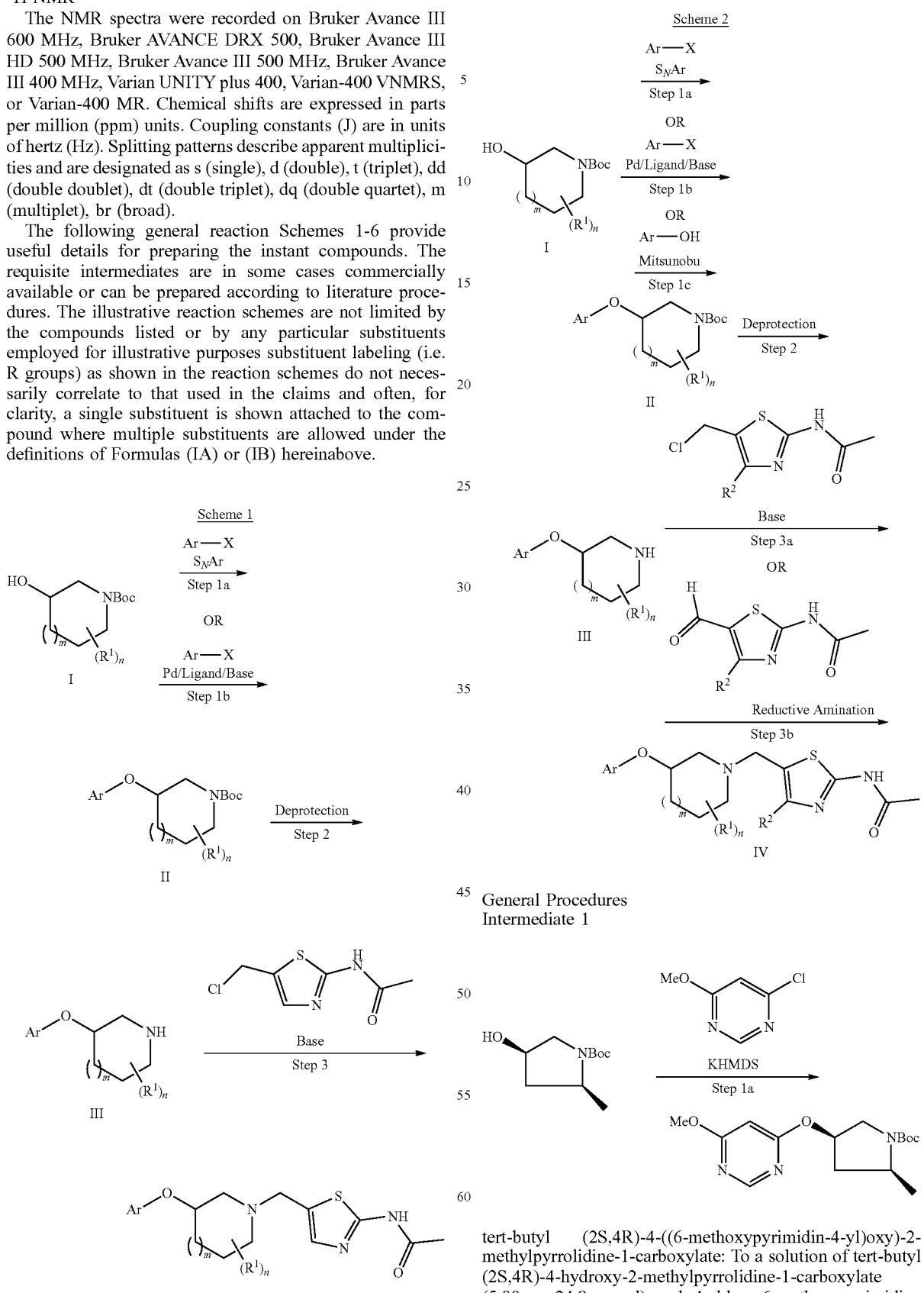

General Procedures

Intermediate 1 tert-butyl (2S,4R)-4-((6-methoxypyrimidin-4-yl)oxy)-2-methylpyrrolidine-1-carboxylate: To a solution of tert-butyl (2S,4R)-4-hydroxy-2-methylpyrrolidine-1-carboxylate (5.00 g, 24.8 mmol) and 4-chloro-6-methoxypyrimidine (3.95 g, 27.3 mmol) in THF (125 mL) at 0° C. was added a solution of KHMDS (1.0 M in THF, 27.3 mL) over 10 minutes. The mixture was warmed to room temperature and stirred for 3 h. To the mixture was added 10 mL of saturated NH₄Cl(aq), and the mixture was subsequently concentrated in vacuo. The residue was dissolved with EtOAc, washed with brine, dried over MgSO₄, filtered, and conc in vacuo. The residue was purified over SiO₂ (0-70% EtOAc/heptane) to provide the titled compound (6.36 g, 82% yield). LCMS (ESI): [M+H] 310. ¹HNMR: (500 MHz, CDCl₃) δ 8.42 (s, 1H), 6.04 (s, 1H), 5.47-5.55 (m, 1H), 3.98-4.13 (m, 1H), 3.95 (s, 3H), 3.76 (br s, 1H), 3.45-3.65 (m, 1H), 2.28-2.46 (m, 1H), 1.90 (br d, J=14.04 Hz, 1H), 1.46 (s, 9H), 1.32 (br d, J=6.10 Hz, 3H).

OR tert-butyl (2S,4R)-4-hydroxy-2-methyl-pyrrolidine-1-carboxylate (150.00 g, 745.3 mmol) was added to a stirred mixture of 60% sodium hydride (44.7 g, 1.12 mol) in THF (800 mL) at rt. The mixture was refluxed for 2 h. A solution of 4-chloro-6-methoxy-pyrimidine (107.7 g, 745.3 mmol) in THF (200 mL) slowly added dropwise to the refluxing mixture. After 3 h at reflux, the reaction was cooled and stirred overnight at rt. A solution of NH₄Cl (sat) (300 ml) was slowly added to the reaction cooled with an ice bath. The layers were separated, and the aqueous layer was extracted (THF 100 mL). The combined organic layers were dried over MgSO₄, filtered and concentrated in vacuo. The residue was purified in 35 g batches on SiO₂ 220 g (5 min at 100% heptane to 20% 3:1 EtOAc:EtOH over 30 min) to afford the title compound (125 g, 54% yield). LCMS (ESI): [M+H] 310. ¹HNMR: (500 MHz, CDCl₃) δ 8.43 (s, 1H), 6.05 (s, 1H), 5.52 (ddd, J=5.5, 3.5, 2.1 Hz, 1H), 3.97-4.14 (m, 1H), 3.90-3.97 (m, 3H), 3.78 (br d, J=17.5 Hz, 1H), 3.56 (br s, 1H), 2.37 (br d, J=5.6 Hz, 1H), 1.91 (br d, J=14.2 Hz, 1H), 1.43-1.51 (m, 9H), 1.33 (br d, J=5.2 Hz, 3H).

Intermediate 2

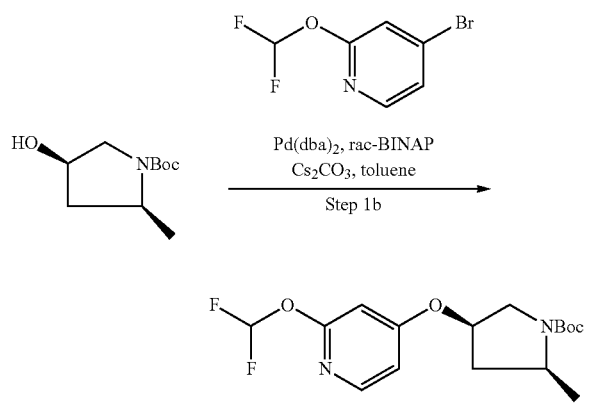

tert-butyl (2S,4R)-4-((2-(difluoromethoxy)pyridin-4-yl)oxy)-2-methylpyrrolidine-1-carboxylate: A suspension of tert-butyl (2S,4R)-4-hydroxy-2-methylpyrrolidine-1-carboxylate (0.30 g, 1.49 mmol), 4-bromo-2-(difluoromethoxy) pyridine (0.33 mg, 1.49 mmol), Pd(dba)₂ (0.086 g, 0.15 mmol), rac-BINAP (0.18 g, 0.298 mmol), and Cs₂CO₃ (0.97 g, 2.98 mmol) in toluene (3.75 mL) was heated to 120° C. and stirred for 16 h. The reaction was diluted with EtOAc, washed with saturated NH₄Cl (aq), dried over MgSO₄, filtered, and concentrated in vacuo. The residue was purified over SiO₂ (0-100% EtOAc/heptane) to provide the titled compound (0.37 g, 72% yield). LCMS (ESI): [M+H]345.

Intermediate 3

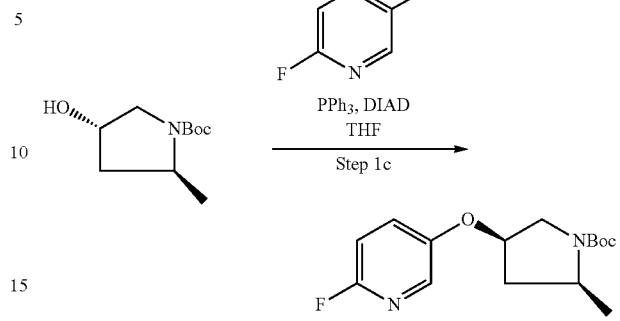

tert-butyl (2S,4R)-4-((6-fluoropyridin-3-yl)oxy)-2-methylpyrrolidine-1-carboxylate: To a solution of 6-fluoropyridin-3-ol (185 mg, 1.64 mmol) and tert-butyl (2S,4S)-4-hydroxy-2-methylpyrrolidine-1-carboxylate (300 mg, 1.49 mmol) in THF (15.0 mL) were added DIAD (603 mg, 2.98 mmol) and triphenylphosphine (782 mg, 2.98 mmol). The mixture was stirred at 60° C. for 2 hrs. The solvent was removed and the residue was purified by column chromatograph on silica gel eluted (Petroleum ether/EtOAc=3/1) to provide the title compound (92.0 mg, 21% yield). ¹HNMR: (400 MHz, CDCl₃) δ 7.78-7.79 (m, 1H), 7.27-7.31 (m, 1H), 6.87 (dd, J=8.8, 3.2 Hz, 1H), 4.82-4.84 (m, 1H), 4.03-4.09 (m, 1H), 3.75-3.76 (m, 1H), 3.62-3.64 (m, 1H), 2.33-2.36 (m, 1H), 1.93-1.96 (m, 1H), 1.47 (s, 9H), 1.32 (d, J=6.4 Hz, 3H).

Intermediate 4

Preparation 1

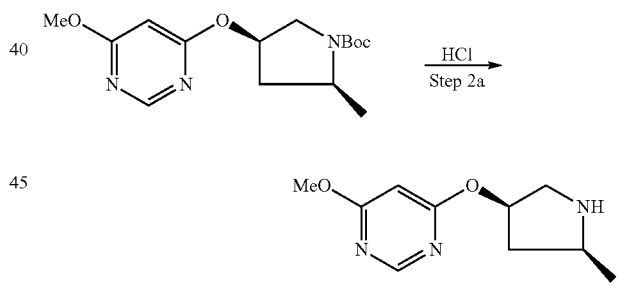

4-methoxy-6-(((3R,5S)-5-methylpyrrolidin-3-yl)oxy)pyrimidine hydrochloride: Acetyl chloride (14.1 mL, 197 mmol) was added dropwise over 10 minutes to MeOH (100 mL) at 0° C. and the mixture was stirred for a further 20 minutes. To the anhydrous HCl solution at 0° C. was added a solution of tert-butyl (2S,4R)-4-((6-methoxypyrimidin-4-yl)oxy)-2-methylpyrrolidine-1-carboxylate (6.09 g, 19.69 mmol) in MeOH (30 mL) dropwise. The resulting mixture was warmed to room temperature and stirred for a further 2 h. The mixture was concentrated in vacuo to provide the titled compound (4.84 g, 99% yield). LCMS (ESI): [M+H] 210. ¹HNMR: (500 MHz, methanol-d₄) δ 8.56 (s, 1H), 6.46 (s, 1H), 5.70-5.78 (m, 1H), 4.03 (s, 3H), 3.83-3.92 (m, 1H), 3.66-3.72 (m, 1H), 3.57-3.63 (m, 1H), 2.81 (ddd, J=6.71, 7.94, 14.65 Hz, 1H), 1.97 (dddd, J=1.22, 3.66, 7.94, 14.65 Hz, 1H), 1.52 (d, J=6.71 Hz, 3H).

Preparation 2

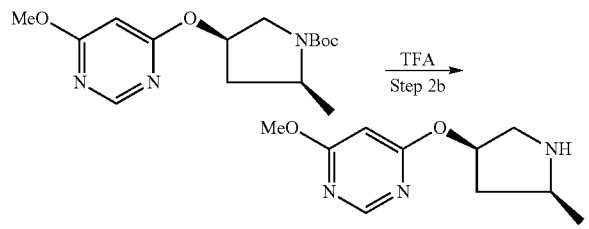

4-Methoxy-6-(((3R,5S)-5-methylpyrrolidin-3-yl)oxy)pyrimidine trifluoroacetate:
To a solution of tert-butyl (2S,4R)-4-(6-methoxypyrimidin-4-yl)oxy-2-methyl-pyrrolidine-1-carboxylate (868 mg, 2.81 mmol) in $CH_2Cl_2$ (10 mL) was added TFA (2.15 mL, 28.1 mmol). The reaction mixture was stirred at room temperature overnight. The mixture was concentrated and co-evaporated with EtOAc to provide the title compound (1.65 g, contains ~3 eq. TFA). LCMS (ESI): [M+H] 210. $^1$H NMR (400 MHz, METHANOL-$d_4$) δ 8.43 (d, J=1.00 Hz, 1H), 6.22 (d, J=1.00 Hz, 1H), 5.69 (dddd, J=2.13, 3.51, 5.62, 6.81 Hz, 1H), 3.95 (s, 3H), 3.74-3.89 (m, 1H), 3.49-3.69 (m, 2H), 2.77 (ddd, 0.1=6.78, 7.97, 14.62 Hz, 1H), 1.85-2.01 (m, 1H), 1.49 (d, J=6.78 Hz, 3H).
OR
TFA (230 g, 2.02 mol, 154.4 mL) was slowly added to a solution of tert-butyl (2S,4R)-4-(6-methoxypyrimidin-4-yl)oxy-2-methyl-pyrrolidine-1-carboxylate (61.7 g, 199.5 mmol) in DCM (154 mL) cooled in an ice bath. The reaction was allowed to warm to rt. After 2 h, the mixture was concentrated in vacuo. The residue was diluted with water (80 ml) and the mixture was cooled with an ice bath. To the mixture was added 50% aqueous NaOH (~20 ml) dropwise, maintaining the internal temperature below 30° C. while the mixture was brought to a final pH~11. The mixture was extracted with DCM, dried over $NaSO_4$, filtered and concentrated in vacuo to afford the title compound (45 g, 100% yield). LCMS (ESI): [M+H] 210. $^1$HNMR: (500 MHz, $CDCl_3$) δ 8.41 (s, 1H), 6.04 (d, J=0.6 Hz, 1H), 5.47 (dtd, J=6.8, 3.4, 3.4, 1.6 Hz, 1H), 3.94 (s, 3H), 3.24-3.32 (m, 2H), 3.14 (dd, J=13.0, 5.3 Hz, 1H), 2.47 (dt, J=14.2, 7.2 Hz, 1H), 1.50-1.61 (m, 1H), 1.32 (d, J=6.4 Hz, 4H).

Example 1-1

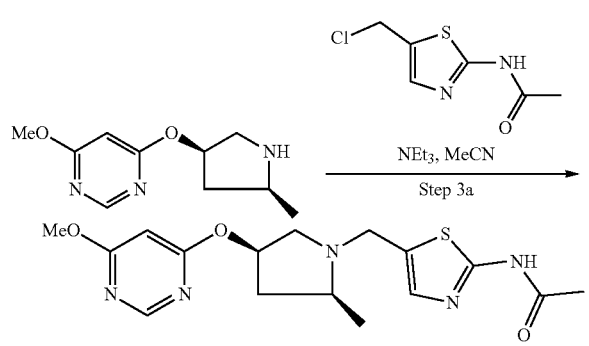

N-(5-(((2S,4R)-4-((6-methoxypyrimidin-4-yl)oxy)-2-methylpyrrolidin-1-yl)methyl)thiazol-2-yl)acetamide: To a suspension of 4-methoxy-6-(((3R,5S)-5-methylpyrrolidin-3-yl)oxy)pyrimidine hydrochloride (9.26 g, 37.7 mmol) and N-[5-(chloromethyl)thiazol-2-yl]acetamide (7.55 g, 39.6 mmol) in acetonitrile (95.0 mL) was added triethylamine (11.4 g, 113.1 mmol) and the mixture was warmed to 55° C. overnight. The reaction was cooled to room temperature, and the mixture was filtered over celite and concentrated in vacuo. The residue was dissolved in EtOAc and washed with saturated $NH_4C_1$ (aq). The aqueous layer was back extracted with EtOAc and the combined organics were dried over $MgSO_4$, filtered, and concentrated in vacuo. The residue was purified over $SiO_2$ (10-70% EtOAc:ethanol (3:1 v/v)/heptane) to provide a foamy white residue. The material was dissolved in warm methanol and upon cooling a solid precipitated. The solid was filtered to provide the titled compound (4.32 g, 31% yield). LCMS (ESI): [M+H] 364. $^1$HNMR: (500 MHz, $CDCl_3$) δ 11.76 (br s, 1H), 8.38 (s, 1H), 7.22 (s, 1H), 6.06 (s, 1H), 5.31-5.38 (m, 1H), 4.08-4.17 (m, 1H), 3.93 (s, 3H), 3.59 (d, J=14.65 Hz, 1H), 3.14 (d, J=11.60 Hz, 1H), 2.61 (dd, J=6.10, 11.60 Hz, 1H), 2.48-2.57 (m, 2H), 2.31 (s, 3H), 1.64-1.72 (m, 1H), 1.26 (d, J=6.10 Hz, 3H).

Example 1-2

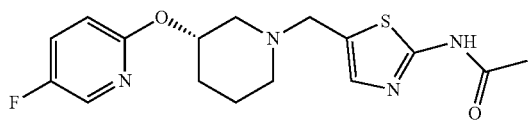 [SMILES: CC(=O)Nc1ncc(CN2CCC[C@H](Oc3ccc(F)cn3)C2)s1]

(S)-N-(5-((3-((5-fluoropyridin-2-yl)oxy)piperidin-1-yl)methyl)thiazol-2-yl)acetamide: The title compound was prepared in an analogous manner of that in scheme 1 from tert-butyl(S)-3-hydroxypiperidine-1-carboxylate, 2,5-difluoropyridine, and N-[5-(chloromethyl)thiazol-2-yl]acetamide. LCMS (ESI): [M+H] 351. $^1$HNMR: (500 MHz, $CDCl_3$) δ 12.55 (s, 1H), 7.93 (d, J=3.05 Hz, 1H), 7.30 (ddd, J=3.36, 7.78, 9.00 Hz, 1H), 7.19 (s, 1H), 6.68 (dd, J=3.66, 8.55 Hz, 1H), 5.07 (tt, J=3.97, 8.24 Hz, 1H), 3.68-3.82 (m, 2H), 2.94-3.01 (m, 1H), 2.62-2.72 (m, 1H), 2.36 (br t, J=9.16 Hz, 1H), 2.31-2.33 (m, 3H), 2.23-2.30 (m, 1H), 1.94-2.06 (m, 1H), 1.78-1.87 (m, 1H), 1.58-1.72 (m, 1H), 1.45-1.56 (m, 1H).

Example 1-3

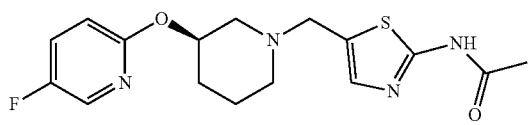 [SMILES: CC(=O)Nc1ncc(CN2CCC[C@@H](Oc3ccc(F)cn3)C2)s1]

(R)-N-(5-((3-((5-fluoropyridin-2-yl)oxy)piperidin-1-yl)methyl)thiazol-2-yl)acetamide: The title compound was prepared in an analogous manner of that in scheme 1 from tert-butyl(R)-3-hydroxypiperidine-1-carboxylate, 2,5-difluoropyridine, and N-[5-(chloromethyl)thiazol-2-yl]acetamide. LCMS (ESI): [M+H] 351. $^1$HNMR: (500 MHz, $CDCl_3$) δ 12.50 (s, 1H), 7.93 (d, J=3.05 Hz, 1H), 7.28-7.33 (m, 1H), 7.19 (s, 1H), 6.68 (dd, J=3.36, 8.85 Hz, 1H), 5.07 (tt, J=3.97, 8.24 Hz, 1H), 3.64-3.86 (m, 2H), 2.90-3.06 (m, 1H), 2.61-2.76 (m, 1H), 2.33-2.43 (m, 1H), 2.32 (s, 3H), 2.24-2.30 (m, 1H), 1.93-2.07 (m, 1H), 1.74-1.91 (m, 1H), 1.61-1.70 (m, 1H), 1.45-1.56 (m, 1H).

Example 1-4

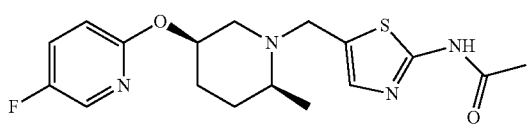 [SMILES: CC(=O)Nc1ncc(CN2C[C@H](Oc3ccc(F)cn3)CC[C@@H]2C)s1]

N-(5-(((2S,5R)-5-((5-fluoropyridin-2-yl)oxy)-2-methylpiperidin-1-yl)methyl)thiazol-2-yl)acetamide: The title compound was prepared in an analogous manner of that in scheme 1 from tert-butyl (2S,5R)-5-hydroxy-2-methylpiperidine-1-carboxylate, 2,5-difluoropyridine, and N-[5-(chloromethyl)thiazol-2-yl]acetamide. LCMS (ESI): [M+H] 365. $^1$HNMR: (500 MHz, CDCl$_3$) δ 12.32 (br s, 1H), 7.90 (d, J=3.1 Hz, 1H), 7.35-7.27 (m, 1H), 7.18 (s, 1H), 6.77 (dd, J=3.7, 9.2 Hz, 1H), 5.17-5.03 (m, 1H), 4.03-3.82 (m, 2H), 2.97 (dd, J=4.3, 12.2 Hz, 1H), 2.60 (m, 2H), 2.31 (s, 3H), 1.95-1.82 (m, 1H), 1.75-1.61 (m, 4H), 1.21 (d, J=6.1 Hz, 3H).

Example 1-5

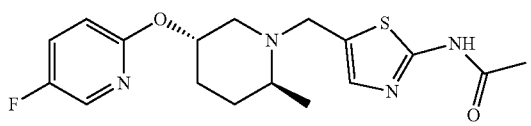 [SMILES: CC(=O)Nc1ncc(CN2C[C@@H](Oc3ccc(F)cn3)CC[C@@H]2C)s1]

N-(5-(((2S,5S)-5-((5-fluoropyridin-2-yl)oxy)-2-methylpiperidin-1-yl)methyl)thiazol-2-yl)acetamide: The title compound was prepared in an analogous manner of that in scheme 1 from tert-butyl (2S,5S)-5-hydroxy-2-methylpiperidine-1-carboxylate, 2,5-difluoropyridine, and N-[5-(chloromethyl)thiazol-2-yl]acetamide. LCMS (ESI): [M+H] 365. $^1$HNMR: (500 MHz, CDCl$_3$) δ 12.15 (br s, 1H), 7.93 (d, J=3.66 Hz, 1H), 7.27-7.32 (m, 1H), 7.19 (s, 1H), 6.61 (dd, J=3.36, 8.85 Hz, 1H), 4.96-5.05 (m, 1H), 4.00 (d, 0.1=14.65 Hz, 1H), 3.89 (d, 0.1=14.65 Hz, 1H), 3.17 (br dd, J=2.75, 10.68 Hz, 1H), 2.33-2.41 (m, 1H), 2.31 (s, 3H), 2.21 (t, J=10.07 Hz, 1H), 2.13-2.18 (m, 1H), 1.75-1.81 (m, 1H), 1.33-1.53 (m, 2H), 1.22 (d, J=6.10 Hz, 3H).

Example 1-6

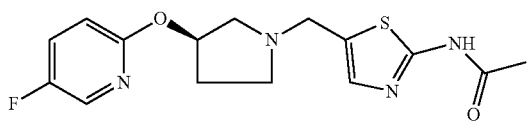 [SMILES: CC(=O)Nc1ncc(CN2CC[C@@H](Oc3ccc(F)cn3)C2)s1]

(R)-N-(5-((3-((5-fluoropyridin-2-yl)oxy)pyrrolidin-1-yl)methyl)thiazol-2-yl)acetamide: The title compound was prepared in an analogous manner of that in scheme 1 from tert-butyl(R)-3-hydroxypyrrolidine-1-carboxylate, 2,5-difluoropyridine, and N-[5-(chloromethyl)thiazol-2-yl]acetamide. LCMS (ESI): [M+H] 337. $^1$HNMR: (500 MHz, CDCl$_3$) δ 12.66 (s, 1H), 7.93 (d, J=3.05 Hz, 1H), 7.30 (ddd, J=3.05, 7.63, 8.85 Hz, 1H), 7.23 (s, 1H), 6.68 (dd, J=3.66, 9.16 Hz, 1H), 5.32-5.43 (m, 1H), 3.71-3.98 (m, 2H), 2.96 (dd, J=6.10, 10.99 Hz, 1H), 2.87 (m, 1H), 2.78 (dd, J=2.75, 10.68 Hz, 1H), 2.51-2.61 (m, 1H), 2.20-2.42 (m, 4H), 1.91-2.02 (m, 1H).

Example 1-7

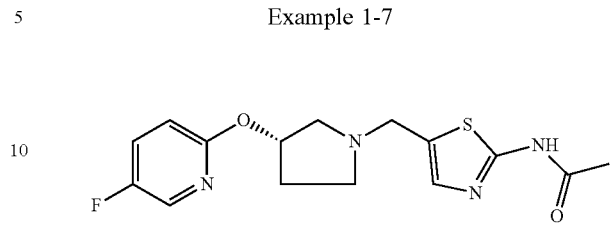

(S)-N-(5-((3-((5-fluoropyridin-2-yl)oxy)pyrrolidin-1-yl)methyl)thiazol-2-yl)acetamide: The title compound was prepared in an analogous manner of that in scheme 1 from tert-butyl(S)-3-hydroxypyrrolidine-1-carboxylate, 2,5-difluoropyridine, and N-[5-(chloromethyl)thiazol-2-yl]acetamide. LCMS (ESI): [M+H] 337. $^1$HNMR: (500 MHz, CDCl$_3$) δ 12.66 (s, 1H), 7.93 (d, J=3.05 Hz, 1H), 7.30 (ddd, J=3.05, 7.94, 9.16 Hz, 1H), 7.23 (s, 1H), 6.68 (dd, J=3.66, 9.16 Hz, 1H), 5.32-5.43 (m, 1H), 3.77-3.92 (m, 2H), 2.96 (dd, J=6.10, 10.38 Hz, 1H), 2.83-2.90 (m, 1H), 2.78 (dd, J=2.75, 10.68 Hz, 1H), 2.51-2.62 (m, 1H), 2.26-2.39 (m, 4H), 1.90-2.02 (m, 1H).

Example 1-8

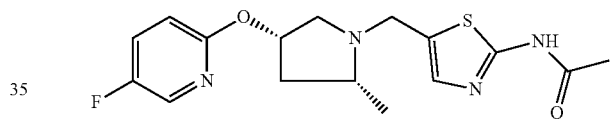

N-(5-(((2R,4S)-4-((5-fluoropyridin-2-yl)oxy)-2-methylpyrrolidin-1-yl)methyl)thiazol-2-yl)acetamide: The title compound was prepared in an analogous manner of that in scheme 1 from tert-butyl (2R,4S)-4-hydroxy-2-methylpyrrolidine-1-carboxylate, 2,5-difluoropyridine, and N-[5-(chloromethyl)thiazol-2-yl]acetamide. LCMS (ESI): [M+H] 351. $^1$HNMR: (500 MHz, CDCl$_3$) δ 11.57 (br s, 1H), 7.92 (d, J=3.05 Hz, 1H), 7.27-7.33 (m, 1H), 7.22 (s, 1H), 6.71 (dd, J=3.66, 9.16 Hz, 1H), 5.22-5.29 (m, 1H), 4.13 (d, J=14.65 Hz, 1H), 3.60 (d, J=14.04 Hz, 1H), 3.14 (d, J=10.99 Hz, 1H), 2.61 (dd, 1-6.41, 11.29 Hz, 1H), 2.47-2.57 (m, 2H), 2.30 (s, 3H), 1.63-1.72 (m, 1H), 1.26 (d, J=6.10 Hz, 3H).

Example 1-9

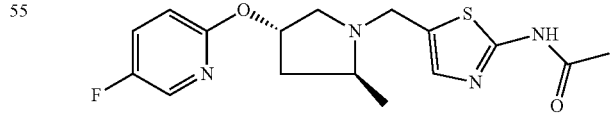

N-(5-(((2S,4S)-4-((5-fluoropyridin-2-yl)oxy)-2-methylpyrrolidin-1-yl)methyl)thiazol-2-yl)acetamide: The title compound was prepared in an analogous manner of that in scheme 1 from tert-butyl (2S,4S)-4-hydroxy-2-methylpyrrolidine-1-carboxylate, 2,5-difluoropyridine, and N-[5-(chloromethyl)thiazol-2-yl]acetamide. LCMS (ESI): [M+H] 351. $^1$HNMR: (500 MHz, CDCl$_3$) δ 12.04 (br s, 1H), 7.93

(d, J=3.05 Hz, 1H), 7.27-7.34 (m, 1H), 7.20 (s, 1H), 6.63 (dd, J=3.66, 9.16 Hz, 1H), 5.22-5.33 (m, 1H), 4.11 (dd, J=1.22, 14.04 Hz, 1H), 3.55-3.67 (m, 2H), 2.79-2.88 (m, 1H), 2.40 (dd, J=4.58, 10.68 Hz, 1H), 2.31 (s, 3H), 2.07 (ddd, J=1.83, 6.26, 13.89 Hz, 1H), 1.90 (ddd, J=7.63, 9.92, 13.58 Hz, 1H), 1.20 (d, J=6.10 Hz, 3H).

Example 1-10

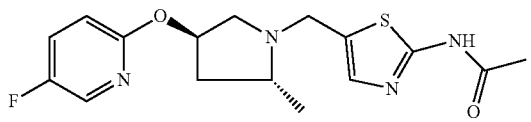 [SMILES: CC(=O)Nc1ncc(CN2C[C@H](Oc3ccc(F)cn3)C[C@H]2C)s1]

N-(5-(((2R,4R)-4-((5-fluoropyridin-2-yl)oxy)-2-methylpyrrolidin-1-yl)methyl)thiazol-2-yl)acetamide: The title compound was prepared in an analogous manner of that in scheme 1 from tert-butyl (2R,4R)-4-hydroxy-2-methylpyrrolidine-1-carboxylate, 2,5-difluoropyridine, and N-[5-(chloromethyl)thiazol-2-yl]acetamide. LCMS (ESI): [M+H] 351. ¹HNMR: (500 MHz, CDCl₃) δ 12.14 (s, 1H), 7.93 (d, J=3.05 Hz, 1H), 7.28-7.33 (m, 1H), 7.20 (s, 1H), 6.63 (dd, J=3.66, 9.16 Hz, 1H), 5.15-5.38 (m, 1H), 4.02-4.25 (m, 1H), 3.46-3.78 (m, 2H), 2.73-3.08 (m, 1H), 2.40 (dd, 0.1=4.27, 10.38 Hz, 1H), 2.31 (s, 3H), 2.03-2.11 (m, 1H), 1.90 (m, 1H), 1.20 (d, J=6.10 Hz, 3H).

Example 1-11

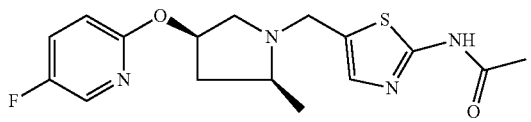 [SMILES: CC(=O)Nc1ncc(CN2C[C@H](Oc3ccc(F)cn3)C[C@@H]2C)s1]

N-(5-(((2S,4R)-4-((5-fluoropyridin-2-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2,5-difluoropyridine, and N-[5-(chloromethyl)thiazol-2-yl]acetamide. LCMS (ESI): [M+H] 351. ¹HNMR: (500 MHz, CDCl₃) δ 12.07 (s, 1H), 7.92 (d, J=1-3.05 Hz, 1H), 7.27-7.33 (m, 1H), 7.22 (s, 1H), 6.71 (dd, J=3.66, 9.16 Hz, 1H), 5.23-5.28 (m, 1H), 4.06-4.18 (m, 1H), 3.59 (d, J=14.65 Hz, 1H), 3.14 (d, J=10.99 Hz, 1H), 2.61 (dd, J=6.41, 11.29 Hz, 1H), 2.48-2.56 (m, 2H), 2.31 (s, 3H), 1.65-1.73 (m, 1H), 1.26 (d, J=5.49 Hz, 3H).

Example 1-12

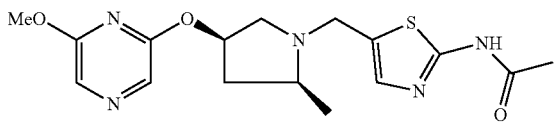 [SMILES: COc1cncc(O[C@@H]2C[C@H](C)N(Cc3cnc(NC(C)=O)s3)C2)n1]

N-(5-(((2S,4R)-4-((6-methoxypyrazin-2-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2-chloro-6-methoxypyrazine, and N-[5-(chloromethyl)thiazol-2-yl]acetamide. LCMS (ESI): [M+H] 364. ¹HNMR: (500 MHz, CDCl₃) δ 11.68 (br s, 1H), 7.78 (s, 1H), 7.76 (s, 1H), 7.23 (s, 1H), 5.22-5.33 (m, 1H), 4.124.17 (m, 1H), 3.90 (s, 3H), 3.61 (d, 0.1=14.04 Hz, 1H), 3.19 (d, J=10.99 Hz, 1H), 2.65 (dd, J=6.10, 10.99 Hz, 1H), 2.52-2.60 (m, 2H), 2.31 (s, 3H), 1.68-1.77 (m, 1H), 1.27 (d, 0.1=5.49 Hz, 3H).

Example 1-13

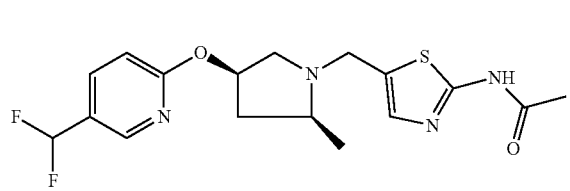 [SMILES: CC(=O)Nc1ncc(CN2C[C@H](Oc3ccc(C(F)F)cn3)C[C@@H]2C)s1]

N-(5-(((2S,4R)-4-((5-(difluoromethyl)pyridin-2-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2-chloro-5-(difluoromethyl)pyridine, and N-[5-(chloromethyl)thiazol-2-yl]acetamide. LCMS (ESI): [M+H] 383. ¹HNMR: (500 MHz, CDCl₃) δ 11.87 (br s, 1H), 8.19-8.23 (m, 1H), 7.69 (dd, J=2.44, 8.55 Hz, 1H), 7.22 (s, 1H), 6.82 (d, J=9.16 Hz, 1H), 6.61 (t, J=56.20 Hz, 1H), 5.34-5.40 (m, 1H), 4.14 (d, J=13.43 Hz, 1H), 3.59 (d, =14.65 Hz, 1H), 3.15 (d, J=10.99 Hz, 1H), 2.63 (dd, J=6.41, 11.29 Hz, 1H), 2.50-2.59 (m, 2H), 2.31 (s, 3H), 1.66-1.75 (m, 1H), 1.27 (d, J=6.10 Hz, 3H).

Example 1-14

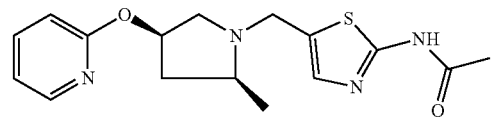 [SMILES: CC(=O)Nc1ncc(CN2C[C@H](Oc3ccccn3)C[C@@H]2C)s1]

N-(5-(((2S,4R)-2-methyl-4-(pyridin-2-yloxy)pyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2-fluoropyridine, and N-[5-(chloromethyl)thiazol-2-yl]acetamide. LCMS (ESI): [M+H] 333. ¹HNMR: (500 MHz, CDCl₃) δ 11.85 (br s, 1H), 8.06-8.12 (m, 1H), 7.47-7.57 (m, 1H), 7.22 (s, 1H), 6.78-6.86 (m, 1H), 6.71-6.76 (m, 1H), 5.28-5.40 (m, 1H), 4.09-4.18 (m, 1H), 3.61 (d, 0.1=14.65 Hz, 1H), 3.16 (d, J=11.60 Hz, 1H), 2.64 (dd, J==6.71, 10.99 Hz, 1H), 2.50-2.58 (m, 2H), 2.30 (s, 3H), 1.66-1.74 (m, 1H), 1.26 (d, J=5.49 Hz, 3H).

Example 1-1

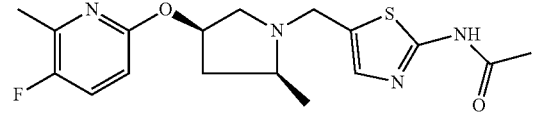 [SMILES: CC(=O)Nc1ncc(CN2C[C@H](Oc3ccc(F)c(C)n3)C[C@@H]2C)s1]

N-(5-(((2S,4R)-4-((5-fluoro-6-methylpyridin-2-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 6-chloro-3-fluoro-2-methylpyridine, and N-[5-(chloromethyl)thiazol-2-yl]acetamide. LCMS (ESI): [M+H] 365. ¹HNMR: (500 MHz, CDCl₃) δ 12.10 (br s, 1H), 7.24 (br s, 1H), 7.20 (t, J=8.37 Hz, 1H), 6.51 (dd, J=2.75, 8.85 Hz, 1H), 5.25-5.32 (m, 1H), 4.14 (br d, 0.1=14.04 Hz, 1H), 3.55-3.67 (m, 1H), 3.13 (br d, J=10.99 Hz, 1H), 2.57-2.69 (m, 1H), 2.49-2.56 (m, 2H), 2.35 (d, J=3.05 Hz, 3H), 2.31 (s, 3H), 1.63-1.74 (m, 1H), 1.24-1.29 (m, 3H).

Example 1-16

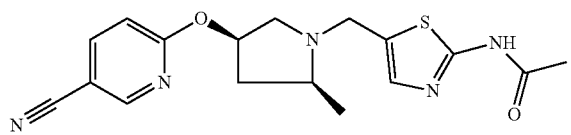 [SMILES: CC(=O)Nc1ncc(CN2C[C@H](Oc3ccc(C#N)cn3)C[C@@H]2C)s1]

N-(5-(((2S,4R)-4-((5-cyanopyridin-2-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 6-fluoronicotinonitrile, and N-[5-(chloromethyl)thiazol-2-yl]acetamide. LCMS (ESI): [M+H] 358. ¹HNMR: (500 MHz, CDCl₃) δ 11.82 (br s, 1H), 8.42 (d, J=2.44 Hz, 1H), 7.68-7.78 (m, 1H), 7.22 (s, 1H), 6.82 (d, J=8.55 Hz, 1H), 5.32-5.43 (m, 1H), 4.07-4.19 (m, 1H), 3.58 (d, J=14.04 Hz, 1H), 3.15 (d, J=10.99 Hz, 1H), 2.49-2.67 (m, 3H), 2.31 (s, 3H), 1.65-1.74 (m, 1H), 1.26 (d, J=5.49 Hz, 3H).

Example 1-17

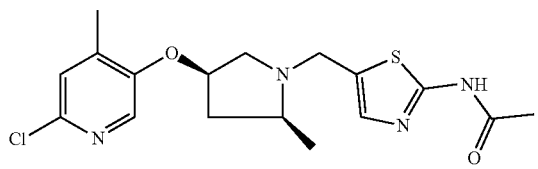 [SMILES: CC(=O)Nc1ncc(CN2C[C@H](Oc3cnc(Cl)cc3C)C[C@@H]2C)s1]

N-(5-(((2S,4R)-4-((6-chloro-4-methylpyridin-3-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2-chloro-5-fluoro-4-methylpyridine, and N-[5-(chloromethyl)thiazol-2-yl]acetamide. LCMS (ESI): [M+H] 381. ¹HNMR: (500 MHz, CDCl₃) δ 11.50 (br s, 1H), 7.72 (s, 1H), 7.21 (s, 1H), 7.08 (s, 1H), 4.67-4.77 (m, 1H), 4.12 (d, J=14.04 Hz, 1H), 3.57 (br d, J=14.04 Hz, 1H), 3.18 (d, J=10.99 Hz, 1H), 2.49-2.66 (m, 3H), 2.31 (s, 3H), 2.23 (s, 3H), 1.74 (ddd, J=3.97, 8.70, 12.97 Hz, 1H), 1.26 (d, J=6.10 Hz, 3H)).

Example 1-18

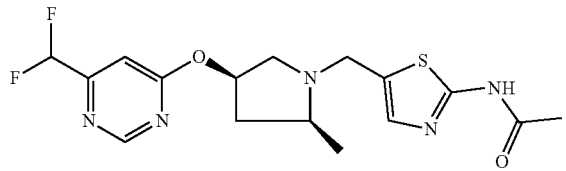 [SMILES: CC(=O)Nc1ncc(CN2C[C@H](Oc3cc(C(F)F)ncn3)C[C@@H]2C)s1]

N-(5-(((2S,4R)-4-((6-(difluoromethyl)pyrimidin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 4-chloro-6-(difluoromethyl)pyrimidine, and N-[5-(chloromethyl)thiazol-2-yl]acetamide. LCMS (ESI): [M+H] 384. ¹HNMR: (500 MHz, CDCl₃) δ 11.98 (br s, 1H), 8.76 (s, 1H), 7.23 (s, 1H), 7.02 (s, 1H), 6.47 (t, J=55.55 Hz, 1H), 5.37-5.49 (m, 1H), 4.14 (d, 0.1=14.65 Hz, 1H), 3.58 (d, J=14.04 Hz, 1H), 3.16 (d, J=11.60 Hz, 1H), 2.50-2.73 (m, 3H), 2.31 (s, 3H), 1.66-1.75 (m, 1H), 1.27 (d, J=5.49 Hz, 3H).

Example 1-19

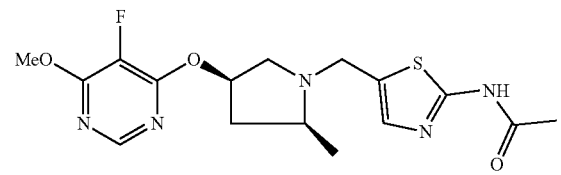 [SMILES: COc1ncnc(O[C@@H]2C[C@H](C)N(Cc3cnc(NC(C)=O)s3)C2)c1F]

N-(5-(((2S,4R)-4-((5-fluoro-6-methoxypyrimidin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 4-chloro-5-fluoro-6-methoxypyrimidine, and N-[5-(chloromethyl)thiazol-2-yl]acetamide. LCMS (ESI): [M+H] 382. ¹HNMR: (500 MHz, CDCl₃) δ 12.07 (br s, 1H), 8.10 (s, 1H), 7.23 (s, 1H), 5.31-5.41 (m, 1H), 4.09-4.14 (m, 1H), 4.02 (s, 3H), 3.60 (d, J=14.65 Hz, 1H), 3.19 (d, J=10.99 Hz, 1H), 2.68 (dd, J=6.41, 11.29 Hz, 1H), 2.51-2.61 (m, 2H), 2.31 (s, 3H), 1.73-1.82 (m, 1H), 1.26 (d, J=6.10 Hz, 3H).

Example 1-20

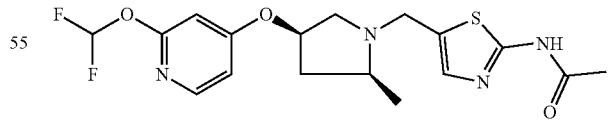

N-(5-(((2S,4R)-4-((2-(difluoromethoxy)pyridin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 4-bromo-2-(difluoromethoxy)pyridine, and N-[5-(chloromethyl)thiazol-2-yl]acetamide. LCMS (ESI): [M+H] 399. ¹HNMR: (500 MHz, CDCl₃) δ 11.38 (br s, 1H), 7.95 (d, J=5.49 Hz, 1H), 7.44 (t, J=72.64

Hz, 1H), 7.23 (s, 1H), 6.58-6.61 (m, 1H), 6.22 (d, J=2.44 Hz, 1H), 4.66-4.75 (m, 1H), 4.11-4.16 (m, 1H), 3.61 (d, J=14.04 Hz, 1H), 3.18 (d, J=10.99 Hz, 1H), 2.49-2.68 (m, 3H), 2.31 (s, 3H), 1.70 (m, 1H), 1.26 (d, J=5.49 Hz, 3H).

Example 1-21

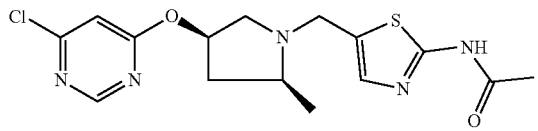 [SMILES: CC(=O)Nc1ncc(CN2C[C@H](Oc3cc(Cl)ncn3)C[C@@H]2C)s1]

N-(5-(((2S,4R)-4-((6-chloropyrimidin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 2,4-dichloropyridine, and N-[5-(chloromethyl)thiazol-2-yl]acetamide. LCMS (ESI): [M+H] 368. $^1$HNMR: (500 MHz, CDCl$_3$) δ 12.13 (br s, 1H), 8.51 (s, 1H), 7.22 (s, 1H), 6.77 (d, J=1.22 Hz, 1H), 5.30-5.48 (m, 1H), 4.13 (d, J=14.04 Hz, 1H), 3.56 (d, J=14.04 Hz, 1H), 3.14 (d, J=10.99 Hz, 1H), 2.47-2.73 (m, 3H), 1.66-1.72 (m, 1H), 1.26 (d, J=6.10 Hz, 3H).

Example 1-22

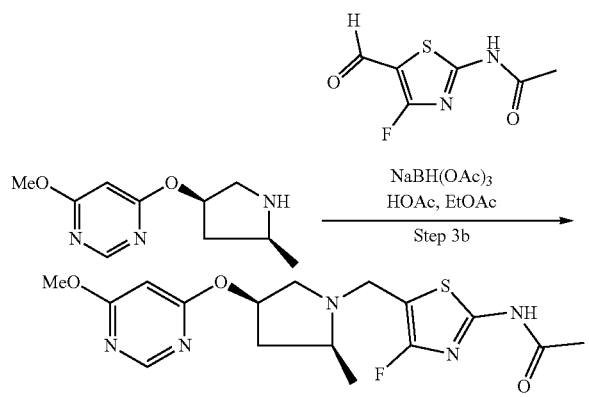

N-(4-Fluoro-5-(((2S,4R)-4-((6-methoxypyrimidin-4-yl)oxy)-2-methylpyrrolidin-1-yl)methyl)thiazol-2-yl)acetamide: To a mixture of the crude 4-methoxy-6-[(3R,5S)-5-methylpyrrolidin-3-yl]oxy-pyrimidine trifluoroacetate (1.65 g, 2.81 mmol; Intermediate 3, Preparation 2) and N-(4-fluoro-5-formyl-thiazol-2-yl)acetamide (429 mg, 2.28 mmol, prepared according to the literature procedure described in WO2018/140299A1) in EtOAc (20 mL) was added N,N-diisopropylethylamine (1.19 mL 6.84 mmol). The mixture was heated to 50° C. for 5 minutes and subsequently cooled to room temperature. To the mixture was added sodium triacetoxyborohydride (1.45 g, 6.84 mmol). The mixture was heated to 50° C. for 1 h, then cooled to room temperature. To the mixture was added saturated NaHCO$_3$(aq) and EtOAc. The aqueous layer was removed and back-extracted with EtOAc. The combined organics were washed with brine, dried over MgSO$_4$, filtered, and concentrated in vacuo. The residue was triturated with heptane/EtOAc to provide a pink solid (329 mg). The mother liquor was concentrated in vacuo and the residue was purified over SiO$_2$(50/EtOAc/heptane) to provide a yellow solid (98 mg). The solid material (427 mg) was dissolved in MeOH (30 mL) and treated with charcoal. The suspension was filtered over celite and the eluent was concentrated in vacuo to provide the title compound (402 mg, yield 46%). LCMS (ESI): [M+H] 382. $^1$H NMR (400 MHz, METHANOL-d$_4$) δ 8.35 (s, 1H), 6.13 (s, 1H), 5.21-5.47 (m, 1H), 3.85-4.03 (m, 4H), 3.55 (d, J=14.56 Hz, 1H), 3.13 (d, J=11.29 Hz, 1H), 2.47-2.73 (m, 3H), 2.17 (s, 3H), 1.52-1.72 (m, 1H), 1.23 (d, J=5.52 Hz, 3H).

OR

N-(4-Fluoro-5-(((2S,4R)-4-((6-methoxypyrimidin-4-yl)oxy)-2-methylpyrrolidin-1-yl)methyl)thiazol-2-yl)acetamide: Sodium triacetoxyborohydride (100.3 g, 473.1 mmol) was added to a mixture of 4-methoxy-6-[(3R,5S)-5-methylpyrrolidin-3-yl]oxy-pyrimidine (33 g, 158 mmol) and acetic acid (18.9 g, 315 mmol, 18.0 mL) in EtOAc (743 mL) at 40° C. After 5 min, N-(4-fluoro-5-formyl-thiazol-2-yl)acetamide (30.7 g, 163 mmol) was added to the mixture. After 2 h at 40° C., the mixture was cooled to rt and stirred overnight. A solution of 1N HCl (315 mL) was slowly added to the reaction. The aqueous layer was separated, and the organic layer was extracted with additional 1N HCl (150 mL). The combined HCl layers were treated with 50% NaOH to a final pH ~11 while being cooled with an ice bath. The mixture was extracted with DCM and the organics were dried over MgSO$_4$, filtered, and concentrated in vacuo. The residue was triturated with MeOH to afford a pink solid. The solid was purified in two batches over SiO$_2$ (220 g, 20%→60% heptane/(3:1 EtOAc:EtOH 2% NH$_4$OH) to afford the title compound (29 g, 48% yield). LCMS (ESI): [M+H] 382. $^1$HNMR: (500 MHz, CDCl$_3$) δ 11.16 (br s, 1H), 8.36-8.41 (m, 1H), 6.04-6.08 (m, 1H), 5.28-5.39 (m, 1H), 3.98 (d, J=14.6 Hz, 1H), 3.89-3.94 (m, 3H), 3.64 (d, J=14.6 Hz, 1H), 3.16 (d, J=11.1 Hz, 1H), 2.65 (dd, J=11.1, 6.1 Hz, 1H), 2.48-2.57 (m, 2H), 2.29-2.34 (m, 3H), 1.60-1.72 (m, 2H), 1.20-1.29 (m, 4H). $^{19}$FNMR: (471 MHz, CDCl$_3$) δ −116 (s, 1F).

Intermediate 5

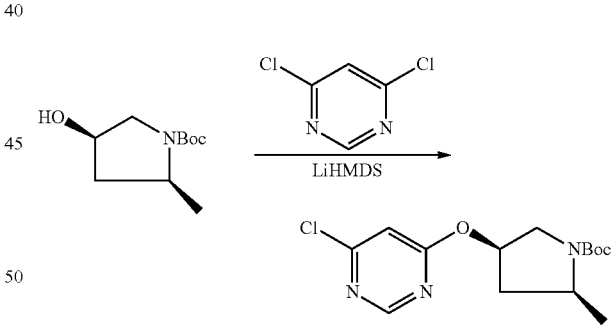

tert-butyl (2S,4R)-4-((6-chloropyrimidin-4-yl)oxy)-2-methylpyrrolidine-1-carboxylate: To a 1 L round bottom flask charged with tert-butyl (2S,4R)-4-hydroxy-2-methyl-pyrrolidine-1-carboxylate (40 g, 198.75 mmol) in THF (100 mL) was added a solution of LiHMDS (1 M, 198.75 mL) at rt and the mixture was warmed to 60° C. and stirred for 30 min. The reaction was cooled to 0° C. and 4,6-dichloropyrimidine (29.61 g, 198.75 mmol) was added and stirred for 2 h at 60° C., and then at rt for 16 h. The mixture was quenched with NH$_4$Cl (sat) at rt, and diluted with EtOAc and the layers were separated. The aqueous phase was extracted with EtOAc (2×), and the combined organics were dried over sodium sulfate and concentrated. The residue was adsorbed onto silica and purified with the following gradient EtOAc/ heptane (0→20→100%) to obtain the title compound (35.5 g, 113.3 mmol, 57% yield). LCMS (ESI): [M+H] 313.1. ¹HNMR: (500 MHz, CDCl₃) δ 8.57 (s, 1H), 6.78 (s, 1H), 5.58 (tt, J=5.5, 2.1 Hz, 1H), 3.95-4.14 (m, 1H), 3.78 (br s, 1H), 3.57 (br s, 1H), 2.36-2.45 (m, 1H), 1.92 (br d, J=14.0 Hz, 1H), 1.59 (s, 1H), 1.43-1.49 (m, 9H), 1.33 ppm (br d, J=6.1 Hz, 3H).
Intermediate 6

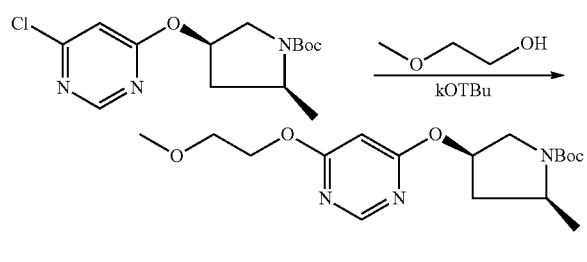

tert-butyl(2S,4R)-4-((6-(2-methoxyethoxy)pyrimidin-4-yl)oxy)-2-methylpyrrolidine-1-carboxylate: To a 500 mL round bottom flask charged with 2-methoxyethanol (6.32 g, 83.08 mmol, 6.52 mL) in THF (200 mL) was added potassium tert-butoxide (9.32 g, 83.08 mmol) at rt, and the mixture was stirred for 30 min. at 60° C. The mixture was cooled to 0° C. and tert-butyl (2S,4R)-4-(6-chloropyrimidin-4-yl)oxy-2-methyl-pyrrolidine-1-carboxylate (23.70 g, 75.53 mmol) was added and stirred at rt for 16 h. The mixture was quenched with water, and EtOAc and brine were subsequently added. The layers were separated, and the aqueous layer was extracted with EtOAc. The combined organics were dried over sodium sulfate and concentrated. The residue was purified over silica gel with a gradient EtOAc/heptane (0→50%) to obtain the title compound (16.5 g, 46.7 mmol, 62% yield).). LCMS (ESI): [M+H] 354.2. ¹HNMR: (500 MHz, CDCl₃) δ 8.40 (s, 1H), 6.10 (s, 1H), 5.48-5.53 (m, 1H), 4.48-4.51 (m, 2H), 3.974.07 (m, 1H), 3.68-3.79 (m, 3H), 3.50-3.63 (m, 1H), 3.42-3.44 (m, 3H), 2.37 (br s, 1H), 1.90 (br d, J=14.0 Hz, 1H), 1.47 (s, 9H), 1.24-1.36 (m, 5H), 0.86-0.90 ppm (m, 1H).
Intermediate 7

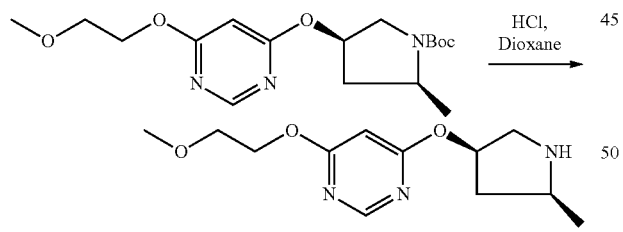

4-(2-methoxyethoxy)-6-(((3R,5S)-5-methylpyrrolidin-3-yl)oxy)pyrimidine: A 2 L round bottom flask charged with tert-butyl (2S,4R)-4-[6-(2-methoxyethoxy)pyrimidin-4-yl]oxy-2-methyl-pyrrolidine-1-carboxylate (28.58 g, 80.87 mmol) in DCM was cooled to 0° C. A solution of hydrogen chloride (4 M in dioxane, 202.18 mL) was subsequently added. Upon completion of the reaction the mixture was concentrated, diluted with water and adjusted the pH ~11 with 50% NaOH. The mixture was extracted with EtOAc, dried over sodium sulfate, filtered and concentrated to obtain the title compound (19.21 g, 75.84 mmol, 93% yield). LCMS (ESI): [M+H] 254.1. ¹HNMR: (500 MHz, CDCl₃) δ 8.39 (s, 1H), 6.08 (s, 1H), 5.40 (dddd, J=6.8, 5.1, 3.4, 1.2 Hz, 1H), 4.47-4.51 (m, 2H), 3.70-3.74 (m, 2H), 3.42-3.43 (m, 3H), 3.22 (d, J=12.8 Hz, 1H), 3.12-3.19 (m, 1H), 3.00-3.05 (m, 1H), 2.42 (dt, J=14.2, 7.2 Hz, 1H), 1.69 (br s, 2H), 1.45 (dddd, J=14.0, 7.9, 3.1, 1.2 Hz, 1H), 1.27 ppm (d, J=6.7 Hz, 3H).

Example 1-23

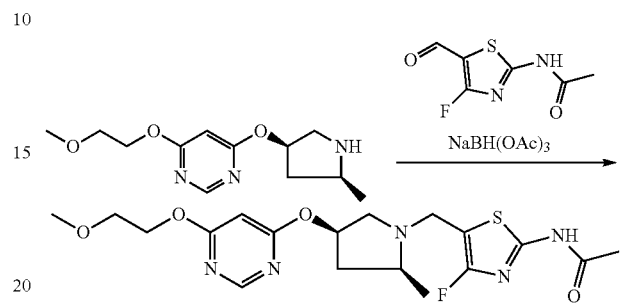

N-(4-fluoro-5-(((2S,4R)-4-((6-(2-methoxyethoxy)pyrimidin-4-yl)oxy)-2-methylpyrrolidin-1-yl)methyl)thiazol-2-yl)acetamide: Sodium triacetoxyborohydride (48.22 g, 227.52 mmol) was added to a mixture of 4-(2-methoxyethoxy)-6-[(3R,5S)-5-methylpyrrolidin-3-yl]oxy-pyrimidine (19.21 g, 75.84 mmol) and acetic acid (9.11 g, 151.68 mmol, 8.7 mL) in EtOAc (321.48 g, 3.65 mol, 357 mL) at 40° C. After 5 min, N-(4-fluoro-5-formyl-thiazol-2-yl)acetamide (14.70 g, 78.12 mmol) was added to the mixture at 40° C. The reaction turned pink after 30 min. After 2 h at 40° C., the reaction was cooled to rt and stirred at rt for 1 h. Added 1M HCl (~50 mL until bubbling ceased) to quench the reaction. Separated the aqueous layer from the organics and extracted the organics with ~75 mL of 1M HCl. Collected the aqueous layer and adjusted the pH to ~11-12 with 50% h NaOH (~75 mL). Extracted the aqueous with EtOAc, dried the organics over sodium sulfate and concentrated. The residue was purified over silica gel with gradient heptane/[EtOAc/EtOH (3:1)] w/1% TEA (0→50→100%) to obtain the title compound (25 g, 58.76 mmol, 77% yield). LCMS (ESI): [M+H] 426.1. ¹HNMR: (400 MHz, CDCl₃) δ 10.48 (br s, 1H), 8.36 (s, 1H), 6.10 (s, 1H), 5.30-5.35 (m, 1H), 4.45-4.48 (m, 2H), 3.97 (d, J=14.7 Hz, 1H), 3.70-3.73 (m, 2H), 3.64 (d, J=14.7 Hz, 1H), 3.49 (d, J=5.5 Hz, 1H), 3.42 (s, 3H), 3.15 (d, J=11.0 Hz, 1H), 2.66 (dd, J=11.0, 6.1 Hz, 1H), 2.48-2.55 (m, 2H), 2.28-2.30 (m, 3H), 1.57-1.62 (m, 6H), 1.24 (d, J=6.1 Hz, 3H), −0.12-0.01 (m, 1H).

Example 1-24

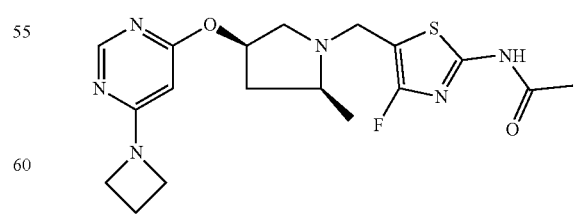

N-(5-(((2S,4R)-4-((6-(azetidin-1-yl)pyrimidin-4-yl)oxy)-2-methylpyrrolidin-1-yl)methyl)-4-fluorothiazol-2-yl)acetamide: The title compound was prepared in an analogous manner to Example 1-23 from tert-butyl (2S,4R)-4-hydroxy- 2-methylpyrrolidine-1-carboxylate, 4,6-dichloropyrimidine, azetidine, and N-(4-fluoro-5-formylthiazol-2-yl)acetamide. LCMS (ESI): [M+H] 407. ¹HNMR: (400 MHz, Methanol-d₄) δ 8.12 (s, 1H), 5.73 (s, 1H), 5.25-5.29 (m, 1H), 4.05-4.09 (m, 4H), 4.07-4.08 (m, 1H), 3.64 (d, J=14.5 Hz, 1H), 3.17 (d, J=11.0 Hz, 1H), 2.59-2.63 (m, 3H), 2.43-2.47 (m, 2H), 2.21 (s, 3H), 1.64-1.67 (m, 1H), 1.28 (d, J=5.5 Hz, 3H).

Example 1-25

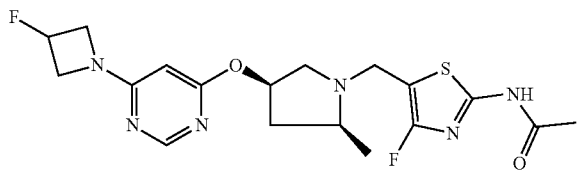 [SMILES: CC(=O)Nc1nc(F)c(CN2C[C@H](Oc3cc(N4CC(F)C4)ncn3)C[C@@H]2C)s1]

N-(4-fluoro-5-(((2S,4R)-4-((6-(3-fluoroazetidin-1-yl)pyrimidin-4-yl)oxy)-2-methylpyrrolidin-1-yl)methyl)thiazol-2-yl)acetamide: The title compound was prepared in an analogous manner to Example 1-23 from tert-butyl (2S,4R)-4-hydroxy-2-methylpyrrolidine-1-carboxylate, 4,6-dichloropyrimidine, 3-fluoroazetidine and N-(4-fluoro-5-formylthiazol-2-yl)acetamide. LCMS (ESI): [M+H] 425. ¹HNMR: (500 MHz, Methanol-d4) δ 8.12 (s, 1H), 5.73 (s, 1H), 5.25-5.29 (m, 1H), 4.05-4.09 (m, 4H), 4.07-4.08 (m, 1H), 3.64 (d, J=14.5 Hz, 1H), 3.17 (d, J=11.0 Hz, 1H), 2.59-2.63 (m, 3H), 2.43-2.47 (m, 2H), 2.21 (s, 3H), 1.64-1.67 (m, 1H), 1.28 (d, J=5.5 Hz, 3H).

Example 1-26

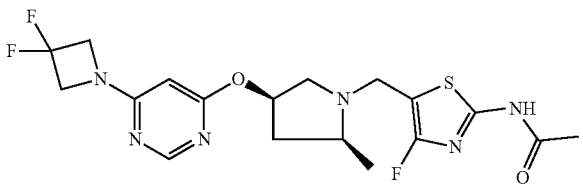 [SMILES: CC(=O)Nc1nc(F)c(CN2C[C@H](Oc3cc(N4CC(F)(F)C4)ncn3)C[C@@H]2C)s1]

N-(5-(((2S,4R)-4-((6-(3,3-difluoroazetidin-1-yl)pyrimidin-4-yl)oxy)-2-methylpyrrolidin-1-yl)methyl)-4-fluorothiazol-2-yl)acetamide: The title compound was prepared in an analogous manner Example 1-23 from tert-butyl (2S,4R)-4-hydroxy-2-methylpyrrolidine-1-carboxylate, 4,6-dichloropyrimidine, 3,3-difluoroazetidine and N-(4-fluoro-5-formylthiazol-2-yl)acetamide. LCMS (ESI): [M+H] 443.1. ¹HNMR: (500 MHz, Methanol-d₄) δ 8.20 (s, 1H), 5.78 (s, 1H), 5.26-5.29 (m, 1H), 4.36-4.41 (m, 4H), 3.93-3.97 (m, 1H), 3.51-3.58 (m, 1H), 3.10-3.12 (m, 1H), 2.45-2.65 (m, 3H), 2.17 (s, 3H), 1.57-1.62 (m, 1H), 1.23 (d, J=5.5 Hz, 3H).

Example 1-27

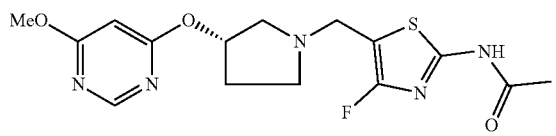 [SMILES: COc1cc(O[C@H]2CCN(Cc3sc(NC(C)=O)nc3F)C2)ncn1]

(S)-N-(4-fluoro-5-((3-((6-methoxypyrimidin-4-yl)oxy)pyrrolidin-1-yl)methyl)thiazol-2-yl)acetamide: The title compound was prepared in an analogous manner of that in Scheme 2 from tert-butyl(S)-3-hydroxypyrrolidine-1-carboxylate, 4-chloro-6-methoxypyrimidine, and N-(4-fluoro-5-formylthiazol-2-yl)acetamide. LCMS (ESI): [M+H] 368. ¹HNMR: (400 MHz, Methanol-d₄) δ 8.36 (s, 1H), 6.14 (s, 1H), 5.42-5.47 (m, 1H), 3.93 (s, 3H), 3.75-3.78 (m, 2H), 2.99-3.02 (m, 1H), 2.83-2.90 (m, 2H), 2.62-2.64 (m, 1H), 2.36-2.38 (m, 1H), 2.19 (s, 3H), 1.96-1.98 (m, 1H).

Example 1-28

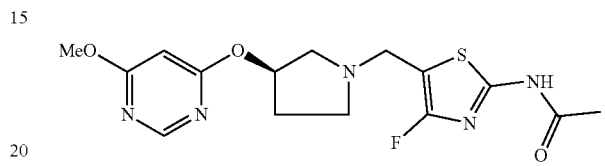

(R)-N-(4-fluoro-5-((3-((6-methoxypyrimidin-4-yl)oxy)pyrrolidin-1-yl)methyl)thiazol-2-yl)acetamide: The title compound was prepared in an analogous manner of that in Scheme 2 from tert-butyl(R)-3-hydroxypyrrolidine-1-carboxylate, 4-chloro-6-methoxypyrimidine, and N-(4-fluoro-5-formylthiazol-2-yl)acetamide. LCMS (ESI): [M+H] 368. ¹HNMR: (500 MHz, Methanol-d₄) δ 8.36 (s, 1H), 6.14 (s, 1H), 5.46-5.42 (m, 1H), 3.93 (s, 3H), 3.78-3.71 (m, 2H), 3.00-2.96 (m, 1H), 2.88-2.87 (m, 1H), 2.83-2.80 (m, 1H), 2.62-2.57 (m, 1H), 2.40-2.32 (m, 1H), 2.18 (s, 3H), 1.99-1.93 (m, 1H).

Example 1-29

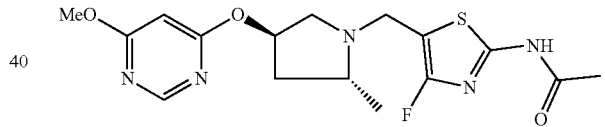

N-(4-fluoro-5-(((2R,4R)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2R,4R)-4-hydroxy-2-methylpyrrolidine-1-carboxylate, 4-chloro-6-methoxypyrimidine, and N-(4-fluoro-5-formylthiazol-2-yl)acetamide. LCMS (ESI): [M+H] 382. ¹HNMR: (500 MHz, CDCl₃) δ:10.71 (br. s, 1H), 8.39 (s, 1H), 5.97 (s, 1H), 5.33-5.35 (m, 1H), 3.93-3.97 (m, 1H), 3.92 (s, 3H), 3.62-3.66 (m, 2H), 2.81-2.86 (m, 1H), 2.41-2.51 (m, 1H), 2.29 (s, 3H), 2.01-2.07 (m, 1H), 1.83-1.91 (m, 1H), 1.15-1.22 (m, 3H).

Example 1-30

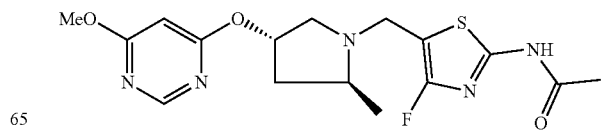

N-(4-fluoro-5-(((2S,4S)-4-((6-methoxypyrimidin-4-yl)oxy)-2-methylpyrrolidin-1-yl)methyl)thiazol-2-yl)acetamide: The title compound was prepared in an analogous manner of that in Scheme 2 from pyrazine tert-butyl (2S,4S)-4-hydroxy-2-methylpyrrolidine-1-carboxylate, 4-chloro-6-methoxypyrimidine, and N-(4-fluoro-5-formylthiazol-2-yl)acetamide. LCMS (ESI): [M+H] 382. $^1$HNMR (400 MHz, Methanol-$d_4$) δ 8.35 (d, J=0.75 Hz, 1H), 6.07 (d, J=1.00 Hz, 1H), 5.28-5.37 (m, 1H), 5.28-5.37 (m, 1H), 3.90-4.00 (m, 4H), 3.67 (d, J=14.81 Hz, 1H), 3.57 (dd, J=6.27, 11.04 Hz, 1H), 2.88 (td, J=6.02, 10.29 Hz, 1H), 2.53 (dd, J=4.02, 11.04 Hz, 1H), 2.18 (s, 3H), 2.09 (ddd, J=1.76, 6.02, 13.80 Hz, 1H), 1.87 (ddd, J=7.28, 10.29, 13.80 Hz, 1H), 1.20 (d, J=6.27 Hz, 3H).

Example 1-31

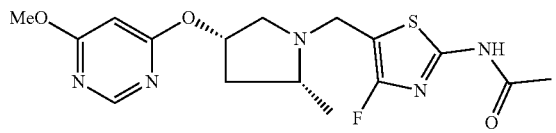 [SMILES: COc1cc(O[C@H]2C[C@@H](C)N(Cc3sc(NC(C)=O)nc3F)C2)ncn1]

N-(4-fluoro-5-(((2R,4S)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2R,4S)-4-hydroxy-2-methylpyrrolidine-1-carboxylate, 4-chloro-6-methoxypyrimidine, and N-(4-fluoro-5-formylthiazol-2-yl)acetamide. LCMS (ESI): [M+H] 382. $^1$HNMR (400 MHz, Methanol-$d_4$) δ 8.35 (s, 1H), 6.14 (s, 1H), 5.31-5.33 (m, 1H), 3.96-4.00 (m, 1H), 3.92 (s, 3H), 3.55-3.59 (m, 1H), 3.13-3.16 (m, 1H), 2.57-2.69 (m, 3H), 2.18 (s, 3H), 1.62-1.65 (m, 1H), 1.25 (d, J=5.6 Hz, 3H).

Example 1-32

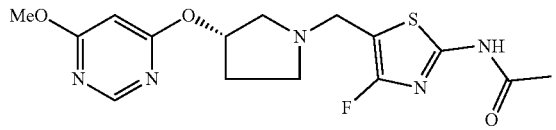 [SMILES: COc1cc(O[C@H]2CCN(Cc3sc(NC(C)=O)nc3F)C2)ncn1]

(S)-N-(4-fluoro-5-((3-((6-methoxypyrimidin-4-yl)oxy)piperidin-1-yl)methyl)thiazol-2-yl)acetamide: The title compound was prepared in an analogous manner of that in Scheme 2 from tert-butyl(S)-3-hydroxypiperidine-1-carboxylate, 4-chloro-6-methoxypyrimidine, and N-(4-fluoro-5-formylthiazol-2-yl)acetamide. LCMS (ESI): [M+H] 382. $^1$HNMR (400 MHz, Methanol-$d_4$) δ 8.33 (s, 1H), 6.14 (s, 1H), 5.17-5.13 (m, 1H), 3.93 (s, 3H), 3.67-3.65 (m, 2H), 2.93-2.90 (m, 1H), 2.66-2.65 (m, 1H), 2.45-2.44 (s, 1H), 2.36-2.35 (s, 1H), 2.18 (s, 3H), 1.96-1.95 (m, 1H), 1.85-1.84 (m, 1H), 1.67-1.58 (m, 2H).

Example 1-33

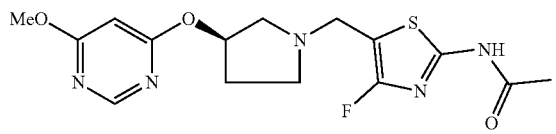 [SMILES: COc1cc(O[C@@H]2CCN(Cc3sc(NC(C)=O)nc3F)C2)ncn1]

(R)-N-(4-fluoro-5-((3-((6-methoxypyrimidin-4-yl)oxy)piperidin-1-yl)methyl)thiazol-2-yl)acetamide: The title compound was prepared in an analogous manner of that in Scheme 2 from tert-butyl(R)-3-hydroxypiperidine-1-carboxylate, 4-chloro-6-methoxypyrimidine, and N-(4-fluoro-5-formylthiazol-2-yl)acetamide. LCMS (ESI): [M+H] 382. $^1$HNMR: (400 MHz, Methanol-$d_4$) δ 8.33 (s, 1H), 6.14 (s, 1H), 5.16-5.12 (m, 1H), 3.93 (s, 3H), 3.65 (s, 2H), 2.91 (d, J=8.4 Hz, 1H), 2.65 (d, J=5.6 Hz, 1H), 2.44-2.35 (m, 2H), 2.18 (s, 3H), 1.99-1.85 (m, 2H), 1.66-1.57 (m, 2H).

Example 1-34

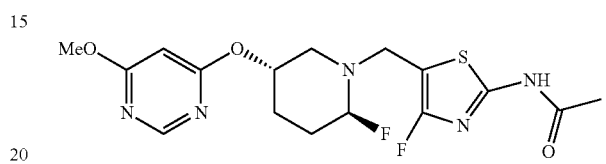

N-(4-fluoro-5-(((2S,5S)-5-((6-methoxypyrimidin-4-yl)oxy)-2-methylpiperidin-1-yl)methyl)thiazol-2-yl)acetamide: The title compound was prepared in an analogous manner of that in Scheme 2 from tert-butyl (2S,5S)-5-hydroxy-2-methylpiperidine-1-carboxylate, 4-chloro-6-methoxypyrimidine, and N-(4-fluoro-5-formylthiazol-2-yl)acetamide. LCMS (ESI): [M+H] 396. $^1$HNMR: (500 MHz, Methanol-$d_4$) δ 8.34 (s, 1H), 6.13 (s, 1H), 5.08-5.12 (m, 1H), 3.94 (s, 3H), 3.83-3.86 (m, 2H), 3.33-3.34 (m, 2H), 3.17-3.19 (m, 1H), 2.39-2.40 (m, 1H), 2.25-2.29 (m, 1H), 2.21 (s, 3H), 2.16 (m, 1H), 1.83-1.86 (m, 1H), 1.23 (d, J=6.0 Hz, 3H).

Example 1-35

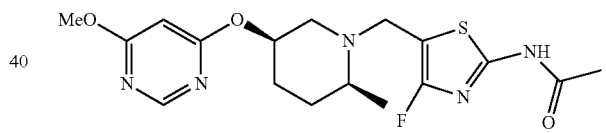

N-(4-fluoro-5-(((2S,5R)-5-((6-methoxypyrimidin-4-yl)oxy)-2-methylpiperidin-1-yl)methyl)thiazol-2-yl)acetamide: The title compound was prepared in an analogous manner of that in Scheme 2 from tert-butyl (2S,5R)-5-hydroxy-2-methylpiperidine-1-carboxylate, 4-chloro-6-methoxypyrimidine, and N-(5-(chloromethyl)-4-fluorothiazol-2-yl)acetamide. LCMS (ESI): [M+H] 396. $^1$HNMR: (500 MHz, CDCl$_3$) δ 10.95 (brs, 1H), 8.37 (s, 1H), 6.14 (s, 1H), 5.20-5.24 (m, 1H), 3.96 (s, 3H), 3.90-3.94 (m, 1H), 3.79 (d, J=15.0 Hz, 1H), 3.98-3.01 (m, 1H), 2.55-2.63 (m, 2H), 2.30 (s, 3H), 1.88-1.91 (m, 1H), 1.62-1.70 (m, 3H), 1.20 (d, J=6.5 Hz, 3H).

Example 1-36

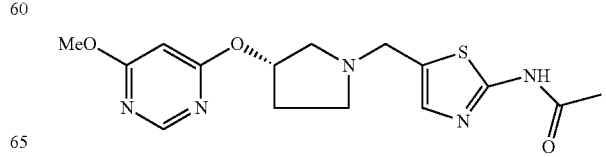

(S)-N-(5-((3-((6-methoxypyrimidin-4-yl)oxy)pyrrolidin-1-yl)methyl)thiazol-2-yl)acetamide: The title compound was prepared in an analogous manner of that in Scheme 2 from tert-butyl(S)-3-hydroxypyrrolidine-1-carboxylate, 4-chloro-6-methoxypyrimidine, and N-(5-formylthiazol-2-yl)acetamide. LCMS (ESI): [M+H] 350. ¹HNMR: (500 MHz, Methanol-d4) δ 8.36 (s, 1H), 7.26 (s, 1H), 6.14 (s, 1H), 5.42-5.46 (m, 1H), 3.93 (s, 3H), 3.80-3.88 (m, 2H), 2.95-2.98 (m, 1H), 2.79-2.82 (m, 1H), 2.58-2.60 (m, 1H), 2.36-2.37 (m, 1H), 2.06-2.11 (m, 1H) 2.20 (s, 3H), 1.83-1.94 (m, 1H).

Example 1-37

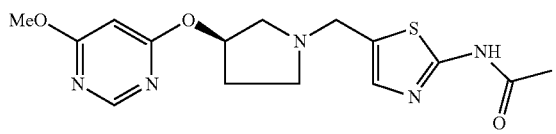 [SMILES: COc1cc(O[C@@H]2CCN(Cc3cnc(NC(C)=O)s3)C2)ncn1]

(R)-N-(5-((3-((6-methoxypyrimidin-4-yl)oxy)pyrrolidin-1-yl)methyl)thiazol-2-yl)acetamide: The title compound was prepared in an analogous manner of that in Scheme 2 from tert-butyl(R)-3-hydroxypyrrolidine-1-carboxylate, 4-chloro-6-methoxypyrimidine, and N-(5-formylthiazol-2-yl)acetamide. LCMS (ESI): [M+H] 350. ¹HNMR: (500 MHz, Methanol-d₄) δ 8.39 (s, 1H), 7.29 (s, 1H), 6.17 (s, 1H), 5.45-5.49 (m, 1H), 3.96 (s, 3H), 3.91-3.83 (m, 2H), 3.01-2.98 (m, 1H), 2.93-2.88 (m, 1H), 2.85-2.82 (m, 1H), 2.64-2.59 (m, 1H), 2.43-2.36 (m, 1H), 2.22 (s, 3H), 2.02-1.96 (m, 1H).

Example 1-38

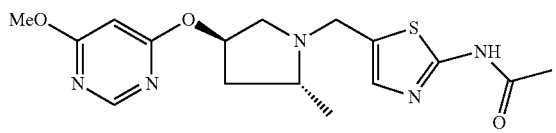 [SMILES: COc1cc(O[C@@H]2C[C@@H](C)N(Cc3cnc(NC(C)=O)s3)C2)ncn1]

N-(5-(((2R,4R)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2R,4R)-4-hydroxy-2-methylpyrrolidine-1-carboxylate, 4-chloro-6-methoxypyrimidine, and N-(5-formylthiazol-2-yl)acetamide. LCMS (ESI): [M+H] 364. ¹HNMR: (500 MHz, Methanol-d₄) δ 8.34 (s, 1H), 7.24 (s, 1H), 6.08 (s, 1H), 5.31-5.33 (m, 1H), 4.12 (d, J=14.5 Hz, 1H), 3.92 (s, 3H), 3.68 (d, J=14.0 Hz, 1H), 3.52-3.56 (m, 1H), 2.85-2.87 (m, 1H), 2.46-2.49 (m, 1H), 2.20 (s, 3H), 2.07-2.11 (m, 1H), 1.85-1.94 (m, 1H), 1.21 (d, J=6.0 Hz, 3H).

Example 1-39

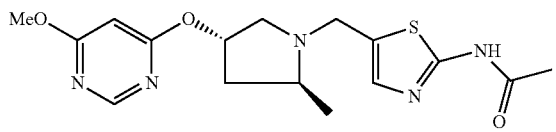 [SMILES: COc1cc(O[C@H]2C[C@H](C)N(Cc3cnc(NC(C)=O)s3)C2)ncn1]

N-(5-(((2S,4S)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2S,4S)-4-hydroxy-2-methylpyrrolidine-1-carboxylate, 4-chloro-6-methoxypyrimidine, and N-(5-formylthiazol-2-yl)acetamide. LCMS (ESI): [M+H] 364. ¹HNMR: (400 MHz, Methanol-d₄) δ 8.37 (s, 1H), 7.27 (s, 1H), 6.11 (s, 1H), 5.34-5.36 (m, 1H), 4.15 (d, J=14.4 Hz, 1H), 3.95 (s, 3H), 3.71 (d, J=14.0 Hz, 1H), 3.55-3.60 (m, 1H), 2.88-2.91 (m, 1H), 2.49-2.53 (m, 1H), 2.23 (s, 3H), 2.11-2.14 (m, 1H), 1.92-1.94 (m, 1H), 1.24 (d, J=6.0 Hz, 3H).

Example 1-40

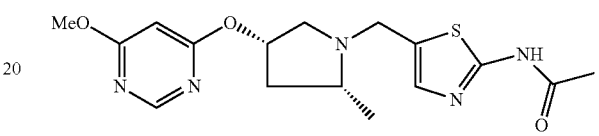

N-(5-(((2R,4S)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2R,4S)-4-hydroxy-2-methylpyrrolidine-1-carboxylate, 4-chloro-6-methoxypyrimidine, and N-(5-formylthiazol-2-yl)acetamide. LCMS (ESI): [M+H] 364. ¹HNMR: (500 MHz, Methanol-d₄) δ 8.34 (s, 1H), 7.26 (s, 1H), 6.13 (s, 1H), 5.30-5.33 (m, 1H), 4.11-4.15 (m, 1H), 3.92 (s, 3H), 3.52-3.55 (m, 1H), 3.08-3.11 (m, 1H), 2.54-2.65 (m, 3H), 2.19 (s, 3H), 1.61-1.65 (m, 1H), 1.24 (d, J=5.5 Hz, 3H).

Example 1-41

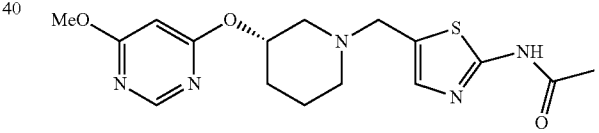

(S)-N-(5-((3-((6-methoxypyrimidin-4-yl)oxy)piperidin-1-yl)methyl)thiazol-2-yl)acetamide: The title compound was prepared in an analogous manner of that in Scheme 2 from tert-butyl(S)-3-hydroxypiperidine-1-carboxylate, 4-chloro-6-methoxypyrimidine, and N-(5-formylthiazol-2-yl)acetamide. LCMS (ESI): [M+H] 364. ¹HNMR: (500 MHz, Methanol-d₄) δ 8.17 (s, 1H), 7.13 (s, 1H), 5.98 (s, 1H), 5.05 (br s, 1H), 3.76 (s, 3H), 3.74-3.76 (m, 2H), 2.84-2.85 (m, 1H), 2.60-2.61 (m, 1H), 2.28-2.46 (m, 2H), 2.03 (s, 3H), 1.71-1.75 (m, 2H), 1.51-1.55 (m, 2H).

Example 1-42

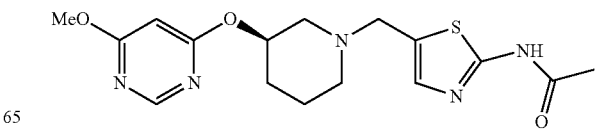

(R)-N-(5-((3-((6-methoxypyrimidin-4-yl)oxy)piperidin-1-yl)methyl)thiazol-2-yl)acetamide: The title compound was prepared in an analogous manner of that in Scheme 2 from tert-butyl(R)-3-hydroxypiperidine-1-carboxylate, 4-chloro-6-methoxypyrimidine, and N-(5-formylthiazol-2-yl)acetamide. LCMS (ESI): [M+H] 364. ¹HNMR: (400 MHz, Methanol-d4) δ 8.32 (s, 1H), 7.23 (s, 1H), 6.13 (s, 1H), 5.13-5.17 (m, 1H), 3.92 (s, 3H), 3.77-3.80 (m, 2H), 2.93 (d, J=10.4 Hz, 1H), 2.67-2.69 (m, 1H), 2.43-2.44 (m, 2H), 2.19 (s, 3H), 1.86-2.00 (m, 2H), 1.59-1.67 (m, 2H).

Example 1-43

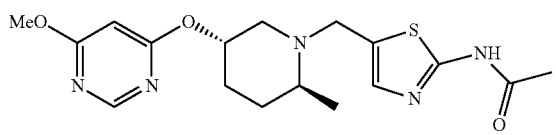 [SMILES: COc1cc(O[C@H]2CC[C@H](C)N(Cc3cnc(NC(C)=O)s3)C2)ncn1]

N-(5-(((2S,5S)-5-((6-methoxypyrimidin-4-yl)oxy)-2-methylpiperidin-1-yl)methyl)thiazol-2-yl)acetamide: The title compound was prepared in an analogous manner of that in Scheme 2 from tert-butyl (2S,5S)-5-hydroxy-2-methylpiperidine-1-carboxylate, 4-chloro-6-methoxypyrimidine, and N-(5-formylthiazol-2-yl)acetamide. LCMS (ESI): [M+H] 378. ¹HNMR: (500 MHz, Methanol-d₄) δ 8.34 (s, 1H), 7.28 (s, 1H), 6.12 (s, 1H), 5.11-5.21 (m, 1H), 4.07-4.17 (m, 1H), 3.97 (s, 3H), 3.89-3.90 (m, 1H), 3.17-3.19 (m, 1H), 2.44-2.45 (m, 1H), 2.22 (s, 3H), 2.17-2.18 (m, 1H), 2.01-2.02 (m, 1H), 1.87-1.88 (m, 1H), 1.48-1.52 (m, 2H), 1.26 (d, J=6.0 Hz, 3H).

Example 1-44

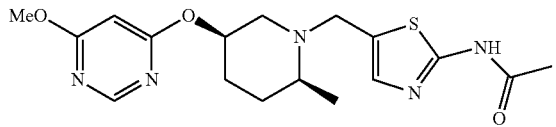 [SMILES: COc1cc(O[C@@H]2CC[C@H](C)N(Cc3cnc(NC(C)=O)s3)C2)ncn1]

N-(5-(((2S,5R)-5-((6-methoxypyrimidin-4-yl)oxy)-2-methylpiperidin-1-yl)methyl)thiazol-2-yl)acetamide: The title compound was prepared in an analogous manner of that in Scheme 2 from tert-butyl (2S,5R)-5-hydroxy-2-methylpiperidine-1-carboxylate, 4-chloro-6-methoxypyrimidine, and N-(5-(chloromethyl)thiazol-2-yl)acetamide. LCMS (ESI): [M+H]378. ¹HNMR: (500 MHz, CDCl₃) δ 11.4 (brs, 1H), 8.36 (s, 1H), 7.18 (s, 1H), 6.12 (s, 1H), 5.19-5.21 (m, 1H), 3.96 (d, J=15.0 Hz, 1H), 3.93 (s, 3H), 3.87 (d, J=15.0 Hz, 1H), 2.93-2.96 (m, 1H), 2.60-2.63 (m, 2H), 2.29 (s, 3H), 1.85-1.89 (m, 1H), 1.63-1.74 (m, 3H), 1.20 (d, J=6.0 Hz, 3H).

Example 1-45

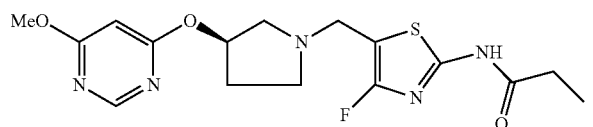

(R)-N-(4-fluoro-5-((3-((6-methoxypyrimidin-4-yl)oxy)pyrrolidin-1-yl)methyl)thiazol-2-yl)propionamide: The title compound was prepared in an analogous manner of that in Scheme 2 from tert-butyl(R)-3-hydroxypyrrolidine-1-carboxylate, 4-chloro-6-methoxypyrimidine, and N-(4-fluoro-5-formylthiazol-2-yl)propionamide. LCMS (ESI): [M+H] 382. ¹HNMR (400 MHz, Methanol-d₄) δ 8.36 (s, 1H), 6.13 (d, J=0.75 Hz, 1H), 5.38-5.49 (m, 1H), 3.93 (s, 3H), 3.68-3.82 (m, 2H), 2.99 (dd, J=6.15, 11.17 Hz, 1H), 2.79-2.93 (m, 2H), 2.55-2.66 (m, 1H), 2.46 (q, J=7.53 Hz, 2H), 2.29-2.40 (m, 1H), 1.91-2.03 (m, 1H), 1.19 (t, J=7.65 Hz, 3H).

Example 1-46

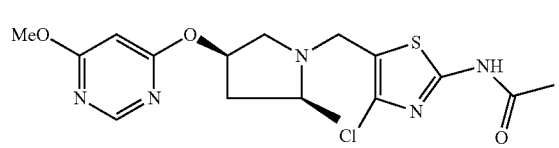 [SMILES: COc1cc(O[C@@H]2C[C@H](C)N(Cc3sc(NC(C)=O)nc3Cl)C2)ncn1]

N-(4-chloro-5-(((2S,4R)-4-((6-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-methylpyridine, and N-(4-chloro-5-formylthiazol-2-yl)acetamide. LCMS (ESI): [M+H] 398. ¹HNMR: (400 MHz, Methanol-d₄) δ 8.34 (d, J=1.00 Hz, 1H), 6.13 (d, J=0.75 Hz, 1H), 5.28-5.40 (m, 1H), 4.04 (d, J=14.56 Hz, 1H), 3.92 (s, 3H), 3.56 (d, J=14.56 Hz, 1H), 3.07-3.17 (m, 1H), 2.51-2.73 (m, 3H), 2.18 (s, 3H), 1.56-1.69 (m, 1H), 1.24 (d, J=5.52 Hz, 3H).

Example 1-47

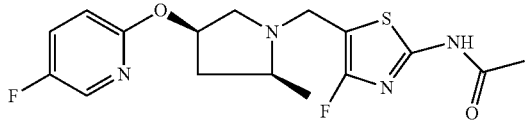 [SMILES: CC(=O)Nc1nc(F)c(CN2C[C@H](Oc3ccc(F)cn3)C[C@@H]2C)s1]

N-(4-fluoro-5-(((2S,4R)-4-((5-fluoropyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2,5-difluoropyridine, and N-(4-fluoro-5-formylthiazol-2-yl)acetamide. LCMS (ESI): [M+H] 369. ¹HNMR: (400 MHz, Methanol-d₄) δ 7.95 (d, J=2.4 Hz, 1H), 7.45-7.49 (m, 1H), 6.77 (dd, J=9.2, 3.2 Hz, 1H), 5.21-5.24 (m, 1H), 3.96 (d, J=14.8 Hz, 1H), 3.56 (d, J=14.8 Hz, 1H), 3.10-3.13 (m, 1H), 2.54-2.68 (m, 3H), 2.18 (s, 3H), 1.56-1.64 (m, 1H), 1.24 (d, J=6.0 Hz, 3H).

Example 1-48

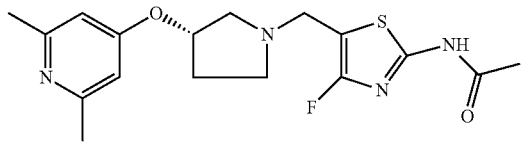 [SMILES: CC(=O)Nc1nc(F)c(CN2CC[C@H](Oc3cc(C)nc(C)c3)C2)s1]

(S)-N-(5-((3-((2,6-dimethylpyridin-4-yl)oxy)pyrrolidin-1-yl)methyl)-4-fluorothiazol-2-yl)acetamide: The title compound was prepared in an analogous manner of that in Scheme 2 from 4-chloro-2,6-dimethylpyridine, tert-butyl (S)-3-hydroxypyrrolidine-1-carboxylate, and N-(4-fluoro-5-formylthiazol-2-yl)acetamide. LCMS (ESI): [M+H] 365.0. $^1$HNMR: (500 MHz, CDCl$_3$) δ 10.27 (br., s., 1H), 6.44 (s, 2H), 4.82-4.86 (m, 1H), 3.76-3.79 (m, 2H), 2.99-3.03 (m, 1H), 2.94-2.98 (m, 1H), 2.82-2.86 (m, 1H), 2.76-2.78 (m, 1H), 2.48 (s, 6H), 2.29-2.34 (m, 4H), 1.95-2.01.

Example 1-49

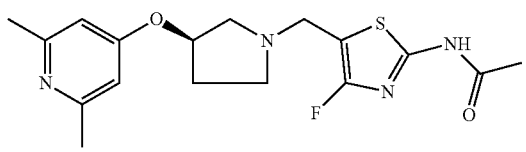

(R)-N-(5-((3-((2,6-dimethylpyridin-4-yl)oxy)pyrrolidin-1-yl)methyl)-4-fluorothiazol-2-yl)acetamide: The title compound was prepared in an analogous manner of that in Scheme 2 from 4-chloro-2,6-dimethylpyridine, tert-butyl (R)-3-hydroxypyrrolidine-1-carboxylate, and N-(4-fluoro-5-formylthiazol-2-yl)acetamide. LCMS (ESI): [M+H] 365.0. $^1$HNMR: (400 MHz, CDCl$_3$) δ 10.71 (br., s., 1H), 6.43 (s, 2H), 4.82-4.83 (m, 1H), 3.75 (s, 2H), 2.84-3.01 (m, 1H), 2.75-2.82 (m, 2H), 2.63-2.64 (m, 1H), 2.47 (s, 6H), 1.97-2.31 (m, 4H), 1.86-1.95 (m, 1H).

Example 1-50

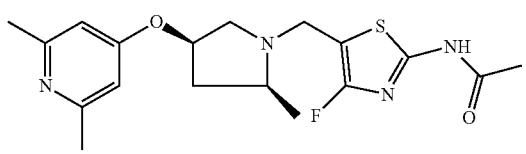 [SMILES: CC(=O)Nc1nc(F)c(CN2C[C@H](Oc3cc(C)nc(C)c3)C[C@@H]2C)s1]

N-(5-(((2S,4R)-4-((2,6-dimethylpyridin-4-yl)oxy)-2-methylpyrrolidin-1-yl)methyl)-4-fluorothiazol-2-yl)acetamide: The title compound was prepared in an analogous manner of that in Scheme 2 from 4-chloro-2,6-dimethylpyridine, tert-butyl (2S,4R)-4-hydroxy-2-methylpyrrolidine-1-carboxylate, N-(4-fluoro-5-formylthiazol-2-yl)acetamide. LCMS (ESI): [M+H] 379.1. $^1$HNMR: (400 MHz, CDCl$_3$) δ 10.67 (br. s., 1H), 6.45 (s, 2H), 4.71-4.73 (m, 1H), 3.96 (d, J=15.2 Hz, 1H), 3.65 (d, J=14.8 Hz, 1H), 3.17 (d, J=10.8 Hz, 1H), 2.53-2.65 (m, 3H), 2.50 (s, 6H), 2.30 (s, 3H), 1.66-1.69 (m, 1H), 1.24 (d, J=6.0 Hz, 3H).

Example 1-51

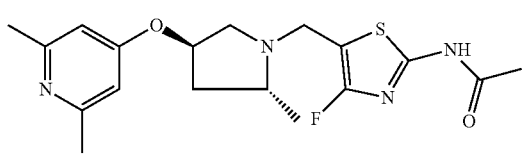 [SMILES: CC(=O)Nc1nc(F)c(CN2C[C@H](Oc3cc(C)nc(C)c3)C[C@H]2C)s1]

N-(5-(((2R,4R)-4-((2,6-dimethylpyridin-4-yl)oxy)-2-methylpyrrolidin-1-yl)methyl)-4-fluorothiazol-2-yl)acetamide: The title compound was prepared in an analogous manner of that in Scheme 2 from 4-chloro-2,6-dimethylpyridine, tert-butyl (2R,4R)-4-hydroxy-2-methylpyrrolidine-1-carboxylate, and N-(4-fluoro-5-formylthiazol-2-yl)acetamide. LCMS (ESI): [M+H] 379.0. $^1$HNMR: (400 MHz, CDCl$_3$) δ 10.09 (br. s, 1H), 6.39 (d, J=2.8 Hz, 2H), 4.75-4.79 (m, 1H), 3.93-3.97 (m, 1H), 3.57-3.64 (m, 2H), 2.80-2.83 (m, 1H), 2.45-2.50 (m, 7H), 2.28 (s, 3H), 2.03-2.05 (m, 1H), 1.82-1.86 (m, 1H), 1.17 (d, J=5.6 Hz, 3H).

Example 1-52

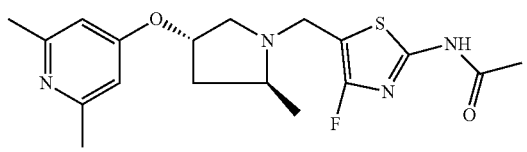 [SMILES: CC(=O)Nc1nc(F)c(CN2C[C@@H](Oc3cc(C)nc(C)c3)C[C@@H]2C)s1]

N-(5-(((2S,4S)-4-((2,6-dimethylpyridin-4-yl)oxy)-2-methylpyrrolidin-1-yl)methyl)-4-fluorothiazole-2-yl)acetamide: The title compound was prepared in an analogous manner of that in Scheme 2 from tert-butyl (2S,4S)-4-hydroxy-2-methylpyrrolidine-1-carboxylate, 4-bromo-2,6-dimethylpyridine, and N-(4-fluoro-5-formylthiazol-2-yl)acetamide. LCMS (ESI): [M+H] 379. $^1$H NMR (400 MHz, Methanol-d$_4$) δ 7.19 (s, 2H), 5.35-5.49 (m, 1H), 4.62-4.74 (m, 1H), 4.50-4.61 (m, 1H), 4.19 (br dd, J=5.14, 13.68 Hz, 1H), 3.93 (td, J=5.99, 11.86 Hz, 1H), 3.63 (br d, J=13.80 Hz, 1H), 2.54-2.72 (m, 7H), 2.22 (s, 4H), 1.56 (d, J=6.27 Hz, 3H).

Example 1-53

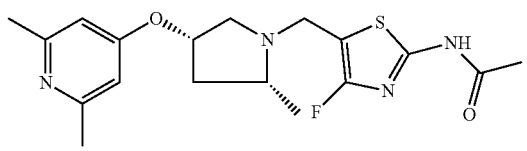 [SMILES: CC(=O)Nc1nc(F)c(CN2C[C@@H](Oc3cc(C)nc(C)c3)C[C@H]2C)s1]

N-(5-(((2R,4)-4-((2,6-dimethylpyridin-4-yl)oxy)-2-methylpyrrolidin-1-yl)methyl)-4-fluorothiazol-2-yl)acetamide: The title compound was prepared in an analogous manner of that in Scheme 2 from 2,6-dimethylpyridin-4-ol tert-butyl (2R,4R)-4-hydroxy-2-methylpyrrolidine-1-carboxylate, and N-(5-formylthiazol-2-yl)acetamide.. LCMS (ESI): [M+H] 379.0. $^1$HNMR: (400 MHz, Methanol-d$_4$) δ 6.58 (s, 2H), 4.83-4.89 (m, 1H), 3.97 (d, J=14.4 Hz, 1H), 3.58 (d, J=14.4 Hz, 1H), 3.12-3.13 (m, 1H), 2.55-2.69 (m, 3H), 2.41 (s, 6H), 2.18 (s, 3H), 1.56-1.61 (m, 1H), 1.23 (d, J=5.6 Hz, 3H).

Example 1-54

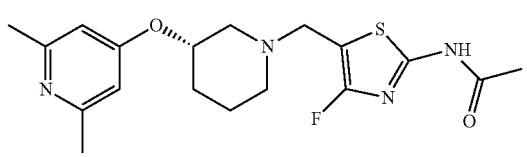 [SMILES: CC(=O)Nc1nc(F)c(CN2CCC[C@H](Oc3cc(C)nc(C)c3)C2)s1]

(S)-N-(5-((3-((2,6-dimethylpyridin-4-yl)oxy)piperidin-1-yl)methyl)-4-fluorothiazol-2-yl)acetamide: The title compound was prepared in an analogous manner of that in Scheme 2 from 4-chloro-2,6-dimethylpyridine, tert-butyl(S)-3-hydroxypiperidine-1-carboxylate, and N-(4-fluoro-5-formylthiazol-2-yl)acetamide. LCMS (ESI): [M+H] 379.1. $^1$HNMR: (500 MHz, Methanol-d$_4$) δ 6.70 (s, 2H), 4.57-4.53 (m, 1H), 3.72-3.68 (m, 2H), 2.97 (d, J=9.5 Hz, 1H), 2.76-2.73 (m, 1H), 2.41-2.35 (m, 6H), 2.33-2.32 (m, 2H), 2.21-2.04 (m, 3H), 1.88 (d, J=4.5 Hz, 1H), 1.70 (m, 1H), 1.69-1.68 (m, 1H), 1.56 (m, 1H).

Example 1-55

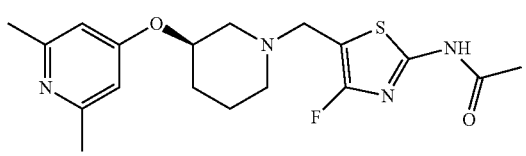 [SMILES: CC(=O)Nc1nc(F)c(CN2CCC[C@@H](Oc3cc(C)nc(C)c3)C2)s1]

(R)-N-(5-((3-((2,6-dimethylpyridin-4-yl)oxy)piperidin-1-yl)methyl)-4-fluorothiazol-2-yl)acetamide: The title compound was prepared in an analogous manner of that in Scheme 2 from 4-chloro-2,6-dimethylpyridine, tert-butyl (R)-3-hydroxypiperidine-1-carboxylate, and N-(4-fluoro-5-formylthiazol-2-yl)acetamide. LCMS (ESI): [M+H] 379.1. $^1$HNMR: (500 MHz, CDCl$_3$) δ 6.65 (s, 2H), 4.57-4.52 (m, 1H), 3.71-3.68 (m, 2H), 2.98-2.96 (m, 1H), 2.76-2.73 (m, 1H), 2.41 (s, 6H), 2.33-2.31 (m, 2H), 2.21 (s, 3H), 2.02-1.99 (m, 1H), 1.88-1.87 (m, 1H), 1.71-1.69 (m, 1H), 1.67-1.55 (m, 1H).

Example 1-56

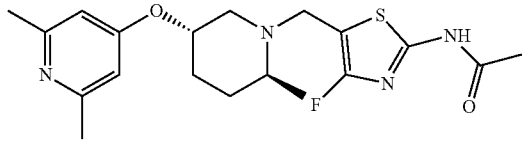 [SMILES: CC(=O)Nc1nc(F)c(CN2C[C@@H](Oc3cc(C)nc(C)c3)CC[C@@H]2C)s1]

N-(5-(((2S,5S)-5-((2,6-dimethylpyridin-4-yl)oxy)-2-methylpiperidin-1-yl)methyl)-4-fluorothiazol-2-yl)acetamide: The title compound was prepared in an analogous manner of that in Scheme 2 from 4-chloro-2,6-dimethylpyridine, tert-butyl (2S,5S)-5-hydroxy-2-methylpiperidine-1-carboxylate, and N-(4-fluoro-5-formylthiazol-2-yl)acetamide. LCMS (ESI): [M+H] 393.1. $^1$HNMR: (400 MHz, Methanol-d$_4$) δ 6.68 (s, 2H), 4.47-4.48 (m, 1H), 3.92-3.96 (m, 1H), 3.72-3.75 (m, 1H), 3.13-3.15 (m, 1H), 2.41 (s, 6H), 2.36-2.37 (m, 1H), 2.19 (s, 3H), 2.14-2.17 (m, 2H), 1.83-1.84 (m, 1H), 1.43-1.48 (m, 2H), 1.22 (d, J=6.4 Hz, 3H).

Example 1-57

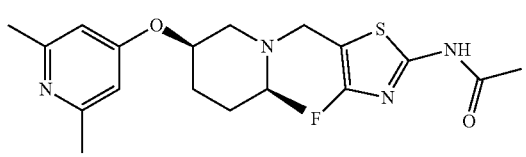 [SMILES: CC(=O)Nc1nc(F)c(CN2C[C@H](Oc3cc(C)nc(C)c3)CC[C@@H]2C)s1]

N-(5-(((2,5R)-5-((2,6-dimethylpyridin-4-yl)oxy)-2-methylpiperidin-1-yl)methyl)-4-fluorothiazol-2-yl)acetamide: The title compound was prepared in an analogous manner of that in Scheme 2 from 2,6-dimethylpyridin-4-ol, tert-butyl (2S,5S)-5-hydroxy-2-methylpiperidine-1-carboxylate, N-(4-fluoro-5-formylthiazol-2-yl)acetamide. LCMS (ESI): [M+H] 393.1. $^1$HNMR: (500 MHz, Methanol-d$_4$) δ 6.66 (s, 2H), 4.61-4.63 (m, 1H), 3.78 (dd, J=15.0, 12.5 Hz, 2H), 2.93-2.96 (m, 1H), 2.55-2.62 (m, 2H), 2.39 (s, 6H), 2.18 (s, 3H), 1.83-1.95 (m, 1H), 1.66-1.73 (m, 3H), 1.20 (d, J=6.0 Hz, 3H).

Example 1-58

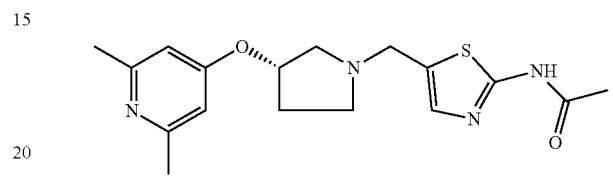

(S)-N-(5-((3-((2,6-dimethylpyridin-4-yl)oxy)pyrrolidin-1-yl)methyl)thiazol-2-yl)acetamide. The title compound was prepared in an analogous manner of that in Scheme 2 from 4-chloro-2,6-dimethylpyridine, tert-butyl(S)-3-hydroxypyrrolidine-1-carboxylate, and N-(5-formylthiazol-2-yl)acetamide. LCMS (ESI): [M+H] 347.1. $^1$HNMR: (400 MHz, CDCl$_3$) δ 11.25 (br., s., 1H), 7.16 (s, 1H), 6.35 (s, 2H), 4.75-4.79 (m, 1H), 3.73-3.81 (m, 2H), 2.94-2.98 (m, 1H), 2.71-2.77 (m, 1H), 2.65-2.68 (m, 1H), 2.56-2.62 (m, 1H), 2.38 (s, 6H), 2.21-2.26 (m, 4H), 1.88-1.95 (m, 1H).

Example 1-59

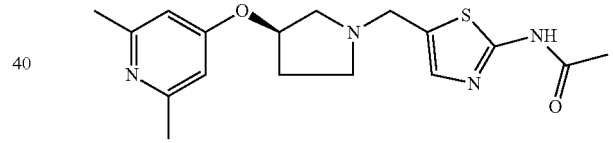

(R)-N-(5-((3-((2,6-dimethylpyridin-4-yl)oxy)pyrrolidin-1-yl)methyl)thiazol-2-yl)acetamide: The title compound was prepared in an analogous manner of that in Scheme 2 from 4-chloro-2,6-dimethylpyridine, tert-butyl(R)-3-hydroxypyrrolidine-1-carboxylate, and N-(5-formylthiazol-2-yl)acetamide. LCMS (ESI): [M+H] 347.0. $^1$HNMR: (500 MHz, CDCl$_3$) δ 11.43 (br s, 1H), 7.23 (s, 1H), 6.42 (s, 2H), 4.85-4.82 (m, 1H), 3.88-3.84 (m, 2H), 3.02-3.01 (m, 1H), 3.04-3.03 (m, 1H), 2.82-2.80 (m, 1H), 2.74-2.73 (m, 1H), 2.72 (s, 6H), 2.45-2.32 (m, 4H), 2.30-1.99 (m, 1H).

Example 1-60

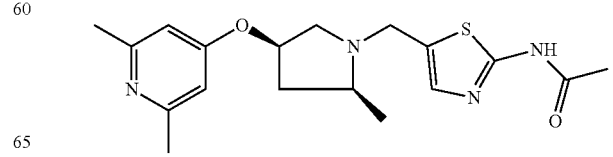

N-(5-(((2S,4R)-4-((2,6-dimethylpyridin-4-yl)oxy)-2-methylpyrrolidin-1-yl)methyl)thiazol-2-yl)acetamide: The title compound was prepared in an analogous manner of that in Scheme 2 from 4-bromo-2,6-dimethylpyridine, tert-butyl (2S,4R)-4-hydroxy-2-methylpyrrolidine-1-carboxylate, and N-(5-(chloromethyl)thiazol-2-yl)acetamide. LCMS (ESI): [M+H] 361. ¹HNMR: (400 MHz, Methanol-d₄) δ 7.29 (s, 1H), 6.58 (s, 2H), 4.70-4.85 (m, 1H), 4.16 (dd, J=1.00, 14.06 Hz, 1H), 3.52-3.64 (m, 1H), 3.04-3.16 (m, 1H), 2.50-2.72 (m, 3H), 2.42 (s, 6H), 2.21 (s, 3H), 1.56-1.71 (m, 1H), 1.26 (d, J=5.77 Hz, 3H).

Example 1-61

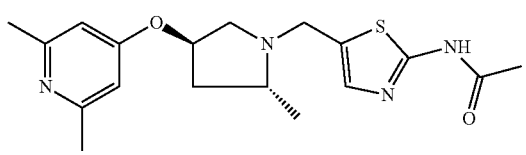 [SMILES: CC(=O)Nc1ncc(CN2C[C@H](Oc3cc(C)nc(C)c3)C[C@H]2C)s1]

N-(5-(((2R,4R)-4-((2,6-dimethylpyridin-4-yl)oxy)-2-methylpyrrolidin-1-yl)methyl)thiazol-2-yl)acetamide: The title compound was prepared in an analogous manner of that in Scheme 2 from 4-chloro-2,6-dimethylpyridine, tert-butyl (2R,4R)-4-hydroxy-2-methylpyrrolidine-1-carboxylate, and N-(5-formylthiazol-2-yl)acetamide. LCMS (ESI): [M+H] 361.0. ¹HNMR: (500 MHz, CDCl₃) δ 11.94 (br s, 1H), 7.20 (s, 1H), 6.42 (s, 2H), 4.77-4.79 (m, 1H), 4.10-4.12 (m, 1H), 3.53-3.60 (m, 2H), 2.46-2.48 (m, 1H), 2.46 (s, 6H), 2.40-2.43 (m, 1H), 2.30 (s, 3H), 2.07-2.10 (m, 1H), 1.86-1.89 (m, 1H), 1.20 (d, J=6.0 Hz, 3H).

Example 1-62

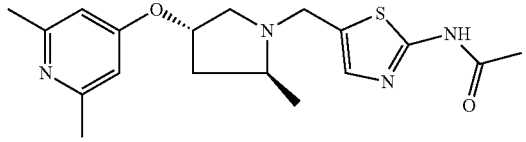 [SMILES: CC(=O)Nc1ncc(CN2C[C@@H](Oc3cc(C)nc(C)c3)C[C@@H]2C)s1]

N-(5-(((2S,4S)-4-((2,6-dimethylpyridin-4-yl)oxy)-2-methylpyrrolidin-1-yl)methyl)thiazol-2-yl)acetamide: The title compound was prepared in an analogous manner of that in Scheme 2 from 2,6-dimethylpyridin-4-ol, tert-butyl (2S,4R)-4-hydroxy-2-methylpyrrolidine-1-carboxylate, and N-(5-formylthiazol-2-yl)acetamide. LCMS (ESI): [M+H] 361.0. ¹HNMR: (500 MHz, Methanol-d₄) δ 7.10 (s, 1H), 6.69 (s, 2H), 4.86 (d, J=3.5 Hz, 1H), 4.01 (d, J=13.5 Hz, 1H), 3.60 (d, J=14.5 Hz, 1H), 3.44 (dd, J=11.5, 6.5 Hz, 1H), 2.78-2.80 (m, 1H), 2.44-2.49 (m, 1H), 2.36 (s, 6H), 2.05 (s, 3H), 1.96-2.00 (m, 1H), 1.77-1.83 (m, 1H), 1.07 (d, J=6.0 Hz, 3H).

Example 1-63

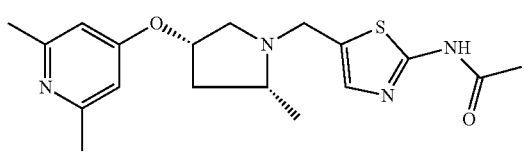 [SMILES: CC(=O)Nc1ncc(CN2C[C@@H](Oc3cc(C)nc(C)c3)C[C@H]2C)s1]

N-(5-(((2R,4S)-4-((2,6-dimethylpyridin-4-yl)oxy)-2-methylpyrrolidin-1-yl)methyl)thiazol-2-yl)acetamide: The title compound was prepared in an analogous manner of that in Scheme 2 from 4-chloro-2,6-dimethylpyridine, tert-butyl (2R,4S)-4-hydroxy-2-methylpyrrolidine-1-carboxylate, and N-(5-formylthiazol-2-yl)acetamide. LCMS (ESI): [M+H] 361.0. ¹HNMR: (500 MHz, Methanol-d₄) δ 7.30 (s, 1H), 6.60 (s, 2H), 4.88-4.94 (m, 1H), 4.15-4.18 (m, 1H), 3.58-3.61 (m, 1H), 3.11-3.13 (m, 1H), 2.61-2.68 (m, 3H), 2.43 (s, 6H), 2.22 (s, 3H), 1.60-1.63 (m, 1H), 1.27 (d, J=5.5 Hz, 3H).

Example 1-64

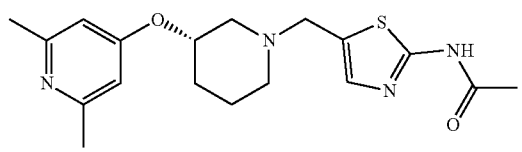 [SMILES: CC(=O)Nc1ncc(CN2CCC[C@H](Oc3cc(C)nc(C)c3)C2)s1]

(S)-N-(5-((3-((2,6-dimethylpyridin-4-yl)oxy)piperidin-1-yl)methyl)thiazol-2-yl)acetamide: The title compound was prepared in an analogous manner of that in Scheme 2 from 4-chloro-2,6-dimethylpyridine, tert-butyl(S)-3-hydroxypiperidine-1-carboxylate, and N-(5-formylthiazol-2-yl)acetamide. LCMS (ESI): [M+H] 361.0. ¹HNMR: (500 MHz, CDCl₃,) δ 11.02 (br s, 1H), 7.18 (s, 1H), 6.50 (s, 2H), 4.44-4.41 (m, 1H), 3.78-3.70 (m, 2H), 3.03 (d, J=9.0 Hz, 1H), 2.78 (d, J=11.5 Hz, 1H), 2.46-2.44 (m, 6H), 2.30-2.28 (m, 3H), 2.18-2.15 (m, 2H), 2.05 (d, J=9.5 Hz, 1H), 1.84-1.82 (m, 1H), 1.68 (m, 1H), 1.46 (m, 1H).

Example 1-65

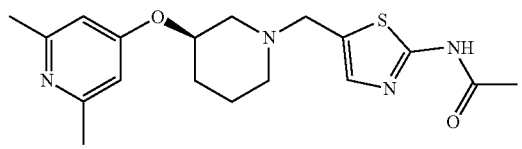 [SMILES: CC(=O)Nc1ncc(CN2CCC[C@@H](Oc3cc(C)nc(C)c3)C2)s1]

(R)-N-(5-((3-((2,6-dimethylpyridin-4-yl)oxy)piperidin-1-yl)methyl)thiazol-2-yl)acetamide: The title compound was prepared in an analogous manner of that in Scheme 2 from 4-chloro-2,6-dimethylpyridine, tert-butyl(R)-3-hydroxypiperidine-1-carboxylate, and N-(5-formylthiazol-2-yl)acetamide. LCMS (ESI): [M+H] 361.0. ¹HNMR: (400 MHz, CDCl₃) δ 11.01 (br s, 1H), 7.18 (s, 1H), 6.54 (s, 2H), 4.44-4.46 (m, 1H), 3.68-3.78 (m, 2H), 2.94-2.96 (m, 1H), 2.74-2.76 (m, 1H), 2.47 (s, 6H), 2.30 (s, 3H), 2.15-2.30 (m, 2H), 2.02-2.14 (m, 2H), 1.51-1.68 (m, 2H).

Example 1-66

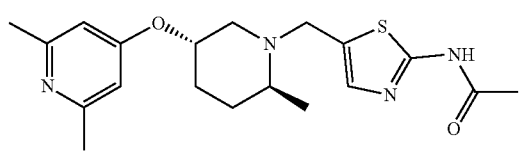 [SMILES: CC(=O)Nc1ncc(CN2C[C@@H](Oc3cc(C)nc(C)c3)CC[C@@H]2C)s1]

N-(5-(((2S,5S)-5-((2,6-dimethylpyridin-4-yl)oxy)-2-methylpiperidin-1-yl)methyl)thiazol-2-yl)acetamide: The title compound was prepared in an analogous manner of that in Scheme 2 from 4-chloro-2,6-dimethylpyridine, tert-butyl (2S,5S)-5-hydroxy-2-methylpiperidine-1-carboxylate, and N-(5-formylthiazol-2-yl)acetamide. LCMS (ESI): [M+H] 375.1. $^1$HNMR: (400 MHz, Methanol-$d_4$) δ 7.23 (s, 1H), 6.55 (s, 2H), 4.38-4.42 (m, 1H), 4.09-4.13 (m, 1H), 3.70-3.74 (m, 1H), 3.13-3.15 (m, 1H), 2.35 (s, 6H), 2.33-2.34 (m, 1H), 2.20 (s, 3H), 2.13-2.14 (m, 1H), 2.01-2.07 (m, 1H), 1.83-1.86 (m, 1H), 1.45-1.53 (m, 2H), 1.24 (d, J=6.4 Hz, 3H).

Example 1-67

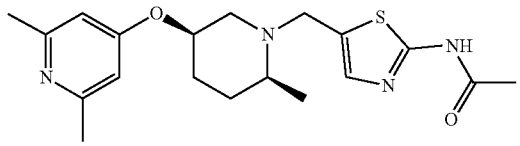 [SMILES: CC(=O)Nc1ncc(CN2C[C@H](Oc3cc(C)nc(C)c3)CC[C@@H]2C)s1]

N-(5-(((2S,5R)-5-((2,6-dimethylpyridin-4-yl)oxy)-2-methylpiperidin-1-yl)methyl)thiazol-2-yl)acetamide: The title compound was prepared in an analogous manner of that in Scheme 2 from 2,6-dimethylpyridin-4-ol, tert-butyl (2S,5S)-5-hydroxy-2-methylpiperidine-1-carboxylate, and N-(5-formylthiazol-2-yl)acetamide. LCMS (ESI): [M+H] 375.1. $^1$HNMR: (400 MHz, Methanol-$d_4$) δ 7.22 (s, 1H), 6.62 (s, 2H), 4.57-4.59 (m, 1H), 3.91-3.95 (m, 1H), 3.79-3.85 (m, 1H), 2.87-2.90 (m, 1H), 2.65-2.67 (m, 1H), 2.53-2.58 (m, 1H), 2.38 (s, 6H), 2.19 (s, 3H), 1.83-1.92 (m, 1H), 1.68-1.80 (m, 3H), 1.20 (d, J=6.0 Hz, 3H).

Example 1-68

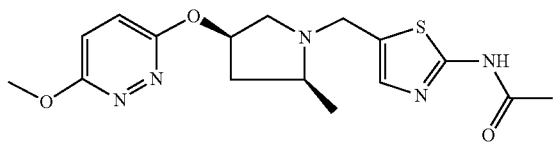 [SMILES: COc1ccc(O[C@@H]2C[C@H](C)N(Cc3cnc(NC(C)=O)s3)C2)nn1]

N-(5-(((2S,4R)-4-((6-methoxypyridazin-3-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 3-chloro-6-methoxypyridazine, and N-(5-formylthiazol-2-yl)acetamide. LCMS (ESI): [M+H] 364. $^1$HNMR: (500 MHz, Methanol-$d_4$) δ 7.11 (s, 2H), 5.33-5.37 (m, 1H), 3.98-4.02 (m, 1H), 3.99 (s, 3H), 3.57-3.60 (m, 1H), 3.20-3.22 (m, 1H), 2.62-2.74 (m, 3H), 2.20 (s, 3H), 1.66-1.68 (m, 1H), 1.27 (d, J=5.5 Hz, 3H).

Example 1-69

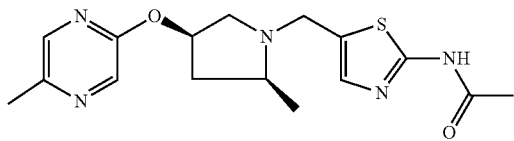 [SMILES: CC(=O)Nc1ncc(CN2C[C@H](Oc3cnc(C)cn3)C[C@@H]2C)s1]

N-(5-(((2S,4R)-2-methyl-4-((5-methylpyrazin-2-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-5-methylpyrazine, and N-(5-formylthiazol-2-yl)acetamide. LCMS (ESI): [M+H] 348.1. $^1$HNMR: (500 MHz, Methanol-$d_4$) δ 8.05 (s, 1H), 7.99 (s, 1H), 7.26 (s, 1H), 5.27-5.30 (m, 1H), 4.13-4.15 (m, 1H), 3.54-3.57 (m, 1H), 3.09-3.12 (m, 1H), 2.57-2.66 (m, 3H), 2.41 (s, 3H), 2.19 (s, 3H), 1.64-1.67 (m, 1H), 1.25 (d, J=6.0 Hz, 3H).

Example 1-70

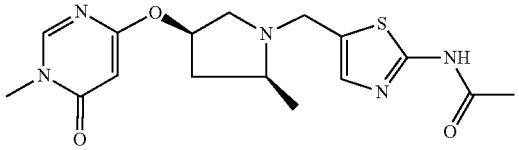 [SMILES: CC(=O)Nc1ncc(CN2C[C@H](Oc3cc(=O)n(C)cn3)C[C@@H]2C)s1]

N-(5-(((2S,4R)-2-methyl-4-((1-methyl-6-oxo-1,6-dihydropyrimidin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 6-chloro-3-methylpyrimidin-4(3H)-one, and N-[5-(chloromethyl)thiazol-2-yl]acetamide. LCMS (ESI): [M+H] 363.1. $^1$HNMR: (500 MHz, DMSO-d6) δ 11.95 (br s, 1H), 8.32 (s, 1H), 7.26 (s, 1H), 5.52 (s, 1H), 4.99 (br d, J=4.3 Hz, 1H), 4.02 (d, J=14.0 Hz, 1H), 2.89 (d, J=11.6 Hz, 1H), 2.37-2.49 (m, 3H), 2.07-2.13 (m, 4H), 1.45 (s, 1H), 1.24 (s, 1H), 1.14 (d, J=6.1 Hz, 4H), 0.01-0.05 (m, 1H).

Example 1-71

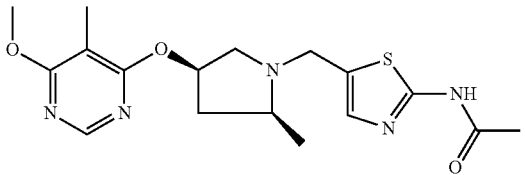 [SMILES: COc1ncnc(O[C@@H]2C[C@H](C)N(Cc3cnc(NC(C)=O)s3)C2)c1C]

N-(5-(((2S,4R)-4-((6-methoxy-5-methylpyrimidin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-6-methoxy-5-methylpyrimidine, and N-[5-(chloromethyl)thiazol-2-yl]acetamide. LCMS (ESI): [M+H] 378.1. $^1$HNMR: (500 MHz, DMSO-d6) δ 12.30 (s, 1H), 7.64 (s, 1H), 5.53 (br s, 1H), 4.77 (br d, J=12.8 Hz, 2H), 4.52 (br dd, J=13.7, 5.2 Hz, 1H), 3.92 (s, 4H), 3.60-3.79 (m, 2H), 2.82 (dt, J=14.2, 7.2 Hz, 1H), 2.16 (s, 4H), 1.96 (s, 3H), 1.85-1.93 (m, 1H), 1.38-1.48 (m, 4H).

Example 1-72

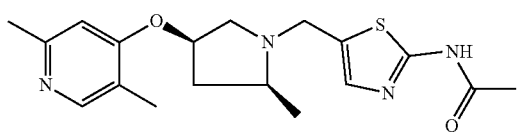 [SMILES: CC(=O)Nc1ncc(CN2C[C@H](Oc3cc(C)ncc3C)C[C@@H]2C)s1]

N-(5-(((2S,4R)-4-((2,5-dimethylpyridin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2,5-dimethylpyridine, and N-(4-fluoro-5-formylthiazol-2-yl)acetamide. LCMS (ESI): [M+H] 361. $^1$HNMR: (400 MHz, Methanol-d$_4$) δ 8.00 (s, 1H), 7.28 (s, 1H), 6.71 (s, 1H), 4.90-4.91 (m, 1H), 4.15 (d, J=14.0 Hz, 1H), 3.61 (d, 0.114.4 Hz, 1H), 3.14 (d, J=10.8 Hz, 1H), 2.62-2.73 (m, 3H), 2.43 (s, 3H), 2.19 (s, 3H), 2.13 (s, 3H), 1.61-1.68 (m, 1H), 1.26 (d, J=5.6 Hz, 3H).

Example 1-73

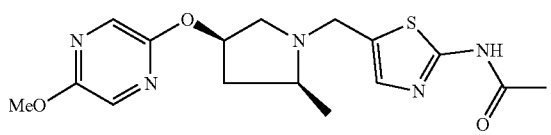 [SMILES: COc1cnc(O[C@@H]2C[C@H](C)N(Cc3cnc(NC(C)=O)s3)C2)cn1]

N-(5-(((2S,4R)-4-((5-methoxypyrazine-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-5-methoxypyrazine, and N-(4-fluoro-5-formylthiazol-2-yl)acetamide. LCMS (ESI): [M+H]364. $^1$HNMR: (400 MHz, DMSO-d6) δ 7.85-7.86 (m, 2H), 7.25 (s, 1H), 5.09-5.14 (m, 1H), 4.01-4.04 (m, 1H), 3.84 (s, 3H), 3.42-3.46 (m, 1H), 2.90-2.93 (m, 1H), 2.39-2.44 (m, 3H), 2.10 (s, 3H), 1.47-1.52 (m, 1H), 1.14 (d, J=6.0 Hz, 3H).

Example 1-74

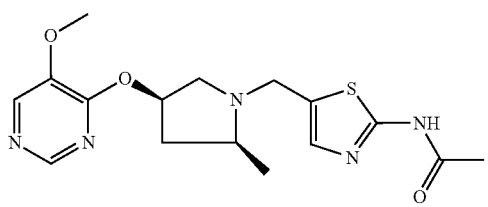 [SMILES: COc1cncnc1O[C@@H]1C[C@H](C)N(Cc2cnc(NC(C)=O)s2)C1]

N-(4-fluoro-5-(((2S,4R)-4-((5-methoxypyrimidin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-5-methoxy-pyrimidine, and N-[5-(chloromethyl)thiazol-2-yl]acetamide. LCMS (ESI): [M+H] 364.1. $^1$HNMR: (500 MHz, DMSO-d6) δ 11.95 (br s, 1H), 8.31 (s, 1H), 8.20 (s, 1H), 7.26 (s, 1H), 5.29-5.36 (m, 1H), 4.03 (d, J=14.0 Hz, 1H), 3.85 (s, 3H), 3.47 (br d, J=14.0 Hz, 1H), 2.95 (d, J=11.6 Hz, 1H), 2.51-2.65 (m, 3H), 2.36-2.48 (m, 1H), 2.07-2.13 (m, 4H), 1.52 (ddd, J=13.3, 9.3, 4.3 Hz, 1H), 1.23 (s, 1H), 1.15 (d, J=6.1 Hz, 4H).

Example 1-75

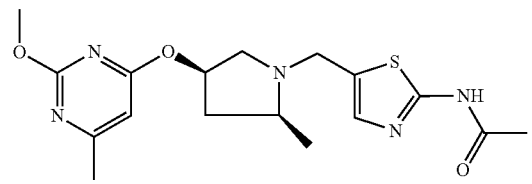 [SMILES: COc1nc(C)cc(O[C@@H]2C[C@H](C)N(Cc3cnc(NC(C)=O)s3)C2)n1]

N-(5-(((2S,4R)-4-((2-methoxy-6-methylpyrimidin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-6-methoxy-2-methylpyrimidine, and N-[5-(chloromethyl)thiazol-2-yl]acetamide. LCMS (ESI): [M+H] 378.1. $^1$HNMR: (500 MHz, DMSO-d6) δ 12.30 (s, 1H), 7.63 (s, 2H), 6.06 (s, 1H), 5.44-5.60 (m, 2H), 4.75 (br d, J=13.4 Hz, 2H), 4.49 (br dd, J=13.1, 4.6 Hz, 2H), 3.45-3.68 (m, 3H), 2.83 (dt, J=14.6, 7.3 Hz, 2H), 2.54-2.62 (m, 2H), 2.44 (s, 5H), 2.16 (s, 3H), 1.75-1.87 (m, 2H), 1.40 (br d, J=6.7 Hz, 3H).

Example 1-76

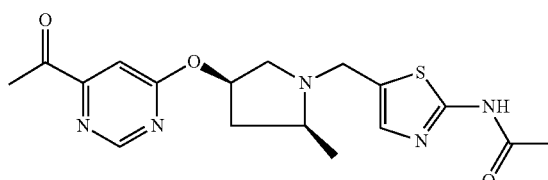

N-(5-(((2S,4R)-((6-acetylpyrimidin-4-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-hydroxy-2-methylpyrrolidine-1-carboxylate, 1-(6-chloropyrimidin-4-yl)ethanone, and N-[5-(chloromethyl)thiazol-2-yl]acetamide. LCMS (ESI): [M+H] 376.1. $^1$HNMR: (500 MHz, DMSO-d6) δ 12.27-12.45 (m, 1H), 9.01 (s, 1H), 7.63 (s, 1H), 7.19-7.29 (m, 1H), 5.26 (s, 1H), 4.67 (br d, J=14.0 Hz, 1H), 4.51 (br s, 1H), 4.35-4.48 (m, 2H), 3.12 (br s, 1H), 2.80-3.00 (m, 2H), 2.60-2.65 (m, 3H), 2.16 (br s, 3H), 1.90 (br s, 2H), 1.36 (br d, J=6.1 Hz, 3H).

Example 1-77

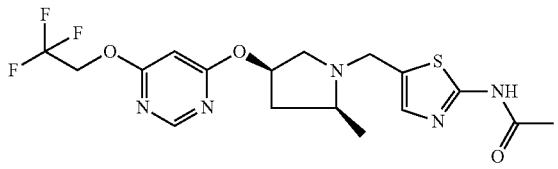 [SMILES: CC(=O)Nc1ncc(CN2C[C@H](Oc3cc(OCC(F)(F)F)ncn3)C[C@@H]2C)s1]

N-(4-fluoro-5-(((2S,4R)-2-methyl-4-((6-(2,2,2-trifluoroethoxy)pyrimidin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate 2,2,2-trifluoroethanol, and N-[5-(chloromethyl)thiazol-2-yl]acetamide. LCMS (ESI): [M+H] 432. $^1$HNMR: (500 MHz, DMSO-d6) δ 12.30 (br s, 1H), 7.63 (br s, 1H), 6.46-6.55 (m, 1H), 5.55 (br s, 1H), 5.02-5.15 (m, 2H), 4.76 (br d, J=12.8 Hz, 1H), 3.49-3.71 (m, 1H), 2.74-2.96 (m, 1H), 2.52-2.71 (m, 3H), 2.16 (s, 3H), 1.78-1.93 (m, 1H), 1.41 (br d, J=6.1 Hz, 4H).

Example 1-78

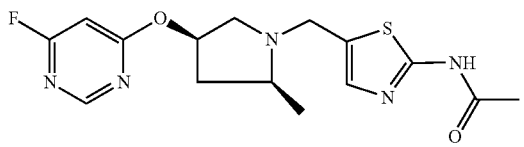 [SMILES: CC(=O)Nc1ncc(CN2C[C@H](Oc3cc(F)ncn3)C[C@@H]2C)s1]

N-(5-(((2S,4R)-4-((6-fluoropyrimidin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4,6-difluoropyrimidine, and N-[5-(chloromethyl)thiazol-2-yl]acetamide. LCMS (ESI): [M+H] 352.1. $^1$HNMR: (500 MHz, DMSO-d6) δ 12.30 (br s, 1H), 8.66 (d, J=1.8 Hz, 1H), 7.63 (s, 1H), 6.80 (s, 1H), 5.52-5.68 (m, 1H), 4.76 (br d, J=14.0 Hz, 1H), 4.42-4.62 (m, 1H), 3.50-3.82 (m, 2H), 2.87 (dt, J=14.6, 7.3 Hz, 1H), 2.16 (s, 3H), 1.77-1.97 (m, 1H), 1.37-1.48 (m, 4H).

Example 1-79

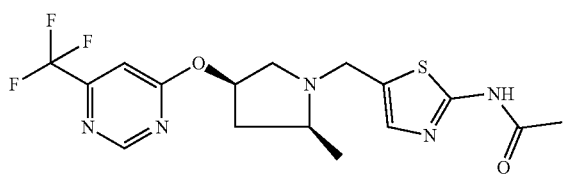 [SMILES: CC(=O)Nc1ncc(CN2C[C@H](Oc3cc(C(F)(F)F)ncn3)C[C@@H]2C)s1]

N-(5-(((2S,4R)-2-methyl-44(6-(trifluoromethyl)pyrimidin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-6-(trifluoromethyl)pyrimidine, and N-[5-(chloromethyl)thiazol-2-yl]acetamide. LCMS (ESI): [M+H] 402.1. $^1$HNMR: (500 MHz, DMSO-d6) δ 12.26-12.37 (m, 1H), 7.55-7.73 (m, 1H), 7.47 (s, 1H), 5.67 (br s, 2H), 4.77 (br d, J=12.8 Hz, 1H), 4.40-4.62 (m, 1H), 2.81-2.95 (m, 2H), 2.13-2.19 (m, 5H), 2.07 (s, 1H), 1.87-2.00 (m, 1H), 1.44 (br d, J=6.1 Hz, 5H).

Example 1-80

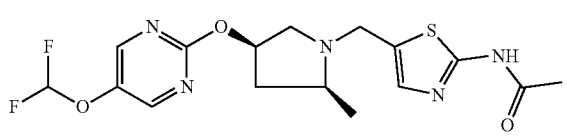 [SMILES: CC(=O)Nc1ncc(CN2C[C@H](Oc3ncc(OC(F)F)cn3)C[C@@H]2C)s1]

N-(5-(((2S,4R)-4-((5-(difluoromethoxy)pyrimidin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-5-(difluoromethoxy)pyrimidine, and N-[5-(chloromethyl)thiazol-2-yl]acetamide. LCMS (ESI): [M+H] 400.1. $^1$HNMR: (500 MHz, DMSO-d6) δ 11.95 (s, 1H), 8.55 (s, 1H), 7.26 (s, 1H), 7.19 (s, 1H), 7.33 (s, 1H), 5.17-5.24 (m, 1H), 4.06 (s, 1H), 4.03 (s, 1H), 3.47 (br d, J=14.0 Hz, 1H), 2.95 (d, J=11.6 Hz, 1H), 2.52-2.62 (m, 3H), 2.42-2.49 (m, 1H), 2.08-2.15 (m, 3H), 1.52 (ddd, J=13.0, 8.7, 4.0 Hz, 1H), 1.17 (d, J=6.1 Hz, 4H).

Example 1-81

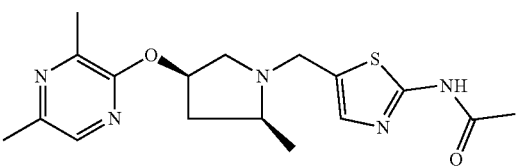 [SMILES: CC(=O)Nc1ncc(CN2C[C@H](Oc3ncc(C)nc3C)C[C@@H]2C)s1]

N-(5-(((2S,4R)-4-((3,5-dimethylpyrazin-2-yl)oxy)-3-methylpyrrolidin-1-yl)methyl)thiazol-2-yl)acetamide: The title compound was prepared in an analogous manner of the in Scheme 2 from tert-butyl (2S,4R)-4-hydroxy-2-methylpyrrolidine-1-carboxylate, 2-chloro-3,5-dimethylpyrizine, and N-(5-(formylthiazol-2-yl)acetamide. LCMS (ESI): [M+H] 362. $^1$HNMR: (400 MHz, Methanol-d$_4$) δ 7.81 (s, 1H), 7.32 (s, 1H), 5.32-5.33 (m, 1H), 4.22-4.23 (m, 1H), 3.69-3.70 (m, 1H), 3.13-3.19 (m, 1H), 2.57-2.65 (m, 3H), 2.41 (s, 3H), 2.37 (s, 3H), 2.19 (s, 3H), 1.72-1.73 (m, 1H), 1.31 (d, J=4.4 Hz, 3H).

Example 1-82

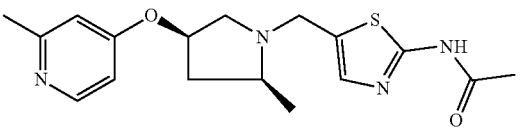 [SMILES: CC(=O)Nc1ncc(CN2C[C@H](Oc3ccnc(C)c3)C[C@@H]2C)s1]

N-(5-(((2S,4R)-2-methyl-4-((2-methylpyridin-4-yl)oxy)pyrrolidin-1-yl)methyl)thiazol-2-yl) acetamide: The title compound was prepared in an analogous manner of that in Scheme 2 from tert-butyl (2S,4R)-4-hydroxy-2-methylpyrrolidine-1-carboxylate, 4-chloro-2-methylpyridine, and N-(5-(chloromethyl)thiazol-2-yl)acetamide. LCMS (ESI): [M+H] 347. $^1$HNMR: (400 MHz, Methanol-d4) δ 8.18 (d, J=5.77 Hz, 1H), 7.29 (s, 1H), 6.67-6.82 (m, 2H), 4.78-4.92 (m, 1H), 4.16 (d, J=15.06 Hz, 1H), 3.52-3.66 (m, 1H), 3.13 (d, J=11.29 Hz, 1H), 2.53-273 (m, 3H), 2.46 (s,3H), 2.21 (s, 3H), 1.57-1.71 (m, 1H), 1.26 (d, J=6.02 Hz, 3H).

Example 1-83

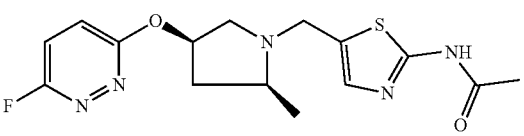 [SMILES: CC(=O)Nc1ncc(CN2C[C@H](Oc3ccc(F)nn3)C[C@@H]2C)s1]

N-(5-(((2S,4R)-4-((6-fluoropyridazin-3-yl)oxy-2-methylpyrrolidin-1-yl)methyl)thiazol 2-yl)acetamide: The title compound was prepared in an analogous manner of that in Scheme 2 from 3,6-difluoropyridazine, tert-butyl (2S,4R)-4-hydroxy-2-methylpyrrolidine-1-carboxylate, and N-(5-formylthiazol-2-yl)acetamide. LCMS (ESI): [M+H] 352.0. $^1$HNMR: (400 MHz, Methanol-d$_4$) δ 7.40 (d, J=9.2 Hz, 1H), 7.29-7.33 (m, 1H), 7.27 (s, 1H), 5.39-5.43 (m, 1H), 4.13-4.17 (m, 1H), 3.53-3.57 (m, 1H), 3.16-3.18 (m, 1H), 2.57-2.68 (m, 3H), 2.19 (s, 3H), 1.67-1.71 (m, 1H), 1.26 (d, J=6.0 Hz, 3H).

Example 1-84

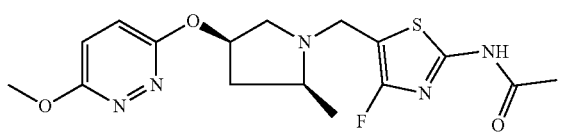 [SMILES: COc1ccc(O[C@@H]2C[C@H](C)N(Cc3sc(NC(C)=O)nc3F)C2)nn1]

N-(4-fluoro-5-(((2S,4R)-4-((6-methoxypyridazin-3-yl)oxy)-2-methylpyrrolidin-1-yl)methy)thiazol-2-yl)acetamide: The title compound was prepared in an analogous manner of that in Scheme 2 from tert-butyl (2S,4R)-4-hydroxy-2-methylpyrrolidine-1-carboxylate, 3-chloro-6-methoxypyridazine, and N-(4-fluoro-5-formylthiazol-2-yl)acetamide. LCMS (ESI): [M+H] 382.1. $^1$HNMR: (500 MHz, Methanol-d$_4$) δ 7.11 (s, 2H), 5.33-5.37 (m, 1H), 3.98-4.02 (m, 1H), 3.99 (s, 3H), 3.57-3.60 (m, 1H), 3.20-3.22 (m, 1H), 2.62-2.74 (m, 3H), 2.20 (s, 3H), 1.66-1.68 (m, 1H), 1.27 (d, J=5.5 Hz, 3H).

Example 1-45

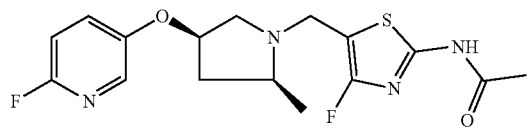 [SMILES: CC(=O)Nc1nc(F)c(CN2C[C@H](Oc3ccc(F)nc3)C[C@@H]2C)s1]

N-(4-fluoro-5-(((2S,4R)-4-((6-fluoropyridin-3-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 6-fluoropyridin-3-ol, and N-(4-fluoro-5-formylthiazol-2-yl)acetamide. LCMS (ESI): [M+H] 369. $^1$HNMR: (500 MHz, Methanol-d$_4$) δ 7.75 (s, 1H), 7.46-7.50 (m, 1H), 6.98 (dd, J=8.8, 3.2 Hz, 1H), 4.78-4.80 (m, 1H), 3.96-4.00 (m, 1H), 3.57-3.60 (m, 1H), 3.15-3.18 (m, 1H), 2.58-2.68 (m, 3H), 2.18 (s, 3H), 1.56-1.63 (m, 1H), 1.25 (d, J=5.6 Hz, 3H).

Example 1-86

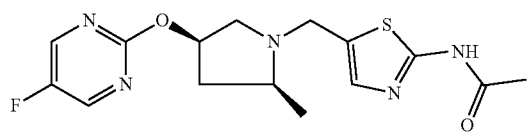 [SMILES: CC(=O)Nc1ncc(CN2C[C@H](Oc3ncc(F)cn3)C[C@@H]2C)s1]

N-(5-(((2S,4R)-4-((5-fluoropyrimidin-2-yl)oxy)-2-methylpyrrolidin-1-yl)methyl)thiazol-2-yl)acetamide: The title compound was prepared in an analogous manner of that in Scheme 2 from 2-chloro-5-fluoropyrimidine, tert-butyl (2S,4R)-4-hydroxy-2-methylpyrrolidine-1-carboxylate, and N-(5-formylthiazol-2-yl)acetamide. LCMS (ESI): [M+H] 352.0. $^1$HNMR: (500 MHz, CDCl$_3$) δ 12.14 (br s, 1H), 8.26 (s, 2H), 7.14 (s, 1H), 5.05-5.19 (m, 1H), 4.02 (d, J=14.50 Hz, 1H), 3.52 (d, J=14.50 Hz, 1H), 3.10 (d, J=11.14 Hz, 1H), 2.62 (dd, J=11.22, 6.48 Hz, 1H), 2.40-2.55 (m, 2H), 2.19-2.28 (m, 3H), 1.70 (ddd, J=13.01, 8.66, 4.27 Hz, 1H), 1.10-1.26 (m, 5H), 0.81 (t, J=6.94 Hz, 1H).

Example 1-87

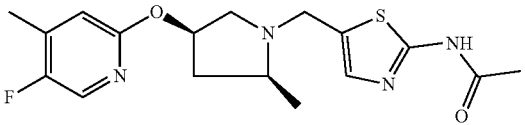 [SMILES: CC(=O)Nc1ncc(CN2C[C@H](Oc3cc(C)c(F)cn3)C[C@@H]2C)s1]

N-(5-(((2S,4R)-4-((5-fluoro-4-methylpyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-bromo-5-fluoro-4-methylpyridine, and N-(5-formylthiazol-2-yl)acetamide. LCMS (ESI): [M+H] 365. $^1$HNMR: (500 MHz, CDCl$_3$) δ 11.46 (brs, 1H), 7.79 (s, 1H), 7.20 (s, 1H), 6.56 (d, J=5.0 Hz, 1H), 5.20-5.23 (m, 1H), 4.10-4.13 (m, 1H), 3.56-3.59 (m, 1H), 3.09-3.12 (m, 1H), 2.56-2.61 (m, 1H), 2.48-2.52 (m, 2H), 2.29 (s, 3H), 2.22 (s, 3H), 1.62-1.66 (m, 1H), 1.24 (d, J=5.5 Hz, 3H).

Example 1-88

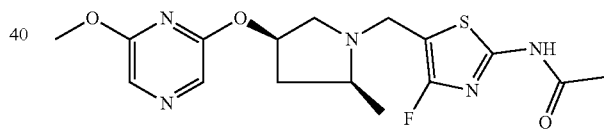

N-(4-fluoro-5-(((2S,4R)-4-((6-methoxypyrazin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-6-methoxypyrazine, and N-(4-fluoro-5-formylthiazol-2-yl)acetamide. LCMS (ESI): [M+H] 382.1. $^1$HNMR: (500 MHz, Methanol-d$_4$) δ 7.70 (s, 2H), 5.29-5.31 (m, 1H), 3.97-4.00 (m, 1H), 3.94 (s, 3H), 3.56-3.60 (m, 1H), 3.18-3.20 (m, 1H), 2.73-2.77 (m, 1H), 2.60-2.65 (m, 2H), 2.18 (s, 3H), 1.64-1.69 (m, 1H), 1.25 (d, J=5.2 Hz, 3H).

Example 1-89

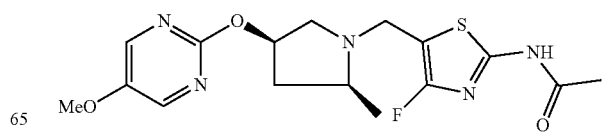

N-(4-fluoro-5-(((2S,4R)-4-((5-methoxypyrimidin-2-yl) oxy)-2-methylpyrrolidin-1-yl)methyl)thiazol-2-yl)acetamide: The title compound was prepared in an analogous manner of that Scheme 2 from tert-butyl (2S,4R)-4-hydroxy-2-methylpyrrolidine-1-carboxylate, 2-chloro-5-methoxypyrimidine, and N-(4-fluoro-5-formylthiazol-2-yl) acetamide. LCMS (ESI): [M+H] 382. $^1$HNMR: (400 MHz, Methanol-$d_4$) δ 8.26 (s, 2H), 5.29-5.30 (m, 1H), 4.07-4.11 (m, 1H), 3.87 (s, 3H), 3.70-3.73 (m, 1H), 3.24-3.25 (m, 1H), 2.64-2.89 (m, 3H), 2.18 (s, 3H), 1.73-1.75 (m, 1H), 1.30 (d, J=5.6 Hz, 3H).

Example 1-90

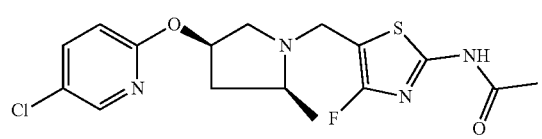 [SMILES: CC(=O)Nc1nc(F)c(CN2C[C@H](Oc3ccc(Cl)cn3)C[C@@H]2C)s1]

N-(5-(((2S,4R) 4-((5-chloropyridin-2-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-hydroxy-2-methylpyrrolidine-1-carboxylate, 5-chloro-2-fluoropyridine, and N-(4-fluoro-5-formylthiazol-2-yl)acetamide. LCMS (ESI): [M+H] 385. $^1$HNMR: (400 MHz, CDCl$_3$) δ 10.57 (br.s, 1H), 8.03 (d, J=2.4 Hz, 1H), 7.48 (dd, J=8.8, 2.4 Hz, 1H), 6.70 (d, J=8.8 Hz, 1H), 5.25-5.27 (m, 1H), 3.97 (d, J=14.4 Hz, 1H), 3.64 (d, J=14.8 Hz, 1H), 3.14-3.17 (m, 1H), 2.62-2.67 (m, 1H), 2.49-2.55 (m, 2H), 2.29 (s, 3H), 1.63-1.67 (m, 1H), 1.24 (d, J=5.2 Hz, 3H).

Example 1-91

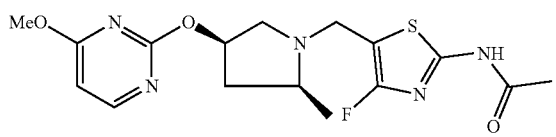 [SMILES: COc1ccnc(O[C@@H]2C[C@H](C)N(Cc3sc(NC(C)=O)nc3F)C2)n1]

N-(4-fluoro-5-(((2S,4R)-4-((4-methoxypyrimidin-2-yl) oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-4-methoxypyrimidine, and N-(4-fluoro-5-formylthiazol-2-yl) acetamide. LCMS (ESI): [M+H] 382. $^1$HNMR: (400 MHz, CDCl$_3$) δ 10.57 (br s, 1H), 8.13 (d, J=5.5 Hz, 1H), 6.33 (d, J=5.5 Hz, 1H), 5.22-5.28 (m, 1H), 3.95-3.96 (m, 1H), 3.94 (s, 3H), 3.62 (d, J=14.5 Hz, 1H), 3.22 (d, J=11.0 Hz, 1H), 2.68-2.73 (m, 1H), 2.47-2.58 (m, 2H), 2.29 (s, 3H), 1.73-1.79 (m, 1H), 1.23 (d, J=5.5 Hz, 3H).

Example 1-92

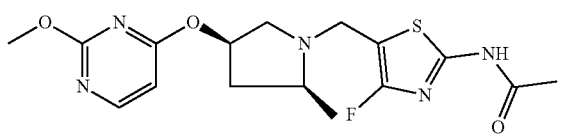

N-(4-fluoro-5-(((2S,4R)-4-((2-methoxypyrimidin-4-yl) oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-methoxypyrimidine, and N-(4-fluoro-5-formylthiazol-2-yl) acetamide. LCMS (ESI): [M+H] 382.0. $^1$HNMR: (400 MHz, Methanol-$d_4$) δ 8.18 (d, J=6.0 Hz 1H), 6.45 (d, J=6.0 Hz, 1H), 5.36-5.40 (m, 1H), 3.97-3.98 (m, 1H), 3.93 (s, 3H), 3.55-3.58 (m, 1H), 3.15-3.18 (m, 1H), 2.59-2.74 (m, 3H), 2.18 (s, 3H), 1.61-1.67 (m, 1H), 1.23 (d, J=5.6 Hz, 3H).

Example 1-93

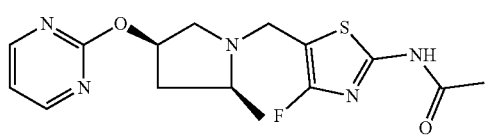 [SMILES: CC(=O)Nc1nc(F)c(CN2C[C@H](Oc3ncccn3)C[C@@H]2C)s1]

N-(4-fluoro-5-(((2S,4R)-2-methyl-4-(pyrimidin-2-yloxy) pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloropyrimidine, and N-(4-fluoro-5-formylthiazol-2-yl)acetamide. LCMS (ESI): [M+H] 352.0. $^1$HNMR: (500 MHz, Methanol-$d_4$) δ 8.53 (d, J=5.0 Hz, 2H), 7.06 (t, J=5.0 Hz, 1H), 5.30-5.34 (m, 1H), 3.93-3.97 (m, 1H), 3.53-3.57 (m, 1H), 3.15-3.18 (m, 1H), 2.58-2.73 (m, 3H), 2.17 (s, 3H), 1.65-1.70 (m, 1H), 1.25 (d, J=6.0 Hz, 3H).

Example 1-94

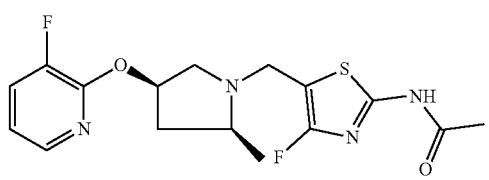 [SMILES: CC(=O)Nc1nc(F)c(CN2C[C@H](Oc3ncccc3F)C[C@@H]2C)s1]

N-(4-fluoro-5-(((2S,4R)-4-((3-fluoropyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2,3-difluoropyridine, and N-(4-fluoro-5-formylthiazol-2-yl)acetamide. LCMS (ESI): [M+H] 369.0. $^1$HNMR: (500 MHz, Methanol-$d_4$) δ 7.87 (d, J=5.0 Hz, 1H), 7.40-7.44 (m, 1H), 6.88-6.92 (m, 1H), 5.34-5.37 (m, 1H), 3.93-3.97 (m, 1H), 3.56-3.59 (m, 1H), 3.15-3.17 (m, 1H), 2.70-2.74 (m, 1H), 2.55-2.61 (m, 2H), 2.18 (s, 3H), 1.66-1.70 (m, 1H), 1.25 (d, J=5.5 Hz, 3H).

Example 1-95

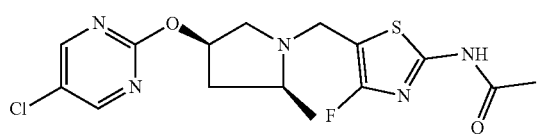 [SMILES: CC(=O)Nc1nc(F)c(CN2C[C@H](Oc3ncc(Cl)cn3)C[C@@H]2C)s1]

N-(5-(((2S,4R)-4-((5-chloropyrimidin-2-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-hydroxy-2-methylpyrrolidine-1-carboxylate, 2,5-dichloropyrimidine, and N-(4-fluoro-5-formylthiazol-2-yl)acetamide. LCMS (ESI): [M+H]385.9. $^1$HNMR: (500 MHz, CDCl$_3$) δ 10.82 (br s, 1H), 8.41 (s, 2H), 5.21-5.22 (m, 1H), 3.93 (d, J=14.5 Hz, 1H), 3.62 (d, 0.1=14.5 Hz, 1H), 3.18-3.20 (m, 1H), 2.69-2.72 (m, 1H), 2.50-2.54 (m, 2H), 2.29 (s, 3H), 1.73-1.74 (m, 1H), 1.24 (d, J=6.0 Hz, 3H).

Example 1-96

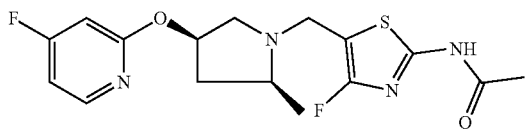 [SMILES: CC(=O)Nc1nc(F)c(CN2C[C@H](Oc3cc(F)ccn3)C[C@@H]2C)s1]

N-(4-fluoro-5-(((2S,4R)-4-((4-fluoropyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2,4-difluoropyridine, and N-(4-fluoro-5-formylthiazol-2-yl)acetamide. LCMS (ESI): [M+H] 368.9. $^1$HNMR: (500 MHz, Methanol-d$_4$) δ 8.07-8.10 (m, 1H), 6.73-6.76 (m, 1H), 6.50-6.53 (m, 1H), 5.29-5.32 (m, 1H), 3.95-3.98 (m, 1H), 3.55-3.58 (m, 1H), 3.12-3.14 (m, 1H), 2.56-2.69 (m, 3H), 2.18 (s, 3H), 1.58-1.64 (m, 1H), 1.23 (d, J=5.5 Hz, 3H).

Example 1-97

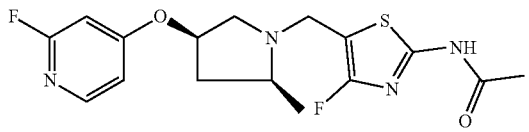 [SMILES: CC(=O)Nc1nc(F)c(CN2C[C@H](Oc3ccnc(F)c3)C[C@@H]2C)s1]

N-(4-fluoro-5-(((2S,4R)-4-((2-fluoropyridin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2,4-difluoropyridine, and N-(4-fluoro-5-formylthiazol-2-yl)acetamide. LCMS (ESI): [M+H] 368.9. $^1$HNMR: (500 MHz, Methanol-d$_4$) δ 7.96 (d, J=4.5 Hz, 1H), 6.82 (d, J=6.0 Hz, 1H), 6.55 (d, J=1.5 Hz, 1H), 4.89-4.92 (m, 1H), 3.96-4.00 (m, 1H), 3.57-3.60 (m, 1H), 3.16-3.18 (m, 1H), 2.61-2.71 (m, 3H), 2.18 (s, 3H), 1.58-1.62 (m, 1H), 1.28 (d, J=5.5 Hz, 3H).

Example 1-98

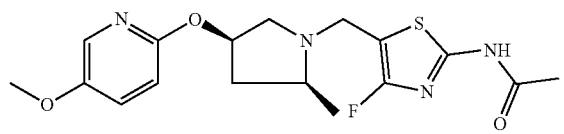 [SMILES: COc1ccc(O[C@@H]2C[C@H](C)N(Cc3sc(NC(C)=O)nc3F)C2)nc1]

N-(4-fluoro-5-(((2S,4R)-4-((5-methoxypyridin-2-yl)oxy)$_2$-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-fluoro-5-methoxypyridine, and N-(5-(chloromethyl)-4-fluorothiazol-2-yl)acetamide. LCMS (ESI): [M+H] 381.1. $^1$HNMR: (500 MHz, Methanol-d$_4$) δ 7.74 (d, J=3.0 Hz, 1H), 7.31 (dd, J=3.0 Hz, 9.0 Hz, 1H), 6.70-6.76 (m, 1H), 5.18-5.19 (m, 1H), 3.96 (d, J=15.0 Hz, 1H), 3.79 (s, 3H), 3.56 (d, J=14.5 Hz, 1H), 3.11 (d, J=11.0 Hz, 1H), 2.65-2.68 (m, 1H), 2.54-2.57 (m, 2H), 2.18 (s, 3H), 1.58-1.63 (m, 1H), 1.24 (d, J=5.5 Hz, 3H).

Example 1-99

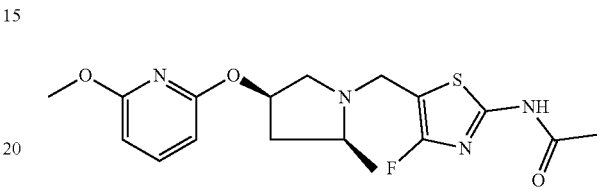

N-(4-fluoro-5-(((2S,4R)-4-((6-methoxypyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-6-methoxypyridine, and N-(4-fluoro-5-formylthiazol-2-yl)acetamide. LCMS (ESI): [M+H] 381.0. $^1$HNMR: (500 MHz, Methanol-d$_4$) δ 7.53 (t, J=8.0 Hz, 1H), 6.30 (d, J=7.5 Hz, 2H), 5.27-5.30 (m, 1H), 3.98-4.01 (m, 1H), 3.87 (s, 3H), 3.58-3.61 (m, 1H), 3.17-3.20 (m, 1H), 2.75-2.78 (m, 1H), 2.57-2.62 (m, 2H), 2.20 (s, 3H), 1.64-1.69 (m, 1H), 1.26 (d, J=5.5 Hz, 3H).

Example 1-100

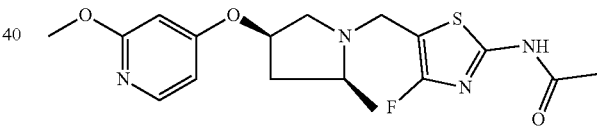

N-(4-fluoro-5-(((2S,4R)-4-((2-methoxypyridin-4-yl)oxy)-2-methylpyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-methoxypyridine, and N-(4-fluoro-5-formylthiazol-2-yl)acetamide. LCMS (ESI): [M+H] 381.0. $^1$HNMR: (500 MHz, Methanol-d$_4$) δ 7.88 (d, J=6.0 Hz, 1H), 6.50 (d, J=4.5 Hz, 1H), 6.20 (s, 1H), 4.81-4.82 (m, 1H), 3.95-3.98 (m, 1H), 3.85 (s, 3H), 3.55-3.58 (m, 1H), 3.13-3.15 (m, 1H), 2.57-2.67 (m, 3H), 2.18 (s, 3H), 1.56-1.61 (m, 1H), 1.23 (d, J=5.5 Hz, 3H).

Example 1-10

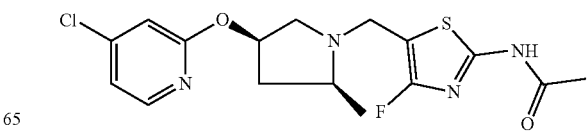

N-(5-(((2S,4R)-4-((4-chloropyridin-2-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-fluoropyridine, and N-(4-fluoro-5-formylthiazol-2-yl)acetamide. LCMS (ESI): [M+H] 384.9. $^{1}$HNMR: (500 MHz, CDCl$_3$) δ 11.18 (br s, 1H), 7.99 (d, J=5.5 Hz, 1H), 6.83 (dd, J=5.5, 2.0 Hz, 1H), 6.76 (d, J=1=1.5 Hz, 1H), 5.30-5.31 (m, 1H), 3.97 (d, 0.1=15.0 Hz, 1H), 3.63 (d, J=14.5 Hz, 1H), 3.14-16 (m, 1H), 2.64-2.67 (m, 1H), 2.49-2.53 (m, 2H), 2.30 (s, 3H), 1.62-1.66 (m, 1H), 1.24 (d, J=5.5 Hz, 3H).

Intermediate 8

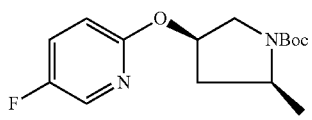

tert-butyl (2S,4R)-4-((5-fluoropyridin-2-yl)oxy)-2-methylpyrrolidine-1-carboxylate: To a mixture of tert-butyl (2S,4R)-4-hydroxy-2-methyl-pyrrolidine-1-carboxylate (262.33 mg, 1.30 mmol) in THF (3.00 mL) was added in NaH (104 mg, 2.61 mmol, 60% purity). After 30 min at room temperature, 2,5-difluoropyridine (150 mg, 1.30 mmol, 118 ulu) was added in the mixture. The resulting mixture was stirred 90° C. for 2 hours. The reaction was concentrated under reduced pressure and the residue was purified by column chromatography (petroleum ether/EtOAc=5/1) on silica gel to provide the title compound (286 mg, 0.965 mmol, 74% yield).

Intermediate 9

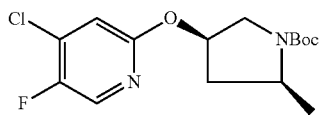 [SMILES: C[C@H]1C[C@@H](Oc2cc(Cl)c(F)cn2)CN1C(=O)OC(C)(C)C]

tert-butyl (2S,4R)-4-((4-chloro-5-fluoropyridin-2-yl)oxy)-2-methylpyrrolidine-1-carboxylate: n-BuLi (2.5 M, 1.94 mL) was added dropwise to a mixture of tert-butyl (2S,4R)-4-[(5-fluoro-2-pyridyl)oxy]-2-methyl-pyrrolidine-1-carboxylate (720 mg, 2.43 mmol) in THF (20.0 mL) at −78° C. under N$_2$. After 0.5 hour, hexachloroethane (1.73 g, 7.29 mmol, 826 uL) was added and the mixture was stirred for another hour. To the mixture was added NH$_4$Cl (saturated aqueous, 15 mL), extracted with EtOAc (3×15 mL), and the combined organics were dried over Na$_2$SO$_4$, filtered and concentrated in vacuo. The residue was purified by column chromatography (petroleum ether/EtOAc=10/1) on silica gel to provide the title compound (430 mg). LCMS (ESI): [M-tBu+H] 275.

Intermediate 10

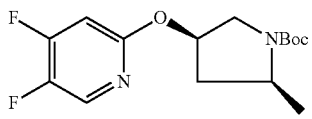 [SMILES: C[C@H]1C[C@@H](Oc2cc(F)c(F)cn2)CN1C(=O)OC(C)(C)C]

tert-butyl (2S,4R)-4-((4,5-difluoropyridin-2-yl)oxy)-2-methylpyrrolidine-1-carboxylate: A mixture of tert-butyl (2S,4R)$^{4}$-[(4-chloro-5-fluoro-2-pyridyl)oxy]-2-methyl-pyrrolidine-1-carboxylate (200 mg, 0.604 mmol) and cesium fluoride (459 mg, 3.02 mmol) in DMSO (3.00 mL) was stirred at 160° C. under N$_2$ in microwave for 2 hours. Water (10 mL) was added and the mixture was extracted with EtOAc (3×10 mL), the combined organic layers were dried over anhydrous Na$_2$SO$_4$, filtered and concentrated. The residue was purified by Prep-HPLC (Column: Welch Xtimate C18 150*25 mm*5 um; Condition: water(10 mM NH$_4$HCO$_3$)-ACN; Begin B: 48; End B: 78; Gradient Time (min): 10; 100% B Hold Time(min): to provide the title compound (101 mg, 0.321 mmol, 53% yield). LCMS (ESI): [M-tBu+H] 259.

Example 1-102

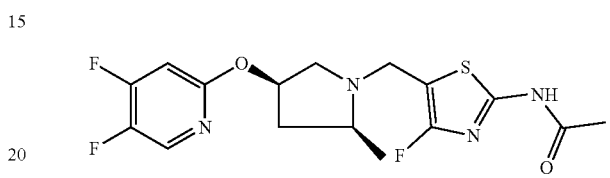

N-(5-(((2S,4R)-4-((4,5-difluoropyridin-2-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-((4,5-difluoropyridin-2-yl)oxy)-2-methylpyrrolidine-1-carboxylate and N-(4-fluoro-5-formylthiazol-2-yl)acetamide. LCMS (ESI): [M+H] 387.0. $^{1}$HNMR: (500 MHz, CDCl$_3$) δ 11.5 (br s, 1H), 7.9 (d, 1H), 6.5 (d, 1H), 5.25 (m, 1H), 3.9 (d, J=14 Hz, 1H), 3.54 (d, J=14 Hz, 1H), 3.10 (d, J=11.14 Hz, 1H), 2.6 (dd, J=11, 6.5 Hz, 1H), 2.40 (m, 2H), 2.19 (s, 3H), 1.10-1.26 (d, 3H).

Intermediate 11

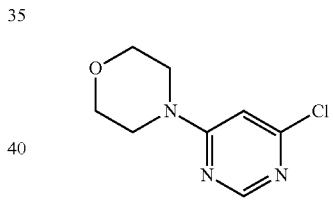

4-(6-chloropyrimidin-4-yl)morpholine: To a solution of 4,6-dichloropyrimidine (500 mg, 3.53 mmol) in EtOH (15.0 mL) was added morpholine (585 mg, 6.71 mmol) and triethylamine (747.2 mg, 7.38 mmol). The mixture was stirred at 20° C. for 3 hours. The reaction mixture was filtered and the residue was washed by EtOH (30 mL) to provide the title compound (826 mg, 62% yield). $^{1}$HNMR: (500 MHz, CDCl$_3$) δ: 8.38 (s, 1H), 6.48 (s, 1H), 3.76-3.80 (m, 4H), 3.62-3.63 (m, 4H).

Example 1-103

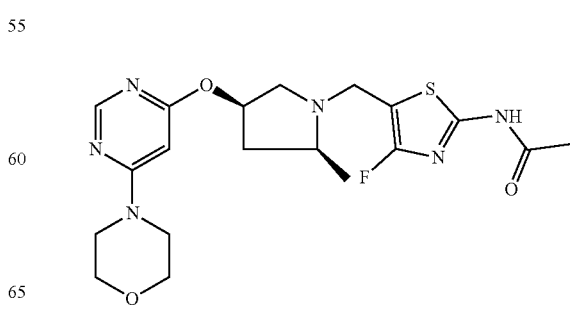

N-(4-fluoro-5-(((2S,4R)-2-methyl-4-((6-morpholinopyrimidin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-(6-chloropyrimidin-4-yl)morpholine, and N-(4-fluoro-5-formylthiazol-2-yl)acetamide. LCMS (ESI): [M+H] 437.1. ¹HNMR: (400 MHz, CDCl₃) δ 10.28 (br., s., 1H), 8.26 (s, 1H), 5.85 (s, 1H), 5.27-5.35 (m, 1H), 3.75-3.97 (m, 1H), 3.64-3.74 (m, 5H), 3.52-3.59 (m, 5H), 3.12-3.16 (m, 1H), 2.51-2.61 (m, 3H), 2.29 (s, 3H), 1.24-1.25 (m, 3H).

Example 1-104

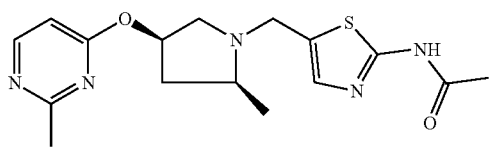 [SMILES: CC(=O)Nc1ncc(CN2C[C@H](Oc3ccnc(C)n3)C[C@@H]2C)s1]

N-(5-(((2S,4R)-2-methyl-4-((2-methylpyrimidin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-methyl-pyrimidine, and N-[5-(chloromethyl)thiazol-2-yl]acetamide. LCMS (ESI): [M+H] 348.1. ¹HNMR: (500 MHz, DMSO-d6) δ 12.30 (s, 1H), 8.45 (d, J=5.5 Hz, 1H), 7.59-7.69 (m, 1H), 5.57 (br s, 1H), 4.75 (br s, 2H), 4.46-4.62 (m, 2H), 2.85 (br d, J=7.3 Hz, 1H), 2.59-2.73 (m, 2H), 2.52-2.55 (m, 5H), 2.12-2.19 (m, 4H), 2.07 (s, 1H), 1.84 (br s, 1H), 1.41 (br d, 1=6.7 Hz, 4H).

Example 1-105

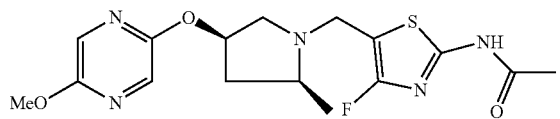 [SMILES: COc1cnc(O[C@@H]2C[C@H](C)N(Cc3sc(NC(C)=O)nc3F)C2)cn1]

N-(4-fluoro-5-(((2S,4R)-4-((5-methoxypyrazin-2-yl)oxy)-2-methylpyrrolidin-1-yl)methyl)thiazol-2-yl)acetamide:
The title compound was prepared in an analogous manner of that in Scheme 2 from tert-butyl (2S,4R)-4-hydroxy-2-methylpyrrolidine-1-carboxylate, 2-chloro-5-methoxypyrazine, and N-(4-fluoro-5-formylthiazol-2-yl)acetamide. LCMS (ESI): [M+H] 382. ¹HNMR: (400 MHz, DMSO-d6) δ 7.85 (s, 2H), 5.10-5.14 (m, 1H), 3.86-3.89 (m, 1H), 3.81 (s, 3H), 3.42-3.46 (m, 1H), 2.94-2.97 (m, 1H), 2.53-2.54 (m, 2H), 2.41-2.46 (m, 1H), 2.10 (s, 3H), 1.44-1.49 (m, 1H), 1.12 (d, J=6.0 Hz, 3H).

Example 1-106

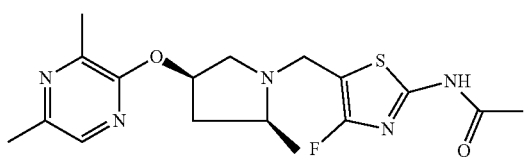 [SMILES: CC(=O)Nc1nc(F)c(CN2C[C@H](Oc3ncc(C)nc3C)C[C@@H]2C)s1]

N-(5-(((2S,4R)-4-((3,5-dimethylpyrazin-2-yl)oxy)-2-methylpyrrolidin-1-yl)methyl)-4-fluorothiazol-2-yl)acetamide:
The title compound was prepared in an analogous manner of that in Scheme 2 from tert-butyl (2S,4R)-4-hydroxy-2-methylpyrrolidine-1-carboxylate, 2-chloro-3,5-dimethylpyrazine, and N-(4-fluoro-5-formylthiazol-2-yl)acetamide. LCMS (ESI): [M+H] 380. ¹HNMR: (400 MHz, Methanol-d₄) δ 7.82 (s, 1H), 5.29-5.30 (m, 1H), 3.39-3.40 (m, 1H), 3.63-3.64 (m, 1H), 3.16-3.17 (m, 1H), 2.60-2.76 (m, 3H), 2.42 (s, 3H), 2.38 (s, 3H), 2.18 (s, 3H), 1.67-1.68 (m, 1H), 1.28 (d, J=5.0 Hz, 3H).

Example 1-107

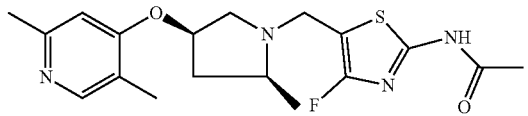 [SMILES: CC(=O)Nc1nc(F)c(CN2C[C@H](Oc3cc(C)ncc3C)C[C@@H]2C)s1]

N-(5-(((2S,4R)-4-((2,5-dimethylpyridin-4-yl)oxy)-2-methylpyrrolidin-1-yl)methyl)-4-fluorothiazol-2-yl)acetamide:
The title compound was prepared in an analogous manner of that in Scheme 2 from tert-butyl (2S,4R)-4-hydroxy-2-methylpyrrolidine-1-carboxylate, 4-chloro-2,5-dimethylpyridine, and N-(4-fluoro-5-formylthiazol-2-yl)acetamide. LCMS (ESI): [M+H] 379. ¹HNMR: (400 MHz, Methanol-d₄) δ 7.99 (s, 1H), 6.69 (s, 1H), 4.86-4.89 (m, 1H), 3.97 (d, J=14.5 Hz, 1H), 3.60 (d, J=15.0 Hz, 1H), 3.16 (d, J=11.0 Hz, 1H), 2.73 (dd, J=11.0, 5.5 Hz, 1H), 2.61-2.64 (m, 2H), 2.43 (s, 3H), 2.18 (s, 3H), 2.12 (s, 3H), 1.60-1.63 (m, 1H), 1.24 (d, J=5.5 Hz, 3H).

Example 1-108

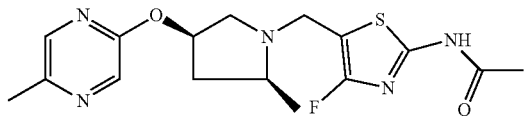 [SMILES: CC(=O)Nc1nc(F)c(CN2C[C@H](Oc3cnc(C)cn3)C[C@@H]2C)s1]

N-(4-fluoro-5-(((2S,4R)-2-methyl-4-((5-methylpyrazin-2-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 2-chloro-5-methylpyrazine, and N-(4-fluoro-5-formylthiazol-2-yl)acetamide. LCMS (ESI): [M+H] 366. ¹HNMR: (400 MHz, Methanol-d₄) δ 8.05 (s, 1H), 8.00 (s, 1H), 5.27-5.29 (m, 1H), 3.96-3.98 (m, 1H), 3.55-3.58 (m, 1H), 3.12-3.15 (m, 1H), 2.57-2.69 (m, 3H), 2.42 (s, 3H), 2.18 (s, 3H), 1.60-1.66 (m, 1H), 1.24 (d, J=6.0 Hz, 3H).

Example 1-109

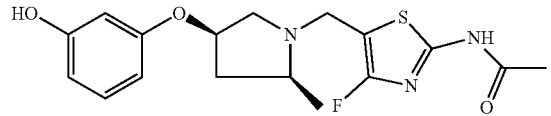 [SMILES: CC(=O)Nc1nc(F)c(CN2C[C@H](Oc3cccc(O)c3)C[C@@H]2C)s1]

N-(4-fluoro-5-(((2S,4R)-4-((6-hydroxypyrimidin-4-yl)oxy)-2-methylpyrrolidin-1-yl)methyl)thiazol-2-yl)acetamide: The title compound was prepared in an analogous manner of that in Scheme 2 (byproduct isolated from Example 1-22). LCMS (ESI): [M+H]368. ¹HNMR: (400 MHz, Methanol-d₄) δ 8.04 (d, J=0.75 Hz, 1H), 5.61 (d, J=0.75 Hz, 1H), 5.08-5.23 (m, 1H), 3.95 (dd, J=0.88, 14.68 Hz, 1H), 3.55 (d, J=14.56 Hz, 1H), 3.13 (d, J=11.55 Hz, 1H), 2.47-2.70 (m, 3H), 2.17 (s, 3H), 1.53-1.71 (m, 1H), 1.16-1.31 (m, 3H)

Example 1-110

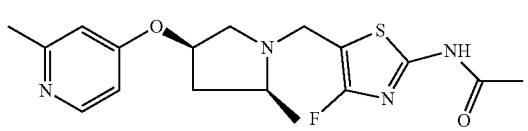 [SMILES: CC(=O)Nc1nc(F)c(CN2C[C@H](Oc3ccnc(C)c3)C[C@@H]2C)s1]

N-(4-fluoro-5-(((2S,4R)-2-methyl-4-((2-methylpyridin-4-yl)oxy)pyrrolidin-1-yl)methyl)thiazol-2-yl)acetamide: The title compound was prepared in an analogous manner of that in Scheme 2 from tert-butyl (2S,4R)-4-hydroxy-2-methylpyrrolidine-1-carboxylate, 4-chloro-2-methylpyridine, and N-(4-fluoro-5-formylthiazol-2-yl)acetamide. LCMS (ESI): [M+H] 365. ¹HNMR: (400 MHz, Methanol-d₄) δ 8.17 (d, J=6.02 Hz, 1H), 6.66-6.85 (m, 2H), 4.87-4.93 (m, 1H), 3.97 (dd, J=1.00, 14.56 Hz, 1H), 3.58 (d, J=14.56 Hz, 1H), 3.15 (d, J=11.04 Hz, 1H), 2.52-2.76 (m, 3H), 2.45 (s, 3H), 2.18 (s, 3H), 1.49-1.70 (m, 1H), 1.24 (d, J=6.02 Hz, 3H)

Example 1-111

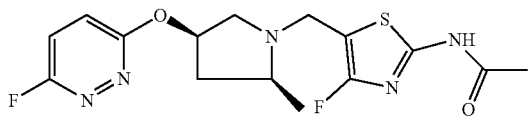 [SMILES: CC(=O)Nc1nc(F)c(CN2C[C@H](Oc3ccc(F)nn3)C[C@@H]2C)s1]

N-(4-fluoro-5-(((2S,4R)-4-((6-fluoropyridazin-3-yl)oxy)-2-methylpyrrolidin-1-yl)methyl)thiazol-2-yl)acetamide: The title compound was prepared in an analogous manner of that in Scheme 2 from 3,6-difluoropyridazine, tert-butyl (2S,4R)-4-hydroxy-2-methylpyrrolidine-1-carboxylate, and N-(5-(chloromethyl)-4-fluorothiazol-2-yl)acetamide. LCMS (ESI): [M+H] 370. ¹HNMR: (400 MHz, Methanol-d₄) δ 7.40 (d, J=9.2, 1.6 Hz, 1H), 7.31-7.33 (m, 1H), 5.39-5.43 (m, 1H), 3.96-4.00 (m, 1H), 3.55-3.58 (m, 1H), 3.19-3.22 (m, 1H), 2.57-2.72 (m, 3H), 2.18 (s, 3H), 1.64-1.69 (m, 1H), 1.25 (d, J=6.0 Hz, 3H).

Example 1-112

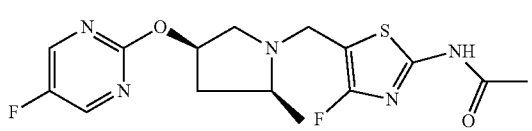 [SMILES: CC(=O)Nc1nc(F)c(CN2C[C@H](Oc3ncc(F)cn3)C[C@@H]2C)s1]

N-(4-fluoro-5-(((2S,4R)-4-((5-fluoropyrimidin-2-yl)oxy)-2-methylpyrrolidin-1-yl)methyl)thiazol-2-yl)acetamide: The title compound was prepared in an analogous manner of that in Scheme 2 from 2-chloro-5-fluoropyrimidine, tert-butyl (2S,4R)-4-hydroxy-2-methylpyrrolidine-1-carboxylate, and N-(4-fluoro-5-formylthiazol-2-yl)acetamide. LCMS (ESI): [M+H] 370.0. ¹HNMR: (400 MHz, Methanol-d₄) δ 8.46 (s, 2H), 5.20-5.29 (m, 1H), 3.93 (d, J=14.4 Hz, 1H), 3.53 (d, J=14.4 Hz, 1H), 3.14 (d, J=11.2 Hz, 1H), 2.64-2.70 (m, 1H), 2.50-2.62 (m, 2H), 2.15 (s, 3H), 1.59-1.68 (m, 1H), 1.22 (d, J=6.0 Hz, 3H).

Example 1-113

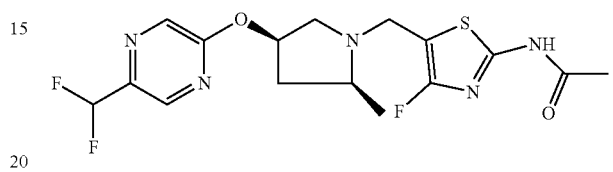

N-(5-(((2S,4R)-4-((5-(difluoromethyl)pyrazin-2-yl)oxy)-2-methylpyrrolidin-1-yl)methyl)-4-fluorothiazol-2-yl)acetamide: The title compound was prepared in an analogous manner of that in Scheme 2 from 2-chloro-5-(difluoromethyl)pyrazine, tert-butyl (2S,4R)-4-hydroxy-2-methylpyrrolidine-1-carboxylate, and N-(4-fluoro-5-formylthiazol-2-yl)acetamide. LCMS (ESI): [M+H] 402.0. ¹HNMR: (400 MHz, Methanol-d₄) δ 8.8 (s, 1H), 8.4 (s, 1H), 6.4 (t), 5.6 (m, 1H), 3.93 (d, J=14.4 Hz, 1H), 3.53 (d, J=14.4 Hz, 1H), 3.3 (d, J=11.2 Hz, 1H), 2.64-2.70 (m, 3H), 2.2 (s, 3H), 1.59-1.68 (m, 1H), 1.22 (d, J=6.0 Hz, 3H).

Example 1-114

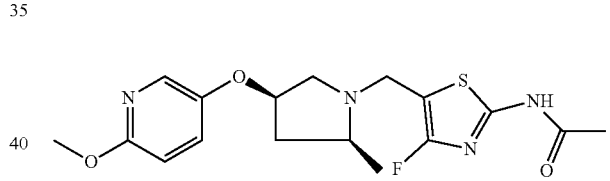

N-(4-fluoro-5-(((2S,4R)-4-((6-methoxypyridin-3-yl)oxy)-2-methylpyrrolidin-1-yl)methyl)thiazol-2-yl)acetamide: The title compound was prepared in an analogous manner of that in Scheme 2 from tert-butyl (2S,4S)-4-hydroxy-2-methylpyrrolidine-1-carboxylate, 6-methoxypyridin-3-ol, and N-(4-fluoro-5-formylthiazol-2-yl)acetamide. LCMS (ESI): [M+H] 380.9. ¹HNMR: (500 MHz, Methanol-d₄) δ 7.68 (d, J=2.5 Hz, 1H), 7.29 (dd, J=9.0, 3.0 Hz, 1H), 6.72 (d, J=9.0 Hz, 1H), 4.72-4.74 (m, 1H), 3.96-3.99 (m, 1H), 3.83 (s, 3H), 3.56-3.59 (m, 1H), 3.14-3.16 (m, 1H), 2.54-2.63 (m, 3H), 2.18 (s, 3H), 1.58-1.64 (m, 1H), 1.23 (d, J=6.0 Hz, 3H).

Example 1-115

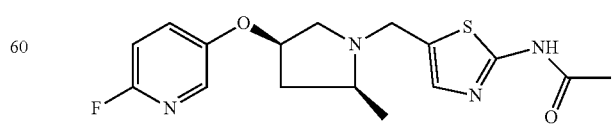

N-(5-(((2S,4R)-4-((6-fluoropyridin-3-yl)oxy)-2-methylpyrrolidin-1-yl)methyl)thiazol-2-yl)acetamide: The title compound was prepared in an analogous manner of that in Scheme 2 from 6-fluoropyridin-3-ol, tert-butyl (2S,4S)-4-hydroxy-2-methylpyrrolidine-1-carboxylate, and N-(5-formylthiazol-2-yl)acetamide. LCMS (ESI): [M+H] 351.1. ¹HNMR: (500 MHz, Methanol-d₄) δ 7.75 (s, 1H), 7.46-7.49 (m, 1H), 7.28 (s, 1H), 6.97 (dd, J=9.0, 3.0 Hz, 1H), 4.79-4.82 (m, 1H), 4.13-4.17 (m, 1H), 3.56-3.59 (m, 1H), 3.12-3.15 (m, 1H), 2.59-2.64 (m, 3H), 2.20 (s, 3H), 1.61-1.65 (m, 1H), 1.26 (d, J=5.5 Hz, 3H).

Example 1-116

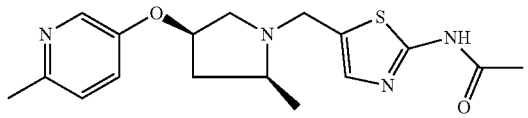 [SMILES: CC(=O)Nc1ncc(CN2C[C@H](Oc3ccc(C)nc3)C[C@@H]2C)s1]

N-(5-(((2R,4S)-2-methyl-4-((6-methylpyridin-3-yl)oxy)pyrrolidin-1-yl)methyl)thiazol-2-yl)acetamide: The title compound was prepared in an analogous manner of that in Scheme 2 from 6-methylpyridin-3-ol, tert-butyl (2S,4S)-4-hydroxy-2-methylpyrrolidine-1-carboxylate, and N-(5-formylthiazol-2-yl)acetamide. LCMS (ESI): [M+H] 347. ¹HNMR: (400 MHz, Methanol-d₄) δ 8.02 (d, J=2.76 Hz, 1H), 7.29 (s, 1H), 7.24-7.28 (m, 1H), 7.18-7.22 (m, 1H), 4.77-4.84 (m, 1H), 4.16 (dd, J=14.18, 0.88 Hz, 1H), 3.59 (d, J=14.31 Hz, 1H), 3.14 (d, J=11.04 Hz, 1H), 2.54-2.68 (m, 3H), 2.45 (s, 3H), 2.21 (s, 3H), 1.64 (s, 1H), 1.27 (d, J=5.77 Hz, 3H).

Example 1-117

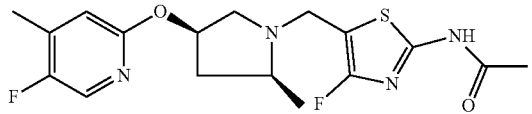 [SMILES: CC(=O)Nc1nc(F)c(CN2C[C@H](Oc3cc(C)c(F)cn3)C[C@@H]2C)s1]

N-(4-fluoro-5-(((2S,4R)-4-((5-fluoro-4-methylpyridin-2-yl)oxy)-2-methylpyrrolidin-1-yl)methyl)thiazol-2-yl)acetamide: The title compound was prepared in an analogous manner of that in Scheme 2 from 2-bromo-5-fluoro-4-methylpyridine, 5 tert-butyl (2S,4R)-4-hydroxy-2-methylpyrrolidine-1-carboxylate and N-(5-(chloromethyl)-4-fluorothiazol-2-yl)acetamide. LCMS (ESI): [M+H] 383. ¹HNMR: (400 MHz, Methanol-d₄) δ 11.08 (brs, 1H), 7.81 (s, 1H), 6.57 (d, J=4.8 Hz, 1H), 5.20-5.25 (m, 1H), 3.95-3.99 (m, 1H), 3.61-3.65 (m, 1H), 3.12-3.15 (m, 1H), 2.61-2.65 (m, 1H), 2.47-2.52 (m, 2H), 2.30 (s, 3H), 2.22 (s, 3H), 1.59-1.62 (m, 1H), 1.24 (d, J=5.6 Hz, 3H).

Example 1-118

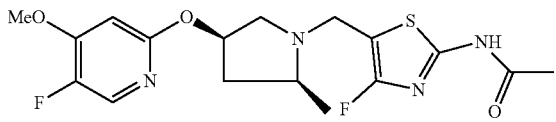 [SMILES: COc1cc(O[C@@H]2C[C@H](C)N(Cc3sc(NC(C)=O)nc3F)C2)ncc1F]

N-(4-fluoro-5-(((2S,4R)-4-((5-fluoro-4-methoxypyridin-2-yl)oxy)-2-methylpyrrolidin-1-yl)methyl)thiazol-2-yl)acetamide: The title compound was prepared in an analogous manner of that in Scheme 2 from 2-bromo-5-fluoro-4-methoxypyridine, tert-butyl (2S,4R)-4-hydroxy-2-methylpyrrolidine-1-carboxylate, and N-(4-fluoro-5-formylthiazol-2-yl)acetamide. LCMS (ESI): [M+H] 399.0. ¹HNMR: (400 MHz, Methanol-d₄) δ 7.75 (s, 1H), 6.45 (s, 1H), 5.25 (m, 1H), 3.9 (d, J=14 Hz, 1H), 3.5 (d, J=14 Hz, 1H), 3.1 (d, J=11 Hz, 1H), 2.49-2.6 (m, 3H), 2.2 (s, 3H), 1.5-1.6 (m, 1H), 1.25 (d, J=6.0 Hz, 3H).

Example 1-119

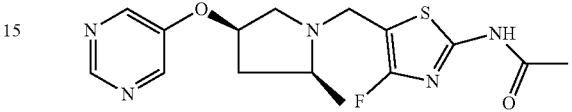

N-(4-fluoro-5-(((2S,4R)-2-methyl-4-(pyrimidin-5-yloxy)pyrrolidin-1-yl)methyl)thiazol-2-yl)acetamide: The title compound was prepared in an analogous manner of that in Scheme 2 from 5-bromopyrimidine, tert-butyl (2S,4R)-4-hydroxy-2-methylpyrrolidine-1-carboxylate, and N-(4-fluoro-5-formylthiazol-2-yl)acetamide. LCMS (ESI): [M+H] 352.0. ¹HNMR: (400 MHz, Methanol-d₄) δ 8.7 (s, 1H), 8.3 (s, 2H), 5.3 (m, 1H), 3.93 (d, J=14.4 Hz, 1H), 3.53 (d, J=14.4 Hz, 1H), 3.3 (d, J=11.2 Hz, 1H), 2.5-2.7 (m, 3H), 2.2 (s, 3H), 1.5-1.6 (m, 1H), 1.2 (d, J=6.0 Hz, 3H).

Scheme 3

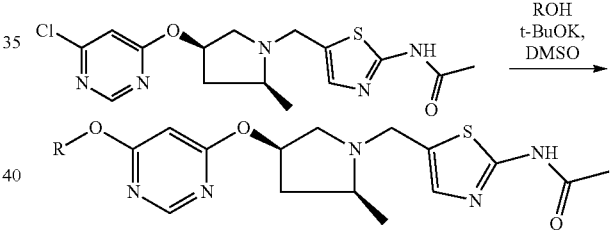

Representative Procedure A: To a solution of alcohol (3 equiv.) in DMSO (0.6 mL) was added tBuOK (2.5 equiv.). The mixture was stirred at ambient temperature for 30 min, followed by addition of N-(5-(((2S,4R)-4-((6-chloropyrimidin-4-yl)oxy)-2-methylpyrrolidin-1-yl)methyl)thiazol-2-yl)acetamide. Stirring was continued under 60° C. for 16-72 h. Upon completion, the mixture was subjected to C18 prep HPLC-MS (gradient mixture H₂O/MeOH or H₂O/MeCN) to afford desired product.

Example 1-120

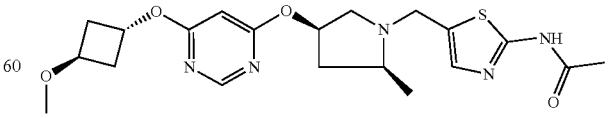

N-(5-(((2S,4R)-4-((6-(((1r,3R)-3-methoxycyclobutoxy)pyrimidin-4-yl)oxy)-2-methylpyrrolidin-1-yl)methyl)thiazol-2-yl)acetamide: The title compound was prepared in an analogous manner of that in scheme 2 from N-(5-(((2S,4R)-

4-((6-chloropyrimidin-4-yl)oxy)-2-methylpyrrolidin-1-yl) methyl)thiazol-2-yl)acetamide and (1r,3r)-3-methoxycyclobutan-1-ol. LCMS (ESI): [M+H] 434.2.

Example 1-121

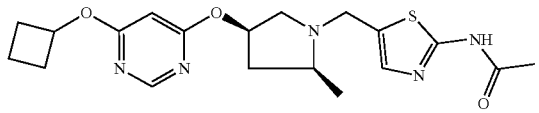 [SMILES: CC(=O)Nc1ncc(CN2C[C@H](Oc3cc(OC4CCC4)ncn3)C[C@@H]2C)s1]

N-(5-(((2S,4R)-4-((6-cyclobutoxypyrimidin-4-yl)oxy)-2-methylpyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and cyclobutanol. LCMS (ESI): [M+H]404.2.

Example 1-122

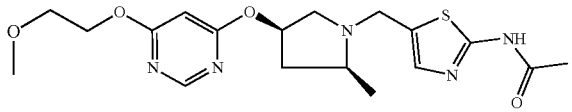 [SMILES: COCCOc1cc(O[C@@H]2C[C@H](C)N(Cc3cnc(NC(C)=O)s3)C2)ncn1]

N-(5-(((2S,4R)-4-((6-(2-methoxyethoxy)pyrimidin-4-yl)oxy)-2-methylpyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and 2-methoxyethan-1-ol. LCMS (ESI): [M+H] 408.2.

Example 1-123

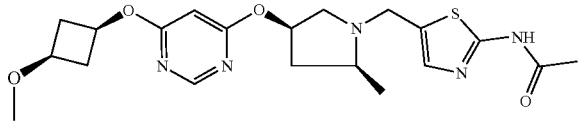 [SMILES: CO[C@H]1C[C@@H](Oc2cc(O[C@@H]3C[C@H](C)N(Cc4cnc(NC(C)=O)s4)C3)ncn2)C1]

N-(5-(((2S,4R)-4-((6-((1S,3S)-3-methoxycyclobutoxy)pyrimidin-4-yl)oxy)-2-methylpyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and (1s,3s)-3-methoxycyclobutan-1-ol. LCMS (ESI): [M+H] 434.2. ¹HNMR: (400 MHz, DMSO+CCl₄) δ11.81 (s, 1H), 8.24 (s, 1H), 7.11 (s, 1H), 5.99 (s, 1H), 5.31-5.26 (m, 1H), 4.83-4.75 (m, 1H), 4.01 (d, J=14.0 Hz, 1H), 3.62-3.55 (m, 1H), 3.46 (d, J=14.0 Hz, 1H), 3.17 (s, 3H), 2.98-2.94 (m, 1H), 2.82-2.78 (m, 2H), 2.59-2.52 (m, 2H), 2.48-2.45 (m, 1H), 2.10 (s, 3H), 1.96-1.92 (m, 2H), 1.59-1.54 (m, 1H), 1.20 (d, J=5.4 Hz, 3H).

Example 1-124

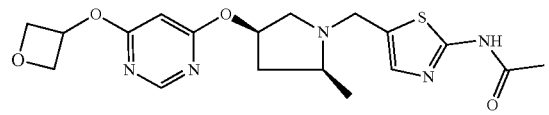 [SMILES: CC(=O)Nc1ncc(CN2C[C@H](Oc3cc(OC4COC4)ncn3)C[C@@H]2C)s1]

N-(5-(((2S,4R)-2-methyl-4-((6-(oxetan-3-yloxy)pyrimidin-4-yl)oxy)pyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and (1s,3s)-3-methoxycyclobutan-1-ol. LCMS (ESI): [M+H] 406.2.

Example 1-125

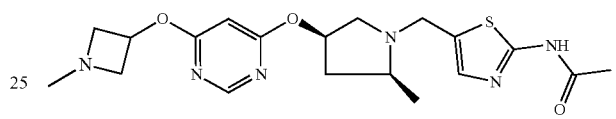

N-(5-(((2S,4R)-2-methyl-4-((6-((1-methylazetidin-3-yl)oxy)pyrimidin-4-yl)oxy)pyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and 1-methylazetidin-3-ol. LCMS (ESI): [M+H] 419.0. ¹HNMR: (400 MHz, DMSO+CCl₄) δ 12.12-11.73 (m, 1H), 8.67 (s, 1H), 7.16 (s, 1H), 6.47 (s, 1H), 5.44-5.40 (m, 1H), 4.40-4.36 (m, 2H), 4.19-4.01 (m, OH), 3.83-3.69 (m, 2H), 3.50-3.40 (m, 5H), 3.17-3.16 (m, 3H), 2.60 (s, 2H), 2.12 (s, 3H), 1.68-1.50 (m, 1H), 1.23 (s, 3H).

Example 1-126

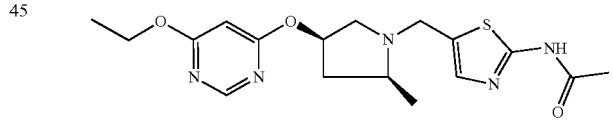

N-(5-(((2S,4R)-4-((6-ethoxypyrimidin-4-yl)oxy)-2-methylpyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and ethanol. LCMS (ESI): [M+H] 378.2.

Example 1-127

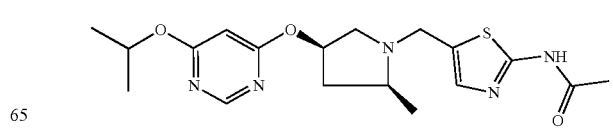

N-(5-(((2S,4R)-4-((6-isopropoxypyrimidin-4yl)oxy)-2-methylpyrrolidin-1-yl)methyl)thiazol-2-yl)acetamide: The title compound was prepared in an analogous manner of that in Scheme 3 from N-(5-(((2S,4R)-4-((6-chloropyrimidin-4-yl)oxy)-2-methylpyrrolidin-1-yl)methyl)thiazol-2-yl)acetamide and isopropanol. LCMS (ESI): [M+H]392.2.

Scheme 4

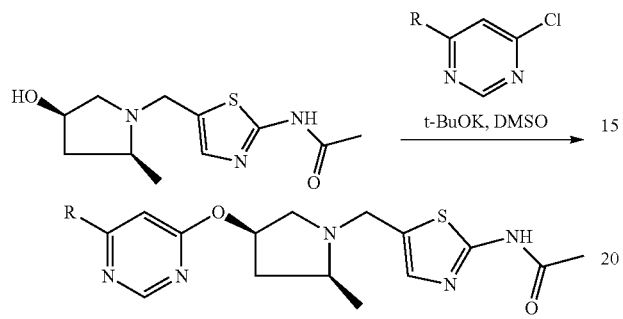

Representative Procedure B: To a solution of N-(5-(((2S,4R)-4-hydroxy-2-methylpyrrolidin-1-yl)methyl)thiazol-2-yl)acetamide (1 equiv.) in DMSO (0.6 mL) was added tBuOK (1.2 equiv.). The mixture was stirred at ambient temperature for 30 min, followed by addition of aryl halide (1.2 equiv.). The mixture was stirred at 60° C. for 16-72 h. Upon completion, the mixture was subjected to C18 prep HPLC-MS (gradient mixture H₂O/MeOH or H₂O/MeCN) to afford desired product.

Intermediate 12

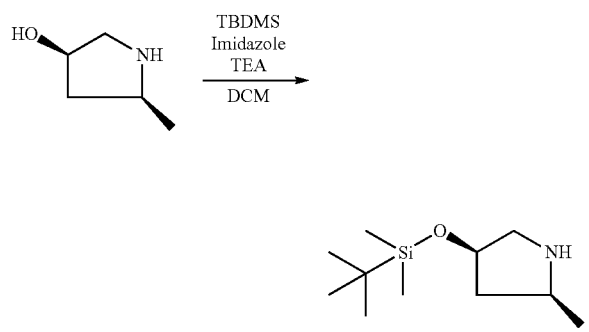

(2S,4R)-4-((tert-butyldimethylsilyl)oxy)-2-methylpyrrolidine: Charged a 1 L round bottom flask with (3R,5S)-5-methylpyrrolidin-3-ol (6.21 g, 45.13 mmol, Hydrochloride) and DCM (150 mL). Added triethylamine (4.57 g, 45.13 mmol, 6.26 mL) and stirred for 10 min. before adding imidazole (737.35 mg, 10.83 mmol) and tert-butyl-chloro-dimethyl-silane (8.16 g, 54.16 mmol). Stirred the reaction for 16 h at rt. Diluted the reaction with DCM and added NaCHO₃ (satd), separated the layers and extracted with DCM (2×). Dried the organics over sodium sulfate, filtered and concentrated to obtain the title compound (9.72 g, 100% yield). LCMS (ESI): [M+H] 216.12. ¹HNMR: (500 MHz, CDCl₃) δ 4.34 (br dd, J=4.9, 2.4 Hz, 1H), 3.11-3.32 (m, 2H), 2.88-3.03 (m, 1H), 2.83 (ddd, J=11.9, 4.9, 1.5 Hz, 1H), 2.15 (ddd, J=13.3, 7.5, 6.1 Hz, 1H), 1.25-1.33 (m, 4H), 0.88 (s, 9H), 0.05 ppm (s, 6H).

Intermediate 13

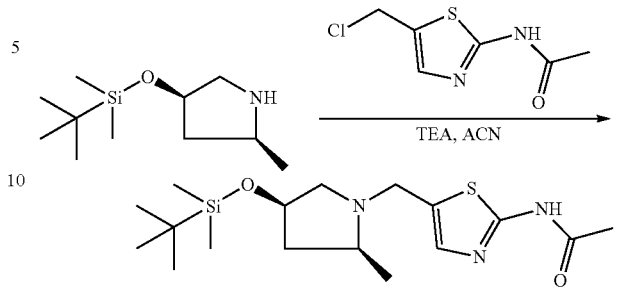

N-(5-(((2S,4R)-4-((tert-butyldimethylsilyl)oxy)-2-methylpyrrolidin-1-yl)methyl)thiazol-2-yl)acetamide: Dissolved (2S,4R)-4-((tert-butyldimethylsilyl)oxy)-2-methylpyrrolidine in acetonitrile (100 mL) and added triethylamine (11.25 g, 111.2 mmol, 15.41 mL). Added N-[5-(chloromethyl)thiazol-2-yl]acetamide (5.30 g, 27.79 mmol) and stirred at rt for 16 h. Filtered the reaction through celite and concentrated. Purified; Gradient Hept/[Ea/EtOH (3:1)] (0-20→50/o) to obtain the desired product (7.2 g, 19.5 mmol, 70% yield). LCMS (ESI): [M+H] 369.1. ¹HNMR: (500 MHz, CDCl₃) δ 7.20 (s, 1H), 4.21-4.41 (m, 1H), 4.01-4.06 (m, 1H), 3.59 (d, J=14.7 Hz, 1H), 2.87 (dd, J=10.1, 2.1 Hz, 1H), 2.43-2.57 (m, 2H), 2.30 (s, 3H), 2.24 (dt, J=12.8, 7.0 Hz, 1H), 1.44-1.68 (m, 3H), 1.22-1.31 (m, 311), 1.18 (d, J=6.1 Hz, 3H), 0.84-0.89 (m, 1H), −0.02-0.02 ppm (m, 8H).

Intermediate 14

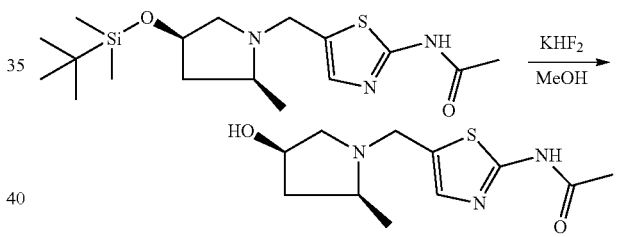

N-(5-(((2S,4R)-4-hydroxy-2-methylpyrrolidin-1-yl)methyl)thiazol-2-yl)acetamide: Charged a 250 ml round bottom flask with N-[5-[[(2S,4R)-4-[tert-butyl(dimethyl)silyl]oxy-2-methyl-pyrrolidin-1-yl]methyl]thiazol-2-yl]acetamide (11.1 g, 29.90 mmol). Added MeOH (119.6 mL) and KHF₂ (5.84 g, 74.8 mmol, 2.46 mL) and stirred at 60° C. for 16 h. Cooled the reaction to room temperature and filtered the reaction through celite and concentrated. Silica gel purification with [[heptane/EtOH (3:1)] with 1% TEA; gradient (0→20→50→100%)]afforded the title compound (5.30 g, 20.76 mmol, 69.42% yield). LCMS (ESI): [M+H] 256.1. ¹HNMR: (500 MHz, MeOD) δ 7.24 (s, 1H), 4.17-4.22 (m, 1H), 4.05-4.10 (m, 1H), 3.48 (d, 0.1=14.0 Hz, 1H), 2.89 (d, J=10.4 Hz, 1H), 2.34-2.49 (m, 3H), 2.19 (s, 3H), 1.39-1.46 (m, 1H), 1.21 ppm (d, J=6.1 Hz, 3H).

Intermediate 15

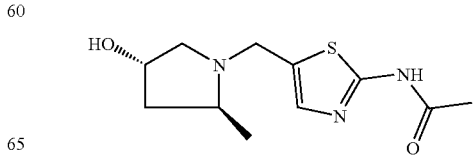

N-(5-(((2S,4S)-4-hydroxy-2-methylpyrrolidin-1-yl)methyl) thiazol-2-yl)acetamide: To a solution of (3S,5S)-5-methylpyrrolidin-3-ol (700 mg, 5.09 mmol, HCl) and N-[5-(chloromethyl)thiazol-2-yl]acetamide (953 mg, 5.00 mmol) in DMF (10.0 mL) was added Hunigs base (1.29 g, 10.0 mmol, 1.75 mL). The mixture was stirred at room temperature overnight, the concentrated in vacuo. To the mixture was added a few drops (~10) of saturated NaHCO₃, and evaporate with MeCN. The residue was purified over SiO₂ (EtOAc/EtOH 3/1) to afford the title compound (430 mg, 34% yield).

Example 1-128

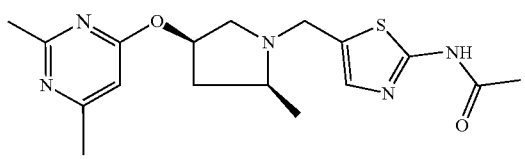 [SMILES: CC(=O)Nc1ncc(CN2C[C@H](Oc3cc(C)nc(C)n3)C[C@@H]2C)s1]

N-(5-(((2S,4R)-4-(2,6-dimethylpyrimidin-4-yl)oxy)₂-methylpyrrolidin-1-yl)methyl)thiazol-2-yl)acetamide: To a mixture of 2,6-dimethylpyrimidin-4-ol (20 mg, 0.163 mmol), N-(5-(((2S,4S)-4-hydroxy-2-methylpyrrolidin-1-yl)methyl) thiazol-2-yl)acetamide (38 mg, 0.149 mmol) and triphenylphosphine (51 mg, 0.193 mmol) in THF (1.0 mL) was added diisopropyl azodicarboxylate (42 mg, 0.208 mmol, 41 uL). The mixture was stirred at room temperature for 40 min. The mixture was purified over SiO₂ (EtOAc 100% to EtOAc/EtOH 3/1) to provide the title compound (23 mg, 43% yield). LCMS (ESI): [M+H] 362. ¹H NMR (400 MHz, Methanol-d₄) δ 7.28 (s, 1H), 6.53 (s, 1H), 5.35-5.46 (m, 1H), 4.15 (dd, J=−1.00, 14.31 Hz, 1H), 3.56 (d, 1=14.31 Hz, 1H), 3.10 (d, J=11.55 Hz, 1H), 2.54-2.71 (m, 3H), 2.51 (s, 3H), 2.38 (s, 3H), 2.21 (s, 3H), 1.58-1.72 (m, 1H), 1.23-1.32 (m, 3H)

Example 1-129

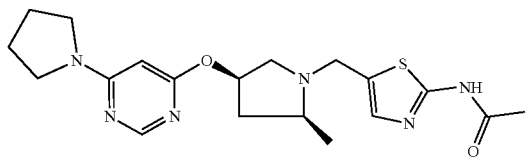 [SMILES: CC(=O)Nc1ncc(CN2C[C@H](Oc3cc(N4CCCC4)ncn3)C[C@@H]2C)s1]

N-(5-(((2S,4R)-2-methyl-4-((6-(pyrrolidin-1-yl)pyrimidin-4-yl)oxy)pyrrolidin-1-yl)methyl)thiazol-2-yl)acetamide: The title compound was prepared in an analogous manner of that in Scheme 4 from N-(5-(((2S,4R)-4-hydroxy-2-methylpyrrolidin-1-yl)methyl)thiazol-2-yl)acetamide and 4-chloro-6-(pyrrolidin-1-yl)pyrimidine. LCMS (ESI): [M+H] 403.

Example 1-130

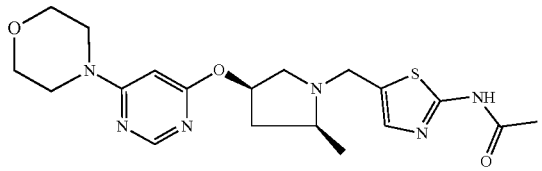 [SMILES: CC(=O)Nc1ncc(CN2C[C@H](Oc3cc(N4CCOCC4)ncn3)C[C@@H]2C)s1]

N-(5-(((2S,4R)-2-methyl-4-((6-morpholinopyrimidin-4-yl) oxy)pyrrolidin-1-yl)methyl)thiazol-2-yl)acetamide: The title compound was prepared in an analogous manner of that in Scheme 4 from N-(5-(((2S,4R)-4-hydroxy-2-methylpyrrolidin-1-yl)methyl)thiazol-2-yl)acetamide and 4-(6-chloropyrimidin-4-yl)morpholine. LCMS (ESI): [M+H] 419.0.

Scheme 5

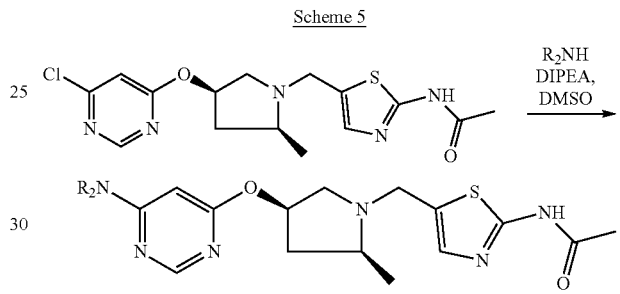

Representative Procedure C: A mixture of N-(5-(((2S,4R)-4-((6-chloropyrimidin-4-yl)oxy)-2-methylpyrrolidin-1-yl) methyl)thiazol-2-yl)acetamide (1 equiv.), amine (1.5 equiv.), and DIPEA (2 equiv.) in DMSO (0.6 mL) was stirred at 90° C. for 16-72 h. Upon completion, the mixture was subjected to C18 prep HPLC-MS (gradient mixture H₂O/MeOH or H₂O/MeCN) to afford desired product.

Example 1-131

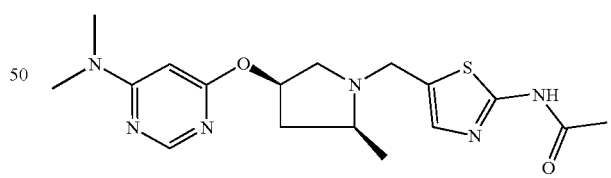

N-(5-(((2S,4R)-4-((6-(dimethylamino)pyrimidin-4-yl)oxy)-2-methylpyrrolin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and dimethylamine. LCMS (ESI): [M+H] 377. ¹HNMR: (400 MHz, DMSO+CCl₄) δ 11.81 (s, 1H), 8.04 (s, 1H), 7.11 (s, 1H), 5.73 (s, 1H), 5.29-5.25 (m, 1H), 4.01 (d, J=14.0 Hz, 1H), 3.42 (d, J=13.9 Hz, 1H), 3.02 (s, 6H), 2.98-2.91 (m, 2H), 2.49-2.41 (m, 2H), 2.10 (s, 3H), 1.58-1.49 (m, 1H), 1.20 (d, J=5.3 Hz, 3H).

Example 1-132

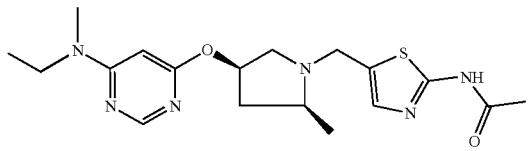 [SMILES: CCN(C)c1cc(O[C@@H]2C[C@H](C)N(Cc3cnc(NC(C)=O)s3)C2)ncn1]

N-(5-(((2S,4R)-4-((6-(ethyl(methyl)amino)pyrimidin-4-yl)oxy)2-methylpyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and N-methylethylamine. LCMS (ESI): [M+H] 391.2. $^1$HNMR: (400 MHz, DMSO+CCl$_4$) δ 11.81 (s, 1H), 8.03 (s, 1H), 7.11 (s, 1H), 5.70 (s, 1H), 5.29-5.24 (m, 1H), 4.01 (d, J=13.9 Hz, 1H), 3.53 (q, J=7.3, 6.5, 6.5 Hz, 2H), 3.42 (d, J=14.0 Hz, 1H), 2.99-2.91 (m, 4H), 2.50-2.42 (m, 3H), 2.10 (s, 3H), 1.55-1.51 (m, 1H), 1.20 (d, J=5.3 Hz, 3H), 1.10 (t, J=7.0, 7.0 Hz, 3H).

Example 1-133

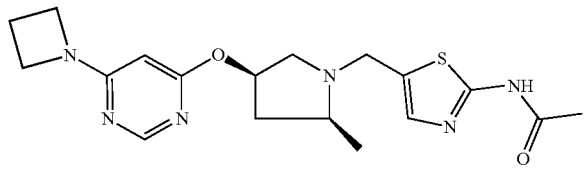 [SMILES: CC(=O)Nc1ncc(CN2C[C@H](Oc3cc(N4CCC4)ncn3)C[C@@H]2C)s1]

N-(5-(((2S,4R)-4-((6-(azetidin-1-yl)pyrimidin-4-yl)oxy)-2-methylpyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and azetidine. LCMS (ESI): [M+H]389.2. $^1$HNMR: (400 MHz, DMSO+CCl$_4$) δ 11.77-11.73 (m, 1H), 8.01 (s, 1H), 7.11 (s, 1H), 5.47 (s, 1H), 5.29-5.22 (m, 1H), 4.05-3.93 (m, 5H), 3.42 (d, J=13.9 Hz, 1H), 2.93 (d, J=11.1 Hz, 1H), 2.51-2.41 (m, 3H), 2.41-2.32 (m, 2H), 2.11 (s, 3H), 1.54-1.46 (m, 1H), 1.19 (d, J=5.4 Hz, 3H).

Example 1-134

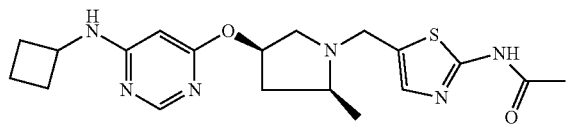 [SMILES: CC(=O)Nc1ncc(CN2C[C@H](Oc3cc(NC4CCC4)ncn3)C[C@@H]2C)s1]

N-(5-(((2S,4R)-4-((6-(cyclobutylamino)pyrimidin-4-yl)oxy)-2-methylpyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and cyclobutanamine. LCMS (ESI): [M+H] 403.2. $^1$HNMR: (400 MHz, DMSO+CCl$_4$) δ 11.81 (s, 1H), 7.95 (s, 1H), 7.11 (s, 1H), 7.04 (d, J=7.2 Hz, 1H), 5.51 (s, 1H), 5.25-5.18 (m, 1H), 4.36-4.03 (m, 1H), 4.00 (d, J=14.0 Hz, 1H), 3.42 (d, J=13.9 Hz, 1H), 2.93 (d, J=11.2 Hz, 1H), 2.51-2.38 (m, 3H), 2.30-2.26 (m, 2H), 2.10 (s, 3H), 1.96-1.86 (m, 2H), 1.74-1.63 (m, 2H), 1.59-1.48 (m, 1H), 1.19 (d, J=5.3 Hz, 3H).

Example 1-135

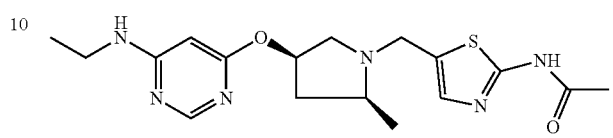

N-(5-(((2S,4R)-4-((6-(ethylamino)pyrimidin-4-yl)oxy)-2-methylpyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and ethylamine hydrochloride. LCMS (ESI): [M+H] 377.2. $^1$HNMR: (400 MHz, DMSO+CCl$_4$) δ 11.81 (s, 1H), 7.96 (s, 1H), 7.11 (s, 1H), 6.74 (t, J=5.6, 5.6 Hz, 1H), 5.57 (s, 1H), 5.25-5.19 (m, 1H), 4.01 (d, J=14.0 Hz, 1H), 3.42 (d, J=14.0 Hz, 1H), 3.02 (s, 2H), 2.93 (d, J=11.1 Hz, 1H), 2.49-2.38 (m, 3H), 2.10 (s, 3H), 1.59-1.48 (m, 1H), 1.20 (d, J=5.3 Hz, 3H), 1.14 (t, J=7.2, 7.2 Hz, 3H).

Example 1-136

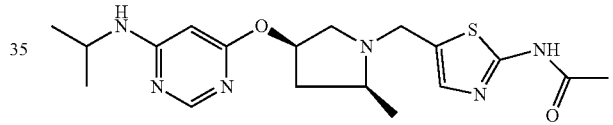

N-(5-(((2S,4R)-4-((6-(isopropylamino)pyrimidin-4-yl)oxy)-2-methylpyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and isopropylamine. LCMS (ESI): [M+H] 391.2. $^1$HNMR: (400 MHz, DMSO+CCl$_4$) δ 11.81 (s, 1H), 7.96 (s, 1H), 7.11 (s, 1H), 6.59 (d, J=7.8 Hz, 1H), 5.56 (s, 1H), 5.25-5.18 (m, 1H), 4.01 (d, J=14.0 Hz, 1H), 3.43 (d, J=13.9 Hz, 1H), 3.19 (d, J=5.2 Hz, 1H), 2.93 (d, J=11.1 Hz, 1H), 2.47-2.42 (m, 3H), 2.10 (s, 3H), 1.61-1.47 (m, 1H), 1.20 (d, J=5.3 Hz, 3H), 1.14 (d, J=6.4 Hz, 6H).

Example 1-137

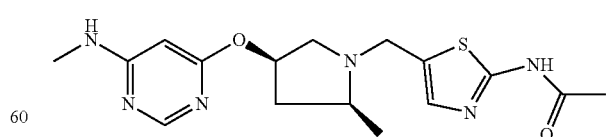

N-(5-(((2S,4R)-2-methyl-4-((6-(methylamino)pyrimidin-4-yl)oxy)pyrrolidin-1-yl)methyl)thiazol-2-yl)acetamide: The title compound was prepared in an analogous manner of that in Scheme 5 from N-(5-(((2S,4R)-4-((6-chloropyrimidin-4-yl)oxy)-2-methylpyrrolidin-1-yl)methyl)thiazol-2-yl)acetamide and methylamine. LCMS (ESI): [M+H]363.2. ¹HNMR: (400 MHz, DMSO+CCl₄) δ 11.82 (s, 1H), 7.97 (s, 1H), 7.12 (s, 1H), 6.76 (s, 1H), 5.57 (s, 1H), 5.24 (s, 1H), 4.02-3.98 (m, 1H), 3.44-3.40 (m, 1H), 2.94-2.90 (m, 2H), 2.75 (d, J=4.8 Hz 3H) 2.50-2.37 (m, 2H) 2.11 (s,3H) 1.56-1.52 (m, 1H), 1.21 (s, 3H), Scheme 6

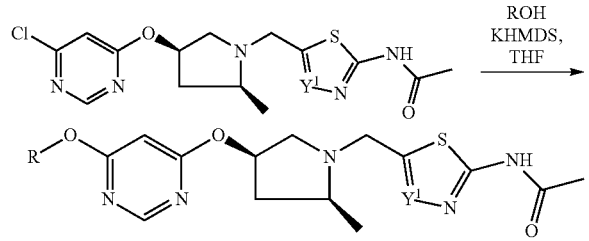

Representative Procedure D: To a solution of alcohol (1.3 equiv.) in THF (2 mL) was added KHMDS (1.2 equiv.), and the solution was stirred at ambient temperature for 1 h. N-(5-(((2S,4R)-4-((6-chloropyrimidin-4-yl)oxy)-2-methylpyrrolidin-1-yl)methyl)thiazol-2-yl)acetamide (1 equiv.) was added, and stirring was continued at room temperature for 2 h, followed by rising the temperature to 60° C. Upon completion, the mixture was then neutralized with AcOH (1 equiv.), concentrated under reduced pressure, and subjected to C18 prep HPLC-MS (gradient mixture H₂O/MeOH or H₂O/MeCN) to afford desired product.

Example 1-138

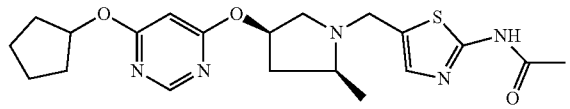 [SMILES: CC(=O)Nc1ncc(CN2C[C@H](Oc3cc(OC4CCCC4)ncn3)C[C@@H]2C)s1]

N-(5-(((2S,4R)-4-((6-(cyclopentyloxy)pyrimidin-4yl)oxy)-2-methylpyrrolidin-1-yl)methyl)thiazol-2-yl)acetamide: The title compound was prepared in an analogous manner of that in Scheme 6 from N-(5-(((2S,4R)-4-((6-chloropyrimidin-4-yl)oxy)-2-methylpyrrolidin-1-yl)methyl)thiazol-2-yl)acetamide and cyclopentanol. LCMS (ESI): [M+H] 418.2.

Example 1-139

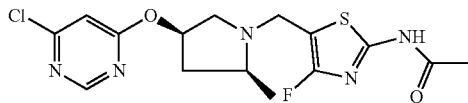 [SMILES: CC(=O)Nc1nc(F)c(CN2C[C@H](Oc3cc(Cl)ncn3)C[C@@H]2C)s1]

N-(5-(((2S,4R)-4-((6-chloropyrimidin-4-yl)oxy)-2-methylpyrrolidin-1-yl)methyl)-4-fluorothiazol-2-yl)acetamide: The title compound was prepared in an analogous manner of that in Scheme 2 from tert-butyl (2S,4R)-4-hydroxy-2-methylpyrrolidine-1-carboxylate, 4,6-dichloropyrimidine, and N-(4-fluoro-5-formylthiazol-2-yl)acetamide. LCMS (ESI): [M+H]385.9.

Example 1-140

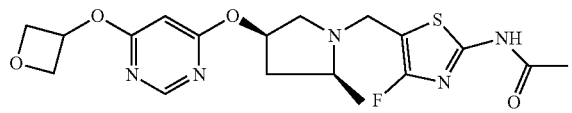 [SMILES: CC(=O)Nc1nc(F)c(CN2C[C@H](Oc3cc(OC4COC4)ncn3)C[C@@H]2C)s1]

N-(4-fluoro-5-(((2S,4)-2-methyl-4-((6-(oxetan-3-yloxy)pyrimidin-4-yl)oxy)pyrrolidin-1-yl)methyl)thiazol-2-yl)acetamide: The title compound was prepared in an analogous manner of that in Scheme 6 from N-(5-(((2S,4R)-4-((6-chloropyrimidin-4-yl)oxy)-2-methylpyrrolidin-1-yl)methyl)-4-fluorothiazol-2-yl)acetamide and oxetan-3-ol. LCMS (ESI): [M+H] 424. ¹HNMR: (500 MHz, CDCl₃) δ 10.78 (br s, 1H), 8.30 (s, 1H), 6.09 (s, 1H), 5.55-5.60 (m, 1H), 5.32-5.35 (m, 1H), 4.94-4.97 (m, 2H), 4.70-4.73 (m, 2H), 3.97 (d, J=15.0 Hz, 1H), 3.63 (d, J=14.5 Hz, 1H), 3.15 (d, J=11.5 Hz, 1H), 2.63-2.66 (m, 1H), 2.49-2.55 (m, 2H), 2.30 (s, 3H), 1.64-1.66 (m, 1H), 1.24 (d, J=5.5 Hz, 3H).

Example 1-141

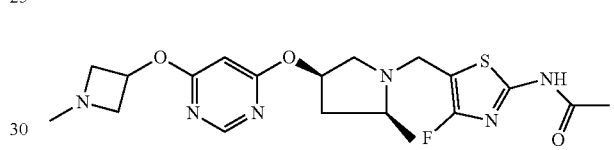

N-(4-fluoro-5-(((2S,4R)-2-methyl-4-((6-((1-methylazetidin-3-yl)oxy)pyrimidin-4-yl)oxy)pyrrolidin-1-yl)methyl)thiazol-2-yl)acetamide: The title compound was prepared in an analogous manner of that in Scheme 6 from N-(5-(((2S,4R)-4-((6-chloropyrimidin-4-yl)oxy)-2-methylpyrrolidin-1-yl)methyl)-4-fluorothiazol-2-yl)acetamide and 1-methylazetidin-3-ol. LCMS (ESI): [M+H] 437.1. ¹HNMR: (400 MHz, Methanol-d₄) δ 8.32 (s, 1H), 6.13 (s, 1H), 5.30-5.33 (m, 1H), 5.17-5.23 (m, 1H), 3.94-3.96 (m, 1H), 3.77-3.81 (m, 2H), 3.53-3.56 (m, 1H), 3.23-3.25 (m, 2H), 3.10-3.22 (m, 1H), 2.55-2.58 (m, 3H), 2.40 (s, 3H), 2.18 (s, 3H), 1.59-1.64 (m, 1H), 1.24 (d, J=6.0 Hz, 3H).

Example 1-142

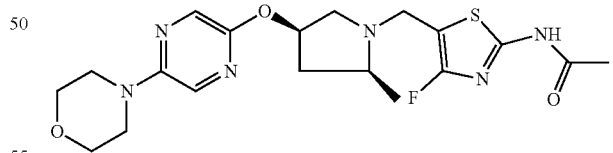

tert-butyl (2S,4R)-4-(5-chloropyrazin-2-yl)oxy-2-methylpyrrolidine-1-carboxylate: To a solution of tert-butyl (2S,4R)-4-hydroxy-2-methyl-pyrrolidine-1-carboxylate (676 mg, 3.36 mmol) in THF (10.0 mL) was added sodium hydride (202 mg, 5.04 mmol, 60% purity), then 2,5-dichloropyrazine (500 mg, 3.36 mmol) was added to the mixture. The resulting mixture was stirred at 90° C. After 2 h, the reaction was concentrated under reduced pressure and the residue was purified by SiO₂ (PE/EtOAc=10/1) to give tert-butyl (2S,4R)-4-(5-chloropyrazin-2-yl)oxy-2-methylpyrrolidine-1-carboxylate (785 mg, 74% yield). tert-butyl (2S,4R)-2-methyl-4-(5-morpholinopyrazin-2-yl)oxy-pyrrolidine-1-carboxylate: A mixture of tert-butyl (2S,4R)-4-(5-chloropyrazin-2-yl)oxy-2-methyl-pyrrolidine-1-carboxylate (200 mg, 0.64 mmol), morpholine (278 mg, 3.19 mmol, 277 uL), Pd$_2$(dba)$_3$ (58 mg, 63.74 umol), t-BuONa (122 mg, 1.27 mmol) and BINAP (40 mg, 63.7 umol) in toluene (10.0 mL) was stirred at 110° C. under N$_2$ for 2 hours. The reaction was concentrated under reduced pressure and the residue was purified over SiO$_2$ (PE/EtOAc=3/1) to give tert-butyl (2S,4R)-2-methyl-4-(5-morpholinopyrazin-2-yl)oxy-pyrrolidine-1-carboxylate (157 mg, 430.80 umol, 68% yield) as a yellow solid.

N-(4-fluoro-5-(((2S,4R)-2-methyl-4-((5-morpholinopyrazin-2-yl)oxy)pyrrolidin-1-yl)methyl)thiazol-2-yl)acetamide: The title compound was prepared in an analogous manner of that in Example 1-22 from tert-butyl (2S,4R)-2-methyl-4-((5-morpholinopyrazin-2-yl)oxy)pyrrolidine-1-carboxylate and N-(4-fluoro-5-formylthiazol-2-yl)acetamide. LCMS (ESI): [M+H] 437. $^1$HNMR: (400 MHz, Methanol-d$_4$) δ ppm 7.81 (d, J=1.17 Hz, 1H), 7.70 (d, J=1.57 Hz, 1H), 5.13-5.23 (m, 1H), 3.97 (d, J=14.48 Hz, 1H), 3.74-3.84 (m, 4H), 3.56 (d, J=14.48 Hz, 1H), 3.32-3.38 (m, 4H), 3.12 (br d, J=10.96 Hz, 1H), 2.65 (dd, 0.1=11.35, 6.26 Hz, 1H), 2.49-2.61 (m, 2H), 2.18 (s, 3H), 1.54-1.69 (m, 1H), 1.25 (d, J=5.48 Hz, 3H).

Example 1-143

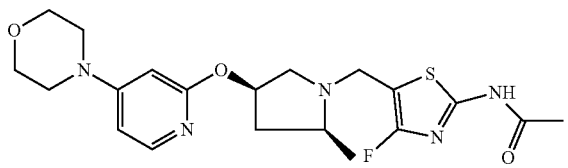 [SMILES: CC(=O)Nc1nc(F)c(CN2C[C@H](Oc3cc(N4CCOCC4)ccn3)C[C@@H]2C)s1]

N-(4-fluoro-5-(((2S,4R)-2-methyl-4-((4-morpholinopyridin-2-yl)oxy)pyrrolidin-1-yl)methyl)thiazol-2-yl)acetamide: The title compound was prepared in an analogous manner of that in Scheme 2 from 4-(2-fluoropyridin-4-yl)morpholine, tert-butyl (2S,4R)-4-hydroxy-2-methylpyrrolidine-1-carboxylate, and N-(4-fluoro-5-formylthiazol-2-yl)acetamide. LCMS (ESI): [M+H] 436. $^1$HNMR: (500 MHz, Methanol-d$_4$) δ ppm 7.75 (d, J=6.26 Hz, 1H), 6.51 (dd, J=6.26, 2.29 Hz, 1H), 6.13 (d, J=2.14 Hz, 1H), 5.09-5.24 (m, 1H), 3.96 (d, 1=14.65 Hz, 1H), 3.71-3.84 (m, 4H), 3.55 (d, J=14.65 Hz, 1H), 3.21-3.29 (m, 4H), 3.10 (d, J=11.14 Hz, 1H), 2.64 (dd, J=11.14, 6.26 Hz, 1H), 2.50-2.59 (m, 2H), 2.18 (s, 3H), 1.54-1.67 (m, 1H), 1.24 (d, J=5.49 Hz, 3H).

Example 1-144

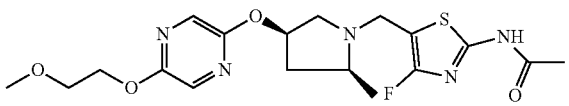 [SMILES: COCCOc1cnc(O[C@@H]2C[C@H](C)N(Cc3sc(NC(C)=O)nc3F)C2)cn1]

N-(4-fluoro-5-(((2S,4R)-4-((5-(2-methoxyethoxy)pyrazin-2-yl)oxy)-2-methylpyrrolidin-1-yl)methyl)thiazol-2-yl)acetamide: The title compound was prepared in an analogous manner of that in Scheme 2 from 2-chloro-5-(2-methoxyethoxy)pyrazine, tert-butyl (2S,4R)-4-hydroxy-2-methylpyrrolidine-1-carboxylate, and N-(4-fluoro-5-formylthiazol-2-yl)acetamide. LCMS (ESI): [M+H] 426. $^1$HNMR: (400 MHz, CDCl$_3$) δ 9.95 (br s, 1H), 7.71 (d, J=1.47 Hz, 1H), 7.68 (d, J=47 Hz, 1H), 5.07-5.17 (m, 1H), 4.25-4.39 (m, 2H), 3.91 (d, J=15.16 Hz, 1H), 3.66 (dd, J=5.26, 3.79 Hz, 2H), 3.58 (d, J=14.67 Hz, 1H), 3.36 (s, 3H), 3.09 (d, J=11.00 Hz, 1H), 2.57 (dd, J=11.13, 6.24 Hz, 1H), 2.36-2.50 (m, 2H), 2.21 (s, 3H), 1.54-1.64 (m, 1H), 1.18 (d, J=5.62 Hz, 3H).

Example 1-145

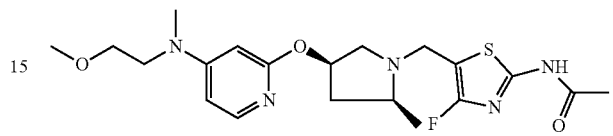

N-(4-fluoro-5-(((2S,4R)-4-((4-((2-methoxyethyl)methyl)amino)pyridin-2-yl)oxy)$_2$-methylpyrrolidin-1-yl)methyl)thiazol-2-yl)acetamide: The title compound was prepared in an analogous manner of that in Scheme 2 from 2-fluoro-N-(2-methoxyethyl)-N-methylpyridin-4-amine, tert-butyl (2S,4R)-4-hydroxy-2-methylpyrrolidine-1-carboxylate, and N-(4-fluoro-5-formylthiazol-2-yl)acetamide. LCMS (ESI): [M+H] 438. $^1$HNMR: (400 MHz, CDCl$_3$) δ ppm 9.72 (br s, 2H), 7.75 (d, J=6.11 Hz, 2H), 6.19 (dd, J=6.11, 2.45 Hz, 1H), 5.89 (d, J=2.20 Hz, 2H), 5.30 (br d, J=3.91 Hz, 2H), 3.95 (br d, J=14.67 Hz, 2H), 3.63 (d, J=14.67 Hz, 1H), 3.41-3.55 (m, 3H), 3.32 (s, 3H), 3.13 (br d, J=11.00 Hz, 1H), 2.95 (s, 3H), 2.56-2.66 (m, 1H), 2.41-2.54 (m, 2H), 2.25 (s, 3H), 1.22 (d, J=5.62 Hz, 4H)

Example 1-146

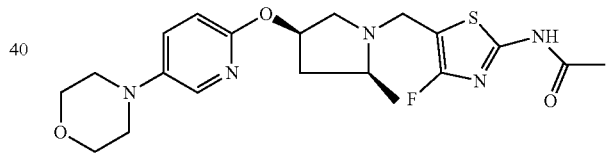

tert-butyl (2S,4R) 4-[(5-bromo-2-pyridyl)oxy]-2-methylpyrrolidine-1-carboxylate: To a solution of 5-bromo-2-fluoro-pyridine (315 mg, 1.79 mmol, 184 uL) in THF (5.0 mL) was added NaH (119 mg, 2.98 mmol, 60% purity) and tert-butyl (2S,4R)-4-hydroxy-2-methyl-pyrrolidine-1-carboxylate (300 mg, 1.49 mmol) and the mixture was stirred at 90° C. for 2 hours. The reaction was quenched by sat. NH$_4$Cl (aq. 4 mL). The mixture was concentrated then treated with H$_2$O (10 mL) and extracted with EtOAc (20 mL×3). The organic phase was washed with brine (10 mL), dried over Na$_2$SO$_4$, filtered and concentrated. The residue was purified over SiO$_2$ (Petroleum ether/EtOAc=15/1 to 5/1) to afford tert-butyl (2S,4R)-4-[(5-bromo-2-pyridyl)oxy]-2-methyl-pyrrolidine-1-carboxylate (458 mg, 86% yield). tert-butyl (2S,4R)-2-methyl-4-[(5-morpholino-2-pyridyl)oxy]pyrrolidine-1-carboxylate: To a solution of morpholine (243.87 mg, 2.80 mmol, 243.87 uL) in Toluene (8.00 mL) was added tert-butyl (2S,4R)-4-[(5-bromo-2-pyridyl)oxy]-2-methyl-pyrrolidine-1-carboxylate (200 mg, 560 umol), [2-(2-aminophenyl)phenyl]-methylsulfonyloxy-palladium; dicyclohexyl-[3,6-dimethoxy-2-(2,4,6-tri isopropylphenyl)phenyl]phosphane (51 mg, 56 umol), Cs$_2$CO$_3$ (365 mg, 1.12 mmol). The mixture was stirred at 110° C. for 15 hours under N₂. The mixture was concentrated and purified on SiO₂ (Petroleum ether/EtOAc=15/1 to 5/1) to afford tert-butyl (2S,4R)-2-methyl-4-[(5-morpholino-2-pyridyl)oxy]pyrrolidine-1-carboxylate (197 mg, 97% yield. LCMS (ESI): [M+H] 359.

N-(4-fluoro-5-(((2S,4R)-2-methyl-4-((5-morpholinopyridin-2-yl)oxy)pyrrolidin-1-yl)methyl)thiazol-2-yl)acetamide: The title compound was prepared in an analogous manner of that in Example 1-22 from tert-butyl (2S,4R)-2-methyl-4-[(5-morpholino-2-pyridyl)oxy]pyrrolidine-1-carboxylate, and N-(4-fluoro-5-formyl-thiazol-2-yl)acetamide. LCMS (ESI): [M+H] 436. ¹HNMR: (400 MHz, Methanol-d₄) δ ppm 7.72 (d, J=2.93 Hz, 1H), 7.41 (dd, J=9.05, 3.18 Hz, 1H), 6.70 (d, J=9.05 Hz, 1H), 5.12-5.24 (m, 1H), 3.95 (d, J=14.67 Hz, 1H), 3.75-3.87 (m, 4H), 3.55 (d, J=14.43 Hz, 1H), 3.10 (br d, J=1.25 Hz, 1H), 2.99-3.07 (m, 4H), 2.65 (dd, J=11.13, 6.24 Hz, 1H), 2.48-2.60 (m, 2H), 2.18 (s, 3H), 1.61 (ddd, J=15.77, 11.86, 3.91 Hz, 1H), 1.24 (d, J=5.62 Hz, 3H).

Example 1-147

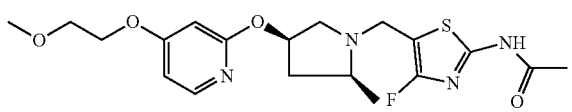 [SMILES: COCCOc1ccnc(O[C@@H]2C[C@H](C)N(Cc3sc(NC(C)=O)nc3F)C2)c1]

tert-butyl (2S,4R)-4-[5-(2-methoxyethoxy)-2-pyridyl)oxy]-2-methyl-pyrrolidine-1-carboxylate: A mixture of tert-butyl (2S,4R)-4-[(5-fluoro-2-pyridyl)oxy]-2-methyl-pyrrolidine-1-carboxylate (200 mg, 675 umol), 2-methoxyethanol (257 mg, 3.37 mmol, 264 uL), potassium t-butoxide (152 mg, 1.35 mmol) in DMSO (8.00 mL) was stirred at 120° C. for 12 hours. The reaction was extracted (EtOAc 3×10 mL), dried over Na₂SO₄), filtered and concentrated. The residue was purified over SiO₂ (Petroleum ether/EtOAc=3/1) to afford tert-butyl (2S,4R)-4-[[5-(2-methoxyethoxy)-2-pyridyl]oxy]-2-methyl-pyrrolidine-1-carboxylate (79 mg, 33% yield). LCMS (EST): [M+H] 353.

N-(4-fluoro-5-(((2S,4R)-4-((4-(2-methoxyethoxy)pyridin-2-yl)oxy)-2-methylpyrrolidin-1-yl)methyl)thiazol-2-yl)acetamide: The title compound was prepared in an analogous manner of that in Example 1-22 from tert-butyl (2S,4R)-4-[[5-(2-methoxyethoxy)-2-pyridyl]oxy]-2-methyl-pyrrolidine-1-carboxylate and N-(4-fluoro-5-formyl-thiazol-2-yl)acetamide. LCMS (ESI): [M+H] 425. ¹HNMR: (400 MHz, Methanol-d₄) δ ppm 7.87 (d, J=5.87 Hz, 1H), 6.54 (dd, J=5.87, 1.96 Hz, 1H), 6.29 (d, J=1.71 Hz, 1H), 5.12-5.29 (m, 1H), 4.08-4.21 (m, 2H), 3.96 (br d, J=14.43 Hz, 1H), 3.69-3.79 (m, 2H), 3.55 (br d, J=14.43 Hz, 1H), 3.40 (s, 3H), 3.11 (br d, J=11.25 Hz, 1H), 2.65 (br dd, J=11.13, 6.24 Hz, 1H), 2.47-2.61 (m, 2H), 2.18 (s, 3H), 1.52-1.69 (m, 1H), 1.24 (br d, J=5.38 Hz, 3H).

Example 1-148

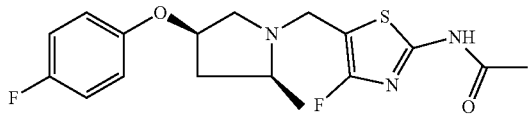 [SMILES: CC(=O)Nc1nc(F)c(CN2C[C@H](Oc3ccc(F)cc3)C[C@@H]2C)s1]

tert-butyl (2S,4R)-4-(4-fluorophenoxy)-2-methyl-pyrrolidine-1-carboxylate: To a solution of 4-fluorophenol (50 mg, 446 umol) in DMF (5.00 mL) was added sodium hydride (36 mg, 892 umol, 60% purity) at 25° C. and stirred for 30 min. tert-butyl (2S,4S)-2-methyl-4-methylsulfonyloxy-pyrrolidine-1-carboxylate (83 mg, 297 umol) was added and the mixture was stirred at 90° C. for 3 h. The reaction mixture was quenched by water (15 mL), extracted with EtOAc (2×15 mL). The combined organic phases were washed with water (2×15 mL), brine (15 mL), dried over Na₂SO₄), filtered and concentrated. The residue was purified over SiO₂ (PE:EtOAc=3:1) to afford tert-butyl (2S,4R)-4-(4-fluorophenoxy)-2-methyl-pyrrolidine-1-carboxylate (35 mg, 40% yield).

N-(4-fluoro-5-(((2S,4R)-4-(4-fluorophenoxy)-2-methylpyrrolidin-1-yl)methyl)thiazol-2-yl)acetamide: The title compound was prepared in an analogous manner of that in Example 1-22 from tert-butyl (2S,4R)-4-(4-fluorophenoxy)-2-methyl-pyrrolidine-1-carboxylate and N-(4-fluoro-5-formyl-thiazol-2-yl)acetamide. LCMS (ESI): [M+H] 368. ¹HNMR: (400 MHz, CDCl₃) δ 10.73 (br s, 1H), 6.88-6.99 (m, 2H), 6.70-6.80 (m, 2H), 4.53-4.67 (m, 1H), 3.98 (d, J=14.48 Hz, 1H), 3.66 (d, J=14.87 Hz, 1H), 3.19 (d, J=10.56 Hz, 1H), 2.61 (dd, 0.1=10.56, 5.87 Hz, 1H), 2.50-2.58 (m, 1H), 2.41-2.49 (m, 1H), 2.30 (s, 3H), 1.66-1.73 (m, 1H), 1.24 (d, J=5.87 Hz, 3H).

Example 1-149

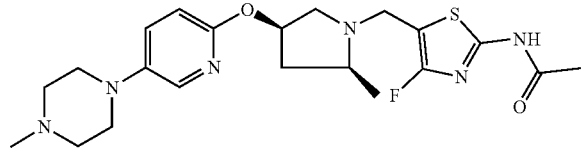 [SMILES: CC(=O)Nc1nc(F)c(CN2C[C@H](Oc3ccc(N4CCN(C)CC4)cn3)C[C@@H]2C)s1]

N-(4-fluoro-5-(((2S,4R)-2-methyl-4-((5(4-methylpiperazin-1-yl)pyridin-2-yl)oxy)pyrrolidin-1-yl)methyl)thiazol-2-yl)acetamide: The title compound was prepared in an analogous manner of that in Example 1-146 from 1-methylpiperazine, tert-butyl (2S,4R)-4-(( 5-bromopyridin-2-yl)oxy)-2-methylpyrrolidine-1-carboxylate, and N-(4-fluoro-5-formylthiazol-2-yl)acetamide. LCMS (ESI): [M+H] 449. ¹HNMR: (400 MHz, Methanol-d₄) δ ppm 7.73 (d, J=2.88 Hz, 1H), 7.42 (dd, J=9.01, 3.00 Hz, 1H), 6.70 (d, J=9.01 Hz, 1H), 5.13-5.23 (m, 1H), 3.95 (d, J=14.51 Hz, 1H), 3.56 (d, J=14.51 Hz, 1H), 3.06-3.15 (m, 5H), 2.49-2.70 (m, 7H), 2.34 (s, 3H), 2.15-2.21 (m, 4H), 1.52-1.69 (m, 1H), 1.23 (d, J=5.63 Hz, 3H).

Example 1-150

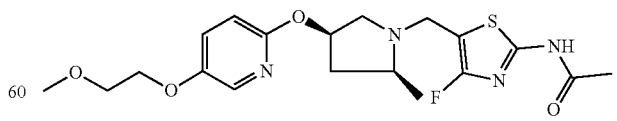

tert-butyl (2S,4R)-4-[[4-(2-methoxyethoxy)-2-pyridyl]oxy]-2-methyl-pyrrolidine-1-carboxylate: tert-butyl (2S,4R)-4-[(4-fluoro-2-pyridyl)oxy]-2-methyl-pyrrolidine-1-carboxylate (100 mg, 337 umol) was added to a mixture of 2-methoxyethanol (51 mg, 675 umol, 53 uL) NaH (34 mg, 844 umol, 60% purity) in THF (5.00 mL). The mixture was stirred at 80° C. for 12 hours. The mixture was quenched (NH₄Cl aq), extracted (EtOAc 3×10 mL), washed with brine (2×20 mL), dried over Na₂SO₄), filtered and concentrated to afford tert-butyl (2S,4R)-4-[[4-(2-methoxyethoxy)-2-pyridyl]oxy]-2-methyl-pyrrolidine-1-carboxylate (106 mg, 88% yield).

N-(4-fluoro-5-(((2S,4R)-4-((5-(2-methoxyethoxy)pyridin-2-yl)oxy)-2-methylpyrrolidin-1-yl)methyl)thiazol-2-yl)acetamide: The title compound was prepared in an analogous manner of that in Scheme 2 from tert-butyl (2S,4R)-4-[[4-(2-methoxyethoxy)-2-pyridyl]oxy]-2-methyl-pyrrolidine-1-carboxylate, and N-(4-fluoro-5-formylthiazol-2-yl)acetamide. LCMS (ESI): [M+H] 425. ¹HNMR: (500 MHz, Methanol-d₄) δ ppm 7.76 (d, J=3.05 Hz, 1H), 7.33 (dd, J=9.00, 3.05 Hz, 1H), 6.70 (d, J=9.00 Hz, 1H), 5.10-5.24 (m, 1H), 4.09 (dd, J=5.26, 3.74 Hz, 2H), 3.97 (d, J=14.65 Hz, 1H), 3.71 (dd, J=5.34, 3.66 Hz, 2H), 3.58 (d, J=14.65 Hz, 1H), 3.41 (s, 3H), 3.12 (d, J=11.29 Hz, 1H), 2.68 (dd, J=11.22, 6.33 Hz, 1H), 2.49-2.62 (m, 2H), 2.18 (s, 3H), 1.55-1.68 (m, 1H), 1.24 (d, J=5.65 Hz, 3H).

Example 1-151

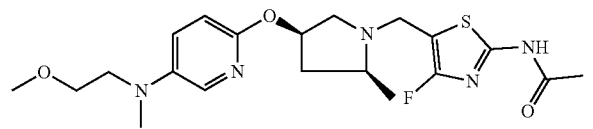 [SMILES: COCCN(C)c1ccc(O[C@@H]2C[C@H](C)N(Cc3sc(NC(C)=O)nc3F)C2)nc1]

N-(4-fluoro-5-(((2S,4R)-4-((5-((2-methoxyethyl)(methyl)amino)pyridin-2-yl)oxy)-2-methylpyrrolidin-1-yl)methyl)thiazol-2-yl)acetamide: The title compound was prepared in an analogous manner of that in Example 1-146 from tert-butyl (2S,4R)-4-((5-bromopyridin-2-yl)oxy)-2-methylpyrrolidine-1-carboxylate, 2-methoxy-N-methylethan-1-amine, and N-(4-fluoro-5-formylthiazol-2-yl)acetamide. LCMS (ESI): [M+H] 438. ¹HNMR: (400 MHz, Methanol-d₄) δ ppm 7.56 (d, J=3.18 Hz, 1H), 7.26 (dd, J=9.05, 3.18 Hz, 1H), 6.66 (d, J=8.80 Hz, 1H), 5.08-5.17 (m, 1H), 3.95 (d, J=14.67 Hz, 1H), 3.48-3.60 (m, 3H), 3.35-3.45 (m, 2H), 3.32 (s, 2H), 3.10 (br d, J=11.25 Hz, 1H), 2.89 (s, 3H), 2.65 (dd, J=11.00, 6.36 Hz, 1H), 2.48-2.59 (m, 2H), 2.18 (s, 3H), 1.54-1.67 (m, 1H), 1.24 (d, J=5.62 Hz, 3H).

Example 1-152

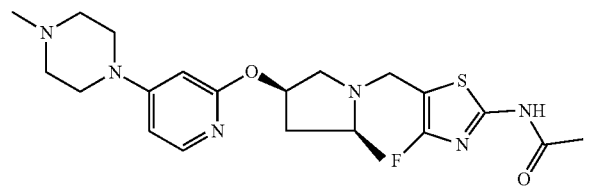 [SMILES: CC(=O)Nc1nc(F)c(CN2C[C@H](Oc3cc(N4CCN(C)CC4)ccn3)C[C@@H]2C)s1]

N-(4-fluoro-5-(((2S,4R)-2-methyl-4-((4-(4-methylpiperazin-1-yl)pyridin-2-yl)oxy)pyrrolidin-1-yl)methyl)thiazol-2-yl)acetamide: The title compound was prepared in an analogous manner of that in Example 1-22 from 1-(2-fluoropyridin-4-yl)-4-methylpiperazine, tert-butyl (2S,4R)-4-hydroxy-2-methylpyrrolidine-1-carboxylate, and N-(4-fluoro-5-formylthiazol-2-yl)acetamide. LCMS (ESI): [M+H] 449. ¹HNMR: (400 MHz, Methanol-d₄) δ ppm 7.74 (d, J=6.11 Hz, 1H), 6.51 (dd, J=6.36, 2.20 Hz, 1H), 6.13 (d, J=1.96 Hz, 1H), 5.14-5.21 (m, 1H), 3.97 (br d, J=14.67 Hz, 1H), 3.56 (br d, J=14.67 Hz, 1H), 3.33-3.39 (m, 4H), 3.11 (br d, J=11.00 Hz, 1H), 2.65 (br dd, J=11.13, 6.24 Hz, 1H), 2.51-2.60 (m, 5H), 2.35 (s, 3H), 2.18 (s, 3H), 1.54-1.67 (m, 2H), 1.24 (d, J=5.62 Hz, 3H).

Intermediate 16

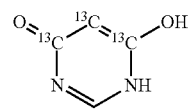

Pyrimidine-4,6-diol-4,5,6-¹³C₃: To a mixture of formamide (2.48 g, 2.19 mL, 55.2 mmol) and a solution of sodium ethoxide (26.0 g, 30 mL, 80.9 mmol) in ethanol (21% wt) was added diethyl malonate-¹³C₃ (4.00 g, 3.72 mL, 24.5 mmol) over 1 hour at 65-70° C. The mixture was stirred at reflux overnight, then cooled to room temperature and concentrated under reduced pressure. The residue was treated with concentrated aq. HCl (5.6 mL) and water (8.8 mL) at 0° C. The resulting precipitate was filtered, washed with cold water, and dried under reduced pressure to provide the title compound (2.81 g; 99%).

Intermediate 17

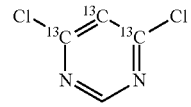

4,6-dichloropyrimidine-4,5,6-¹³C: To a solution of phosphorus oxychloride (40.4 g, 24.5 mL, 263 mmol) was added pyrimidine-4,6-diol-4,5,6-¹³C₃ (2.82 g, 24.5 mmol) in one portion, followed by N,N-dimethylaniline (4.75 g, 4.97 mL, 39.2 mmol). The resulting mixture was heated to reflux for 2 hours. The mixture was cooled to room temperature, concentrated under reduced pressure, and poured into water (50 mL). The solids were filtered and dried to provide 1.26 g of the title compound. The solution that remained was extracted with EtOAc (2×100 mL). The organic layer was dried over Na₂SO₄, filtered and concentrated under reduced pressure to give additional 1.2 g. The crude products were combined and purified over SiO₂ to provide the title compound (1.85 g; 50%).

Intermediate 18

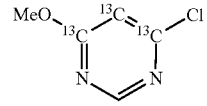

4-chloro-6-methoxypyrimidine-4,5,6-¹³C₃: A solution of sodium methoxide, prepared from sodium (95 mg, 4.11 mmol) and methanol (1.2 g, 1.53 mL, 38 mmol), was added dropwise to a solution of 4,6-dichloropyrimidine-4,5,6-¹³C₃ (624 mg, 4.11 mmol) in methanol (4.6 mL), maintaining the temperature at RT. The resulting solution was stirred at RT for 1 hour and then additional sodium methoxide (0.5 eq) was added. The mixture was stirred for 30 min and then diluted with DCM (12 mL) and washed with water (10 mL).

The organic layer was dried over Na₂SO₄, filtered and concentrated under reduced pressure to provide the title compound (426 mg, 70%).

Intermediate 19

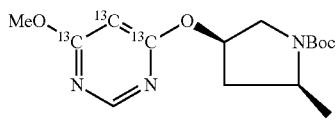 [SMILES: CO[13c]1[13cH][13c](O[C@@H]2CC[C@H](C)N(C(=O)OC(C)(C)C)C2)ncn1]

tert-butyl (2S,4R)-4-((6-methoxypyrimidin-4-yl-4,5,6-$^{13}C_3$)oxy)-2-methylpyrrolidine-1-carboxylate: To a 3-necked round bottom flask was charged with THF (10.3 mL), NaH (60% in mineral oil, 0.43 g, 10.8 mmol) was added slowly. t-Butyl (2S,4R)-4-hydroxy-2-methylpyrrolidine-1-carboxylate (1.60 g, 7.71 mmol) was added and the mixture was allowed to stir for 30 minutes. Another round bottomed flask was charged with 4-chloro-6-methoxypyrimidine-4,5,6-$^{13}C_3$ (1.14 g, 7.71 mmol) in THF (3.43 mL). The solution was heated to 60° C. and the previously mentioned mixture was added slowly at this temperature. The resulting mixture was heated to 60° C. for 1.5 hours and then the mixture was cooled to room temperature and saturated aq. NH₄C₁ was added (4 mL). The organic layer was dried over Na₂SO₄, filtered and concentrated. The residue was purified over SiO₂ to provide the title compound (1.30 g, 54%).

Intermediate 20

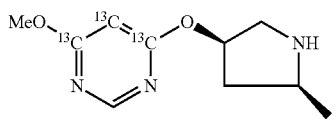 [SMILES: CO[13c]1[13cH][13c](O[C@@H]2CC[C@H](C)NC2)ncn1]

4-methoxy-6-(((3R,5S)-5-methylpyrrolidin-3-yl)oxy)pyrimidine-4,5,6-$^{13}C_3$: In a 3-necked round-bottom flask tert-butyl (2S,4R)-4-((6-methoxypyrimidin-4-yl-4,5,6-$^{13}C_3$)oxy)-2-methylpyrrolidine-1-carboxylate (1.30 g, 4.20 mmol) was dissolved in DCM. The solution was cooled to 0° C. and TFA (2.90 g, 1.9 mL, 25.0 mmol) was added dropwise. The mixture was allowed to stir overnight at RT. Another portion of TFA (1.5 equiv) was added and stirring was continued at RT overnight. The mixture was cooled to 0° C. 2 M NaOH (aq) was added until pH=11. The layers were separated and the alkaline water layer was extracted using DCM (2×50 mL). The combined organic layers were dried over Na₂SO₄, filtered and concentrated in vacuo to provide 786 mg of the title compound.

Example 1-153

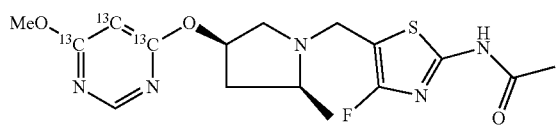 [SMILES: CO[13c]1[13cH][13c](O[C@@H]2CC[C@H](C)N(Cc3sc(NC(C)=O)nc3F)C2)ncn1]

N-(4-fluoro-5-(((2S,4R)-4-((6-methoxypyrimidin-4-yl-4,5,6-$^{13}C_3$)oxy)-2-methylpyrrolidin-1-yl)methyl)thiazol-2-yl)acetamide: Sodium triacetoxyborohydride (2.40 g, 11.1 mmol), 4-methoxy-6-(((3R,5S)-5-methylpyrrolidin-3-yl)oxy)pyrimidine-4,5,6-$^{13}C_3$ (0.786 g, 3.70 mmol) and acetic acid (445 mg, 424 μL, 7.41 mmol) were dissolved in ethyl acetate (15.7 g, 17 mL, 178 mmol). The mixture was warmed to 40° C. and stirred for 5 min at that temperature. Then, N-(4-fluoro-5-formylthiazol-2-yl)acetamide (718 mg, 3.81 mmol) was added in one portion. The reaction was stirred between 40-50° C. for 2 h. 1 M aqueous HC (5 mL) was added slowly. The layers were separated, and the organic layer was extracted again with 1 M aqueous HCl (10 mL). The combined acidic layers were cooled to 0° C. and basified with 2 M aqueous NaOH (20 mL) until pH=11. A solid precipitated; the mixture was stirred and cooled to room temperature before DCM (50 mL) was added to the mixture; the layers were separated. The aqueous layer was extracted again with DCM (50 mL) and the combined organic layers were dried over sodium sulfate, filtered and concentrated to give the crude product (1.36 g). The solid was suspended in MeOH (5 mL) and stirred at reflux for 10 min. The mixture was filtered off and the solid was washed with cold MeOH to provide 485 mg of the title compound. The solution was concentrated and more solid precipitated. This solid was filtered to give additional 217 mg. In total 702 mg of the titled compound were obtained. LCMS (EI): [M+H] 385.4.

Intermediate 21

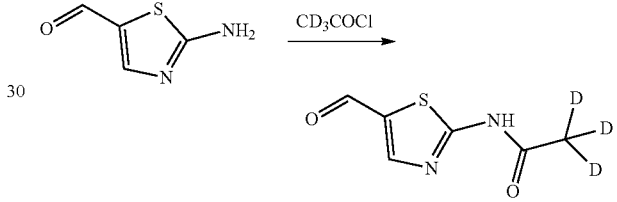

N-(5-formylthiazol-2-yl)acetamide-2,2,2-d₃: To a solution of 2-aminothiazole-5-carbaldehyde (491 mg, 3.83 mmol) and pyridine (930 uL, 11 mmol) in DCM (10. mL) was added acetyl-d3 chloride (550 uL, 7.7 mmol) dropwise at 0° C. The reaction mixture was stirred at room temperature for 3 d then was evaporated to dryness. Residue purified by silica gel chromatography using ethyl acetate in dichloromethane as eluent to give the title compound (452 mg, 68% yield). LCMS (ESI): [M+H] 174.1. ¹HNMR: (400 MHz, Methanol-d₄) δ 9.93 (s, 1H), 8.23 (s, 1H).

Intermediate 22

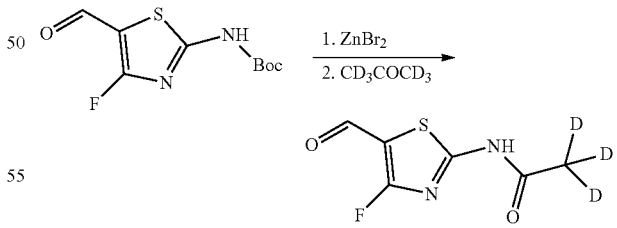

N-(4-fluoro-5-formylthiazol-2-yl)acetamide-2,2,2-d₃: Step 1: 2-amino-4-fluorothiazole-5-carbaldehyde: Zinc bromide (1.38 g, 6.13 mmol) was added to a mixture of tert-butyl (4-fluoro-5-formylthiazol-2-yl)carbamate (503 mg, 2.04 mmol) in DCM (12.5 mL) at rt. The reaction was stirred at 40° C. overnight then cooled to rt. 20% of the mixture was removed. The remaining mixture was diluted with ether and filtered, then washed with ether to give the title compound (376 mg, 158% yield, adjusted) as a light yellow solid which was used in the next step without further purifications. LCMS (ESI): [M+H] 146.9. ¹HNMR: (400 MHz, Methanol-d₄) δ 9.60 (s, 1H). ¹⁹F NMR (376 MHz, METHANOL-d₄) δ −95.27 (br s, 1F).
Step 2: N-(4-fluoro-5-formylthiazol-2-yl)acetamide-2,2,2-d₃: 2-amino-4-fluorothiazole-5-carbaldehyde (100 mg, 0.684 mmol) and pyridine (170 uL, 2.1 mmol) in DCM (2.5 mL) was cooled to 0° C. Acetic-2,2,2-d₃ anhydride (130 uL, 1.4 mmol) was slowly added then stirred at rt for 1 d. Reaction was evaporated, then the residue was partitioned between water, ethyl acetate. Organics were washed with saturated sodium chloride, dried over magnesium sulfate, filtered and evaporated. Sample purified by silica gel chromatography to the title compound (23 mg, 18% yield or 28% yield over 2 steps). ¹HNMR: (600 MHz, Methanol-d₄) δ 9.89 (s, 1H). ¹⁹FNMR: (565 MHz, Methanol-d₄) δ −100.90 (br s, 1F).
Intermediate 23

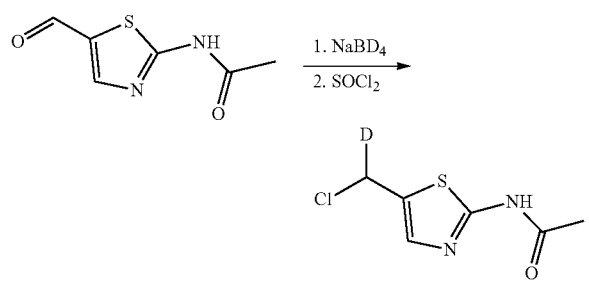

N-(5-(chloromethyl-d)thiazol-2-yl)acetamide: Step 1: N-(5-(hydroxymethyl-d)thiazol-2-yl)acetamide: To a solution of N-(5-formylthiazol-2-yl)acetamide (300. mg, 1.76 mmol) in MeOH (3.3 mL) and THF (5.0 mL) stirred at 0° C. was slowly added sodium borodeuteride (147 mg, 3.51 mmol), and the mixture was stirred at rt for 2 h. The reaction was quenched by addition of saturated aqueous NH₄Cl solution. The reaction was concentrated and treated with aqueous NH₄Cl, extracted with EtOAc (3×), washed with saturated NaCl solution, dried over MgSO₄, filtered and evaporated to give the title compound (221 mg, 72% yield). LCMS (ESI): [M+H] 174.1. ¹HNMR: (400 MHz, Methanol-d₄) δ 7.28 (d, J=1.00 Hz, 1H), 4.68-4.70 (m, 1H), 2.20 (s, 3H).
Intermediate 24

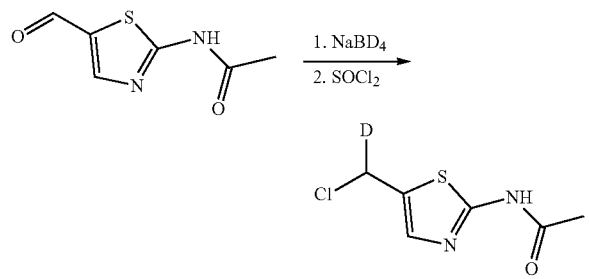

N-(5-(chloromethyl-d)thiazol-2-yl)acetamide:
Step 1: N-(5-(hydroxymethyl-d)thiazol-2-yl)acetamide: To a solution of N-(5-formylthiazol-2-yl)acetamide (300. mg, 1.76 mmol) in MeOH (3.3 mL) and THF (5.0 mL) stirred at 0° C. was slowly added sodium borodeuteride (147 mg, 3.51 mmol), and the mixture was stirred at rt for 2 h. The reaction was quenched by addition of saturated aqueous NH₄Cl solution. The reaction was concentrated and treated with aqueous NH₄Cl, extracted with EtOAc (3×), washed with saturated NaCl solution, dried over MgSO₄, filtered and evaporated to give the title compound (221 mg, 72% yield). LCMS (ESI): [M+H] 174.1. ¹HNMR: (400 MHz, Methanol-d₄) δ 7.28 (d, J=1.00 Hz, 1H), 4.68-4.70 (m, 1H), 2.20 (s, 3H).
Intermediate 25

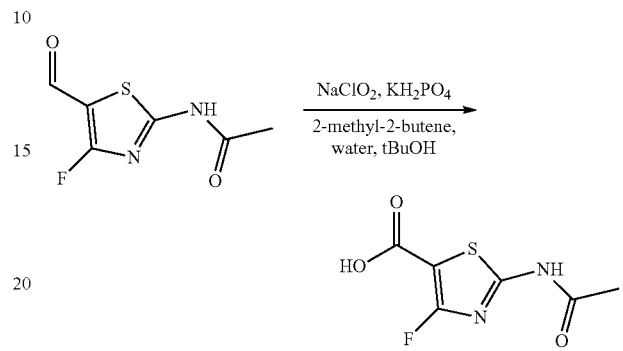

2-acetamido-4-fluorothiazole-5-carboxylic acid: To a stirred mixture of N-(4-fluoro-5-formylthiazol-2-yl)acetamide (500. mg, 2.66 mmol), monopotassium phosphate (1.09 g, 7.98 mmol) solution in water (5.0 mL) and 2-methyl-2-butene (3.7 mL, 35 mmol) in tert-butanol (28 mL) was added dropwise sodium chlorite (1.80 g, 16.0 mmol, 80% purity) in water (3.0 mL) under ice-bath cooling. The mixture was stirred at room temperature overnight. To the reaction mixture was added ethyl acetate and the mixture was washed with 5% citric acid solution, then with saturated sodium chloride. Organics were dried over sodium sulfate, filtered and evaporated. Sample was purified by silica gel chromatography using 0-50% methanol in methylene chloride as eluent. 450 mg isolated of material isolated, containing 25% starting material. 320 mg was repurified by preparative HPLC (ACN/H2O, 0.1% TFA modifier) to give the title compound (174 mg, 45% yield adjusted). LCMS (ESI): [M+H]205.0. ¹HNMR: (400 MHz, Methanol-d₄) δ 2.22 (s, 3H). ¹⁹FNMR: (376 MHz, Methanol-d4) δ −97.03 (s, 1F).
Intermediate 26

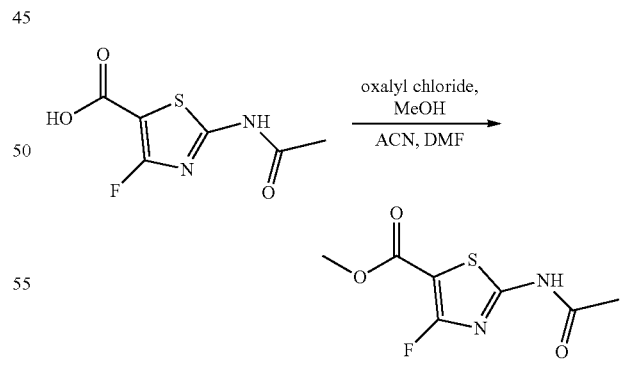

Methyl 2-acetamido-4-fluorothiazole-5-carboxylate: In a 20 mL vial, 2-acetamido-4-fluorothiazole-5-carboxylic acid (50. mg, 0.25 mmol) and oxalyl chloride (26 uL, 0.31 mmol) were dissolved in acetonitrile (1.0 mL). After 5 min, DMF (10. uL, 0.13 mmol) was added dropwise at RT with much gas evolution. The reaction was allowed to stir at RT for 2 hr. Methanol (1.0 mL) was added in one portion and the reaction was allowed to stir at rt overnight. The solvent was removed in vacuo and the resulting residue was then diluted with EtOAc and washed with sat NaHCO$_3$ solution and then with brine. The organics were dried over Na$_2$SO$_4$, filtered and evaporated under vacuum to give the crude title compound (33 mg, 63% yield). LCMS (ESI): [M+H] 219.1. $^1$HNMR: (400 MHz, Methanol-d$_4$) δ 3.83 (s, 3H), 2.22 (s, 3H). $^{19}$FNMR: (376 MHz, Methanol-d$_4$) δ −96.25 (s, 1F).
Intermediate 27

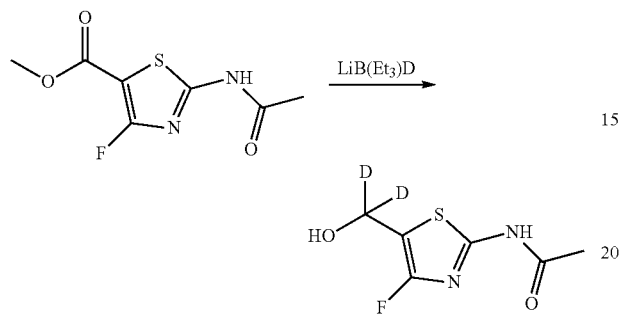

N-(4-fluoro-5-(hydroxymethyl-d$_2$)thiazol-2-yl)acetamide:
To a stirred mixture of methyl 2-acetamido-4-fluorothiazole-5-carboxylate (33 mg, 0.15 mmol) in toluene (1.0 mL), was added lithium triethylborodeuteride (310 uL, 1M in THF) slowly at 0° C. Reaction mixture was stirred 1 h at RT then was cooled to 0° C. and additional lithium triethylborodeuteride (310 uL, 1M in THF) was added slowly and the reaction was allowed to stir for 3 d at rt. The reaction was cooled to 0° C. and methanol (0.2 mL) was added very slowly followed by 5% citric acid solution (4 mL) (with gas evolution). The mixture was stirred for 10 minutes at rt then was extracted with ethyl acetate, washed with saturated sodium chloride, dried over sodium sulfate, filtered and evaporated. Purification was by silica gel chromatography using ethyl acetate in heptanes as eluent to give the title compound (11 mg, 38% yield). LCMS (ESI): [M+H] 193.1. $^1$HNMR (400 MHz, Methanol-d$_4$) δ 2.18 (s, 3H). $^9$FNMR: (376 MHz, Methanol-d$_4$) δ −118.83 (s, 1F).
Intermediate 28

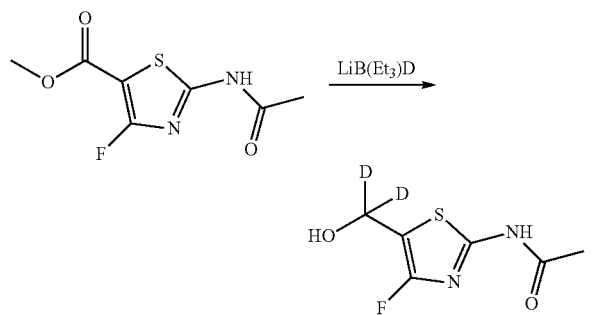

N-(4-fluoro-5-(hydroxymethyl-d$_2$)thiazol-2-yl)acetamide:
To a stirred mixture of methyl 2-acetamido-4-fluorothiazole-5-carboxylate (33 mg, 0.15 mmol) in toluene (1.0 mL), was added lithium triethylborodeuteride (310 uL, 1M in THF) slowly at 0° C. Reaction mixture was stirred 1 h at RT then was cooled to 0° C. and additional lithium triethylborodeuteride (310 uL, 1M in THF) was added slowly and the reaction was allowed to stir for 3 d at rt. The reaction was cooled to 0° C. and methanol (0.2 mL) was added very slowly followed by 5% citric acid solution (4 mL) (with gas evolution). The mixture was stirred for 10 minutes at rt then was extracted with ethyl acetate, washed with saturated sodium chloride, dried over sodium sulfate, filtered and evaporated. Purification was by silica gel chromatography using ethyl acetate in heptanes as eluent to give the title compound (11 mg, 38% yield). LCMS (ESI): [M+H] 193.1. $^1$HNMR (400 MHz, Methanol-d$_4$) δ 2.18 (s, 3H). $^{19}$FNMR: (376 MHz, Methanol-d$_4$) δ −118.83 (s, 1F).
Intermediate 29

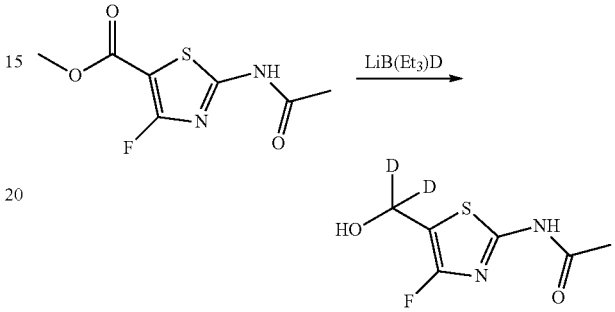

N-(4-fluoro-5-(hydroxymethyl-d$_2$)thiazol-2-yl)acetamide:
To a stirred mixture of methyl 2-acetamido-4-fluorothiazole-5-carboxylate (33 mg, 0.15 mmol) in toluene (1.0 mL), was added lithium triethylborodeuteride (310 uL, 1M in THF) slowly at 0° C. Reaction mixture was stirred 1 h at RT then was cooled to 0° C. and additional lithium triethylborodeuteride (310 uL, 1M in THF) was added slowly and the reaction was allowed to stir for 3 d at rt. The reaction was cooled to 0° C. and methanol (0.2 mL) was added very slowly followed by 5% citric acid solution (4 mL) (with gas evolution). The mixture was stirred for 10 minutes at rt then was extracted with ethyl acetate, washed with saturated sodium chloride, dried over sodium sulfate, filtered and evaporated. Purification was by silica gel chromatography using ethyl acetate in heptanes as eluent to give the title compound (11 mg, 38% yield). LCMS (ESI): [M+H] 193.1. $^1$HNMR (400 MHz, Methanol-d$_4$) δ 2.18 (s, 3H). $^{19}$FNMR: (376 MHz, Methanol-d$_4$) δ −118.83 (s, 1F).

Example 1-154

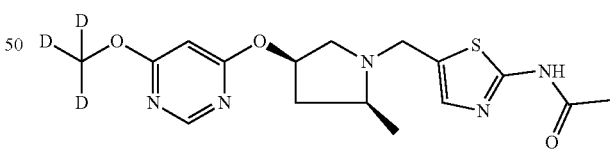

N-(5-(((2S,4R)-4-((6-(methoxy-da)pyrimidin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 4-bromo-6-(methoxy-d$_3$)pyrimidine, and N-(5-(chloromethyl)thiazol-2-yl)acetamide. LCMS (ESI): [M+H] 367.2. $^1$HNMR: (400 MHz, Methanol-d$_4$) δ 8.33 (d, J=1.00 Hz, 1H), 7.26 (s, 1H), 6.12 (d, J=0.75 Hz, 1H), 5.29-5.36 (m, 1H), 4.13 (dd, J=1.13, 14.18 Hz, 1H), 3.54 (d, J=14.31 Hz, 1H), 3.10 (d, J=11.55 Hz, 1H), 2.50-2.66 (m, 3H), 2.19 (s, 3H), 1.57-1.67 (m, 1H), 1.24 (d, J=5.77 Hz, 3H).

Example 1-155

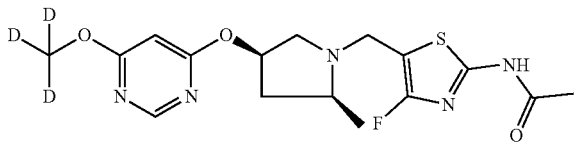 [SMILES: [2H]C([2H])([2H])Oc1cc(O[C@@H]2C[C@H](C)N(Cc3cnc(NC(C)=O)s3)C2)ncn1]

N-(4-fluoro-5-(((2S,4R)-4-((6-(methoxy-d₃)pyrimidin-4-yl)oxy)-2-methylpyrrolidin-1-yl)methyl)thiazol-2-yl)acetamide: The title compound was prepared in an analogous manner of that in scheme 1 from tert-butyl (2S,4R)-4-hydroxy-2-methylpyrrolidine-1-carboxylate, 4-bromo-6-(methoxy-d₃)pyrimidine, and N-(5-(chloromethyl)-4-fluorothiazol-2-yl)acetamide. LCMS (ESI): [M+H] 385.2. ¹HNMR: (400 MHz, Methanol-d₄) δ 8.35 (d, J=1.00 Hz, 1H), 6.13 (d, J=1.00 Hz, 1H), 5.28-5.37 (m, 1H), 3.96 (dd, J=1.00, 14.56 Hz, 1H), 3.56 (d, J=14.31 Hz, 1H), 3.13 (d, J=11.29 Hz, 1H), 2.67 (dd, J=5.77, 11.04 Hz, 1H), 2.51-2.63 (m, 2H), 2.18 (s, 3H), 1.56-1.66 (m, 1H), 1.24 (d, J=5.77 Hz, 3H). ¹⁹FNMR: (376 MHz, Methanol-d₄) δ −117.94 (s, 1F).

Example 1-156

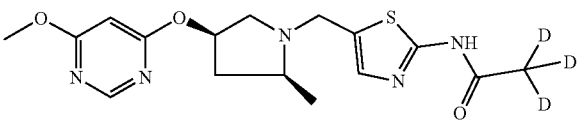 [SMILES: [2H]C([2H])([2H])C(=O)Nc1ncc(CN2C[C@H](Oc3cc(OC)ncn3)C[C@@H]2C)s1]

N-(5-(((2S,4R)-4-((6-methoxypyrimidin-4-yl)oxy)-2-methylpyrrolidin-1-yl)methyl)thiazol-2-yl)acetamide-2,2,2-d₃: The title compound was prepared in an analogous manner of that in scheme 1 from tert-butyl (2S,4R)-4-hydroxy-2-methylpyrrolidine-1-carboxylate, 4-chloro-6-methoxypyrimidine, and N-(5-formylthiazol-2-yl)acetamide-2,2,2-d₃. LCMS (ESI): [M+H] 367.2. ¹HNMR: (400 MHz, Methanol-d₄) δ 8.34 (d, J=0.75 Hz, 1H), 7.26 (s, 1H), 6.13 (d, J=0.75 Hz, 1H), 5.27-5.37 (m, 1H), 4.13 (dd, J=1.00, 14.31 Hz, 1H), 3.92 (s, 3H), 3.55 (d, J=14.31 Hz, 1H), 3.10 (d, J=11.29 Hz, 1H), 2.51-2.67 (m, 3H), 1.57-1.69 (m, 1H), 1.25 (d, J=6.02 Hz, 3H).

Example 1-157

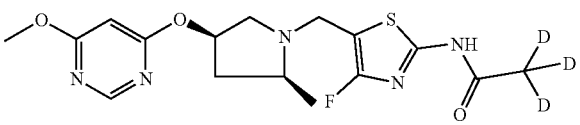

N-(4-fluoro-5-(((2S,4R)-4-((6-methoxypyrimidin-4-yl)oxy)-2-methylpyrrolidin-1-yl)methyl)thiazol-2-yl)acetamide-2,2,2-d₃ trifluoroacetate salt: The title compound was prepared in an analogous manner of that in scheme 1 from tert-butyl (2S,4R)-4-hydroxy-2-methylpyrrolidine-1-carboxylate, 4-chloro-6-methoxypyrimidine, and N-(4-fluoro-5-formylthiazol-2-yl)acetamide-2,2,2-d₃. LCMS (ESI): [M+H] 385.2. ¹HNMR: (600 MHz, Methanol-d₄) δ 8.43 (br s, 1H), 6.21 (br s, 1H), 5.66 (br s, 1H), 4.70 (br d, J=14.67 Hz, 1H), 4.46 (br d, J=14.67 Hz, 1H), 3.95 (br s, 3H), 3.60-3.81 (m, 3H), 2.95 (br s, 1H), 1.94-2.05 (m, 1H), 1.55 (br s, 3H). ¹⁹FNMR: (565 MHz, Methanol-d₄) 5-77.14 (br s, 3F), -110.91 (br s, 1F).

Example 1-158

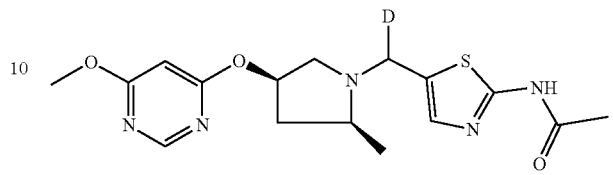

N-(5-(((2S,4R)-4-((6-methoxypyrimidin-4-yl)oxy)-2-methylpyrrolidin-1-yl)methyl-d)thiazol-2-yl)acetamide: The title compound was prepared in an analogous manner of that in scheme 1 from tert-butyl (2S,4R)-4-hydroxy-2-methylpyrrolidine-1-carboxylate, 4-chloro-6-methoxypyrimidine, and N-(5-(chloromethyl-d)thiazol-2-yl)acetamide. LCMS (ESI): [M+H] 365.1. ¹HNMR: (400 MHz, Methanol-d₄) δ 8.34 (d, J=1.00 Hz, 1H), 7.26 (d, J=0.75 Hz, 1H), 6.13 (s, 1H), 5.28-5.37 (m, 1H), 4.11 (s, 0.5H), 3.92 (s, 3H), 3.53 (s, 0.5H), 3.10 (d, J=11.29 Hz, 1H), 2.51-2.69 (m, 3H), 2.19 (s, 3H), 1.58-1.68 (m, 1H), 1.25 (dd, J=0.75, 5.77 Hz, 3H).

Example 1-159

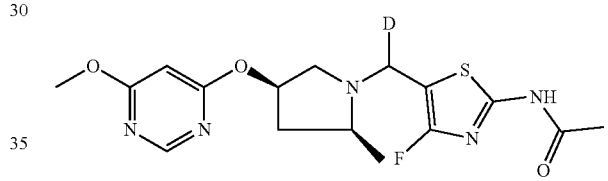

N-(4-fluoro-5-(((2S,4R)-4-((6-methoxypyrimidin-4-yl)oxy)-2-methylpyrrolidin-1-yl)methyl-d)thiazol-2-yl)acetamide: The title compound was prepared in an analogous manner of that in scheme 1 from tert-butyl (2S,4R)-4-hydroxy-2-methylpyrrolidine-1-carboxylate, 4-chloro-6-methoxypyrimidine, and N-(5-(chloromethyl-d)-4-fluorothiazol-2-yl)acetamide. LCMS (ESI): [M+H] 383.1. ¹HNMR: (400 MHz, Methanol-d₄) δ 8.35 (d, J=1.00 Hz, 1H), 6.14 (d, J=1.00 Hz, 1H), 5.29-5.37 (m, 1H), 3.95 (s, 0.5H), 3.92 (s, 3H), 3.54 (s, 0.5H), 3.10-3.16 (m, 1H), 2.68 (td, J=5.55, 11.23 Hz, 1H), 2.53-2.64 (m, 2H), 2.18 (s, 3H), 1.56-1.67 (m, 1H), 1.24 (d, J=5.52 Hz, 3H). ⁹FNMR: (376 MHz, Methanol-d₄) δ−117.92 (br s, 1F).

Intermediate 30

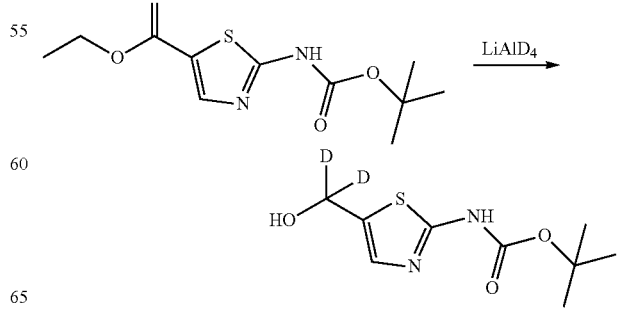

tert-butyl (5-(hydroxymethyl-d₂)thiazol-2-yl)carbamate: Lithium aluminum deuteride (54 mg, 1.3 mmol) was added to a 0° C. solution of ethyl 2-((tert-butoxycarbonyl)amino) thiazole-5-carboxylate (300. mg, 1.10 mmol) in THF (5.0 mL). The reaction mixture was stirred at RT for 1 h, then was diluted with 5 mL ether, cooled to 0° C. and carefully quenched by dropwise addition of water (55 uL). After 10 min, 15% aqueous NaOH (55 uL) was added then 165 uL water. After another 10 min, the mixture was filtered through a pad of CELITE®, washed with ether and the filtrate was concentrated in vacuo. The crude product was purified by silica gel chromatography using EtOAc in heptanes as eluent to give the title compound (93 mg, 37% yield). LCMS (ESI): [M+Na] 255.1. ¹HNMR: (400 MHz, Methanol-d4) δ 7.19 (s, 1H), 1.54 (s, 9H).

Intermediate 31

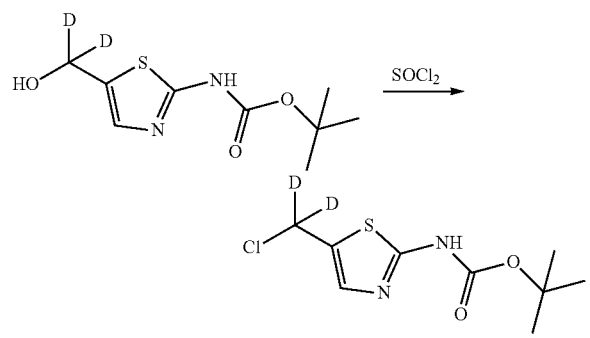

tert-butyl (5-(chloromethyl-d₂)thiazol-2-yl)carbamate: Thionyl chloride (120 uL, 1.6 mmol) was added to a 0° C. mixture of tert-butyl (5-(hydroxymethyl-d₂)thiazol-2-yl)carbamate (93 mg, 0.40 mmol) in DCM (1.0 mL). The reaction mixture was stirred at 0° C. for 2 h then was concentrated vacuo to give the title compound (111 mg). LCMS (ESI): [M-C₄H₈+H] 191.1 for methyl ether (LCMS sample in MeOH).

Intermediate 32

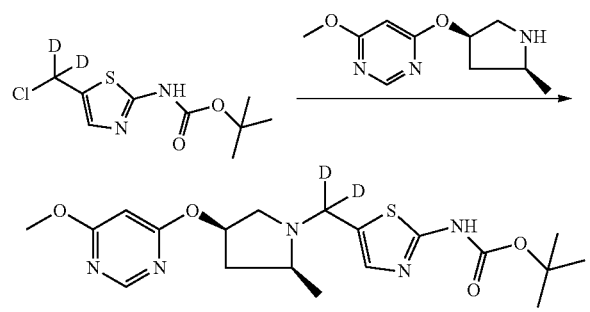

tert-butyl(S-(((2S,4R)-4-((6-methoxypyrimidin-4-yl)oxy)-2-methylpyrrolidin-1-yl)methyl-d₂)thiazol-2-yl)carbamate: 4-methoxy-6-(((3R,5S)-5-methylpyrrolidin-3-yl)oxy)pyrimidine (93 mg, 0.44 mmol) was dissolved in acetonitrile (1.0 mL) and TEA (250 uL, 1.8 mmol) was added dropwise. tert-butyl (5-(chloromethyl-d₂)thiazol-2-yl)carbamate (111 mg, 0.44 mmol) was added dropwise as a solution in acetonitrile (2.0 mL). After 2 h, reaction was evaporated to dryness, partitioned between water and ethyl acetate. Organics washed with saturated sodium chloride, dried over MgSO₄, filtered and evaporated. Residue was purified by silica gel chromatography using 3:1 ethyl acetate/ethanol (with 2% NH₄OH) in heptane as eluent to give the title compound (110 mg, 59% yield). LCMS (ESI): [M+H]424.2. ¹HNMR: (600 MHz, Methanol-d₄) δ 8.34 (s, 1H), 7.17 (s, 1H), 6.14 (s, 1H), 5.29-5.38 (m, 1H), 3.92 (s, 3H), 3.10 (d, J=11.74 Hz, 1H), 2.53-2.68 (m, 3H), 1.63 (ddd, J=3.67, 8.99, 13.02 Hz, 1H), 1.54 (s, 9H), 1.25 (d, J=5.87 Hz, 3H).

Intermediate 33

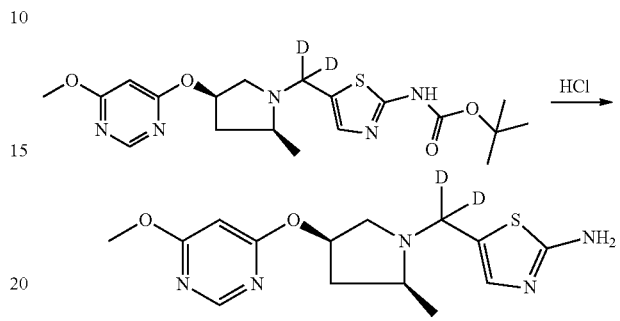

5-(((2S,4R)-4-((6-methoxypyrimidin-4-yl)oxy)-2-methylpyrrolidin-1-yl)methyl-D d₂)thiazol-2-amine hydrochloride salt: Tert-butyl (5-(((2S,4R)-4-((6-methoxypyrimidin-4-yl)oxy)-2-methylpyrrolidin-1-yl)methyl-d₂)thiazol-2-yl)carbamate (50. mg, 0.12 mmol) was dissolved in DCM (1.0 mL) and to this was added hydrogen chloride (0.30 mL, 4 M in dioxane). The reaction was stirred at rt for 4 h then was evaporated to dryness and co-distilled with DCM to give the title compound as an HCl salt. LCMS (ESI): [M+H] 324.1.

Example 1-160

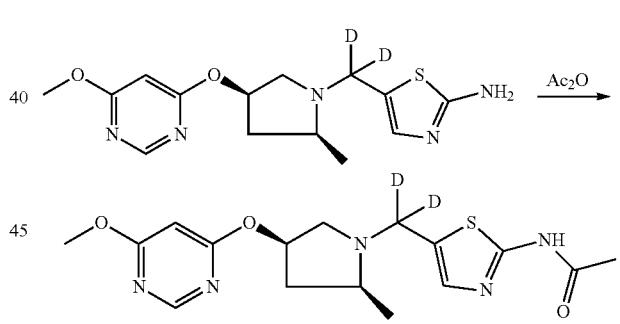

N-(5-(((2S,4R)-4-((6-methoxypyrimidin-4-yl)oxy)-2-methylpyrrolidin-1-yl)methyl-d₂)thiazol-2-yl)acetamide: 5-(((2S,4R)-4-((6-methoxypyrimidin-4-yl)oxy)-2-methylpyrrolidin-1-yl)methyl-d₂)thiazol-2-amine (0.12 mmol, x hydrochloride salt) was taken up in DCM (2.0 mL) and pyridine (50. uL, 0.62 mmol). To this was added acetic anhydride (27 uL, 0.29 mmol) followed by additional pyridine (1 mL, 12 mmol) and acetic anhydride (35 uL, 0.38 mmol). The reaction was stirred at RT overnight then was evaporated to dryness, diluted with water, extracted with EtOAc, washed with saturated sodium chloride, dried over magnesium sulfate, filtered and evaporated. Sample was purified by silica gel chromatography using 3:1 ethyl acetate/ethanol (with 2% NH₄OH) in heptane as eluent to give the title compound (17 mg, 32% yield over 2 steps). LCMS (ESI): [M+H] 366.1. ¹HNMR: (600 MHz, Methanol-d₄) δ 8.34 (s, 1H), 7.27 (s, 1H), 6.13 (s, 1H), 5.29-5.36 (m, 1H), 3.92 (s, 3H), 3.09 (d, J=11.01 Hz, 1H), 2.52-2.68 (m, 3H), 2.19 (s, 3H), 1.58-1.68 (m, 1H), 1.25 (d, J=5.14 Hz, 3H).

Example 1-161

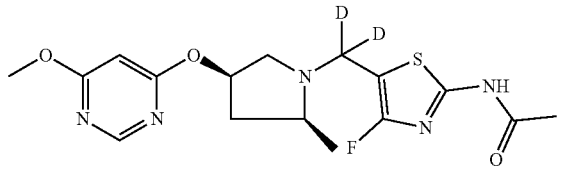 [SMILES: [2H]C([2H])(c1sc(NC(C)=O)nc1F)N1C[C@H](Oc2cc(OC)ncn2)C[C@@H]1C]

N-(4-fluoro-5-(((2S,4R)-4-((6-methoxypyrimidin-4-yl)oxy)-2-methylpyrrolidin-1-yl)methyl-d$_2$)thiazol-2-yl)acetamide: The title compound was prepared in an analogous manner of that in scheme 1 from tert-butyl (2S,4R)-4-hydroxy-2-methylpyrrolidine-1-carboxylate, 4-chloro-6-methoxypyrimidine, and N-(5-(chloromethyl-d$_2$)-4-fluorothiazol-2-yl)acetamide. LCMS (ESI): [M+H] 384.2. $^1$HNMR: (400 MHz, Methanol-d$_4$) δ 8.35 (d, J=0.75 Hz, 1H), 6.13 (d, J=1.00 Hz, 1H), 5.27-5.38 (m, 1H), 3.92 (s, 3H), 3.13 (d, J=11.55 Hz, 1H), 2.68 (dd, J=6.27, 11.29 Hz, 1H), 2.51-2.63 (m, 2H), 2.18 (s, 3H), 1.56-1.66 (m, 1H), 1.24 (d, J=5.77 Hz, 3H). $^{19}$FNMR: (376 MHz, Methanol-d$_4$) 5-117.92 (s, 1F).

Intermediate 34

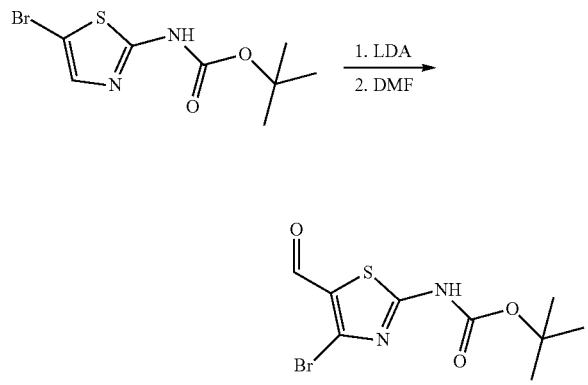

tert-butyl (4-bromo-5-formylthiazol-2-yl)carbamate: To a solution of diisopropylamine (3.3 mL, 23 mmol) in THF (20. mL) at 0° C. was added n-butyllithium (14.8 mL, 1.6 M in hexanes) slowly. The reaction was stirred for 20 minutes and then tert-butyl (5-bromothiazol-2-yl)carbamate (2.00 g, 7.16 mmol) was added slowly as a solution in THF (20. mL). The mixture was stirred for 30 minutes at 0° C. and then DMF (1.8 mL, 23 mmol) was added. The solution was stirred for 2 h at rt. EA and water were added, the layers were separated, and the organics were washed with brine. The organics were dried over sodium sulfate, filtered and concentrated. The crude material was purified by silica gel chromatography using ethyl acetate in heptane as eluent to yield the title compound (1.53 g, 70% yield). LCMS (ESI): [M+H] 308.9 for $^{81}$Br. $^1$HNMR: (400 MHz, Methanol-d$_4$) δ 9.83 (s, 1H), 1.56 (s, 9H).

Intermediate 35

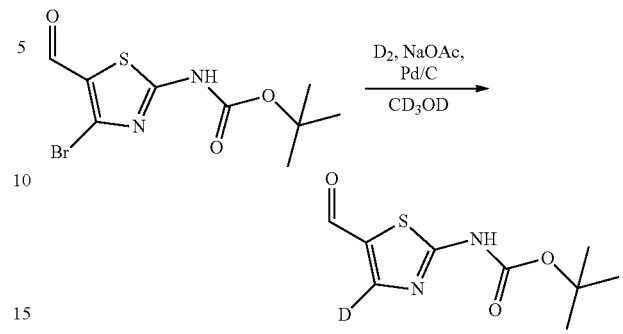

tert-butyl (5-formylthiazol-2-yl-4-d)carbamate: Into a flask under nitrogen with a mixture of tert-butyl (4-bromo-5-formylthiazol-2-yl)carbamate (202 mg, 0.66 mmol) and sodium acetate (113 mg, 1.38 mmol) was added palladium on carbon (91 mg, 10%) and anhydrous methanol-d4 (5.0 mL). Deuterium gas was slowly bubbled into the suspension under stirring for 15 minutes, and then the reaction flask under vigorous agitation was connected to a balloon filled with deuterium gas overnight. The palladium black was filtered off and rinsed with methanol. The filtrate was concentrated. Residue taken up in water, EtOAc. Organics washed with saturated sodium chloride, dried over sodium sulfate, filtered and evaporated to give the title compound (131 mg, 87% yield). LCMS (ESI): [M-C$_4$H$_8$+H] 174.1. $^1$HNMR: (400 MHz, Methanol-d$_4$) δ 9.87 (s, 1H), 1.56 (s, 9H).

Intermediate 36

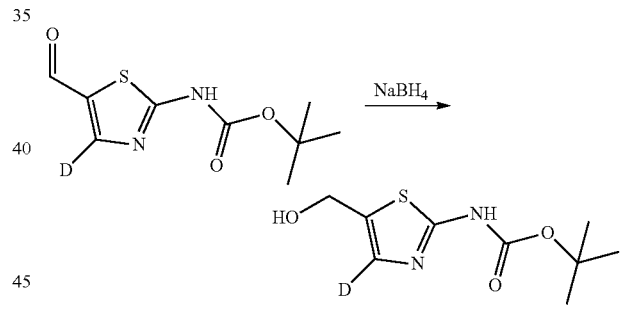

tert-butyl (5-(hydroxymethyl)thiazol-2-yl-4-d)carbamate: To a stirred 0° C. solution of tert-butyl (5-formylthiazol-2-yl-4-d)carbamate (131 mg, 0.57 mmol) in MeOH (1.4 mL) and THF (2.2 mL) was added slowly sodium borohydride (58 mg, 1.5 mmol) and the mixture was stirred at rt for 2 h. The reaction was quenched by dropwise addition of saturated aqueous NH$_4$C (2 mL). The reaction was concentrated and treated with aqueous NH$_4$Cl, extracted with EtOAc (3×), washed with saturated NaCl solution, dried over MgSO$_4$, filtered and evaporated to give the title compound (128 mg, 97% yield). LCMS (ESI): [M+Na] 254.1. $^1$HNMR: (400 MHz, Methanol-d$_4$) δ 4.68 (s, 2H), 1.54 (s, 9H).

Intermediate 37

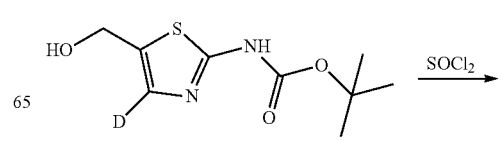

-continued

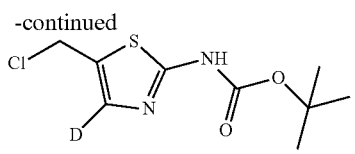

tert-butyl (5-(chloromethyl)thiazol-2-yl-4-d)carbamate: Thionyl chloride (160 uL, 2.2 mmol) was added to a 0° C. mixture of tert-butyl (5-(hydroxymethyl)thiazol-2-yl-4-d) carbamate (128 mg, 0.55 mmol) in DCM (1.4 mL). The reaction mixture was stirred at 0° C. for 2 h then was concentrated in vacuo to give the crude title compound. LCMS (ESI): [M-$C_4H_8$+H] 190.1 for methyl ether (LCMS sample in methanol).
Intermediate 38

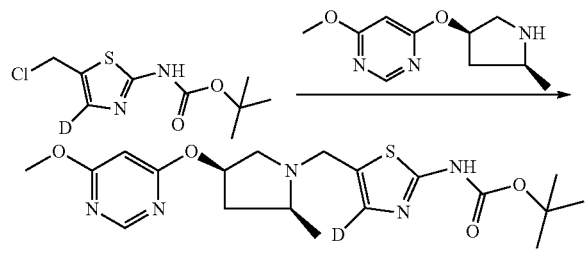

tert-butyl(S-(((2S,4R)-4-((6-methoxypyrimidin-4-yl)oxy)-2-methylpyrrolidin-1-yl)methyl)thiazol-2-yl-4-d)carbamate: 4-methoxy-6-(((3R,5S)-5-methylpyrrolidin-3-yl)oxy) pyrimidine (128 mg, 0.61 mmol) was dissolved in acetonitrile (1.5 mL) and to this was added TEA (340 uL, 2.45 mmol) dropwise. tert-butyl (5-(chloromethyl)thiazol-2-yl-4-d)carbamate (0.55 mmol) was added dropwise as an acetonitrile (1.5 mL) solution with stirring. After 2 h, reaction was evaporated to dryness, partitioned between water and ethyl acetate. Organics washed with saturated sodium chloride, dried over $MgSO_4$, filtered and evaporated. Crude material was purified by silica gel chromatography using 3:1 ethyl acetate/ethanol (with 2% $NH_4OH$) in heptane as eluent to give the title compound (177 mg, 68% yield over 2 steps). LCMS (ESI): [M+H] 423.2. ¹HNMR: (400 MHz, Methanol-$d_4$) δ 8.34 (d, J=0.75 Hz, 1H), 6.14 (d, J=0.75 Hz, 1H), 5.29-5.35 (m, 1H), 4.11 (d, J=14.06 Hz, 1H), 3.92 (s, 3H), 3.54 (d, J=14.31 Hz, 1H), 3.11 (d, J=11.29 Hz, 1H), 2.50-2.68 (m, 3H), 1.57-1.66 (m, 1H), 1.54 (s, 9H), 1.24 (d, J=5.77 Hz, 3H).
Intermediate 39

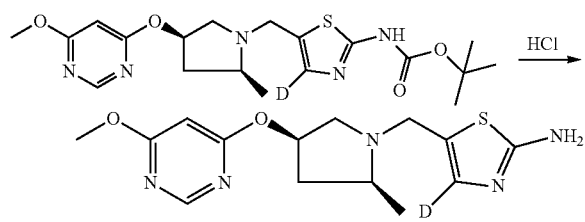

5-((2S,4R)-4-((6-methoxypyrimidin-4-yl)oxy)-2-methylpyrrolidin-1-yl)methyl)thiazol-4-d-2-amine hydrochloride salt: Tert-butyl (5-(((2S,4R)-4-((6-methoxypyrimidin-4-yl) oxy)-2-methylpyrrolidin-1-yl)methyl)thiazol-2-yl-4-d)carbamate (78 mg, 0.18 mmol) was dissolved in DCM (1.5 mL) and hydrogen chloride (460 uL, 4M in dioxane) was added. The reaction was stirred at rt for 4 h, then the reaction was evaporated to dryness, co-distilled 1× MeOH, then co-distilled 2× DCM to give the title compound. LCMS (ESI): [M+H] 323.1.

Example 1-162

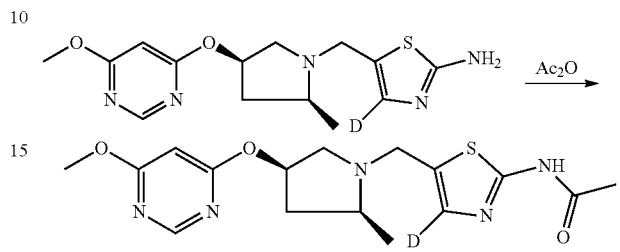

N-(5-(((2S,4R)-4-((6-methoxypyrimidin-4-yl)oxy)-2-methylpyrrolidin-1-yl)methyl)thiazol-2-yl-4-d)acetamide: 5-(((2S,4R)-4-((6-methoxypyrimidin-4-yl)oxy)-2-methylpyrrolidin-1-yl)methyl)thiazol-4-d-2-amine (0.18 mmol, x hydrochloride salt) was taken up in DCM (1.5 mL) and pyridine (1.0 mL). To this was added acetic anhydride (52 uL, 0.55 mmol). The reaction was stirred at rt overnight then was evaporated to dryness, diluted with water, extracted with EtOAc, washed with saturated sodium chloride, dried over sodium sulfate, filtered and evaporated. Residue was purified by silica gel chromatography using 3:1 ethyl acetate/ethanol (with 2% $NH_4OH$) in heptane as eluent to give the title compound (22 mg, 32% yield over 2 steps). LCMS (ESI): [M+H] 365.2. ¹HNMR: (400 MHz, Methanol-$d_4$) δ 8.33 (d, J=1.00 Hz, 1H), 6.13 (d, J=0.75 Hz, 1H), 5.29-5.35 (m, 1H), 4.13 (d, J=14.06 Hz, 1H), 3.92 (s, 3H), 3.55 (d, J=14.05 Hz, 1H), 3.10 (d, J=11.55 Hz, 1H), 2.50-2.67 (m, 3H), 2.19 (s, 3H), 1.58-1.67 (m, 1H), 1.24 (d, J=5.77 Hz, 3H).

Example 1-163

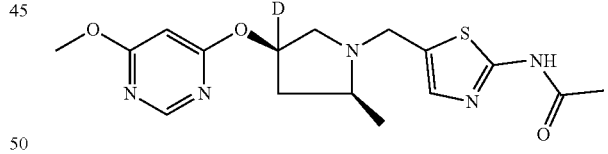

N-(5-(((2S,4R)-4-((6-methoxypyrimidin-4-yl)oxy)-2-methylpyrrolidin-1-yl-4-d)methyl)thiazol-2-yl)acetamide: The title compound was prepared in an analogous manner of that in scheme 1 from tert-butyl (2S)-4-hydroxy-2-methylpyrrolidine-1-carboxylate-4-d, 4-chloro-6-methoxypyrimidine, and N-(5-(chloromethyl)thiazol-2-yl)acetamide. Product mixture was separated into individual diastereomers by HPLC [XSelect CSH Prep C18 OBD 5 um 30×100 mm; Method: (A) 95% {$H_2O$}//(B) 5% {Acetonitrile} w/0.2% $NH_4OH$ (initial conditions hold for 0.5 min) then a linear gradient to 50% (A)/50% (B) over 12 min (flow rate: 50 mL/min)] followed by SFC [CHIRALPAK AD-H 30×250 mm, 5 um; Method: 40% IPA w/0.1% DEA in $CO_2$ (flow rate: 100 mL/min, ABPR 120 bar, MBPR 60 psi, column temp 40 deg C.)]. LCMS (ESI): [M+H] 365.2. ¹HNMR: (400 MHz, Methanol-$d_4$) δ 8.33 (d, J=0.75 Hz, 1H), 7.26 (s, 1H), 6.13 (d, J=0.75 Hz, 1H), 4.13 (dd, J=0.88, 14.18 Hz, 1H), 3.92 (s, 3H), 3.54 (d, J=14.06 Hz, 1H), 3.09 (d, J=11.29 Hz, 1H), 2.63 (d, J=11.55 Hz, 1H), 2.51-2.60 (m, 2H), 2.19 (s, 3H), 1.56-1.67 (m, 1H), 1.23-1.27 (m, 3H).

Example 1-164

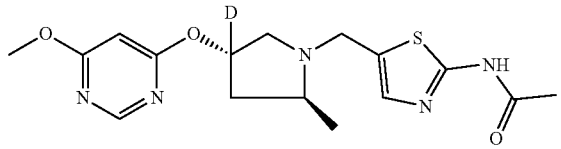 [SMILES: [2H][C@]1(Oc2cc(OC)ncn2)C[C@H](C)N(Cc2cnc(NC(C)=O)s2)C1]

N-(5-(((2S,4S)-4-((6-methoxypyrimidin-4-yl)oxy)-2-methylpyrrolidin-1-yl-4-d)methyl)thiazol-2-yl)acetamide: The title compound was prepared in an analogous manner of that in scheme 1 from tert-butyl (2S)-4-hydroxy-2-methylpyrrolidine-1-carboxylate-4-d, 4-chloro-6-methoxypyrimidine, and N-(5-(chloromethyl)thiazol-2-yl)acetamide. Product mixture was separated into individual diastereomers by HPLC [XSelect CSH Prep C18 OBD 5 um 30×100 mm; Method: (A) 95% ($H_2O$)//(B) 5% (Acetonitrile) w/0.2% $NH_4OH$ (initial conditions hold for 0.5 min) then a linear gradient to 50% (A)/50% (B) over 12 min (flow rate: 50 mL/min)] followed by SFC [CHIRALPAK AD-H 30×250 mm, 5 um; Method: 40% IPA w/0.1% DEA in $CO_2$ (flow rate: 100 mL/min, ABPR 120 bar, MBPR 60 psi, column temp 40 deg C.)]. LCMS (ESI): [M+H] 365.2. $^1$HNMR: (400 MHz, Methanol-$d_4$) δ 8.34 (s, 1H), 7.24 (s, 1H), 6.08 (d, J=0.75 Hz, 1H), 4.13 (d, J=14.05 Hz, 1H), 3.92 (s, 3H), 3.69 (d, J=14.31 Hz, 1H), 3.54 (d, J=11.04 Hz, 1H), 2.84-2.93 (m, 1H), 2.50 (d, J=11.29 Hz, 1H), 2.20 (s, 3H), 2.10 (dd, J=6.15, 13.93 Hz, 1H), 1.89 (dd, J=10.29, 13.80 Hz, 1H), 1.21 (d, J=6.02 Hz, 3H).

Example 1-165

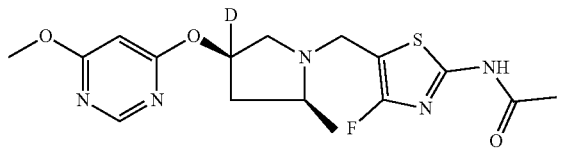 [SMILES: [2H][C@@]1(Oc2cc(OC)ncn2)C[C@H](C)N(Cc2sc(NC(C)=O)nc2F)C1]

N-(4-fluoro-5-(((2S,4R)-4-((6-methoxypyrimidin-4-yl)oxy)-2-methylpyrrolidin-1-yl-4-d)methyl)thiazol-2-yl)acetamide: The title compound was prepared in an analogous manner of that in scheme 1 from tert-butyl (2S)-4-hydroxy-2-methylpyrrolidine-1-carboxylate-4-d, 4-chloro-6-methoxypyrimidine, and N-(5-(chloromethyl)-4-fluorothiazol-2-yl)acetamide. Product mixture was separated into individual diastereomers by SFC [CHIRALPAK AD-H 30×250 mm, 5 um; Method: 45% MeOH w/0.1% DEA in $C_{O2}$ (flow rate: 100 mL/min, ABPR 120 bar, MBPR 40 psi, column temp 40 deg C.)]. LCMS (ESI): [M+H] 383.2. $^1$HNMR: (400 MHz, Methanol-$d_4$) δ 8.35 (d, J=1.00 Hz, 1H), 6.13 (d, J=1.00 Hz, 1H), 3.96 (dd, J=1.00, 14.56 Hz, 1H), 3.92 (s, 3H), 3.55 (d, J=14.56 Hz, 1H), 3.12 (d, J=11.29 Hz, 1H), 2.66 (d, J=11.29 Hz, 1H), 2.50-2.62 (m, 2H), 2.18 (s, 3H), 1.55-1.66 (m, 1H), 1.24 (d, J=5.77 Hz, 3H). $^{19}$FNMR: (376 MHz, Methanol-$d_4$) δ -117.94 (s, 1F).

Example 1-166

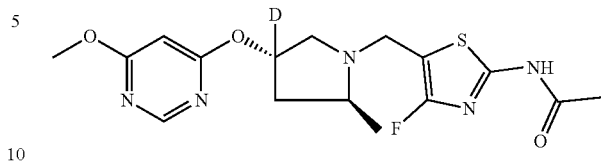

N-(4-fluoro-5-(((2S,4S)-4-((6-methoxypyrimidin-4-yl)oxy)-2-methylpyrrolidin-1-yl-4-d)methyl)thiazol-2-yl)acetamide: The title compound was prepared in an analogous manner of that in scheme 1 from tert-butyl (2S)-4-hydroxy-2-methylpyrrolidine-1-carboxylate-4-d, 4-chloro-6-methoxypyrimidine, and N-(5-(chloromethyl)-4-fluorothiazol-2-yl)acetamide. Product mixture was separated into individual diastereomers by SFC [CHIRALPAK AD-H 30×250 mm, 5 um; Method: 45% MeOH w/0.1% DEA in $C_{O2}$ (flow rate: 100 mL/min, ABPR 120 bar, MBPR 40 psi, column temp 40 deg C.)]. LCMS (ESI): [M+H] 383.2. $^1$HNMR: (400 MHz, Methanol-$d_4$) δ 8.34 (d, J=0.75 Hz, 1H), 6.07 (d, J=1.00 Hz, 1H), 3.95 (dd, J=0.75, 14.81 Hz, 1H), 3.92 (s, 3H), 3.66 (d, J=14.56 Hz, 1H), 3.56 (d, J=10.79 Hz, 1H), 2.80-2.92 (m, 1H), 2.52 (d, J=10.79 Hz, 1H), 2.18 (s, 3H), 2.08 (dd, J=6.15, 13.93 Hz, 1H), 1.86 (dd, J=10.16, 13.93 Hz, 1H), 1.20 (d, J=6.02 Hz, 3H). $^{19}$FNMR: (376 MHz, Methanol-$d_4$) δ -118.18 (s, 1F).

Biological Data

OGA Enzyme Inhibition Biochemical Assay

Recombinant full length human OGA enzyme was purchased from Origene. 4-MUGlcNAc substrate was purchased from Sigma. All other reagents were purchased from Sigma or Fisher. Assay buffer consists of the McIlvaine buffer system, pH 6.4 (0.2M $Na_2HPO_4$ mixed with 0.1M citric acid) and 0.01% BSA. Reactions consist of 1 nM OGA, 100 μM 4-MUGlcNAc ($K_m$), and compound in a final volume of 0 μl. Reactions were incubated for 90 minutes at room temperature and quenched with 40 μl of 3M glycine, pH 10 and read on a Perkin Elmer Envision plate reader (Ex: 355 nm/Em: 460 nm). Compounds were tested with a 10-point dose-response starting from 20 μM with a 4-fold dilution. Data was fit using GraphPad Prism using a 4-parameter fit with variable slope.

Description of Cellular OGA-Tau MSD Assay

HEK-293T cells were transfected with OGT and Tau-V5 plasmids using Lipofectamine and grown overnight. Next day, the cells were collected and re-plated at 1×10$^5$ cells per well in 96 well plates. Cells were incubated for 4 hr at 37° C., before compounds were added at 1 uM, with 3-fold dilutions in a 10-point titration. Cell plates were incubated with compounds overnight at 37° C. The next day media was removed from wells by gentle aspiration and 120 ul of 1× Cell Lysis buffer mixed with protease and phosphatase cocktail added to each well. A freeze thaw was performed at −80° C., then mixed before transferring 50 ul to MSD plates coated with V5-tag antibody to capture Tau. MSD Plates were incubated overnight at 4° C., on a plate shaker. The following day, plates were washed and incubated with Tau-S400-GlcNAc antibody for 2 hr and then developed with rabbit Sulfo-tag antibody. Final read out was carried out on an MSD 600 reader. The data was analyzed using Graph Pad or Genedata, the data was normalized and % activity versus log of compound concentration was plotted. The $IC_{50}$ values were obtained from a 4 parameter fit.

Description of Rat Liver Microsome Stability Assay

Compound (1 uM final concentration) was incubated with rat liver microsomes (0.5 mg/mL) in 0.1M sodium phosphate buffer (pH 7.4) plus 3.3 mM magnesium chloride in the presence or absence of 1 mM nicotinamide adenine dinucleotide phosphate (NADPH) at 37° C. Aliquots (40 uL) at 0, 5, 10, 15, 25 and 40 minutes post NADPH addition (or compound addition for reactions in absence of NADPH) were transferred into individual 96-well plate wells containing 40 ng/ml of 8-cyclopentyl-1,3-dipropylxanthine (CPDPX, internal standard) in 160 uL acetonitrile:methanol (1:1 v/v). The sample-containing plates were centrifuged (10 minutes, 3220×g) and 50 uL of the supernatant from each well was transferred into a clean analytical sample 96-well plate well containing 300 uL of 20:80:0.1 acetonitrile/water/formic acid, mixed, then directly injected onto an LC/MS/MS system for sample analysis.

HPLC and Mass Spectrometer Conditions for Stability Assays

The LC/MS/MS system consisted of an ultra high throughput RapidFire® 300 system (Agilent Technologies, Santa Clara, CA) coupled to a Triple Quad 5500 mass spectrometer (ABSciex, Foster City, CA). Sample load and wash were performed on a RapidFire® $C_4$ cartridge using 0.1% formic acid in water as mobile phase A and sample elution using 0.1% formic acid in acetonitrile:methanol (1:1 v/v) as mobile phase B.

RapidFire® Operating Conditions:

TABLE 1

| RapidFire ® Flow Program Process | Duration (ms) | Mobile Phase | Flow Rate (mL/min) |
|---|---|---|---|
| Aspirate | 1200 | A | 1.0 |
| Load/Wash | 4000 | A | 1.0 |
| Elute | 7000 | B | 1.0 |
| Re-equilibrate | 500 | A | 1.0 |

TABLE 2

| MRM Parameters Q1 Mass (amu) | Q3 Mass (amu) | Dwell (msec) | Declustering Potential | Collision Energy | Collision Exit Potential | |
|---|---|---|---|---|---|---|
| 305.2 | 263.1 | 50 | 180 | 30 | 15 | CPDPX |

| Source Parameters | Parameter Setting |
|---|---|
| CAD Gas | 9 |
| Curtain Gas | 30 |
| Ion Source Gas 1 | 60 |
| Ion Source Gas 2 | 70 |
| Ion Spray Voltage | 5500 |
| Temperature | 600 |

Data Analysis:

CLint,app (apparent intrinsic clearance) was calculated using the following equation for microsome stability:

$$CL_{int,app} = \frac{0.693}{T_{\frac{1}{2}}^{in\ vitro}} \times \frac{\text{incubation volume}}{\text{mg of microsomal protein}} \times$$

$$\frac{45\ \text{mg microsomal protein}}{\text{grant liver}} \times \frac{20^a\ \text{grams of liver}}{\text{kg body weight}}$$

where "a" represents 45 grams of liver/kg of body weight for rat.

$CL_{int,app}$ (apparent intrinsic clearance) was calculated using the following equation for hepatocyte stability:

$CL_{hep}$(hepatic clearance) was calculated using the following equation for microsomes:

$$CL_{hep} = \frac{Q_h \times CL_{int,app}}{Q_h + CL_{int,app}}$$

using 55 mL/minute/kg as Qh (hepatic blood flow) for rat.

Description of the MDR1-MDCK Efflux Ratio Assay

MDR1-MDCK cell monolayers were grown to confluence on microporous polyester membranes in 96-well Corning insert plates. The permeability assay buffer was Hanks' Balanced Salt Solution containing 10 mM HEPES at pH of 7.4. Loperamide (11M) was used as a positive control P-gp substrate. Propranolol and Bestatin (1 μM) were used as high and low permeability comparators, respectively.

Test compounds or positive control P-gp substrate/permeability comparators were added to respective apical and basolateral chambers for bidirectional assessment of permeability. Receiver buffer (transport buffer supplemented with 1% bovine serum albumin) was added to respective receiver chambers. MDR1-MDCK cells were incubated with test compounds at 37° C. with 5% $CO_2$ for 2 hr. Samples were collected from the donor chamber at both 0 and 120 minutes, and from the receiver chamber at 120 minutes. Test and control compound concentrations were determined using LC-MS/MS analysis. Each determination was performed in triplicate. The apparent permeability ($P_{app}$), efflux ratio and mass balance (percent recovery) were calculated as follows:

$P_{app} = (dC_r/dt) \times V_r/(A \times C_E)$

Mass balance $= 100 \times ((V_r \times C_r^{final}) + (V_d \times C_d^{final}))/(V_d \times C_E)$ Efflux ratio $= P_{app(B-A)}/P_{app(A-B)}$ where:

$dC_r/dt$ is the cumulative concentration in the receiver compartment versus time in μM s$^{-1}$ $V_r$ is the volume of the receiver compartment in cm$^3$ $V_d$ is the volume of the donor compartment in cm$^3$ A is the area of the insert (0.143 cm$^2$ for 96-well insert)

$C_E$ is the estimated experimental concentration (Time=0) of the dosing solution $C_r^{final}$ is the concentration of the receiver at the end of the incubation period $C_d^{final}$ is the concentration of the donor at the end of the incubation period.

The following Table 1 shows the activity data for some of the compounds of the present invention. In some instances, the OGA inhibition, MDR1-MDCK efflux ratio, and rat liver microsome stability assays were repeated and whenever the final data in subsequent assays was different, the data is provided below and indicated with an asterisk (*). The symbol "-" indicates that the data is not available.

| Example | OGA Biochemical IC$_{50}$ (nM) | OGA (S400 O-GLCNAC) IC$_{50}$ (μM) | MDR1-MDCK Efflux Ratio (B-A/A-B) | RLM % Qh (%) |
|---|---|---|---|---|
| 1-1 | <1 | 0.002 | 4.8 | 31 |
| 1-2 | 210 | 0.035 | 2.3 | 86 |
|  |  |  | 2.1* |  |
| 1-3 | 140 | 0.038 | 2.3 | 82 |
|  |  |  | 2.2* |  |

| Example | OGA Biochemical IC$_{50}$ (nM) | OGA (S400 O-GLCNAC) IC$_{50}$ (μM) | MDR1-MDCK Efflux Ratio (B-A/A-B) | RLM % Qh (%) |
|---|---|---|---|---|
| 1-4 | 1.2 | 0.006 | 6.1 | 94 |
| 1-5 | 1.6 | 0.004 | 3.1 | 93 |
| 1-6 | 80 | 0.037 | 1.7 | 40 |
| 1-7 | >1000 2000* | — | — | — |
| 1-8 | 460 | >1.000 | 2.3 | 76 |
| 1-9 | 39 | 0.032 | 1.9 | 87 |
| 1-10 | 28 | 0.115 | 1.9 | 76 |
| 1-11 | <1 | 0.003 | 1.1 1.9* | 73 |
| 1-12 | <1 | 0.003 0.002* | 10.0 8.9* | 97 98* |
| 1-13 | 1.1 | 0.002 | 2.4 | 90 |
| 1-14 | 1.3 | 0.005 | 2.9 | 68 |
| 1-15 | <1 | 0.002 | 2.2 | 95 |
| 1-16 | <1 | 0.001 | 9.7 | 50 51* |
| 1-17 | <1 | 0.002 | 12.0 12.4* | 88 |
| 1-18 | 2.4 | 0.012 | 11.7 | 48 |
| 1-19 | 1.2 | — 0.006* | 3.2 | 60 |
| 1-20 | <1 | — 0.007* | 2.9 3.0* | 63 |
| 1-21 | <1 | 0.007 0.008* | 3.8 | — |
| 1-22 | <1 | 0.002 | 2.8 2.9* | 44 48* |
| 1-23 | <1 | 0.003 | 7.7 | 31 |
| 1-24 | <1 | 0.001 | 21.9 | 51 |
| 1-25 | <1 | <0.001 | 25.4 | 46 |
| 1-26 | <1 | 0.001 | 10.1 | 53 |
| 1-27 | 850 | — | — | — |
| 1-28 | 16 | 0.047 | 1.8 | 33 |
| 1-29 | 58 | 0.097 | 2.9 | 63 |
| 1-30 | 15 | 0.021 | 3.0 | 73 |
| 1-31 | 2900 | >1.000 | 2.9 | 40 |
| 1-32 | 14 | 0.032 | 3.1 | 83 |
| 1-33 | 17 | 0.051 | 2.9 | 65 |
| 1-34 | <1 | 0.002 | 4.1 | 90 |
| 1-35 | <1 | 0.002 | 4.3 | 92 |
| 1-36 | 1700 | — | — | — |
| 1-37 | 36 | 0.027 | 2.4 | 16 |
| 1-38 | 250 | >1.000 | 3.9 | 32 |
| 1-39 | 55 | 0.030 | 4.5 | 57 |
| 1-40 | 720 | >1.000 | 5.3 | 20 |
| 1-41 | 24 | 0.029 | 4.3 | 80 |
| 1-42 | 39 | 0.081 | 3.9 | 61 |
| 1-43 | <1 | 0.001 | 6.9 | 81 |
| 1-44 | <1 | 0.002 | 9.3 | 88 |
| 1-45 | 47 | 0.966 | 1.7 | 61 |
| 1-46 | 1 | 0.038 | 3.2 | 55 |
| 1-47 | <1 | 0.001 | 1.5 | 76 |
| 1-48 | 150 | 0.821 | 24.1 | 57 |
| 1-49 | <1 | 0.010 | 18.9 | 34 |
| 1-50 | <1 | 0.001 | 22.4 | 47 |
| 1-51 | 2 | 0.024 | 23.3 | 51 |
| 1-52 | 33 | 0.055 | 12.9 | 76 |
| 1-53 | 1700 | >1.000 | 21.8 | 26 |
| 1-54 | 11 | 0.070 | 25.4 | 78 |
| 1-55 | 1.1 | 0.013 | 19.0 | 85 |
| 1-56 | <1 | — | 21.8 | 91 |
| 1-57 | <1 | 0.003 | 26.4 | 93 |
| 1-58 | 520 | >1.000 | 28.5 | 16 |
| 1-59 | 1.9 | 0.008 | 22.2 | 55 |
| 1-60 | <1 | 0.001 | 21.3 | 56 |
| 1-61 | 7 | 0.039 | 45.2 | 31 |
| 1-62 | 26 | 0.089 | 65.0 | 32 |
| 1-63 | 420 | >1.000 | 45.3 | 16 |
| 1-64 | 23 | 0.031 | 35.3 | 67 |
| 1-65 | 2.1 | 0.018 | 17.0 | 85 |
| 1-66 | <1 | 0.004 | 37.9 | 82 |
| 1-67 | <1 | 0.003 | 4.9 | 90 |
| 1-68 | <1 | 0.002 | 28.6 | 34 |
| 1-69 | <1 | 0.003 | 6.1 | 59 |
| 1-70 | <1 | 0.005 | 19.7 | 16 |
| 1-71 | 1.7 | 0.016 | 3.5 | 76 |
| 1-72 | 7.2 | 0.008 | 55.1 | 64 |
| 1-73 | <1 | 0.003 | 2.9 | 57 |
| 1-74 | 6.4 | 0.013 | 50.7 | 94 |
| 1-75 | <1 | 0.002 | 6.7 | 58 |
| 1-76 | 2.6 | 0.025 | 6.0 | 65 |
| 1-77 | <1 | 0.010 | | 58 |
| 1-78 | 2.4 | 0.006 | 4.1 | 47 |
| 1-79 | 11 | 0.041 | 3.6 | 41 |
| 1-80 | 1.2 | <0.001 | 18.1 | 65 |
| 1-81 | 8.4 | — | 7.3 | 74 |
| 1-82 | <1 | 0.002 | 16.7 | 38 |
| 1-83 | <1 | 0.001 | 38.6 | 16 |
| 1-84 | <1 | 0.001 | 20.5 | 48 |
| 1-85 | <1 | 0.002 | 3.8 | 60 |
| 1-86 | <1 | <0.001 | 11.2 | 26 |
| 1-87 | <1 | <0.001 | 1.8 | 81 |
| 1-88 | <1 | 0.001 | 4.7 | 98 |
| 1-89 | <1 | <0.001 | 19.7 | 66 |
| 1-90 | <1 | <0.001 | 1.1 | 88 |
| 1-91 | <1 | <0.001 | 9.9 | 81 |
| 1-92 | <1 | 0.001 | 10.0 | 54 |
| 1-93 | <1 | 0.002 | 14.3 | 42 |
| 1-94 | <1 | 0.002 | 1.8 | 91 |
| 1-95 | <1 | 0.001 | 3.6 | 72 |
| 1-96 | <1 | 0.001 | 1.2 | 86 |
| 1-97 | <1 | 0.003 | 3.7 | 52 |
| 1-98 | <1 | 0.001 | 2.1 | 93 |
| 1-99 | <1 | 0.001 | 2.2 | 95 |
| 1-100 | <1 | 0.001 | 4.4 | 56 |
| 1-101 | <1 | 0.003 | 1.5 | 88 |
| 1-102 | <1 | 0.002 | 1.2 | 82 |
| 1-103 | <1 | 0.003 | 15.9 | 45 |
| 1-104 | <1 | 0.002 | 16.0 | 30 |
| 1-105 | <1 | 0.002 | 2.4 | 74 |
| 1-106 | 2.4 | — | 4.6 | 86 |
| 1-107 | 1.7 | — | 17.2 | 58 |
| 1-108 | <1 | 0.002 | 3.4 | 79 |
| 1-109 | <1 | 0.008 | 12.7 | 16 |
| 1-110 | <1 | 0.001 | 34.4 | 39 |
| 1-111 | <1 | 0.001 | 19.5 | 30 |
| 1-112 | <1 | 0.001 | 5.3 | 45 |
| 1-113 | 2.1 | 0.005 | 2.1 | 61 |
| 1-114 | <1 | 0.002 | 1.9 | 69 |
| 1-115 | <1 | 0.002 | 4.7 | 54 |
| 1-116 | <1 | 0.001 | 19.6 | 55 |
| 1-117 | <1 | — | 1.4 | 93 |
| 1-118 | <1 | 0.001 | 3.5 | 85 |
| 1-119 | 1.3 | 0.019 | 6.3 | 50 |
| 1-120 | <1 | 0.002 | 10.3 | 64 |
| 1-121 | <1 | 0.003 | 3.4 | 77 |
| 1-122 | <1 | 0.003 | 2.1 | 32 |
| 1-123 | 1.1 | 0.005 | 5.7 | 55 |
| 1-124 | <1 | 0.003 | 11.2 | 16 |
| 1-125 | 1.4 | — | 1.0 | 54 |
| 1-126 | <1 | 0.002 | 3.8 | 48 |
| 1-127 | 1.9 | 0.008 | 3.1 | 62 |
| 1-128 | <1 | 0.001 | 26.3 | 48 |
| 1-129 | <1 | 0.001 | 25.5 | 65 |
| 1-130 | <1 | 0.003 | 30.3 | 37 |
| 1-131 | <1 | 0.001 | 17.8 | 58 |
| 1-132 | <1 | 0.002 | 19.7 | 76 |
| 1-133 | <1 | 0.001 | 23.6 | 43 |
| 1-134 | <1 | 0.001 | 53.4 | 70 |
| 1-135 | <1 | 0.001 | 76.5 | 36 |
| 1-136 | <1 | 0.002 | 32.0 | 24 |
| 1-137 | <1 | 0.002 | 154.8 | 41 |
| 1-138 | <1 | 0.028 | 2.6 | 87 |
| 1-140 | <1 | 0.004 | 8.4 | 43 |
| 1-141 | 1.0 | 0.007 | 27.1 | 53 |
| 1-142 | <1 | 0.002 | 8.3 | 59 |
| 1-143 | <1 | 0.004 | 25.6 | 75 |

-continued

| Example | OGA Biochemical IC$_{50}$ (nM) | OGA (S400 O-GLCNAC) IC$_{50}$ (µM) | MDR1-MDCK Efflux Ratio (B-A/A-B) | RLM % Qh (%) |
|---|---|---|---|---|
| 1-144 | <1 | — | — | — |
| 1-145 | <1 | — | — | — |
| 1-146 | <1 | — | — | — |
| 1-147 | <1 | — | — | — |
| 1-153 | <1 | 0.001 | 2.3 | 39 |
| 1-154 | <1 | 0.002 | 4.3 | 27 |
| 1-155 | <1 | 0.002 | 2.8 | 37 |
| 1-156 | <1 | 0.002 | 5.2 | 35 |
| 1-157 | <1 | 0.003 | 2.6 | 35 |
| 1-158 | <1 | 0.003 | 5.2 | 29 |
| 1-159 | <1 | 0.001 | 2.6 | — |
| 1-160 | <1 | 0.003 | 4.6 | 29 |
| 1-161 | <1 | 0.004 | 3.4 | 37 |
| 1-162 | <1 | 0.019 | 6.2 | 35 |
| 1-163 | <1 | 0.004 | 5.9 | 30 |
| 1-164 | 9.7 | 0.035 | 3.8 | 49 |
| 1-165 | <1 | 0.002 | 3.4 | 37 |
| 1-166 | 13 | 0.011 | 3.0 | 71 |

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound represented by the following structural formula:

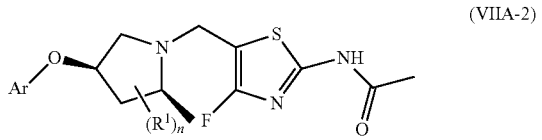

(VIIA-2)

or a pharmaceutically acceptable salt thereof, wherein:
Ar is optionally substituted pyridinyl, optionally substituted pyrimidinyl, optionally substituted pyrazinyl, or optionally substituted pyridazinyl;
n is 0, 1, or 2; and
when n is other than 0, $R^1$, for each occurrence, is independently halo or $C_1$-$C_4$ alkyl.

2. A compound represented by the following structural formula:

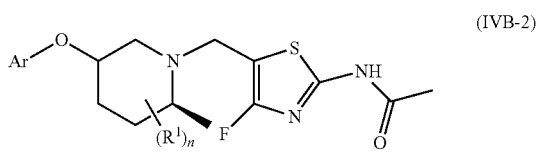

(IVB-2)

or a pharmaceutically acceptable salt thereof, wherein:
Ar is optionally substituted pyridinyl, optionally substituted pyrimidinyl, optionally substituted pyrazinyl, or optionally substituted pyridazinyl;
n is 0, 1, or 2; and
when n is other than 0, $R^1$, for each occurrence, is independently halo or $C_1$-$C_4$ alkyl.

3. The compound according to claim 1 or a pharmaceutically acceptable salt thereof, wherein:
Ar is an optionally substituted pyridinyl, optionally substituted pyrimidinyl, or optionally substituted pyrazinyl.

4. The compound according to claim 1 or a pharmaceutically acceptable salt thereof, wherein:
Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl;
wherein
the $C_1$-$C_4$ alkyl group substituent on Ar is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$—NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy and halomethoxy) or phenyl (optionally substituted with one or more groups selected from —CH$_3$, halomethyl, halo, methoxy and halomethoxy);
the $C_3$-$C_6$ cycloalkyl, $C_3$-$C_6$ heterocyclyl, phenyl and monocyclic heteroaryl group substituent on Ar are optionally and independently substituted with $C_1$-$C_4$ alkyl, $C_1$-$C_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, or —C(=O)R$^x$;
each $R^x$ and each $R^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by $R^x$ or $R^y$ is optionally substituted with one or more substituents selected from halo, hydroxyl, $C_1$-$C_4$ alkyl, $C_1$-$C_4$ alkoxy, $C_3$-$C_6$ cycloalkyl and phenyl (optionally substituted with one or more groups selected from —CH$_3$, halomethyl, halo, methoxy and halomethoxy);
$R^z$ is —H, $C_1$-$C_4$ alkyl, $C_3$-$C_8$ cycloalkyl, or $C_3$-$C_8$ heterocyclyl; wherein the $C_1$-$C_4$ alkyl, $C_3$-$C_8$ cycloalkyl, or $C_3$-$C_8$ heterocyclyl group represented by $R^z$ is optionally substituted with one or more substituents selected from —CN, halo, hydroxyl, $C_1$-$C_4$alkyl, $C_1$-$C_4$alkoxy, $C_3$-$C_6$ cycloalkyl and phenyl (optionally substituted with one or more groups selected from —$CH_3$, halomethyl, halo, methoxy and halomethoxy); and i is 0, 1, or 2.

5. The compound according to claim 1 or a pharmaceutically acceptable salt thereof, wherein:

Ar is optionally substituted with one or more groups selected from optionally substituted $C_1$-$C_4$ alkyl, $C_1$-$C_4$ haloalkyl, optionally substituted $C_3$-$C_6$ cycloalkyl, optionally substituted $C_3$-$C_6$ heterocyclyl, halo, —CN, —$OR^z$, —$NR^xR^y$, —C(=O)$NR^xR^y$, —C(=S)$NR^xR^y$, —O(C=O)$NR^xR^y$, —O(C=S)$NR^xR^y$, —C(=O)$R^x$, —C(=O)$OR^x$, —$NR^xC$(=O)$R^y$, phenyl and optionally substituted monocyclic heteroaryl.

6. The compound according to claim 1 or a pharmaceutically acceptable salt thereof, wherein:

Ar is optionally substituted with one or more groups selected from $C_1$-$C_4$ alkyl, $C_1$-$C_4$ haloalkyl, halo, —CN, and —$OR^z$; wherein $R^z$ is $C_1$-$C_4$ alkyl optionally substituted with one or more halo groups.

7. The compound of claim 1 or a pharmaceutically acceptable salt thereof, wherein n is 0.

8. The compound according to claim 1, wherein the compound is represented by the following structural formula:

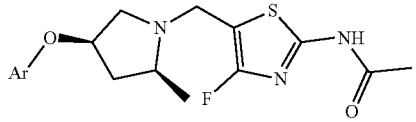

(VIIIA-2)

or a pharmaceutically acceptable salt thereof, wherein:
Ar is

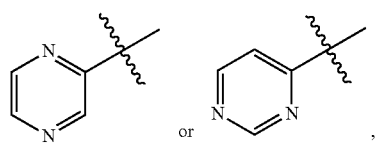 [SMILES: *c1cnccn1 ; *c1ccncn1]

or , each of which is optionally substituted with one substituent $R^{Ar}$ selected from selected from $C_1$-$C_4$ alkyl, $C_1$-$C_4$ haloalkyl, halo, —CN, and —$OR^z$; $R^z$ is H, $C_1$-$C_4$ alkyl, $C_3$-$C_8$ cycloalkyl or $C_3$-$C_6$ heterocyclyl, wherein the $C_1$-$C_4$ alkyl, $C_3$-$C_8$ cycloalkyl and $C_3$-$C_6$ heterocyclyl represented by $R^z$ are each optionally and independently substituted with one or more substituents independently selected from halo, —CN, $C_1$-$C_4$ alkyl and $C_1$-$C_4$ alkoxy.

9. The compound according to claim 1, wherein the compound is selected from

N-(4-fluoro-5-(((2S,4R)-4-((6-(2-methoxyethoxy)pyrimidin-4-yl)oxy)-2-methylpyrrolidin-1-yl)methyl)thiazol-2-yl)acetamide;

N-(5-(((2S,4R)-4-((6-(azetidin-1-yl)pyrimidin-4-yl)oxy)-2-methylpyrrolidin-1-yl)methyl)-4-fluorothiazol-2-yl)acetamide;

N-(4-fluoro-5-(((2S,4R)-4-((6-(3-fluoroazetidin-1-yl)pyrimidin-4-yl)oxy)-2-methylpyrrolidin-1-yl)methyl)thiazol-2-yl)acetamide;

N-(5-(((2S,4R)-4-((6-(3,3-difluoroazetidin-1-yl)pyrimidin-4-yl)oxy)-2-methylpyrrolidin-1-yl)methyl)-4-fluorothiazol-2-yl)acetamide;

N-(4-fluoro-5-(((2S,4R)-4-((5-fluoropyridin-2-yl)oxy)-2-methylpyrrolidin-1-yl)methyl)thiazol-2-yl)acetamide;

N-(5-(((2S,4R)-4-((2,6-dimethylpyridin-4-yl)oxy)-2-methylpyrrolidin-1-yl)methyl)-4-fluorothiazol-2-yl)acetamide;

N-(4-fluoro-5-(((2S,4R)-4-((5-methoxypyrimidin-4-yl)oxy)-2-methylpyrrolidin-1-yl)methyl)thiazol-2-yl)acetamide;

N-(5-(((2S,4R)-4-((6-acetylpyrimidin-4-yl)oxy)-2-methylpyrrolidin-1-yl)methyl)-4-fluorothiazol-2-yl)acetamide;

N-(4-fluoro-5-(((2S,4R)-2-methyl-4-((6-(2,2,2-trifluoroethoxy)pyrimidin-4-yl)oxy)pyrrolidin-1-yl)methyl)thiazol-2-yl)acetamide;

N-(4-fluoro-5-(((2S,4R)-4-((6-methoxypyridazin-3-yl)oxy)-2-methylpyrrolidin-1-yl)methyl)thiazol-2-yl)acetamide;

N-(4-fluoro-5-(((2S,4R)-4-((6-fluoropyridin-3-yl)oxy)-2-methylpyrrolidin-1-yl)methyl)thiazol-2-yl)acetamide;

N-(4-fluoro-5-(((2S,4R)-4-((6-methoxypyrazin-2-yl)oxy)-2-methylpyrrolidin-1-yl)methyl)thiazol-2-yl)acetamide;

N-(4-fluoro-5-(((2S,4R)-4-((5-methoxypyrimidin-2-yl)oxy)-2-methylpyrrolidin-1-yl)methyl)thiazol-2-yl)acetamide;

N-(5-(((2S,4R)-4-((5-chloropyridin-2-yl)oxy)-2-methylpyrrolidin-1-yl)methyl)-4-fluorothiazol-2-yl)acetamide;

N-(4-fluoro-5-(((2S,4R)-4-((4-methoxypyrimidin-2-yl)oxy)-2-methylpyrrolidin-1-yl)methyl)thiazol-2-yl)acetamide;

N-(4-fluoro-5-(((2S,4R)-2-methyl-4-(pyrimidin-2-yloxy)pyrrolidin-1-yl)methyl)thiazol-2-yl)acetamide;

N-(4-fluoro-5-(((2S,4R)-4-((3-fluoropyridin-2-yl)oxy)-2-methylpyrrolidin-1-yl)methyl)thiazol-2-yl)acetamide;

N-(5-(((2S,4R)-4-((5-chloropyrimidin-2-yl)oxy)-2-methylpyrrolidin-1-yl)methyl)-4-fluorothiazol-2-yl)acetamide;

N-(4-fluoro-5-(((2S,4R)-4-((4-fluoropyridin-2-yl)oxy)-2-methylpyrrolidin-1-yl)methyl)thiazol-2-yl)acetamide;

N-(4-fluoro-5-(((2S,4R)-4-((2-fluoropyridin-4-yl)oxy)-2-methylpyrrolidin-1-yl)methyl)thiazol-2-yl)acetamide;

N-(4-fluoro-5-(((2S,4R)-4-((5-methoxypyridin-2-yl)oxy)-2-methylpyrrolidin-1-yl)methyl)thiazol-2-yl)acetamide;

N-(4-fluoro-5-(((2S,4R)-4-((6-methoxypyridin-2-yl)oxy)-2-methylpyrrolidin-1-yl)methyl)thiazol-2-yl)acetamide;

N-(4-fluoro-5-(((2S,4R)-4-((2-methoxypyridin-4-yl)oxy)-2-methylpyrrolidin-1-yl)methyl)thiazol-2-yl)acetamide;

N-(5-(((2S,4R)-4-((4-chloropyridin-2-yl)oxy)-2-methylpyrrolidin-1-yl)methyl)-4-fluorothiazol-2-yl)acetamide;

N-(5-(((2S,4R)-4-((4,5-difluoropyridin-2-yl)oxy)-2-methylpyrrolidin-1-yl)methyl)-4-fluorothiazol-2-yl)acetamide;

N-(4-fluoro-5-(((2S,4R)-2-methyl-4-((6-morpholinopyrimidin-4-yl)oxy)pyrrolidin-1-yl)methyl)thiazol-2-yl)acetamide;

N-(4-fluoro-5-(((2S,4R)-4-((5-methoxypyrazin-2-yl)oxy)-2-methylpyrrolidin-1-yl)methyl)thiazol-2-yl)acetamide;

N-(5-(((2S,4R)-4-((3,5-dimethylpyrazin-2-yl)oxy)-2-methylpyrrolidin-1-yl)methyl)-4-fluorothiazol-2-yl)acetamide;
N-(5-(((2S,4R)-4-((2,5-dimethylpyridin-4-yl)oxy)-2-methylpyrrolidin-1-yl)methyl)-4-fluorothiazol-2-yl)acetamide;
N-(4-fluoro-5-(((2S,4R)-2-methyl-4-((5-methylpyrazin-2-yl)oxy)pyrrolidin-1-yl)methyl)thiazol-2-yl)acetamide;
N-(4-fluoro-5-(((2S,4R)-4-((6-hydroxypyrimidin-4-yl)oxy)-2-methylpyrrolidin-1-yl)methyl)thiazol-2-yl)acetamide;
N-(4-fluoro-5-(((2S,4R)-2-methyl-4-((2-methylpyridin-4-yl)oxy)pyrrolidin-1-yl)methyl)thiazol-2-yl)acetamide;
N-(4-fluoro-5-(((2S,4R)-4-((6-fluoropyridazin-3-yl)oxy)-2-methylpyrrolidin-1-yl)methyl)thiazol-2-yl)acetamide;
N-(4-fluoro-5-(((2S,4R)-4-((5-fluoropyrimidin-2-yl)oxy)-2-methylpyrrolidin-1-yl)methyl)thiazol-2-yl)acetamide;
N-(5-(((2S,4R)-4-((5-(difluoromethyl)pyrazin-2-yl)oxy)-2-methylpyrrolidin-1-yl)methyl)-4-fluorothiazol-2-yl)acetamide;
N-(4-fluoro-5-(((2S,4R)-4-((6-methoxypyridin-3-yl)oxy)-2-methylpyrrolidin-1-yl)methyl)thiazol-2-yl)acetamide;
N-(4-fluoro-5-(((2S,4R)-4-((5-fluoro-4-methylpyridin-2-yl)oxy)-2-methylpyrrolidin-1-yl)methyl)thiazol-2-yl)acetamide;
N-(4-fluoro-5-(((2S,4R)-4-((5-fluoro-4-methoxypyridin-2-yl)oxy)-2-methylpyrrolidin-1-yl)methyl)thiazol-2-yl)acetamide;
N-(4-fluoro-5-(((2S,4R)-2-methyl-4-(pyrimidin-5-yloxy)pyrrolidin-1-yl)methyl)thiazol-2-yl)acetamide;
N-(5-(((2S,4R)-4-((6-chloropyrimidin-4-yl)oxy)-2-methylpyrrolidin-1-yl)methyl)-4-fluorothiazol-2-yl)acetamide;
N-(4-fluoro-5-(((2S,4R)-2-methyl-4-((6-(oxetan-3-yloxy)pyrimidin-4-yl)oxy)pyrrolidin-1-yl)methyl)thiazol-2-yl)acetamide;
N-(4-fluoro-5-(((2S,4R)-2-methyl-4-((6-((1-methylazetidin-3-yl)oxy)pyrimidin-4-yl)oxy)pyrrolidin-1-yl)methyl)thiazol-2-yl)acetamide;
N-(4-fluoro-5-(((2S,4R)-2-methyl-4-((5-morpholinopyrazin-2-yl)oxy)pyrrolidin-1-yl)methyl)thiazol-2-yl)acetamide;
N-(4-fluoro-5-(((2S,4R)-2-methyl-4-((4-morpholinopyridin-2-yl)oxy)pyrrolidin-1-yl)methyl)thiazol-2-yl)acetamide;
N-(4-fluoro-5-(((2S,4R)-4-((5-(2-methoxyethoxy)pyrazin-2-yl)oxy)-2-methylpyrrolidin-1-yl)methyl)thiazol-2-yl)acetamide;
N-(4-fluoro-5-(((2S,4R)-4-((4-((2-methoxyethyl(methyl)amino)pyridin-2-yl)oxy)-2-methylpyrrolidin-1-yl)methyl)thiazol-2-yl)acetamide;
N-(4-fluoro-5-(((2S,4R)-2-methyl-4-((5-morpholinopyridin-2-yl)oxy)pyrrolidin-1-yl)methyl)thiazol-2-yl)acetamide;
N-(4-fluoro-5-(((2S,4R)-4-((4-(2-methoxyethoxy)pyridin-2-yl)oxy)-2-methylpyrrolidin-1-yl)methyl)thiazol-2-yl)acetamide;
N-(4-fluoro-5-(((2S,4R)-4-(4-fluorophenoxy)-2-methylpyrrolidin-1-yl)methyl)thiazol-2-yl)acetamide;
N-(4-fluoro-5-(((2S,4R)-2-methyl-4-((5-(4-methylpiperazin-1-yl)pyridin-2-yl)oxy)pyrrolidin-1-yl)methyl)thiazol-2-yl)acetamide;
N-(4-fluoro-5-(((2S,4R)-4-((5-(2-methoxyethoxy)pyridin-2-yl)oxy)-2-methylpyrrolidin-1-yl)methyl)thiazol-2-yl)acetamide;
N-(4-fluoro-5-(((2S,4R)-4-((5-((2-methoxyethyl(methyl)amino)pyridin-2-yl)oxy)-2-methylpyrrolidin-1-yl)methyl)thiazol-2-yl)acetamide;
N-(4-fluoro-5-(((2S,4R)-2-methyl-4-((4-(4-methylpiperazin-1-yl)pyridin-2-yl)oxy)pyrrolidin-1-yl)methyl)thiazol-2-yl)acetamide;

or a pharmaceutically acceptable salt thereof.

10. A pharmaceutical composition comprising the compound according to claim 1 or a pharmaceutically acceptable salt thereof and a pharmaceutically acceptable carrier or diluent.

11. The compound according to claim 1 or a pharmaceutically acceptable salt thereof, wherein Ar is optionally substituted

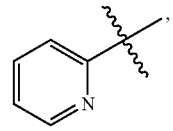 [SMILES: *c1ccccn1]

optionally substituted

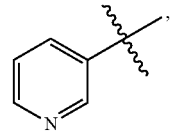 [SMILES: *c1cccnc1]

optionally substituted

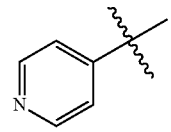

optionally substituted N

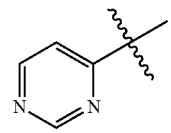

optionally substituted

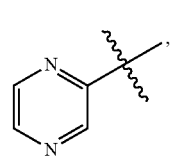 [SMILES: *c1cnccn1]

or optionally substituted

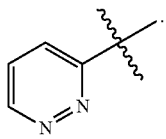 [SMILES: *c1cccnn1]

12. The compound according to claim 2 or a pharmaceutically acceptable salt thereof, wherein Ar is optionally substituted

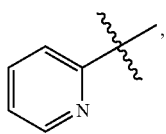

optionally substituted,

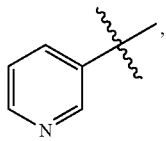 [SMILES: *c1cccnc1]

optionally substituted

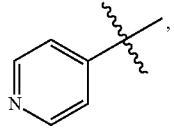

optionally substituted

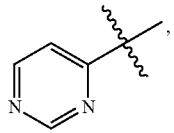

optionally substituted

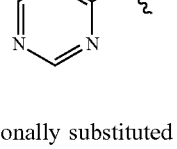

or optionally substituted

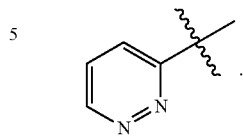

13. The compound according to claim 1 or a pharmaceutically acceptable salt thereof, wherein Ar is optionally substituted

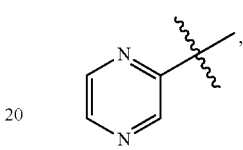

optionally substituted

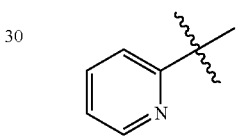

or optionally substituted

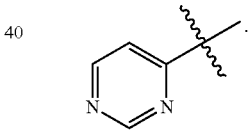

14. The compound according to claim 2 or a pharmaceutically acceptable salt thereof, wherein Ar is optionally substituted

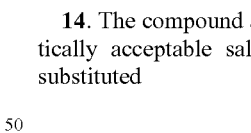

optionally substituted

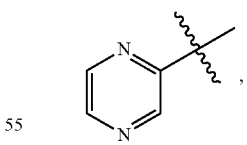

or optionally substituted

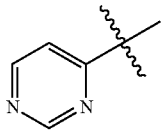

15. The compound according to claim 2 or a pharmaceutically acceptable salt thereof, wherein Ar is optionally substituted with one or more groups selected from optionally substituted $C_1$-$C_4$ alkyl, $C_1$-$C_4$ haloalkyl, optionally substituted $C_3$-$C_6$ cycloalkyl, optionally substituted $C_3$-$C_6$ heterocyclyl, halo, —CN, —$OR^z$, —$NR^xR^y$, —C(=O)$NR^xR^y$, —C(=S)$NR^xR^y$, —O(C=O)$NR^xR^y$, —O(C=S)$NR^xR^y$, —C(=O)$R^x$, —C(=O)$OR^x$, —$NR^xC$(=O)$R^y$, phenyl and optionally substituted monocyclic heteroaryl.

16. The compound according to claim 1 or a pharmaceutically acceptable salt thereof, wherein Ar is optionally substituted with one or more groups selected from —$CH_3$, —$CF_3$, —$CHF_2$, —F, —Cl, —CN, —$OCH_3$, —$OCHF_2$, —$OC_2H_5$, —$OCH_2CF_3$, —$O(CH_2)_2(O)CH_3$, —OCH($CH_3)_2$, —O-(3-methoxycyclobutyl), —O-cyclobutyl, —O-cyclopentyl,

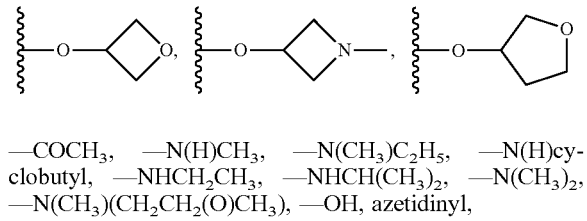

—$COCH_3$, —N(H)$CH_3$, —N($CH_3$)$C_2H_5$, —N(H)cyclobutyl, —$NHCH_2CH_3$, —$NHCH(CH_3)_2$, —N($CH_3)_2$, —N($CH_3$)($CH_2CH_2$(O)$CH_3$), —OH, azetidinyl,

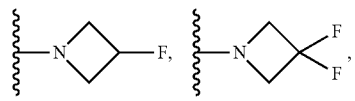

oxetanyl, pyrrolidinyl, morpholinyl, 4-methylpiperazinyl, and piperazinyl.

17. The compound according to claim 2 or a pharmaceutically acceptable salt thereof, wherein Ar is optionally substituted with one or more groups selected from —$CH_3$, —$CF_3$, —$CHF_2$, —F, —Cl, —CN, —$OCH_3$, —$OCHF_2$, —$OC_2H_5$, —$OCH_2CF_3$, —$O(CH_2)_2(O)CH_3$, —OCH($CH_3)_2$, —O-(3-methoxycyclobutyl), —O-cyclobutyl, —O-cyclopentyl,

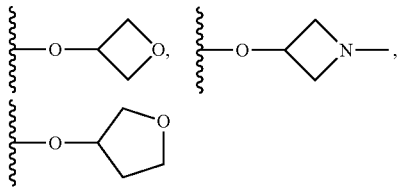

—$COCH_3$, —N(H)$CH_3$, —N($CH_3$)$C_2H_5$, —N(H)cyclobutyl, —$NHCH_2CH_3$, —$NHCH(CH_3)_2$, —N($CH_3)_2$, —N($CH_3$)($CH_2CH_2$(O)$CH_3$), —OH, azetidinyl,

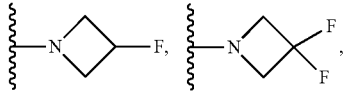

oxetanyl, pyrrolidinyl, morpholinyl, 4-methylpiperazinyl, and piperazinyl.

18. The compound according to claim 1 or a pharmaceutically acceptable salt thereof, wherein Ar is optionally substituted with one or more groups selected from —$CH_3$, —$CF_3$, —$CHF_2$, —F, —Cl, —CN, —$OCH_3$, —$O(CH_2)_2$(O)$CH_3$, and —$OCHF_2$.

19. The compound according to claim 2 or a pharmaceutically acceptable salt thereof, wherein Ar is optionally substituted with one or more groups selected from —$CH_3$, —$CF_3$, —$CHF_2$, —F, —Cl, —CN, —$OCH_3$, —$O(CH_2)_2$(O)$CH_3$, and —$OCHF_2$.

20. The compound according to claim 8 or a pharmaceutically acceptable salt thereof, wherein Ar is represented by the following formula:

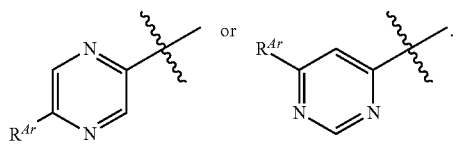

* * * * *

UNITED STATES PATENT AND TRADEMARK OFFICE
CERTIFICATE OF CORRECTION

PATENT NO. : 12,180,205 B2
APPLICATION NO. : 17/276502
DATED : December 31, 2024
INVENTOR(S) : Nathan Genung et al.

Page 1 of 1

It is certified that error appears in the above-identified patent and that said Letters Patent is hereby corrected as shown below:

In the Claims

At Column 132, Claim number 4, Line number 20, please replace "–C(=S)OR$^x$" with ---C(=S)OR$^y$--.

At Column 136, Claim number 9, Line numbers 8-12, please replace "N-(4-fluoro-5-(((2S,4R)-2-methyl-4-((4-(4-methylpiperazin-1-yl)pyridin-2-yl)oxy)pyrrolidin-1-yl)methyl)thiazol-2-yl)acetamide; or a pharmaceutically acceptable salt thereof." with --N-(4-fluoro-5-(((2S,4R)-2-methyl-4-((4-(4 methylpiperazin-1-yl)pyridin-2-yl)oxy)pyrrolidin-1-yl)methyl)thiazol-2-yl)acetamide; and
 N-(4-Fluoro-5-(((2S,4R)-4-((6-methoxypyrimidin-4-yl)oxy)-2-methylpyrrolidin-1-yl)methyl)thiazol-2-yl)acetamide,
 or a pharmaceutically acceptable salt thereof.--.

At Column 136, Claim number 11, Line number 48, please replace "optionally substituted N" with --optionally substituted--.

Signed and Sealed this
Twenty-fourth Day of June, 2025

Coke Morgan Stewart
*Acting Director of the United States Patent and Trademark Office*